United States Patent
Devare et al.

(10) Patent No.: US 6,172,189 B1
(45) Date of Patent: Jan. 9, 2001

(54) HEPATITIS C ASSAY UTILIZING RECOMBINANT ANTIGENS

(75) Inventors: Sushil G. Devare, Northbrook; Suresh M. Desai, Libertyville; James M. Casey, Zion; Stephen H. Dailey, Vernon Hills; George J. Dawson, Libertyville; Robin A. Gutierrez, Gurnee, all of IL (US); Richard R. Lesniewski, Kenosha, WI (US); James L. Stewart, Gurnee; Kevin R. Rupprecht, Grayslake, both of IL (US)

(73) Assignee: Abbott Laboratories, Abbott Park, IL (US)

( * ) Notice: Under 35 U.S.C. 154(b), the term of this patent shall be extended for 0 days.

(21) Appl. No.: 08/867,611

(22) Filed: Jun. 2, 1997

Related U.S. Application Data

(63) Continuation of application No. 08/646,757, filed on May 1, 1996, now abandoned, which is a continuation of application No. 08/179,896, filed on Jan. 10, 1994, now abandoned, which is a continuation of application No. 07/989,843, filed on Nov. 19, 1992, now abandoned, which is a continuation-in-part of application No. 07/748,561, filed on Aug. 21, 1991, now abandoned, and a continuation-in-part of application No. 07/748,565, filed on Oct. 29, 1991, now abandoned, and a continuation-in-part of application No. 07/748,566, filed on Aug. 21, 1991, now abandoned, which is a continuation-in-part of application No. 07/614,069, filed on Nov. 7, 1990, now abandoned, and a continuation-in-part of application No. 07/572,822, filed on Aug. 24, 1990, now abandoned, and a continuation-in-part of application No. 07/748,561, filed on Aug. 21, 1991, and a continuation-in-part of application No. 07/748,565, filed on Aug. 21, 1991, and a continuation-in-part of application No. 07/748,566, filed on Aug. 21, 1991, which is a continuation-in-part of application No. 07/614,069, filed on Nov. 7, 1990, and a continuation-in-part of application No. 07/572,822, filed on Aug. 24, 1990, now abandoned.

(51) Int. Cl.[7] ............... A61K 38/04; A61K 39/29; C07K 5/00; C12N 15/01

(52) U.S. Cl. ............ 530/350; 424/228.1; 435/5; 435/7.1; 435/69.3; 435/172.3; 530/300; 530/326; 530/327

(58) Field of Search ............... 435/5, 7.1, 69.3, 435/172.3; 530/300, 326, 327, 350; 424/228.1

(56) References Cited

U.S. PATENT DOCUMENTS

| | | | |
|---|---|---|---|
| 5,106,726 | * 4/1992 | Wang | 435/5 |
| 5,124,255 | * 6/1992 | Bolling et al. | 435/69.3 |
| 5,350,671 | * 9/1994 | Houghton et al. | 435/5 |

FOREIGN PATENT DOCUMENTS

| | | | |
|---|---|---|---|
| 0318216 | * 5/1989 | (EP) | C12N/15/00 |
| 0331961 | * 9/1989 | (EP) | C12P/21/00 |
| 0388232 | * 9/1990 | (EP) | C12N/15/00 |
| 2212511 | * 7/1989 | (GB) . | |

OTHER PUBLICATIONS

Chou, Q. et al. (91) Proc. Natl. Acad. Sci. USA 88:2451–2455.*
Kremsdorf, O. et al. (91) J. Gen. Virol. 72:2557–2561.*
Takamizawa, A. et al. (91) J. Virol. 65:1105–1113.*

(List continued on next page.)

Primary Examiner—Michael P. Woodward
Assistant Examiner—Mary K. Zeman
(74) Attorney, Agent, or Firm—Dianne Casuto; Priscilla E. Porembski

(57) ABSTRACT

The present invention provides unique recombinant antigens representing distinct antigenic regions of the Hepatitis C Virus (HCV) genome which can be used as reagents for the detection of antibodies and antigen in body fluids from individuals exposed to HCV. The present invention also provides an assay for detecting the presence of an antibody to an HCV antigen in a sample by contacting the sample with the recombinant antigens. Preferred assay formats include a screening assay, a confirmatory assay, a competition or neutralization assay and an immunodot assay.

4 Claims, 60 Drawing Sheets

OTHER PUBLICATIONS

Kato, N. et al. (90) Proc. Natl. Acad. Sci USA 87:9524–9528.*

Okamoto, H. et al. (91) J. Gen. Virol. 72:2697–2704.*

Bolling, T.J. et al (90) Biotechniques 8:488–492.*

T. J. Bolling et al., "An *Escherichia coli* Expression Vector . . .", *BioTechniques*, vol. 8, No. 5 (1990), 488–492.

* cited by examiner

SEROLOGIC PROFILE OF CHIMPANZEES INOCULATED WITH HEPATITIS C VIRUS

| ID # | NAME | ALT (mIU/ml) ELEVATION* (DPI) | | | | | DETECTION OF SEROCONVERSION TO HCV PROTEINS | | |
|---|---|---|---|---|---|---|---|---|---|
| | | Pre ** (range) | First | Peak | Duration | Maximum value | C100-3 (DPI) | pHCV-31 pHCV-34 (DPI) | DAYS DIFFERENT |
| CH 427 | COLONEL | 29 - 53 | 56 | 75 | 24 | 280 | 77 | 56 | 21 |
| CH 479 | JR | 14 - 20 | 91 | 91 | 7 | 156 | 133 | 98 | 35 |
| CH 477 | KIST | 17 - 31 | 30 | 35 | 12 | 107 | 70 | 70 | 0 |
| CH 335 | LEO | 16 - 20 | 38 | 46 | 21 | 295 | 59 | 38 | 21 |
| CH 120 | LOLITA | 15 - 28 | 33 | 65 | 39 | 435 | 65 | 100 | 35 |
| CH 21 | MEULOT | 12 - 30 | 68 | 75 | 14 | 190 | 82 | 66 | 16 |
| CH 379 | PAN | 19 - 27 | 49 | 68 | 28 | 250 | 119 | 98 | 21 |

* twice the upper limit of normal values
** eleven preinoculation samples per animal

*FIG. 2*

| SAMPLE | ASSAY WITH C100-3 MANUAL S/CO | ASSAY WITH pHCV-31 pHCV-34 MANUAL S/CO | CONFIRMATORY RESULTS |
|---|---|---|---|
| 1 | >5.88 (+) | >5.65 (+) | + |
| 2 | 0.63 | 0.54 | |
| 3 | >5.88 (+) | >5.65 (+) | + |
| 4 | >5.88 (+) | >5.65 (+) | + |
| 5 | 0.43 | 0.46 | |
| 6 | >5.88 (+) | >5.65 (+) | + |
| 7 | 0.46 | 0.61 | |
| 8 | 0.41 | 0.70 | |
| 9 | 1.87 (+) | 1.83 (+) | + |
| 10 | 0.35 | 4.88 (+) | + |
| 11 | 0.48 | 0.49 | |
| 12 | 0.32 | 0.50 | |
| 13 | 0.48 | 0.83 | |
| 14 | 0.37 | 0.37 | |
| 15 | >5.88 (+) | >5.65 (+) | + |
| 16 | >5.88 (+) | >5.65 (+) | + |
| 17 | 0.34 | 0.44 | |
| 18 | 3.01 (+) | 2.33 (+) | + |
| 19 | 0.74 | 0.72 | |
| 20 | 0.53 | 0.76 | |
| 21 | >5.88 (+) | >5.65 (+) | + |
| 22 | 0.24 | 0.30 | |
| 23 | >5.88 (+) | >5.65 (+) | + |
| 24 | 0.69 | 0.84 | |
| 25 | 0.50 | 0.75 | |
| 26 | 3.41 (+) | 2.38 (+) | + |
| 27 | 0.62 | 0.82 | |
| 28 | 0.61 | 0.53 | |
| 29 | 0.34 | 4.94 (+) | + |
| 30 | 1.58 (+) | 1.85 (+) | + |
| 31 | 0.32 | 0.52 | |
| 32 | >5.88 (+) | >5.65 (+) | + |
| 33 | 0.45 | 0.58 | |

FIG.14A

| 34 | >5.88 (+) | >5.65 (+) | + |
|---|---|---|---|
| 35 | >5.88 (+) | >5.65 (+) | + |
| 36 | 0.37 | 0.44 | |
| 37 | 0.40 | 0.40 | |
| 38 | >5.88 (+) | >5.65 (+) | + |
| 39* | 0.40 | 1.10 (+) | - |
| 40 | 0.53 | 0.63 | |
| 41 | 0.41 | 0.34 | |
| 42 | 0.52 | 0.70 | |
| 43 | 0.28 | 0.44 | |
| 44 | 0.44 | 0.70 | |

$S/CO = \dfrac{\text{Sample OD}}{\text{Cutoff OD}}$

S/CO = <1.0 is non-reactive
S/CO = ≥1.0 is reactive
*This specimen was negative when retested in duplicate. (S/CO values 0.56 and 0.51.)

FIG.14B

| PANEL MEMBER (LOT #) | IDENTITY | ASSAY WITH C-100-3 | ASSAY WITH pHCV-31 AND pHCV-34 | ORTHO ELISA | CONFIRMATORY RESULTS |
|---|---|---|---|---|---|
| | | | SAMPLE TO CUTOFF VALUES | | |
| 701 | WEAK REACTIVE | 1.819 (+) | 4.469 (+) | 1.239 (+) | + |
| 702 | BORDERLINE REACTIVE | 1.711 (+) | 4.738 (+) | 1.130 (+) | + |
| 703 | NEGATIVE | 0.443 | 0.348 | 0.256 | − |
| 704 | WEAK REACTIVE | 2.220 (+) | 4.738 (+) | 1.639 (+) | + |
| 705 | BORDERLINE REACTIVE | 1.648 (+) | 1.736 (+) | 0.911 | + |
| 706 | NEGATIVE | 0.221 | 0.369 | 0.340 | − |
| 707 | STRONG REACTIVE | 5.713 (+) | 4.738 (+) | 4.272 (+) | + |
| 708 | STRONG REACTIVE | 5.713 (+) | 4.738 (+) | 4.272 (+) | + |
| 709 | NON-REACTIVE* | 0.401 | 0.533 | 0.650 | − |
| 710 | NON-REACTIVE* | 0.582 | 0.419 | 0.423 | − |

* CONTAINS VERY LOW LEVELS OF ANTI-HCV. NOT REQUIRED TO BE DETECTED BY CURRENT HCV ASSAYS.

FIG.15

ANTI-HCV RESULTS ON NON-A, NON-B HEMODIALYSIS PATIENTS

| PATIENT # | DATE | ALT IU/L | ASSAY WITH C-100-3 | | ASSAY WITH pHCV-31, pHCV-34 | | CONFIRMATORY RESULTS |
|---|---|---|---|---|---|---|---|
| 1 | 10/28/85 | 474 | 0.30 | (−) | 2.12 | (+) | + |
|  | 11/11/85 | 113 | 0.38 | (−) | 4.72 | (+) | + |
|  | 12/03/85 | 86 | 3.13 | (+) | >5.65 | (+) | + |
|  | 01/09/86 | 142 | >5.61 | (+) | NT | | NT |
|  | 03/19/86 | 90 | >5.61 | (+) | >5.65 | (+) | + |
|  | 09/30/86 | 25 | >5.61 | (+) | >6.67 | (+) | + |
| 2 | 09/14/87 | 217 | 5.02 | (+) | 5.84 | (+) | + |
|  | 09/17/87 | 210 | >5.61 | (+) | 6.58 | (+) | + |
| 3 | 10/02/87 | 116 | 1.61 | (+) | 1.69 | (+) | + |
| 4 | 11/24/87 | NA | 0.41 | (−) | 2.13 | (+) | + |
|  | 12/17/87 | NA | 0.47 | (−) | 1.27 | (+) | + |
|  | 01/13/88 | NA | 0.46 | (−) | 1.56 | (+) | + |
|  | 02/21/88 | NA | 0.34 | (−) | 1.45 | (+) | + |
| 7 | 10/02/85 | 298 | 0.79 | (−) | 2.94 | (+) | + |
|  | 10/07/85 | 548 | 0.86 | (−) | 2.68 | (+) | + |
|  | 10/23/85 | 334 | 2.06 | (+) | 2.32 | (+) | + |
| 10 | 01/25/89 | NA | 0.57 | (−) | 2.66 | (+) | + |
|  | 02/01/89 | NA | 1.08 | (+) | 2.80 | (+) | + |
|  | 02/08/89 | NA | 1.75 | (+) | 3.38 | (+) | + |
|  | 02/23/89 | NA | 2.22 | (+) | 2.56 | (+) | + |
|  | 03/01/89 | NA | 1.94 | (+) | 3.21 | (+) | + |
|  | 03/08/89 | NA | 1.64 | (+) | 2.52 | (+) | + |
|  | 03/22/89 | NA | 1.49 | (+) | 1.76 | (+) | + |
|  | 04/12/89 | NA | 2.69 | (+) | 5.29 | (+) | + |
|  | 04/26/89 | NA | 2.77 | (+) | >5.65 | (+) | + |
|  | 05/17/89 | NA | 2.19 | (+) | 2.82 | (+) | + |
| 13 | 10/05/88 | NA | 0.31 | (−) | 0.51 | (−) | NT |
|  | 10/19/88 | NA | 0.40 | (−) | 0.61 | (−) | NT |
|  | 10/28/88 | NA | 0.33 | (−) | 0.53 | (−) | NT |
|  | 11/09/88 | NA | 0.33 | (−) | 0.64 | (−) | NT |
|  | 11/11/88 | NA | 0.37 | (−) | 0.66 | (−) | NT |

FIG. 16

|   | 11/18/88 | NA | 0.42 | (−) | 0.57 | (−) | NT |
|---|---|---|---|---|---|---|---|
|   | 11/25/88 | NA | 0.44 | (−) | 0.65 | (−) | NT |
|   | 12/05/88 | NA | 0.51 | (−) | 0.74 | (−) | NT |
|   | 12/16/88 | NA | 0.28 | (−) | 0.68 | (−) | NT |
|   | 12/23/88 | NA | 0.29 | (−) | 0.64 | (−) | NT |
|   | 01/04/89 | NA | 0.29 | (−) | 0.77 | (−) | NT |
|   | 01/13/89 | NA | 0.33 | (−) | 1.11 | (+) | + |
|   | 01/20/89 | NA | 0.30 | (−) | 1.11 | (+) | + |
|   | 02/08/89 | NA | 0.26 | (−) | 1.81 | (+) | + |
|   | 02/10/89 | NA | 0.26 | (−) | 1.88 | (+) | + |
|   | 02/17/89 | NA | 0.26 | (−) | 2.23 | (+) | + |
|   | 02/24/89 | NA | 0.28 | (−) | 3.75 | (+) | + |
|   | 03/08/89 | NA | 0.28 | (−) | 5.25 | (+) | + |
|   | 03/17/89 | NA | 0.22 | (−) | >5.65 | (+) | + |
|   | 04/03/89 | NA | 0.26 | (−) | >5.65 | (+) | + |
|   | 04/14/89 | NA | 0.26 | (−) | >5.65 | (+) | + |
|   | 04/20/89 | NA | 0.29 | (−) | >5.65 | (+) | + |
|   | 04/28/89 | NA | 0.31 | (−) | >5.65 | (+) | + |
|   | 05/05/89 | NA | 0.28 | (−) | >5.65 | (+) | + |
|   | 07/03/89 | NA | 0.23 | (−) | 5.32 | (+) | + |
|   |   |   |   |   |   |   |   |
| 17 | 10/05/88 | 1454 | 0.53 | (−) | 0.95 | (−) | NT |
|   | 10/20/88 | 612 | 0.57 | (−) | 2.04 | (+) | + |
|   | 10/28/88 | 576 | 0.56 | (−) | 1.26 | (+) | + |
|   | 11/09/88 | 306 | 0.54 | (−) | 1.39 | (+) | + |
|   | 11/11/88 | 321 | 0.73 | (−) | 1.34 | (+) | + |
|   | 11/18/88 | 341 | 0.83 | (−) | 1.43 | (+) | + |
|   | 11/25/88 | 333 | 0.73 | (−) | 1.83 | (+) | + |
|   | 12/05/88 | 232 | 0.75 | (−) | 1.92 | (+) | + |
|   | 12/16/88 | 239 | 0.81 | (−) | 2.75 | (+) | + |
|   | 12/23/88 | 198 | 1.20 | (+) | 3.42 | (+) | + |
|   | 01/13/89 | 146 | 3.17 | (+) | >5.65 | (+) | + |
|   | 01/27/89 | 104 | 4.36 | (+) | >6.67 | (+) | + |
|   | 02/17/89 | 113 | >5.61 | (+) | >6.67 | (+) | + |
|   | 02/24/89 | 120 | >5.61 | (+) | >6.67 | (+) | + |
|   |   |   |   |   |   |   |   |
| 18 | 01/13/89 | 112 | >5.61 | (+) | >5.65 | (+) | + |
|   | 01/21/89 | 72 | >5.61 | (+) | >5.65 | (+) | + |
|   | 01/28/89 | 181 | >5.61 | (+) | >6.67 | (+) | + |
|   | 02/08/89 | 106 | >5.61 | (+) | >5.65 | (+) | + |

FIG. 16A

|     | 02/18/89 | 82 | >5.61 | (+) | >5.65 | (+) | + |
| --- | --- | --- | --- | --- | --- | --- | --- |
|     | 03/08/89 | 62 | >5.61 | (+) | >5.65 | (+) | + |
|     | 03/18/89 | 41 | >5.61 | (+) | NT    |     | NT |
|     | 03/25/89 | 37 | >5.61 | (+) | >5.65 | (+) | + |
|     | 04/04/89 | 37 | >5.61 | (+) | >5.65 | (+) | + |
|     | 04/15/89 | 35 | >5.61 | (+) | >5.65 | (+) | + |
|     | 04/22/89 | 27 | >5.61 | (+) | >5.65 | (+) | + |
|     | 04/29/89 | 24 | >5.61 | (+) | >5.65 | (+) | + |
|     | 05/06/89 | 25 | >5.61 | (+) | >5.65 | (+) | + |
|     | 07/03/89 | 31 | >5.61 | (+) | >5.65 | (+) | + |
|     |          |    |       |     |       |     |   |
| 19  | 02/17/89 | NA | 0.33  | (-) | 0.75  | (-) | NT |
|     | 02/24/89 | NA | 0.35  | (-) | 0.62  | (-) | NT |
|     | 03/08/89 | NA | 0.38  | (-) | 0.69  | (-) | NT |
|     | 04/03/89 | NA | 0.13  | (-) | 0.87  | (-) | NT |
|     | 04/14/89 | NA | 0.35  | (-) | 1.07  | (+) | + |
|     | 04/21/89 | NA | 0.32  | (-) | 1.54  | (+) | + |
|     | 04/28/89 | NA | 0.29  | (-) | 1.04  | (+) | + |
|     | 05/05/89 | NA | 0.36  | (-) | 1.16  | (+) | + |
|     | 07/03/89 | NA | 0.30  | (-) | 1.24  | (+) | + |

NT = Not Tested
NA = Not Available

*FIG. 16B*

| CATEGORY | No. SPECIMENS | No. SPECIMENS REPEATABLY REACTIVE BY C-100-3 ASSAY | No. CONFIRMED | No. SPECIMENS REPEATABLY REACTIVE BY ASSAY WITH pHCV-31, pHCV-34 | No. SPECIMENS REPEATABLY REACTIVE WHICH CONFIRMED (%) |
|---|---|---|---|---|---|
| ACUTE POST-TRANSFUSION NANBH | 32 | 4 (12.50%) | 4 | 14* (43.75%) | 11/12** (91.67%) |
| COMMUNITY ACQUIRED NANBH (ACUTE) | 10 | 2 (20.00%) | 2 | 4 (40.00%) | 4 (100.00%) |

FIG.18

| CATEGORY | No. SPECIMENS FOUND ADDITIONALLY REACTIVE ASSAY pHCV-31, pHCV34 | No. SPECIMENS CONFIRMED BY sp67 PEPTIDE | No. SPECIMENS CONFIRMED BY CORE PEPTIDE(sp7.5) | No. SPECIMENS CONFIRMED BY SOD-33c ANTIGEN |
|---|---|---|---|---|
| ACUTE POST-TRANSFUSION NANBH | 11 | 0 | 8* | 0 |
| COMMUNITY ACQUIRED NANBH (ACUTE) | 2 | 0 | 2 | ND** |

FIG.19

| CATEGORY | No. TESTED | C-100-3 ASSAY | | pHCV-34, pHCV-31 ASSAY | |
|---|---|---|---|---|---|
| | | REPEAT REACTIVE | CONFIRMED | REPEAT REACTIVE | CONFIRMED |
| CHRONIC ACTIVE NANBH | 102 | 89 (87.3%) | 88 | 98 (96.1%) | 98 |
| CHRONIC PERSISTENT NANBH | 10 | 9 (90.0%) | 9 | 9 (90.0%) | 9 |
| CHRONIC NANBH WITH CIRRHOSIS | 17 | 15 (88.2%) | 15 | 15 (88.2%) | 15 |
| CHRONIC NANBH (UNDEFINED) | 35 | 25 (71.4%) | 25 | 33 (94.3%) | 33 |
| TOTAL CHRONIC NANBH | 164 | 138 (84.1%) | 137 | 155 (94.5%) | 155 |

FIG. 20

HCV POLYPEPTIDE SPOTTING CONDITIONS

| PLASMID/PROTEIN | ng/SPOT | SPOTTING BUFFER |
| --- | --- | --- |
| c100 | 100-150 | 20mM Tris-HCl, 0.9% NaCl, 0.015% SDS, pH 8.3 |
| pHCV-23/CKS-BCD | 100-150 | 20mM Tris-HCl, 0.9% NaCl, 0.015% SDS, pH 8.3 |
| pHCV-29/CKS-33c | 100-150 | 50mM Naphosphate, 0.01% Triton X100, pH 6.5 |
| pHCV-34/CKS-CORE | 75-100 | 50mM Naphosphate, 0.0025% Tween20, pH12.0 |

FIG. 21

|  | REFLECTANCE DENSITY VALUES | | LIMITING DILUTION | |
|---|---|---|---|---|
| ANTIGEN | NEGATIVE MEAN | CUTOFF | A00642 | 423 |
| c100-3 | 0.023 | 0.129 | 1600 | 40 |
| pHCV-23 | 0.011 | 0.050 | 3200 | 320 |
| pHCV-29 | 0.005 | 0.031 | 12800 | 2560 |
| pHCV-34 | 0.027 | 0.166 | 400 | 320 |

FIG. 22

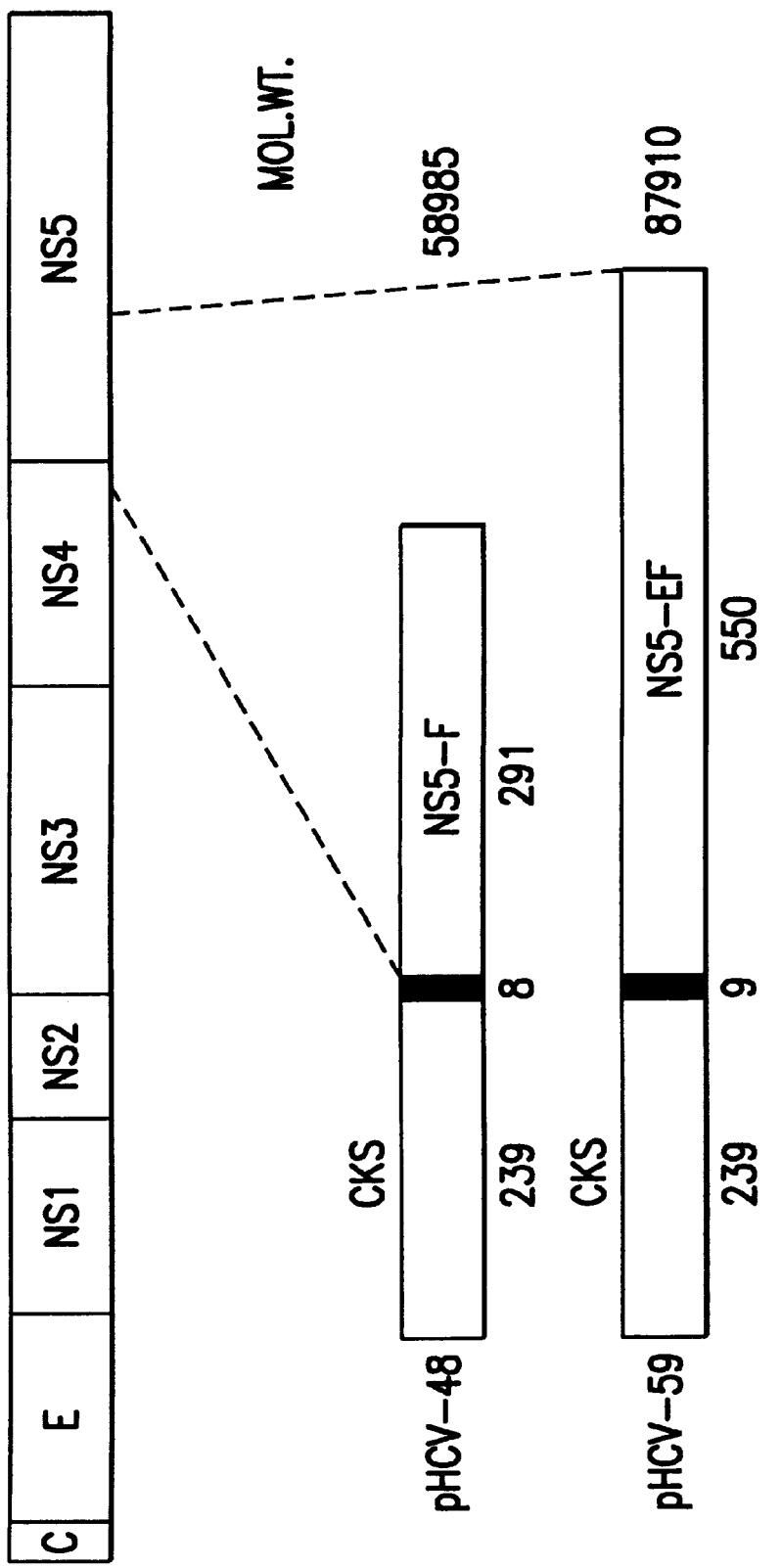

HEPATITIS C ASSAY UTILIZING RECOMBINANT ANTIGENS

This Application is a continuation of application Ser. No. 08/646,757, filed May 1, 1996, now abandoned, which is a continuation of application Ser. No. 08/179,896, filed Jan. 10, 1994, now abandoned, which is a continuation of application Ser. No. 07/989,843, filed Nov. 19, 1992, now abandoned, which is a CIP of application Ser. No. 07/748,561, filed Aug. 21, 1991, now abandoned, and a CIP of application Ser. No. 07/48,565, filed Oct. 29, 1991, now abandoned, and a CIP of application Ser. No. 07/748,566, filed Aug. 21, 1991, now abandoned, which is a CIP of application Ser. No. 07/614,069, filed Nov. 7, 1990, now abandoned, and a CIP of application Ser. No. 07/572,822, filed Aug. 24, 1990, now abandoned.

This application is a continuation-in-part application of pending U.S. patent applications Ser. No. 07/48,561 entitled Hepatitis C Assay Utilizing Recombinant Antigens to NS1, U.S. Ser. No. 07/748,565 entitled Hepatitis C Assay Utilizing Recombinant Antigens From NS5 Region and U.S. Ser. No. 07/748,566 entitled Hepatitis C Assay Utilizing Recombinant Antigens to C-100 Region, each of which was filed on Aug. 21, 1991 and each of which is a continuation-in-part application of pending U.S. Ser. No. 07/614,069 filed Nov. 7, 1990 and U.S. Ser. No. 07/572,822 filed Aug. 24, 1990, abandoned, all of which enjoy common ownership and are incorporated herein by reference.

This invention relates generally to an assay for identifying the presence in a sample of an antibody which is immunologically reactive with a hepatitis C virus antigen and specifically to an assay for detecting a complex of an antibody and recombinant antigens representing distinct regions of the HCV genome. Recombinant antigens derived from the molecular cloning and expression in a heterologous expression system of the synthetic DNA sequences representing distinct antigenic regions of the HCV genome can be used as reagents for the detection of antibodies and antigen in body fluids from individuals exposed to hepatitis C virus (HCV).

BACKGROUND OF THE INVENTION

Acute viral hepatitis is clinically diagnosed by a well-defined set of patient symptoms, including jaundice, hepatic tenderness, and an increase in the serum levels of alanine aminotransferase (ALT) and aspartate aminotransferase. Additional serologic immunoassays are generally performed to diagnose the specific type of viral causative agent. Historically, patients presenting clinical hepatitis symptoms and not otherwise infected by hepatitis A, hepatitis B, Epstein-Barr or cytomegalovirus were clinically diagnosed as having non-A non-B hepatitis (NANBH) by default. The disease may result in chronic liver damage.

Each of the well-known, immunologically characterized hepatitis-inducing viruses, hepatitis A virus (HAV), hepatitis B virus (HBV), and hepatitis D virus (HDV) belongs to a separate family of viruses and has a distinctive viral organization, protein structure, and mode of replication.

Attempts to identify the NANBH virus by virtue of genomic similarity to one of the known hepatitis viruses have failed, suggesting that NANBH has a distinct organization and structure. [Fowler, et al., *J. Med. Virol.*, 12:205–213 (1983) and Weiner, et al., *J. Med. Virol.*, 21:239–247 (1987)].

Progress in developing assays to detect antibodies specific for NANBH has been particularly hampered by difficulties in correctly identifying antigens associated with NANBH. See, for example, Wands, J., et al., U.S. Pat. No. 4,870,076, Wands, et al., *Proc. Nat'l. Acad. Sci.*, 83:6608–6612 (1986), Ohori, et al., *J. Med. Virol.*, 12:161–178 (1983), Bradley, et al., *Proc. Nat'l. Acad. Sci.*, 84:6277–6281, (1987), Akatsuka, T., et al., *J. Med. Virol*, 20:43–56 (1986), Seto, B., et al., U.S. patent application Ser. No. 07/234,641 (available from U.S. Department of Commerce National Technical Information Service, Springfield, Va., No. 89138168), Takahashi, K., et al., European Patent Application No. 0 293 274, published Nov. 30, 1988, and Seelig, R., et al., in PCT Application PCT/EP88/00123.

Recently, another hepatitis-inducing virus has been unequivocally identified as hepatitis C virus (HCV) by Houghton, M., et al., European Patent Application publication number 0 318 216, May 31, 1989. Related papers describing this virus include Kuo, G., et al., *Science*, 244:359–361 (1989) and Choo, Q., et. al, *Science*, 244:362–364 (1989). Houghton, M., et al. reported isolating cDNA sequences from HCV which encode antigens which react immunologically with antibodies present in patients infected with NANBH, thus establishing that HCV is one of the viral agents causing NANBH. The cDNA sequences associated with HCV were isolated from a cDNA library prepared from the RNA obtained from pooled serum from a chimpanzee with chronic HCV infection. The cDNA library contained cDNA sequences of approximate mean size of about 200 base pairs. The cDNA library was screened for encoded epitopes expressed in clones that could bind to antibodies in sera from patients who had previously experienced NANBH.

In the European Patent Application, Houghton, M., et al. also described the preparation of several superoxide dismutase fusion polypeptides (SOD) and the use of these SOD fusion polypeptides to develop an HCV screening assay. The most complex SOD fusion polypeptide described in the European Patent Application, designated c100-3, was described as containing 154 amino acids of human SOD at the aminoterminus, 5 amino acid residues derived from the expression of a synthetic DNA adapter containing a restriction site, EcoRI, 363 amino acids derived from the expression of a cloned HCV cDNA fragment, and 5 carboxyl terminal amino acids derived from an MS2 cloning vector nucleotide sequence. The DNA sequence encoding this polypeptide was transformed into yeast cells using a plasmid. The transformed cells were cultured and expressed a 54,000 molecular weight polypeptide which was purified to about 80% purity by differential extraction.

Other SOD fusion polypeptides designated SOD-NANB$_{5-1-1}$ and SOD-NANB$_{81}$ were expressed in recombinant bacteria. The *E.coli* fusion polypeptides were purified by differential extraction and by chromatography using anion and cation exchange columns. The purification procedures were able to produce SOD-NANB$_{5-1-1}$ as about 80% pure and SOD-NAN38, as about 50% pure.

The recombinant SOD fusion polypeptides described by Houghton, M., et al. were coated on microtiter wells or polystyrene beads and used to assay serum samples. Briefly, coated microtiter wells were incubated with a sample in a diluent. After incubation, the microtiter wells were washed and then developed using either a radioactively labelled sheep anti-human antibody or a mouse antihuman IgG-HRP (horseradish peroxidase) conjugate. These assays were used to detect both post acute phase and chronic phase HCV infection.

Due to the preparative methods, assay specificity required adding yeast or *E. coli* extracts to the samples in order to prevent undesired immunological reactions with any yeast or *E.coli* antibodies present in samples.

Ortho Diagnostic Systems Inc. have developed a immunoenzyme assay to detect antibodies to HCV antigens. The Ortho assay procedure is a three-stage test for serum/plasma carried out in a microwell coated with the recombinant yeast/hepatitis C virus SOD fusion polypeptide c100-3.

In the first stage, a test specimen is diluted directly in the test well and incubated for a specified length of time. If antibodies to HCV antigens are present in the specimen, antigen-antibody complexes will be formed on the microwell surface. If no antibodies are present, complexes will not be formed and the unbound serum or plasma proteins will be removed in a washing step.

In the second stage, anti-human IgG murine monoclonal antibody horseradish peroxidase conjugate is added to the microwell. The conjugate binds specifically to the antibody portion of the antigen-antibody complexes. If antigen-antibody complexes are not present, the unbound conjugate will also be removed by a washing step.

In the third stage, an enzyme detection system composed of o-phenylenediamine 2HCl (OPD) and hydrogen peroxide is added to the test well. If bound conjugate is present, the OPD will be oxidized, resulting in a colored end product. After formation of the colored end product, dilute sulfuric acid is added to the microwell to stop the color-forming detection reaction.

The intensity of the colored end product is measured with a microwell reader. The assay may be used to screen patient serum and plasma It is established that HCV may be transmitted by contaminated blood and blood products. In transfused patients, as many as 10% will suffer from post-transfusion hepatitis. Of these, approximately 90% are the result of infections diagnosed as HCV. The prevention of transmission of HCV by blood and blood products requires reliable, sensitive and specific diagnosis and prognostic tools to identify HCV carriers as well as contaminated blood and blood products. Thus, there exists a need for an HCV assay which uses reliable and efficient reagents and methods to accurately detect the presence of HCV antibodies in samples.

SUMMARY OF THE INVENTION

The present invention provides an improved assay for detecting the presence of an antibody to an HCV antigen in a sample by contacting the sample with at least one recombinant protein representing a distinct antigenic region of the HCV genome. The recombinant antigens include SEQ. ID. NO 2, SEQ. ID. NO 4, SEQ. ID. NO 6, SEQ. ID. NO 8, SEQ. ID. NO 10, SEQ. ID. NO 12, SEQ. ID. NO 14, SEQ. ID. NO 16, SEQ. ID. NO 18, SEQ. ID. NO 20, SEQ. ID. NO 22, SEQ. ID. NO 24, SEQ. ID. NO 26, SEQ. ID. NO 28, SEQ. ID. NO 30, SEQ. ID. NO 58, SEQ. ID. NO 59, SEQ. ID. NO. 31, SEQ. ID. NO. 32, SEQ. ID. NO. 33, SEQ. ID. NO. 34, SEQ. ID. NO. 35, SEQ. ID. NO. 36, SEQ. ID. NO 47, SEQ. ID. NO. 48, SEQ. ID. NO. 49, SEQ. ID. NO. 50, SEQ. ID. NO. 52, SEQ. ID. NO. 53 and SEQ. ID. NO. 54.

One assay format according to the invention provides a screening assay for identifying the presence of an antibody that is immunologically reactive with an HCV antigen. Briefly, a fluid sample is incubated with a solid support containing the two commonly bound recombinant proteins HCV pHCV-34 (SEQ. ID. NO. 2) and pHCV-31 (SEQ. ID. NO. 4). Finally, the antibody-antigen complex is detected. In a modification of the screening assay the solid support additionally contains recombinant polypeptide c100-3.

Another assay format provides a confirmatory assay for unequivocally identifying the presence of an antibody that is immunologically reactive with an HCV antigen. The confirmatory assay includes synthetic peptides or recombinant antigens representing major epitopes contained within the three distinct regions of the HCV genome, which are the same regions represented by the two recombinant proteins described in the screening assay. These regions include NS4 (the c100-3 region) represented by pHCV-23 (SEQ. ID. NO 58), NS3 (the 33c region) represented by pHCV-29 (SEQ. ID. NO. 59), and together with pHCV-23 (the c100-3 region) represented by pHCV-31, and a region near the 5' end of the HCV genome believed to be the core structural protein of HCV (pHCV-34). Recombinant proteins used in the confirmatory assay should have a heterologous source of antigen to that used in the primary screening assay (i.e. should not be an *E.coli*-derived recombinant antigen nor a recombinant antigen composed in part, of CKS sequences). Briefly, specimens repeatedly reactive in the primary screening assay are retested in the confimnatory assay. Aliquots containing identical amounts of specimen are contacted with a synthetic peptide or recombinant antigen individually coated onto a solid support Finally, the antibody-antigen complex is detected. Seroreactivity for epitopes within the c100-3 region of the HCV genome are confirmed by use of the synthetic peptides sp67 and sp65. The synthetic peptide sp 117 can also be used to confirm seroreactivity within the c100-3 region. Seroreactivity for HCV epitopes within the putative core region of HCV are confirmed by the use of the synthetic peptide sp75. In order to confirm seroreactivity for HCV epitopes within the 33c region of HCV, a recombinant antigen is expressed as a chimeric protein with superoxide dismutase (SOD) in yeast. The synthetic peptide sp65 (representing amino acids p1866–1930 of the HCV sequence), sp67 (representing amino acids p1684–1750), sp75 (representing amino acids p1–75), and sp117 (representing amino acids p1689–1805) are described in U.S. Ser. No. 456,162 entitled "Hepatitis C Assay", filed Dec. 22, 1989, which enjoys common ownership and is incorporated herein by reference.

Another assay format provides a competition assay or neutralization assay directed to the confirmation that positive results are not false by identifying the presence of an antibody that is immunologically reactive with an HCV antigen in a fluid sample where the sample is used to prepare first and second immunologically equivalent aliquots. The first aliquot is contacted with solid support containing a bound polypeptide which contains at least one epitope of an HCV antigen under conditions suitable for complexing with the antibody to form a detectable antibody-polypeptide complex and the second aliquot is first contacted with the same solid support containing bound polypeptide. The preferred recombinant polypeptide is derived from pHCV-23.

Another assay format provides an immunodot assay for identifying the presence of an antibody that is immunologically reactive with an HCV antigen by concurrently contacting a sample with recombinant polypeptides each containing distinct epitopes of an HCV antigen under conditions suitable for complexing the antibody with at least one of the polypeptides and detecting the antibody polypeptide complex by reacting the complex with color producing reagents. The preferred recombinant polypeptides employed include those recombinant polypeptides derived from pHCV-23, pHCV-29, pHCV-31, pHCV-34, as well as c100-3 expressed as a chimeric protein with superoxide dismutase (SOD) in yeast.

In all of the assays, the sample is preferably diluted before contacting the polypeptide absorbed on a solid support.

Samples may be obtained from different biological samples such as whole blood, serum, plasma, cerebral spinal fluid, and lymphocyte or cell culture supernatants. Solid support materials may include cellulose materials, such as paper and nitrocellulose, natural and synthetic polymeric materials, such as polyacrylamide, polystyrene, and cotton, porous gels such as silica gel, agarose, dextran and gelatin, and inorganic materials such as deactivated alumina, magnesium sulfate and glass. Suitable solid support materials may be used in assays in a variety of well known physical configurations, including microtiter wells, test tubes, beads, strips, membranes, and microparticles. A preferred solid support for a non-immunodot assay is a polystyrene bead. A preferred solid support for an immunodot assay is nitrocellulose.

Suitable methods and reagents for detecting an antibody-antigen complex in an assay of the present invention are commercially available or known in the relevant art Representative methods may employ detection reagents such as enzymatic, radioisotopic, fluorescent, luminescent, or chemiluminescent reagents. These reagents may be used to prepare hapten-labelled antihapten detection systems according to known procedures, for example, a biotin-labelled antibiotin system may be used to detect an antibody-antigen complex.

Polypeptides also are provided. These include SEQ. ID. NO 2, SEQ. ID. NO 4, SEQ. ID. NO 6, SEQ. ID. NO 8, SEQ. ID. NO 10, SEQ. ID. NO 12, SEQ. ID. NO 14, SEQ. ID. NO 16, SEQ. ID. NO 18, SEQ. ID. NO 20, SEQ. ID. NO 22, SEQ. ID. NO 24, SEQ. ID. NO 26, SEQ. ID. NO 28, SEQ. ID. NO 30, SEQ. ID. NO 58, SEQ. ID. NO 59, SEQ. ID. NO. 31, SEQ. ID. NO. 32, SEQ. ID. NO. 33, SEQ. ID. NO. 34, SEQ. ID. NO. 35, SEQ. ID. NO. 36, SEQ. ID. NO 47, SEQ. ID. NO. 48, SEQ. ID. NO. 49, SEQ. ID. NO. 50, SEQ. ID. NO. 52, SEQ. ID. NO. 53 and SEQ. ID. NO. 54.

The present invention in addition provides plasmids. These plasmids include those with the following sequences: SEQ. ID. NO. 58, SEQ. ID. NO. 59, SEQ. ID. NO. 4 and SEQ. ID. NO. 2.

The present invention also encompasses assay kits including containers containing polypeptides or recombinant proteins which contain at least one epitope of an HCV antigen bound to a solid support as well as a containers containing needed sample preparation reagents, wash reagents, detection reagents and signal producing reagents.

Other aspects and advantages of the invention will be apparent to those skilled in the art upon consideration of the following detailed description which provides illustrations of the invention in its presently preferred embodiments.

*E.coli* strains containing plasmids useful for constructs of the invention were deposited at the American Type Culture Collection, 12301 Parklawn Drive, Rockville, Md. on Aug. 10, 1990, under the accession Nos. ATCC 68380 (pHCV-23), ATCC 68381 (pHCV-29), ATCC 68382 (pHCV-31), ATCC 68383 (pHCV-34, and on Nov. 6, 1990 for *E.coli* strains containing plasmids useful for constructs under the accession Nos. ATCC 68458 (pHCV-50), ATCC 68459 (pHCV-57), ATCC 68460 (pHCV-103), ATCC 68461 (pHCV-102), ATCC 68462 (pHCV-51), ATCC 68463 (pHCV-105), ATCC 68464 (pHCV-107), ATCC 68465 (pHCV-104), ATCC 68466 (pHCV-45), ATCC 68467 (pHCV-48),ATCC 68468 (pHCV-49), ATCC 68469 (pHCV-58) and ATCC 68470 (pHCV-101). *E. coli* strains containing plasmids useful for constructs of the invention also were deposited at the A.T.C.C. on Sep. 26, 1991 under deposit numbers ATCC 68690 (pHCV-77), ATCC 68696 (pHCV-65), ATCC 68689 (pHCV-78), ATCC 68688 (pHCV-80) and ATCC 68695 (pHCV-92), ATCC 68691 (pHCV-59), ATCC 68692 (pHCV-62), ATCC 68687 (pHCV-63), ATCC 68685 (pHCV-72), ATCC 68684 (pHCV-73), ATCC 68694 (pHCV-204), ATCC 68693 (pHCV-205) and ATCC 68686 (pHCV-112).

BRIEF DESCRIPTION OF THE DRAWINGS

FIG. 2 illustrates the use of recombinant polypeptides to identify the presence of antibodies in a chimpanzee inoculated with HCV.

FIG. 14 illustrates the increased sensitivity using the screening assay utilizing the pHCV-34.

FIG. 15 illustrates the increased specificity with the screening assay utilizing pHCV-34 and pHCV-31.

FIGS. 16, 16A and B illustrate the results in hemodialysis patients using the screening and confirmatory assays.

FIG. 18 illustrates the results of the screening assay utilizing pHCV-34 and pHCV-31 on samples from individuals with acute NANBH.

FIG. 19 illustrates the results of the confirmatory assay of the same population group as in FIG. 18.

FIG. 20 illustrates the results of the screening and confirmatory assays on individuals infected with chronic NANBH.

FIG. 21 illustrates preferred buffers, pH conditions, and spotting concentrations for the HCV immunodot assay.

FIG. 22 illustrates the results of the HCV immunodot assay.

FIG. 50 illustrates the NS5 region of the HCV genome, and in particular, the location of pHCV-48 and pHCV-59.

DETAILED DESCRIPTION OF THE INVENTION

The present invention is directed to an assay to detect an antibody to an HCV antigen in a sample. Human serum or plasma is preferably diluted in a sample diluent and incubated with a polystyrene bead coated with a recombinant polypeptide that represents a distinct antigenic region of the HCV genome. If antibodies are present in the sample they will form a complex with the antigenic polypeptide and become affixed to the polystyrene bead. After the complex has formed, unbound materials and reagents are removed by washing the bead and the bead-antigen-antibody complex is reacted with a solution containing horseradish peroxidase labeled goat antibodies directed against human antibodies. This peroxidase enzyme then binds to the antigen-antibody complex already fixed to the bead. In a final reaction the horseradish peroxidase is contacted with o-phenylenediamine and hydrogen peroxide which results in a yellow-orange color. The intensity of the color is proportional to the amount of antibody which initially binds to the antigen fixed to the bead.

The preferred recombinant polypeptides having HCV antigenic epitopes were selected from portions of the HCV genome which encoded polypeptides which possessed amino acid sequences similar to other known immunologically reactive agents and which were identified as having some immunological reactivity. The immunological reactivity of a polypeptide was initially identified by reacting the cellular extract of *E.coli* clones which had been transformed with cDNA fragments of the HCV genome with HCV infected serum. Polypeptides expressed by clone containing the incorporated cDNA were immunologically reactive with serum known to contain antibody to HCV antigens. An analysis of a given amino acid sequence, however, only provides rough guides to predicting immunological reactivity. There is no invariably predictable way to ensure immunological activity short of preparing a given amino acid sequence and testing the suspected sequence in an assay.

Figure 1:
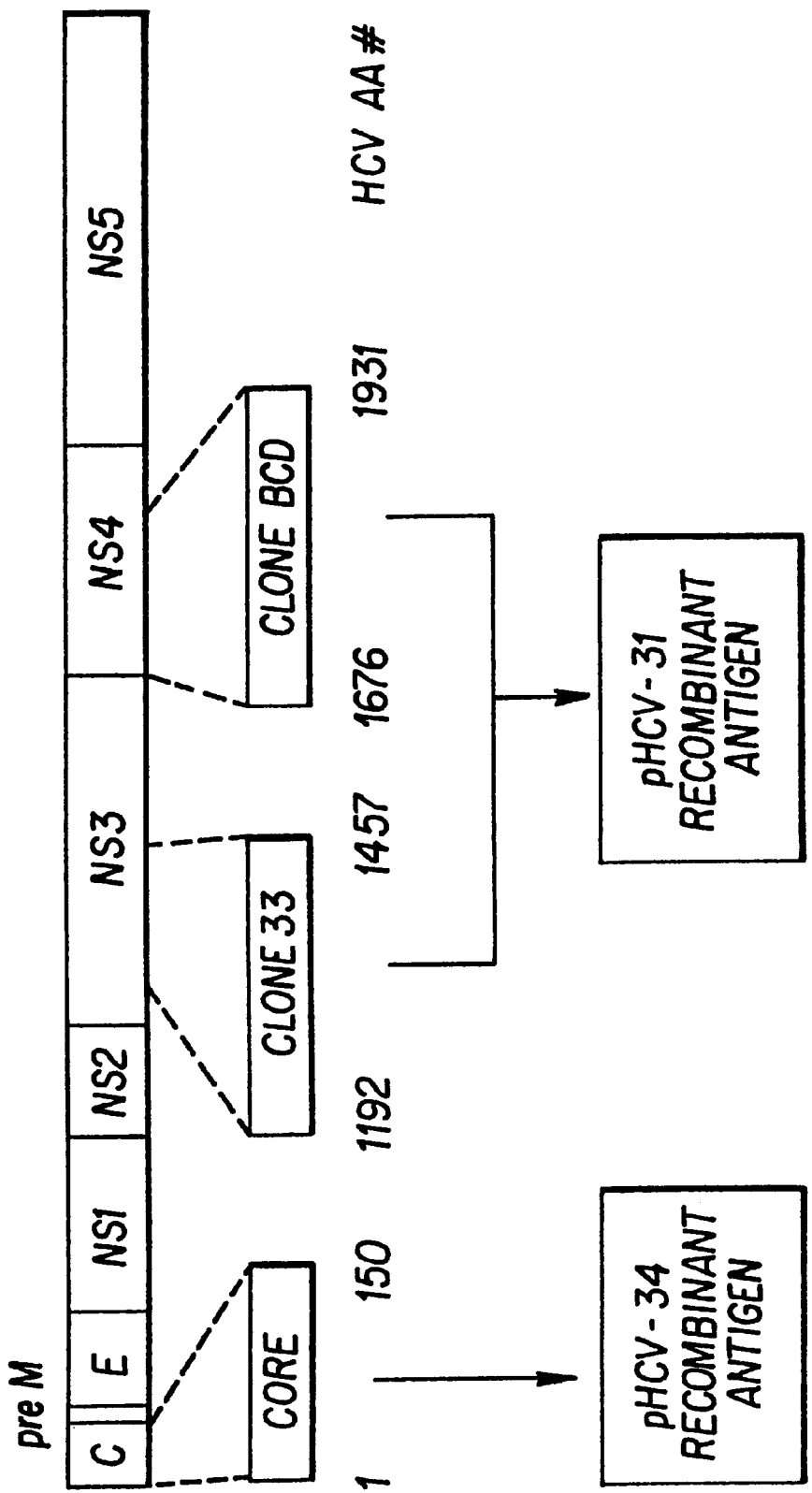
FIG. 1 illustrates the HCV genome.

Recombinant antigens which are derived from the molecular cloning and expression of synthetic DNA sequences in heterologous hosts are provided. Briefly, synthetic DNA sequences which encode the desired proteins representing distinct antigenic regions of the HCV genome are optimized for expression in *E.coli* by specific codon selection. Specifically, two recombinant proteins representing three distinct antigenic regions of the HCV genome, including immunogenic regions of the c100-3 antigen and two additional non-overlapping regions upstream from the c100-3 region are described. Both proteins are expressed as chimeric fusions with *E.coli* CMP-KDO synthetase (CKS) gene. The first protein, expressed by plasmid pHCV-34 represents amino acids 1–150 of the HCV sequence and, based on analogy to the genomic organization of other flaviviruses, has been named HCV CKS-Core. Note that the term pHCV-34 will also refer to the fusion protein itself and that pHCV-34' will be the designation for a polypeptide representing the core region from about amino acids 1–150 of the HCV sequence prepared using other recombinant or synthetic methodologies. Other recombinant methodologies would include the preparation of pHCV-34', utilizing different expression systems. The methodology for the preparation of synthetic peptides of HCV is described in U.S. Ser. No. 456,162, filed Dec. 22, 1989, which enjoys common ownership and is incorporated herein by reference. The other protein is expressed by plasmid pHCV-31 and is composed of two non-contiguous coding regions located in the putative non-structural regions of HCV designated NS-3 and NS-4. The first of the two regions represents amino acids 1192–1457 of the HCV sequence (known as Clone 33) and is expressed by the plasmid pHCV-29. The fusion protein itself will also be referred to as pHCV-29 and pHCV-29' shall be the designation for a polypeptide from the NS-3 region representing from about amino acids 1192–1457 of the HCV sequence prepared using other recombinant or synthetic methodologies. The second region represents amino acids 1676–1931 of the HCV sequence and is expressed by the plasmid pHCV-23. The fusion protein will be referred to as pHCV-23 and pHCV-23' shall be the designation for a polypeptide from the NS4 region representing from about amino acids 1676–1931 of the HCV sequence prepared using other recombinant or synthetic methodologies. It has been designated Clone BCD based on the strategy used in its construction. Clone BCD represents the carboxyl-terminal 256 amino acids of c100-3: the amino terminal 108 amino acids of c100-3 are not represented in Clone BCD. The recombinant antigen produced by pHCV-31 is designated CKS-33c-BCD. The fusion protein is also designated by pHCV-31 and pHCV-31' refers to the polypeptide composed of two noncontiguous coding regions located in the putative nonstructural regions of HCV designated NS-3 and NS-4, representing from about amino acids 1192–1457 and from about 1676–1931 of the HCV sequence prepared using different recombinator synthetic methodologies. FIG. 1 illustrates the position of the three HCV regions within the HCV genome. These antigens are used in the inventive immunoassays to detect the presence of HCV antibodies in samples.

Figure 44:
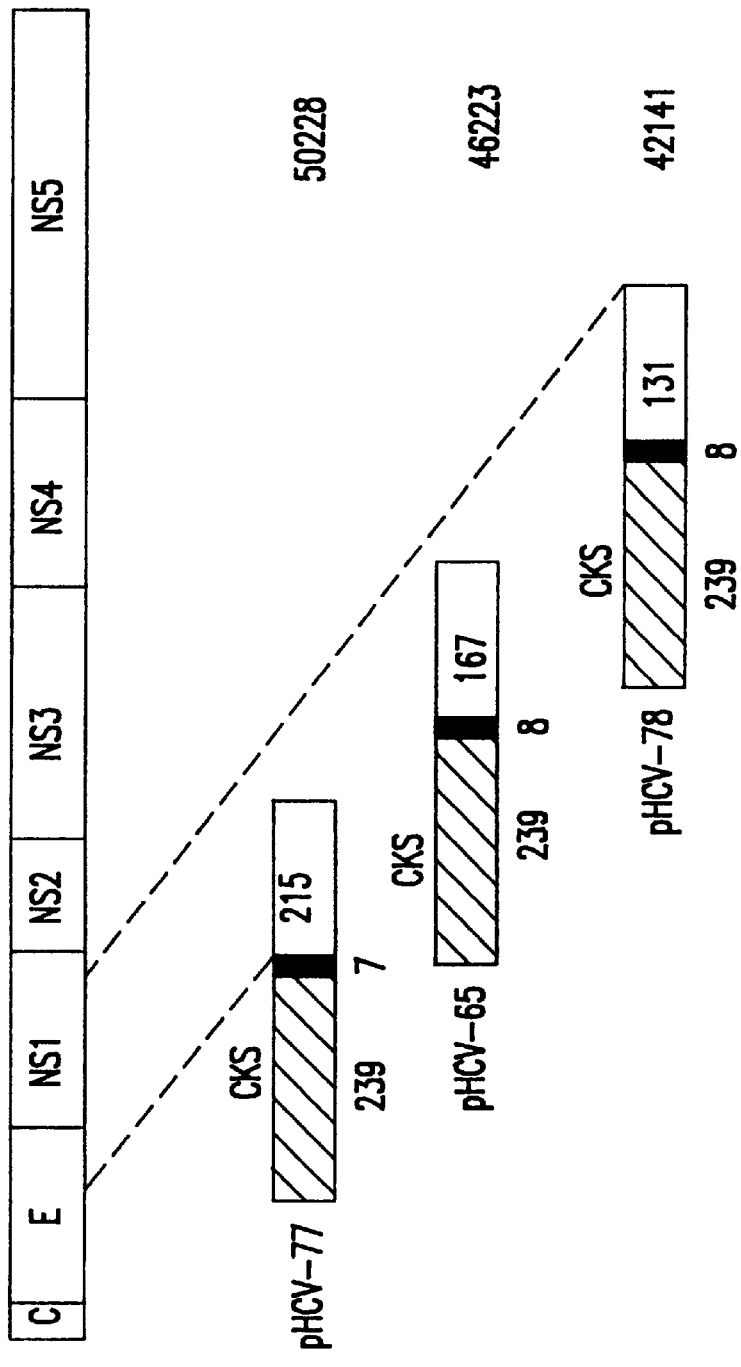
FIG. 44 illustrates the NS1 region of the HCV genome, and in particular, the locations of pHCV-77, pHCV-65 and pHCV-78.
Figure 45:
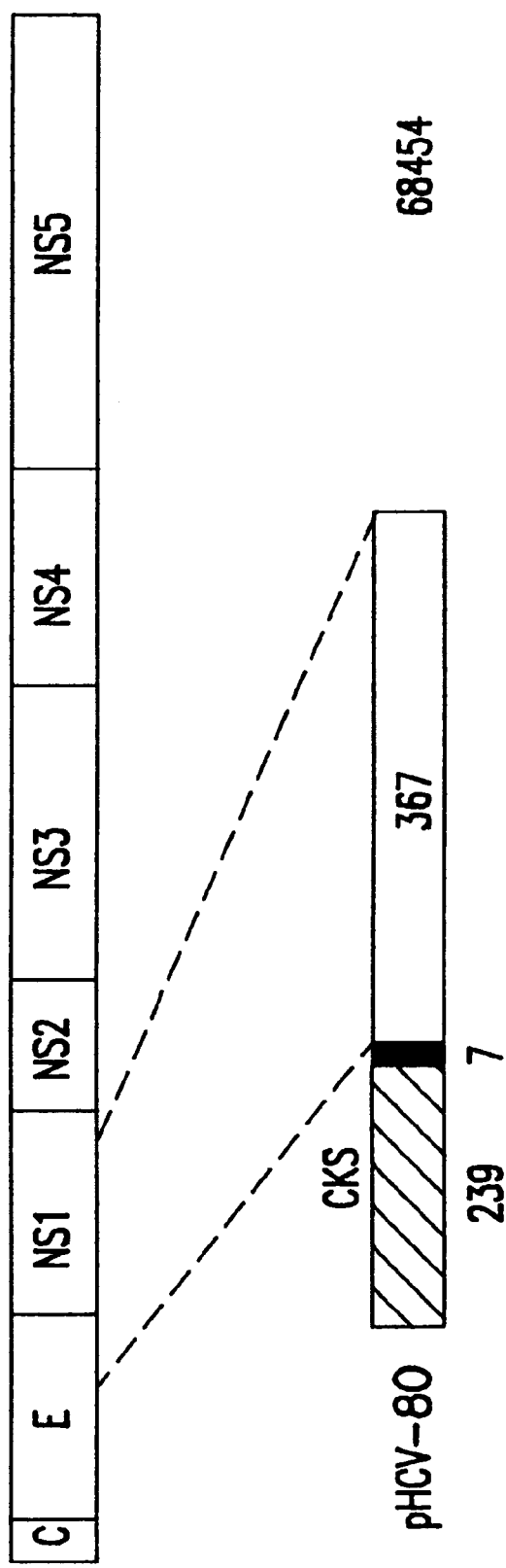
FIG. 45 illustrates the NS1 region of the HCV genome, and in particular, the location of pHCV-80.
Figure 46:
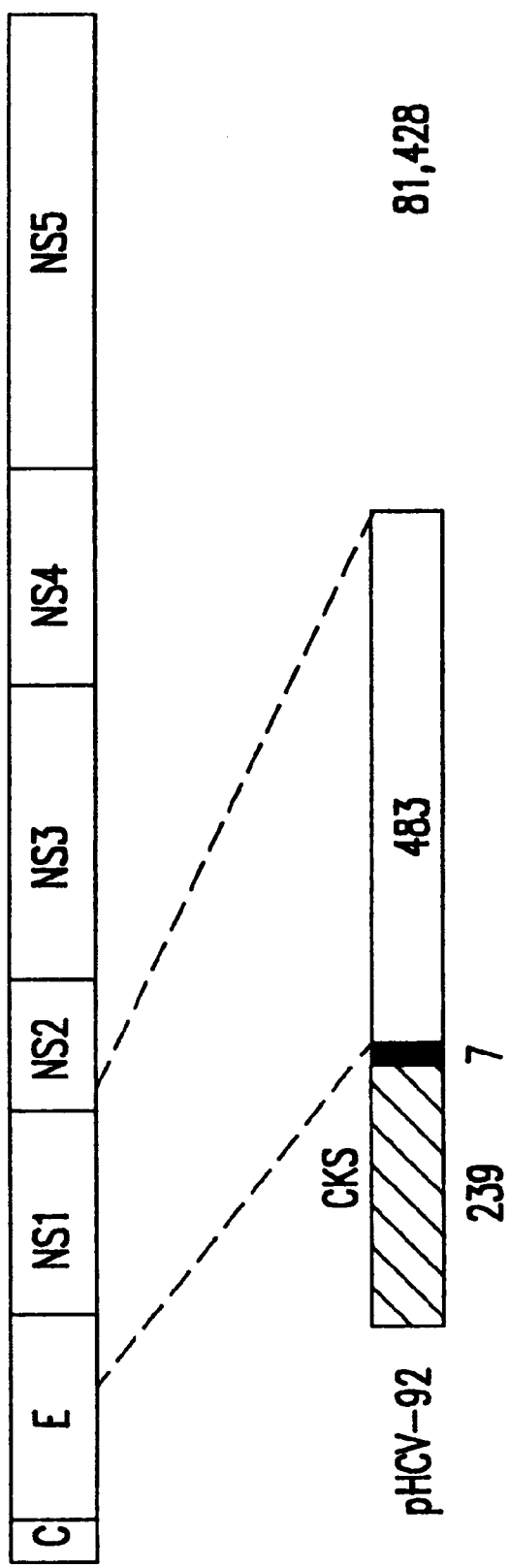
FIG. 46 illustrates the NS1 region of the HCV genome, and in particlar, the location of pHCV-92.

Also, the present invention provides recombinant proteins representing five distinct antigenic regions of NS1 of the HCV genome. The proteins are expressed as chimeric fusions with *E.coli* CMP-KDO synthetase (CKS) gene. The first protein, expressed by plasmid pHCV-77 (identified as SEQ. ID. NO. 31) represents amino acids 365–579 of the HCV sequence of NS1 and, based on analogy to the genomic organization of other flaviviruses, has been named HCV CKS-NS1S1. Note that the term pHCV-77 will also refer to the fusion protein itself and that pHCV-77' will be the designation for a polypeptide representing the NS1 region from about amino acids 365–579 of the HCV sequence prepared using other recombinant or synthetic methodologies. Other recombinant methodologies would include the preparation of pHCV-77', utilizing different expression systems. The next protein is expressed by plasmid pHCV-65, identified as SEQ. ID. NO. 32, and represents amino acids 565–731 of the NS1 region of the HCV genome. pHCV-65 has been named HCV CKS-NS1S2 and is expressed by the plasmid pHCV-65. The fusion protein itself will also be referred to as pHCV-65 and pHCV-65' shall be the designation for a polypeptide from the NS-1 region representing from about amino acids 565–731 of the HCV sequence prepared using other recombinant or synthetic methodologies. The next recombinant antigen represents amino acids 717–847 of the NS1 region of the HCV sequence, and is expressed by the plasmid pHCV-78 (identified by SEQ. ID. NO. 33). The fusion protein will be referred to as pHCV-78 and pHCV-78' shall be the designation for a polypeptide from the NS1 region representing from about amino acids 717–847 of the HCV sequence prepared using other recombinant or synthetic methodologies. It has been designated clone HCV CKS-NS1S3 based on the strategy used in its construction. FIG. 44 illustrates the position of pHCV-77, pHCV-65 and pHCV-78 in the NS1 region of the HCV genome. The recombinant antigen produced by pHCV-80 is identified as SEQ. ID. NO. 34 and is designated HCV CKS-NS1S1-NS1S2. The fusion protein is also designated by pHCV-80 and pHCV-80' refers to the polypeptide located in the NS1 region of HCV, representing amino acids 365–731 of the HCV genome prepared using different recombinant methodologies. FIG. 45 illustrates the position of pHCV-80 within the HCV genome. HCV CKS-Full Length NS1 is the designation for the recombinant protein pHCV-92 (SEQ. ID. NO. 35). It represents amino acids 365–847 of the HCV genome. The fusion proteins will be referred to as pHCV-92 and pHCV 92' shall be the designation for the polypeptide from the NS1 region representing amino acids 365–847 of the HCV sequence prepared using other recombinant or synthetic methodologies. FIG. 46 illustrates the position of pHCV-92 in the HCV genome.

The present invention moreover provides a recombinant protein representing a distinct antigenic region of the HCV NS5 genome. The protein is expressed as a chimeric fusion with *E.coli* CMP-KDO synthetase (CKS) gene. The protein, expressed by plasmid pHCV-59 represents amino acids 1932–2491 of the HCV sequence and, based on analogy to the genomic organization of other flaviviruses, has been named HCV CKS-NS5EF (SEQ. ID. NO. 36). Note that the term pHCV-59 will also refer to the fusion protein itself and that pHCV-59' will be the designation for a polypeptide representing the NS5 region from about amino acids 1932–2491 of the HCV sequence prepared using other recombinant or synthetic methodologies. Other recombinant methodologies would include the preparation of pHCV-59', utilizing different expression systems. FIG. 50 illustrates the position of the HCV region, especially pHCV-59 of NS5, within the HCV genome.

In addition, the present invention provides a protein expressed by plasmid pHCV-62 and identified by SEQ. ID. NO.47. Note that the term pHCV-62 will also refer to the fusion protein itself and that pHCV-62' will be the designation for the polypeptide using other recombinant or synthetic methodologies. Other recombinant methodologies would include the preparation of pHCV-62', utilizing different expression systems. The next protein is expressed by plasmid pHCV-63 and is identified by SEQ. ID. NO.48. The fusion protein itself will also be referred to as pHCV-63 and pHCV-63' shall be the designation for the polypeptide identified by SEQ. ID. NO. 48 prepared using other recombinant or synthetic methodologies. SEQ. ID. NO. 49 shall identify the recombinant protein and fusion protein of pHCV-204. The polypeptide pHCV-204' also shall be identified by SEQ. ID. NO. 49. The next protein is expressed by plasmid pHCV-112 and is identified by SEQ. ID. NO. 50. The fusion protein itself will also be referred to as pHCV-112 and pHCV-112' shall be the designation for the polypeptide identified by SEQ. ID. NO. 50 prepared using other recombinant or synthetic methodologies. SEQ. ID. 52 shall identify the recombinant protein and fusion protein of pHCV-72. The polypeptide pHCV-72' also shall be identified by SEQ. ID. NO. 52. The protein pHCV-72 is expressed by plasmid pHCV-72 and is identified by SEQ. ID. NO. 17. The fusion protein itself will also be referred to as pHCV-72 and pHCV-72' shall be the designation for the polypeptide identified by SEQ. ID. NO. 17 prepared using other recombinant or synthetic methodologies. SEQ. ID. 54 shall identify the recombinant protein and fusion protein of pHCV-205. The polypeptide pHCV-205' also shall be identified by SEQ. ID. NO. 54. The antigens are used in the inventive immunoassays to detect the presence of HCV antibodies in samples.

These antigens are used in the inventive immunoassays to detect the presence of HCV antibodies in samples. Sequence identification numbers for these recombinant polypeptides useful according to the present invention are presented in Table 1.

TABLE 1

Polypeptides Designation and Corresponding Sequence I.D. Number

| Name | Sequence I.D. Number |
|---|---|
| pHCV-34 | SEQ. ID. NO. 1 |
| pHCV-34 | SEQ. ID. NO. 2 |
| pHCV-31 | SEQ. ID. NO. 3 |
| pHCV-31 | SEQ. ID. NO. 4 |
| pHCV-45 | SEQ. ID. NO. 5 |
| pHCV-45 | SEQ. ID. NO. 6 |
| pHCV-48 | SEQ. ID. NO. 7 |
| pHCV-48 | SEQ. ID. NO. 8 |
| pHCV-51 | SEQ. ID. NO. 9 |
| pHCV-51 | SEQ. ID. NO. 10 |
| pHCV-50 | SEQ. ID. NO. 11 |
| pHCV-50 | SEQ. ID. NO. 12 |
| pHCV-49 | SEQ. ID. NO. 13 |
| pHCV-49 | SEQ. ID. NO. 14 |
| pHCV-57 | SEQ. ID. NO. 15 |
| pHCV-57 | SEQ. ID. NO. 16 |
| pHCV-58 | SEQ. ID. NO. 17 |
| pHCV-58 | SEQ. ID. NO. 18 |
| pHCV-105 | SEQ. ID. NO. 19 |
| pHCV-105 | SEQ. ID. NO. 20 |
| pHCV-103 | SEQ. ID. NO. 21 |
| pHCV-103 | SEQ. ID. NO. 22 |
| pHCV-101 | SEQ. ID. NO. 23 |
| pHCV-101 | SEQ. ID. NO. 24 |
| pHCV-102 | SEQ. ID. NO. 25 |
| pHCV-102 | SEQ. ID. NO. 26 |
| pHCV-107 | SEQ. ID. NO. 27 |
| pHCV-107 | SEQ. ID. NO. 28 |
| pHCV-104 | SEQ. ID. NO. 29 |
| pHCV-104 | SEQ. ID. NO. 30 |
| pHCV-77 | SEQ. ID. NO. 31 |
| pHCV-65 | SEQ. ID. NO. 32 |
| pHCV-78 | SEQ. ID. NO. 33 |
| pHCV-80 | SEQ. ID. NO. 34 |
| pHCV-92 | SEQ. ID. NO. 35 |
| pHCV-59 | SEQ. ID. NO. 36 |
| pHCV-54 | SEQ. ID. NO. 37 |
| pHCV-55 | SEQ. ID. NO. 38 |
| pHCV-94 | SEQ. ID. NO. 39 |
| pHCV-95 | SEQ. ID. NO. 40 |
| PHCV-96 | SEQ. ID. NO. 41 |
| pHCV-97 | SEQ. ID. NO. 42 |
| pHCV-202 | SEQ. ID. NO. 43 |
| pHCV-203 | SEQ. ID. NO. 44 |
| — | SEQ. ID. NO. 45 |
| — | SEQ. ID. NO. 46 |
| pHCV-62 | SEQ. ID. NO. 47 |
| pHCV-63 | SEQ. ID. NO. 48 |
| pHCV-204 | SEQ. ID. NO. 49 |
| pHCV-112 | SEQ. ID. NO. 50 |
| pHCV-68 | SEQ. ID. NO. 51 |
| pHCV-72 | SEQ. ID. NO. 52 |
| pHCV-73 | SEQ. ID. NO. 53 |
| pHCV-205 | SEQ. ID. NO. 54 |
| — | SEQ. ID. NO. 55 |
| pHCV-108 | SEQ. ID. NO. 56 |
| pHCV-69 | SEQ. ID. NO. 57 |
| pHCV-23 | SEQ. ID. NO. 58 |
| pHCV-29 | SEQ. ID. NO. 59 |

The use of recombinant polypeptides representing distinct antigenic regions of the HCV genome to detect the presence of an antibody to an HCV antigen is illustrated, for example, in FIG. 2. The course of HCV infection in the chimpanzee, Pan, was followed with one assay using recombinant c100-3 polypeptide and with another improved assay, using the two recombinant antigens CKS-Core (pHCV-34) and pHCV-33c-BCD (pHCV-31) expressed by the plasmids pHCV-34 and pHCV-31, respectively. The assay utilizing the recombinant pHCV-34 and pHCV-31 proteins detected plasma antibody three weeks prior to detection of antibody by the assay using c100-3.

Figure 3:
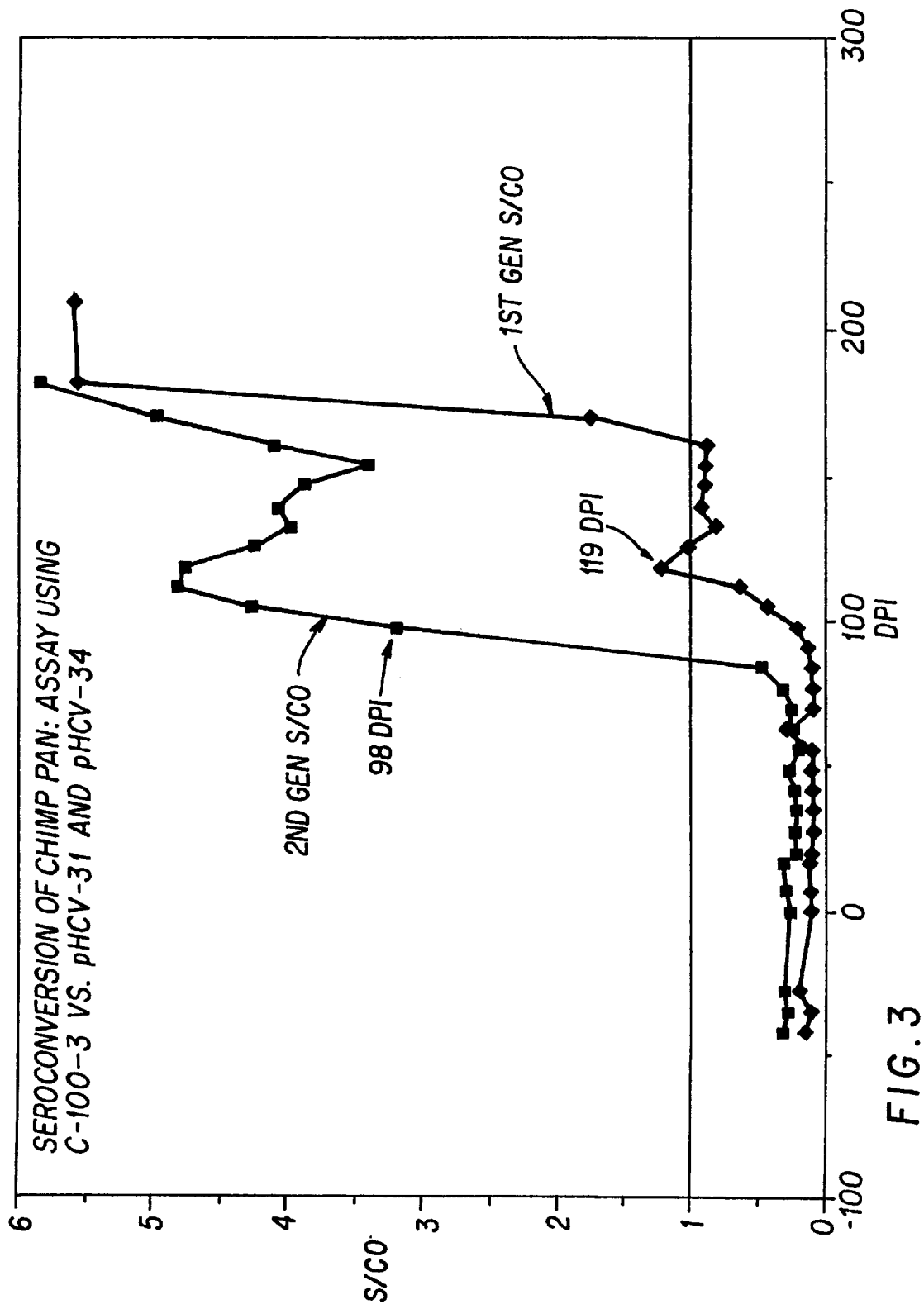
FIG. 3 illustrates the sensitivity and specificity increase in using the screening assay using pHCV-34 and pHCV-31 antigens.

A summary of the results of a study which followed the course of HCV infection in Pan and six other chimpanzees using the two assays described above is summarized in FIG. 3. Both assays gave negative results before inoculation and both assays detected the presence of antibodies after the animal had been infected with HCV. However, in the comparison of the two assays, the improved screening assay using pHCV-34 and pHCV-31 detected seroconversion to HCV antigens at an earlier or equivalent bleed date in six of the seven chimpanzees. Data from these chimpanzee studies clearly demonstrate that overall detection of HCV antibodies is greatly increased with the assay utilizing the pHCV-34 and pHCV-31 proteins. This test is sufficiently sensitive to detect seroconversion during the acute phase of this disease, as defined as an elevation in ALT levels, in most animals. Equally important is the high degree of specificity of the test as no pre-inoculation specimens were reactive.

The polypeptides useful in the practice of this invention are produced using recombinant technologies. The DNA sequences which encode the desired polypeptides are preferably assembled from fragments of the total desired sequence. Synthetic DNA fragments of the HCV genome can be synthesized based on their corresponding amino acid sequences. Once the amino acid sequence is chosen, this is then reverse translated to determine the complementary DNA sequence using codons optimized to facilitate expression in the chosen system. The fragments are generally prepared using well known automated processes and apparatus. After the complete sequence has been prepared the desired sequence is incorporated into an expression vector which is transformed into a host cell. The DNA sequence is then expressed by the host cell to give the desired polypeptide which is harvested from the host cell or from the medium in which the host cell is cultured. When smaller peptides are to be made using recombinant technologies it may be advantageous to prepare a single DNA sequence which encodes several copies of the desired polypeptide in a connected chain. The long chain is then isolated and the chain is cleaved into the shorter, desired sequences.

The methodology of polymerase chain reaction (PCR) may also be employed to develop PCR amplified genes from any portion of the HCV genome, which in turn may then be cloned and expressed in a manner similar to the synthetic genes.

Vector systems which can be used include plant, bacterial, yeast, insect, and mammalian expression systems. It is preferred that the codons are optimized for expression in the system used.

A preferred expression system utilizes a carrier gene for a fusion system where the recombinant HCV proteins are expressed as a fusion protein of an *E.coli* enzyme, CKS (CTP:CMP-3-deoxy-manno-octulosonate cytidylyl transferase or CMP-KDO synthetase). The CKS method of protein synthesis is disclosed in U.S. patent applications Ser. Nos. 167,067 and 276,263 filed Mar. 11, 1988 and Nov. 23, 1988, respectively, by Bolling (EPO 891029282) which enjoy common ownership and are incorporated herein by reference.

Other expression systems may be utilized including the lambda PL vector system whose features include a strong lambda pL promoter, a strong three-frame translation terminator rrnBt1, and translation starting at an ATG codon.

In the present invention, the amino acid sequences encoding for the recombinant HCV antigens of interest were reverse translated using codons optimized to facilitate high level expression in *E.coli*. Individual oligonucleotides were synthesized by the method of oligonucleotide directed double-stranded break repair disclosed in U.S. patent application Ser. No. 883,242, filed Jul. 8, 1986 by Mandecki (EPO 87109357.1) which enjoys common ownership and is incorporated herein by reference. Alternatively, the individual oligonucleotides may be synthesized on the Applied Biosystem 380A DNA synthesizer using methods and reagents recommended by the manufacturer. The DNA sequences of the individual oligonucleotides were confirmed using the Sanger dideoxy chain termination method (Sanger et al., *J. Mole. Biol.*, 162:729 (1982)). These individual gene fragments were then annealed and ligated together and cloned as EcoRl-BamHl subfragments in the CKS fusion vector pJO200. After subsequent DNA sequence confirmation by the Sanger dideoxy chain termination method, the subfragments were digested with appropriate restriction enzymes, gel purified, ligated and cloned again as an EcoRl-BamHl fragment in the CKS fusion vector pJO200. The resulting clones were mapped to identify a hybrid gene consisting of the EcoRl-BamHl HCV fragment inserted at the 3' end of the CKS (CMP-KDO synthetase) gene. The resultant fusion proteins, under control of the lac promoter, consist of 239 amino acids of the CKS protein fused to the various regions of HCV.

The synthesis, cloning, and characterization of the recombinant polypeptides as well as the preferred formats for assays using these polypeptides are provided in the following examples. Examples 1 and 2 describe the synthesis and cloning of CKS-Core and CKS-33-BCD, respectively. Example 3 describes a screening assay. Example 4 describes a confnmatory assay. Example 5 describes a competition assay. Example 6 describes an immunodot assay. Example 7 describes the synthesis and cloning of HCV CKS-NS5E, CKS-NS5F, CKS-NS5G, CKS-NS5H and CKS-NS5I. Example 8 describes the preparation of HCV CKS-C100 vectors. Example 9 describes the preparation of HCV PCR derived expression vectors. Example 10 describes the synthesis and characterization of pHCV-77 of NS1. Example 11 describes the synthesis and characterization of pHCV-65 of NS1. Example 12 describes the synthesis and characterization of pHCV-78 of NS1. Example 13 describes the synthesis and characterization of pHCV-80 of NS1. Example 14 describes the synthesis and characterization of pHCV-92 of NS1. Example 15 describes the synthesis and characterization of pHCV-77 of NS5 EF expression vector and the production of characerization of the recombinant antigen HCV-NS5 EF. Example 16 describes the preparation of HCV CKS-C100A deletion clones. Example 17 describes the construction of HCV CKS-C200 expression clones.

Reagents and Enzymes

Media such as Luria-Bertani (LB) and Superbroth II (Dri Form) were obtained from Gibco Laboratories Life Technologies, Inc., Madison Wis. Restriction enzymes, Klenow fragment of DNA polymerase I, T4 DNA ligase, T4 polynucleotide kinase, nucleic acid molecular weight standards, M13 sequencing system, X-gal (5-bromo-4-chloro-3-indonyl-β-D-galactoside), IPTG (isopropyl-β-D-thiogalactoside), glycerol, Dithioffireitol, 4-chloro-1-naphthol were purchased from Boehringer Mannheim Biochemicals, Indianapolis, Ind.; or New England Biolabs, Inc., Beverly, Mass.; or Bethesda Research Laboratories Life Technologies, Inc., Gaithersburg, Md. Prestained protein molecular weight standards, acrylamide (crystallized, electrophoretic grade>99%); N-N'-Methylene-bis-acrylamide (BIS); N,N,N',N',-Tetramethylethylenediamine (TEMED) and sodium dodecylsulfate (SDS) were purchased from BioRad Laboratories, Richmond, Calif. Lysozyme and ampicillin were obtained from Sigma Chemical Co., St. Louis, Mo. Horseradish peroxidase (HRPO) labeled secondary antibodies were obtained from Kirkegaard & Perry Laboratories, Inc., Gaithersburg, Maryland. Seaplaque® agarose (low melting agarose) was purchased from FMC Bioproducts, Rockland, Me.

T50E10 contained 50 mM Tris, pH 8.0, 10 mM EDTA; 1× TG contained 100 mM Tris, pH 7.5 and 10% glycerol; 2× SDS/PAGE loading buffer consisted of 15% glycerol, 5% SDS, 100 mM Tris base, 1M-mercaptoethanol and 0.8% Bromophenol blue dye; TBS container 50 mM Tris, pH 8.0, and 150 mM sodium chloride; Blocking solution consisted of 5% Carnation nonfat dry milk in TBS.

Host Cell Cultures, DNA Sources and Vectors

*E.coli* JM103 cells, pUC8, pUC18, pUCl9 and M13 cloning vectors were purchased from Pharmacia LKB Biotechnology, Inc., Piscataway, N.J.; Competent Epicurean™ coli stains XL1-Blue and JM109 were purchased from Stratagene Cloning Systems, LaJolla, Calif. RR1 cells were obtained from Coli Genetic Stock Center, Yale University, New Haven, Conn.; and *E.coli* CAG456 cells from Dr. Carol Gross, University of Wis., Madison, Wis. Vector pRK248.clts was obtained from Dr. Donald R. Helinski, University of California, San Diego, Calif.

General Methods

All restriction enzyme digestion were performed according to suppliers' instructions. At least 5 units of enzyme were used per microgram of DNA, and sufficient incubation was allowed to complete digestion of DNA. Standard procedures were used for minicell lysate DNA preparation, phenol-chloroform extraction, ethanol precipitation of DNA, restriction analysis of DNA on agarose, and low melting agarose gel purification of DNA fragments (Maniatis et al., Molecular Cloning. A Laboratory Manual [New York: Cold Spring Harbor, 1982]). Plasmid isolations from *E.coli* strains used the alkali lysis procedure and cesium chloride-ethidium bromide density gradient method (Maniatis et al., supra). Standard buffers were used for T4 DNA ligase and T4 polynucleotide kinase (Maniatis et al., supra).

EXAMPLE 1

CKS-CORE

A. Construction of the Plasmid pJO200

The cloning vector pJO200 allows the fusion of recombinant proteins to the CKS protein. The plasmid consists of the plasmid pBR322 with a modified lac promoter fused to a KdsB gene fragment (encoding the first 239 of the entire 248 amino acids of the *E.coli* CMP-KDO synthetase of CKS protein), and a synthetic linker fused to the end of the KdsB gene fragment. The cloning vector pJO200 is a modification of vector pTB210. The synthetic linker includes: multiple restriction sites for insertion of genes; translational stop signals, and the trpA rho-independent transcriptional terminator. The CKS method of protein synthesis as well as CKS vectors including pTB210 are disclosed in U.S. patent application Ser. Nos. 167,067 and 276,263, filed Mar. 11, 1988 and Nov. 23, 1988, respectively, by Bolling (EPO 891029282) which enjoy common ownership, and are herein incorporated by reference.

B. Preparation of HCV CKS-Core Expression Vector

Figure 4:
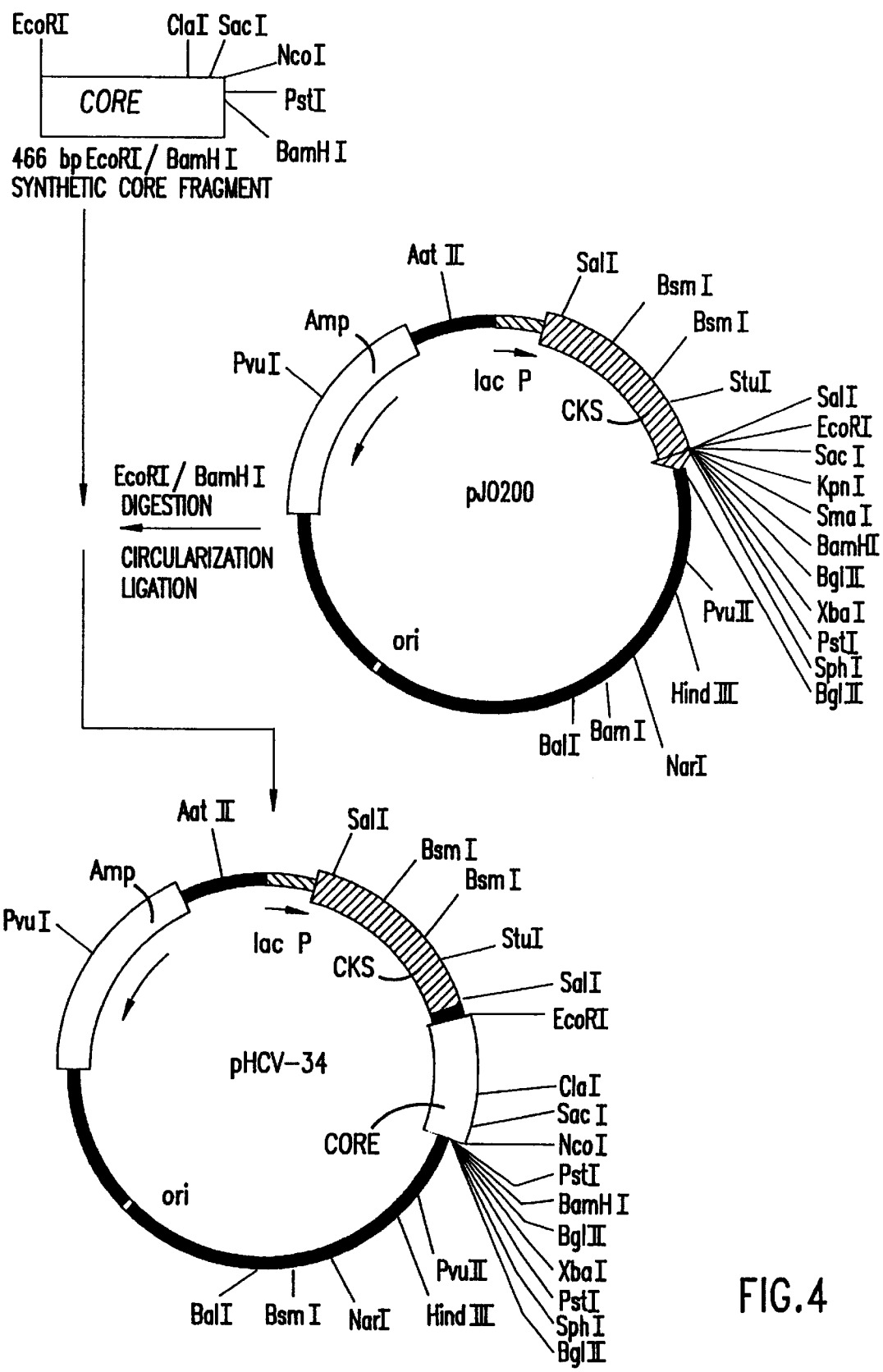
FIG. 4 illustrates the construction of plasmid pHCV-34.
Figure 5:
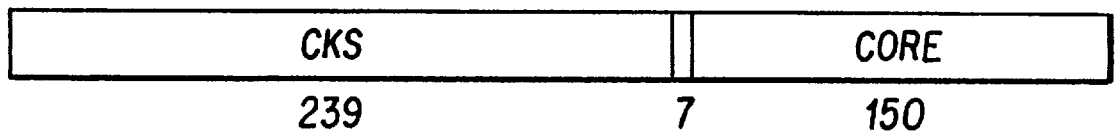
FIG. 5 illustrates fusion protein pHCV-34.

Six individual nucleotides representing amino acids 1–150 of the HCV genome were ligated together and cloned as a 466 base pair EcoRl-BamHl fragment into the CKS fusion vector pJO200 as presented in FIG. 4. The complete DNA sequence of this plasmid, designated pHCV-34, and the entire amino acid sequence of the pHCV-34 recombinant antigen produced is presented in SEQ. ID. NOS. 1 and 2. The resultant fusion protein HCV CKS-Core, consists of 239 amino acids of CKS, seven amino acids contributed by linker DNA sequences, and the first 150 amino acids of HCV as illustrated in FIG. 5.

The pHCV-34 plasmid and the CKS plasmid pTB210 were transformed into E.coli K-12 strain xL-1 (recA1, endA1, gyrA96, thi-1, hsdR17, supE44, relA1, lac/F', proAB, laclqZDM15, TN10) cells made competent by the calcium chloride method. In these constructions the expression of the CKS fusion proteins was under the control of the lac promoter and was induced by the addition of IPTG. These plasmids replicated as independent elements, were nonmobilizable and were maintained at approximately 10–30 copies per cell.

C. Characterization of Recombinant HCV-Core

In order to establish that clone pHCV-34 expressed the unique HCV-CKS Core protein, the pHCV-34/XL-1 culture was grown overnight at 37° C. in growth media consisting of yeast extract, trytone, phosphate salts, glucose, and ampicillin. When the culture reached an OD600 of 1.0, IPTG was added to a final concentration of 1 mM to induce expression. Samples (1.5 ml) were removed at 1 hour intervals, and cells were pelleted and resuspended to an OD600 of 1.0 in 2× SDS/PAGE loading buffer. Aliquots (15 ul) of the prepared samples were separated on duplicate 12.5% SDS/PAGE gels.

One gel was fixed in a solution of 50% methanol and 10% acetic acid for 20 minutes at room temperature, and then stained with 0.25% Coomassie blue dye in a solution of 50% methanol and 10% acetic acid for 30 minutes. Destaining was carried out using a solution of 10% methanol and 7% acetic acid for 3–4 hours, or until a clear background was obtained.

Figure 6:
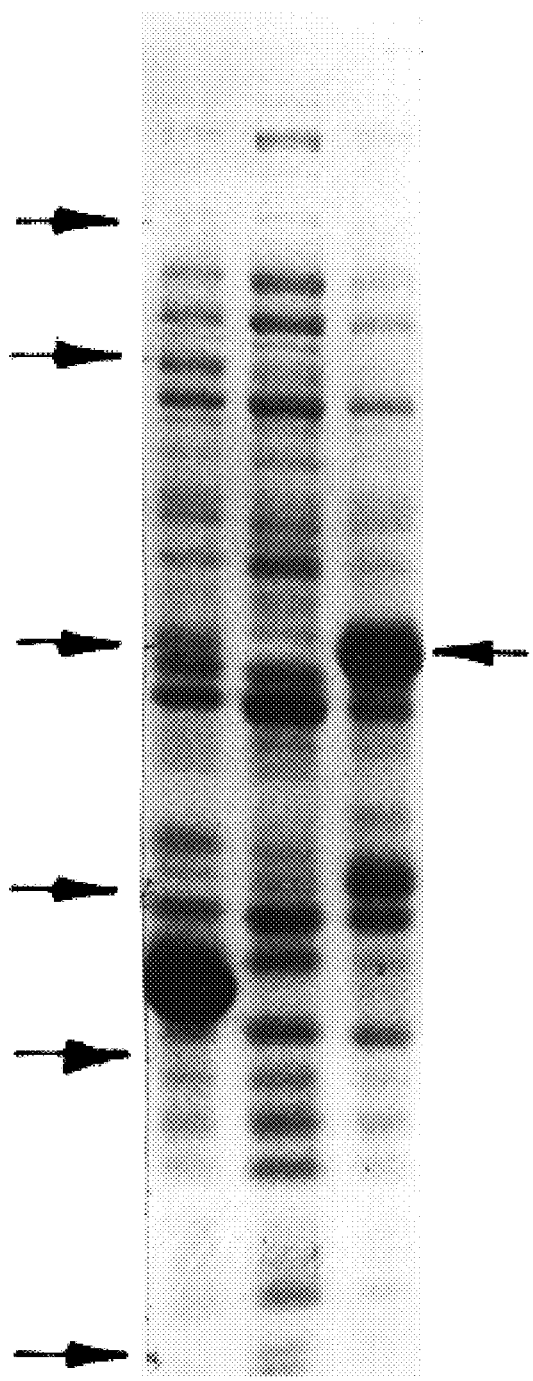
FIG. 6 illustrates the expression of pHCV-34 proteins in *E.coli*.
Figure 7:
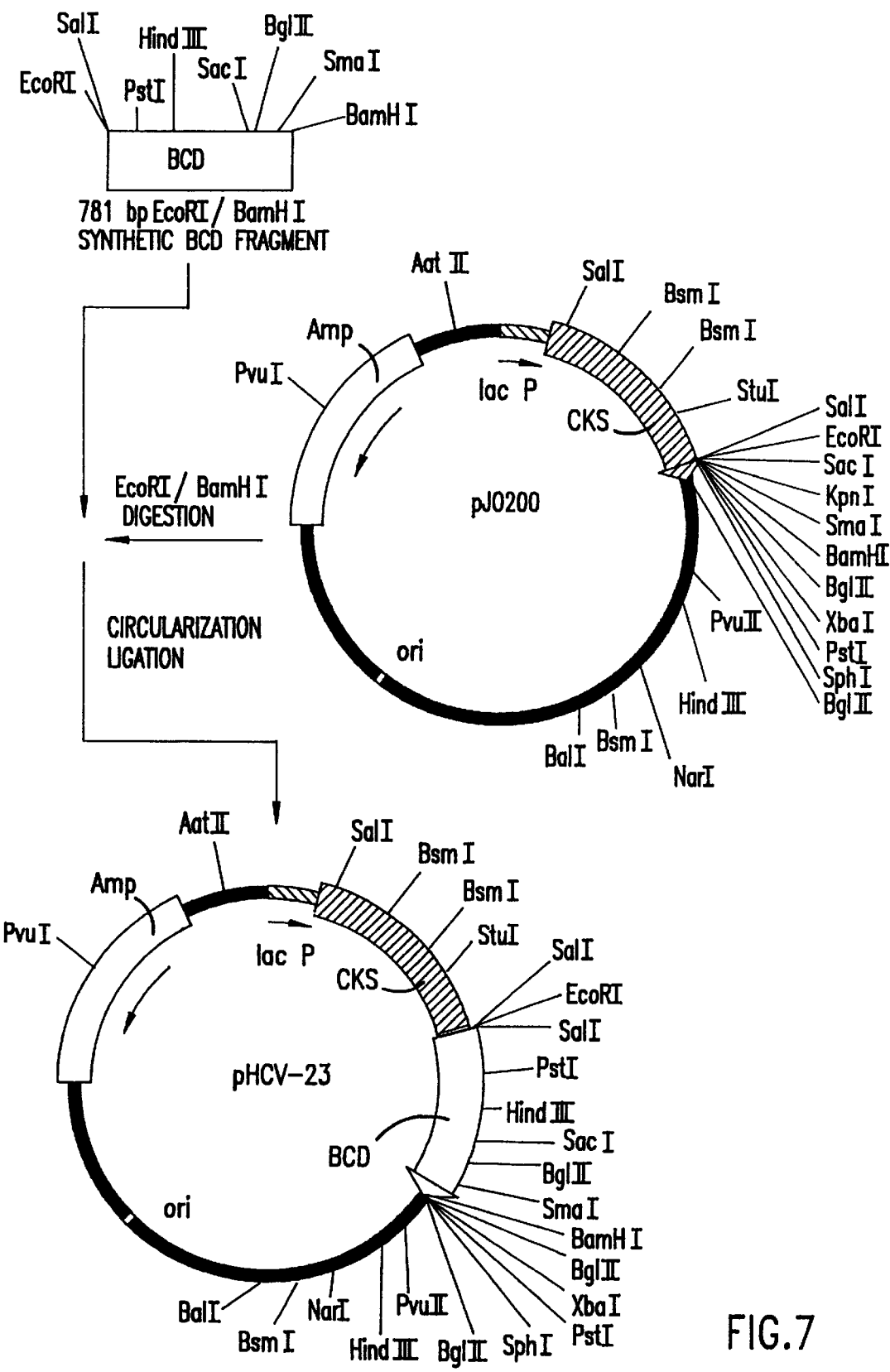
FIG. 7 illustrates the construction of plasmid pHCV-23.

FIG. 6 presents the expression of pHCV-34 proteins in E.coli. Molecular weight standards were run in Lane M. Lane 1 contains the plasmid pJO200-the CKS vector without the HCV sequence. The arrows on the left indicate the mobilities of the molecular weight markers from top to bottom: 110,000; 84,000; 47,000; 33,000; 24,000; and 16,000 daltons. The arrows on the right indicate the mobilities of the recombinant HCV proteins. Lane 2 contains the E.coli lysate containing pHCV-34 expressing CKS-Core (amino acids 1 to 150) prior to induction; and Lane 3 after 3 hours of induction. The results show that the recombinant protein pHCV-34 has an apparent mobility corresponding to a molecular size of 48,000 daltons. This compares acceptably with the predicted molecular mass of 43,750 daltons.

Proteins from the second 12.5% SDSIPAGE gel were electrophoretically transferred to nitrocellulose for immunoblotting. The nitrocellulose sheet containing the transferred proteins was incubated with Blocking Solution for one hour and incubated overnight at 4° C. with HCV patients' sera diluted in TBS containing E.coli K-12 strain XL-1 lysate. The nitrocellulose sheet was washed three times in TBS, then incubated with HRPO-labeled goat anti-human IgG, diluted in TBS containing 10% fetal calf sera. The nitrocellulose was washed three times with TBS and the color was developed in TBS containing 2 mg/ml 4-chloro-1-napthol, 0.02% hydrogen peroxide and 17% methanol. Clone HCV-34 demonstrated a strong immunoreactive band at 48,000 daltons with the HCV patients' sera. Thus, the major protein in the Coomassie stained protein gel was immunoreactive. Normal human serum did not react with any component of pHCV-34.

EXAMPLE 2

HCV CKS-33C-BCD

A. Preparation of HCV CKS-33c-BCD Expression Vector

The construction of this recombinant clone expressing the HCV CKS-33-BCD antigen was carried out in three steps described below. First, a clone expressing the HCV CKS-BCD antigen was constructed, designated pHCV-23. Second, a clone expressing the HCV CKS-33 antigen was constructed, designated pHCV-29. Lastly, the HCV BCD region was excised from pHCV-23 and inserted into pHCV-29 to construct a clone expressing the HCV CKS-33-BCD antigen, designated pHCV-31.

Figure 8:
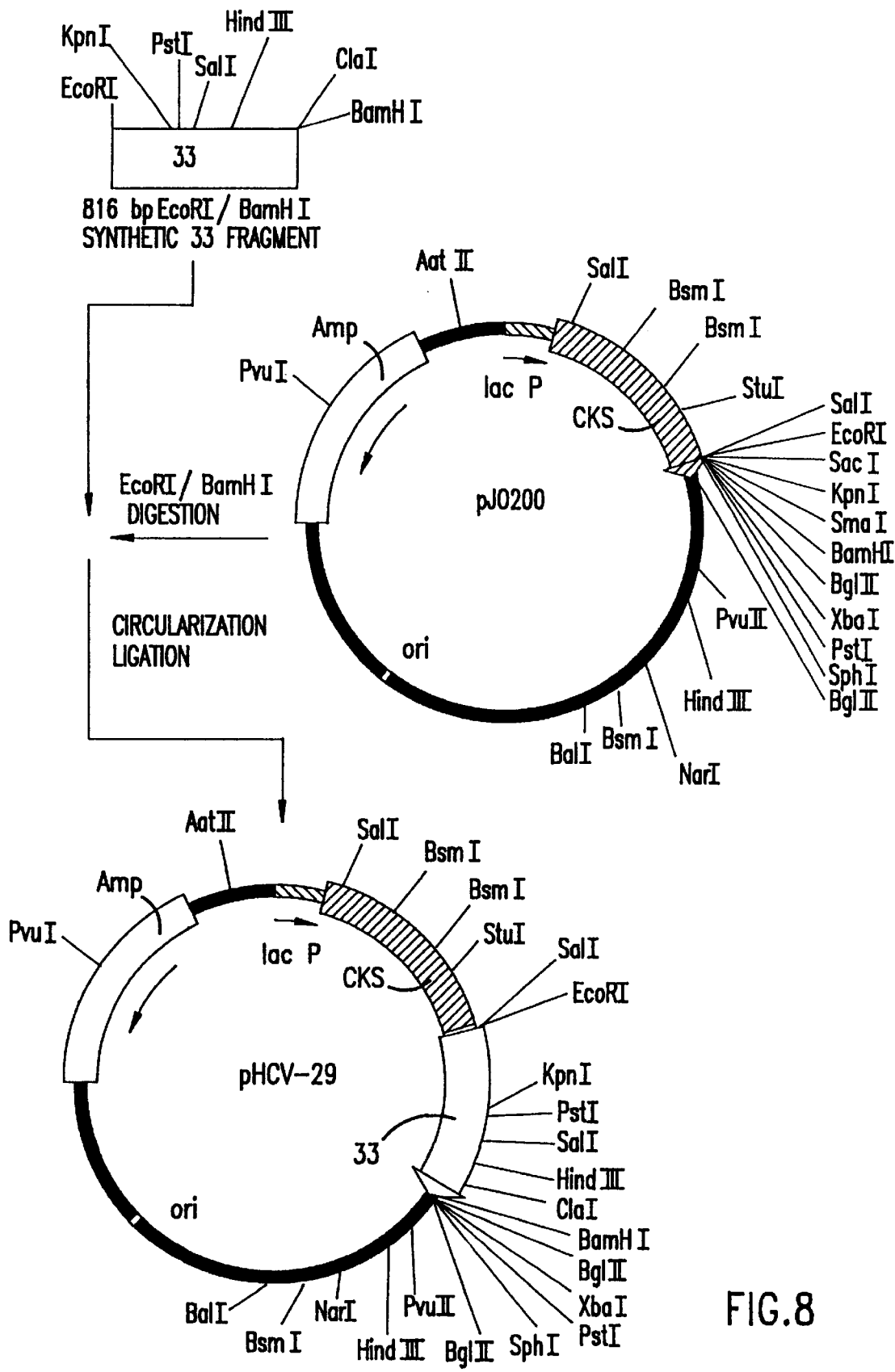
FIG. 8 illustrates the construction of plasmid pHCV-29.

To construct the plasmid pHCV-23, thirteen individual oligonucleotides representing amino acids 1676–1931 of the HCV genome were ligated together and cloned as three separate EcoRl-BamHl subfragments into the CKS fusion vector pJO200. After subsequent DNA sequence confirmation, the three subfragments, designated B, C, and D respectively, were digested with the appropriate restriction enzymes, gel purified, ligated together, and cloned as a 781 base pair EcoRl-BamHl fragment in the CKS fusion vector pJO200, as illustrated in FIG. 8. The resulting plasmid, designated pHCV-23, expresses the HCV CKS-BCD antigen under control of the lac promoter. The HCV CKS-BCD antigen consists of 239 amino acids of CKS, seven amino acids contributed by linker DNA sequences, 256 amino acids from the HCV NS4 region (amino acids 1676–1931, and 10 additional amino acids contributed by linker DNA sequences. The amino acid sequence of pHCV-23 is presented in SEQ. ID. NO. 58.

To construct the plasmid pHCV-29 twelve individual oligonucleotides representing amino acids 1192–1457 of the HCV genome were ligated together and cloned as two separate EcoRl-BamHl subfragments in the CKS fusion vector pJO200. After subsequent DNA sequence confirmation, the two subfragments were digested with the appropriate restriction enzymes, gel purified, ligated together and cloned again as an 816 base pair EcoRl-BamHl fragment in the CKS fusion vector pJO200, as illustrated in FIG. 8. The resulting plasmid, designated pHCV-29, expresses the CKS-33 antigen under control of the lac promoter. The HCV CKS-33 antigen consists of 239 amino acids of CKS, eight amino acids contributed by linker DNA sequences, and 266 amino acids from the HCV NS3 region (amino acids 1192–1457). The amino acid sequence of pHCV-29 is presented in SEQ. ID. NO. 59.

Figure 9A:
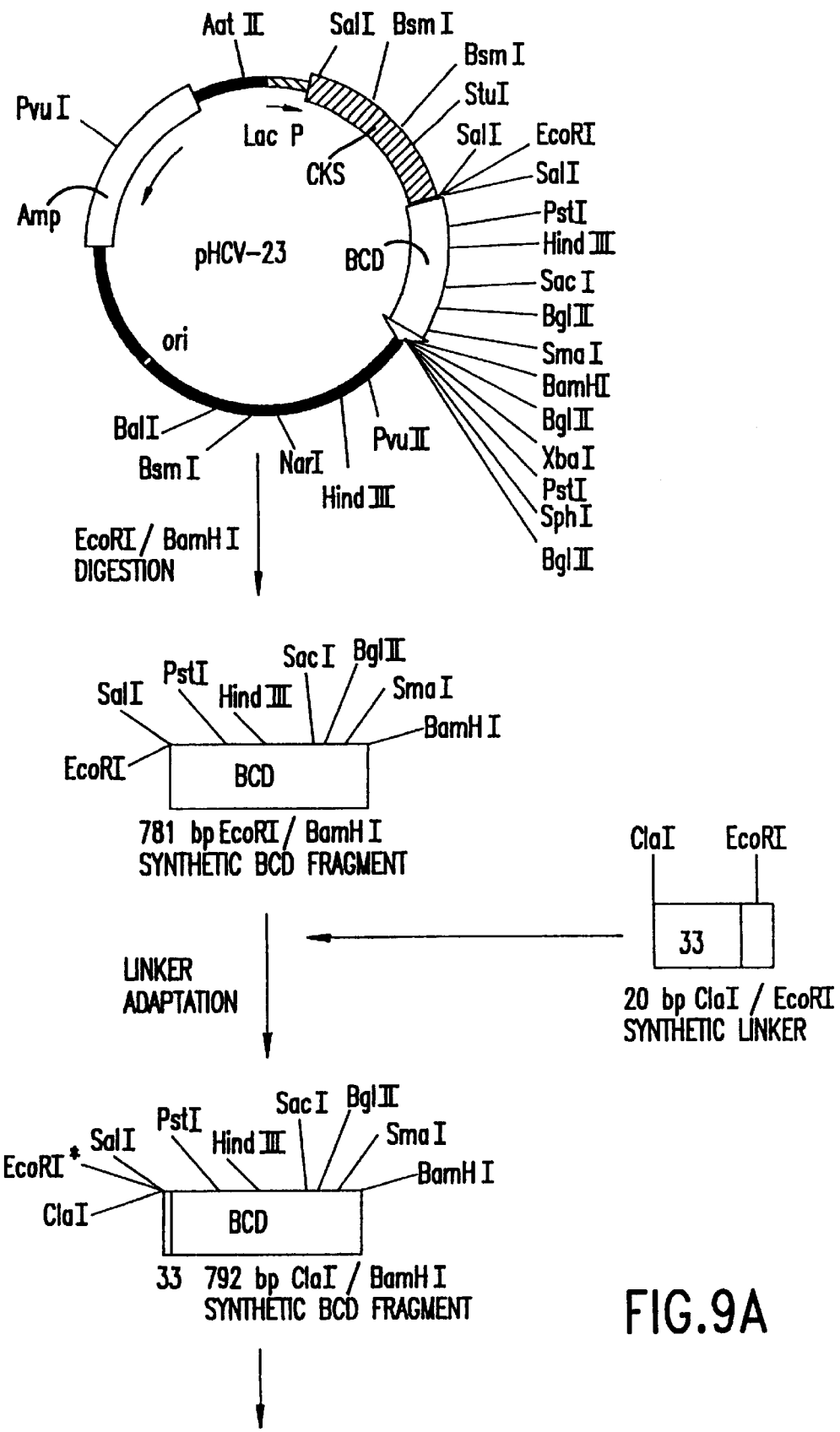
FIG. 9 illustrates the construction of plasmid pHCV-31.
Figure 9B:
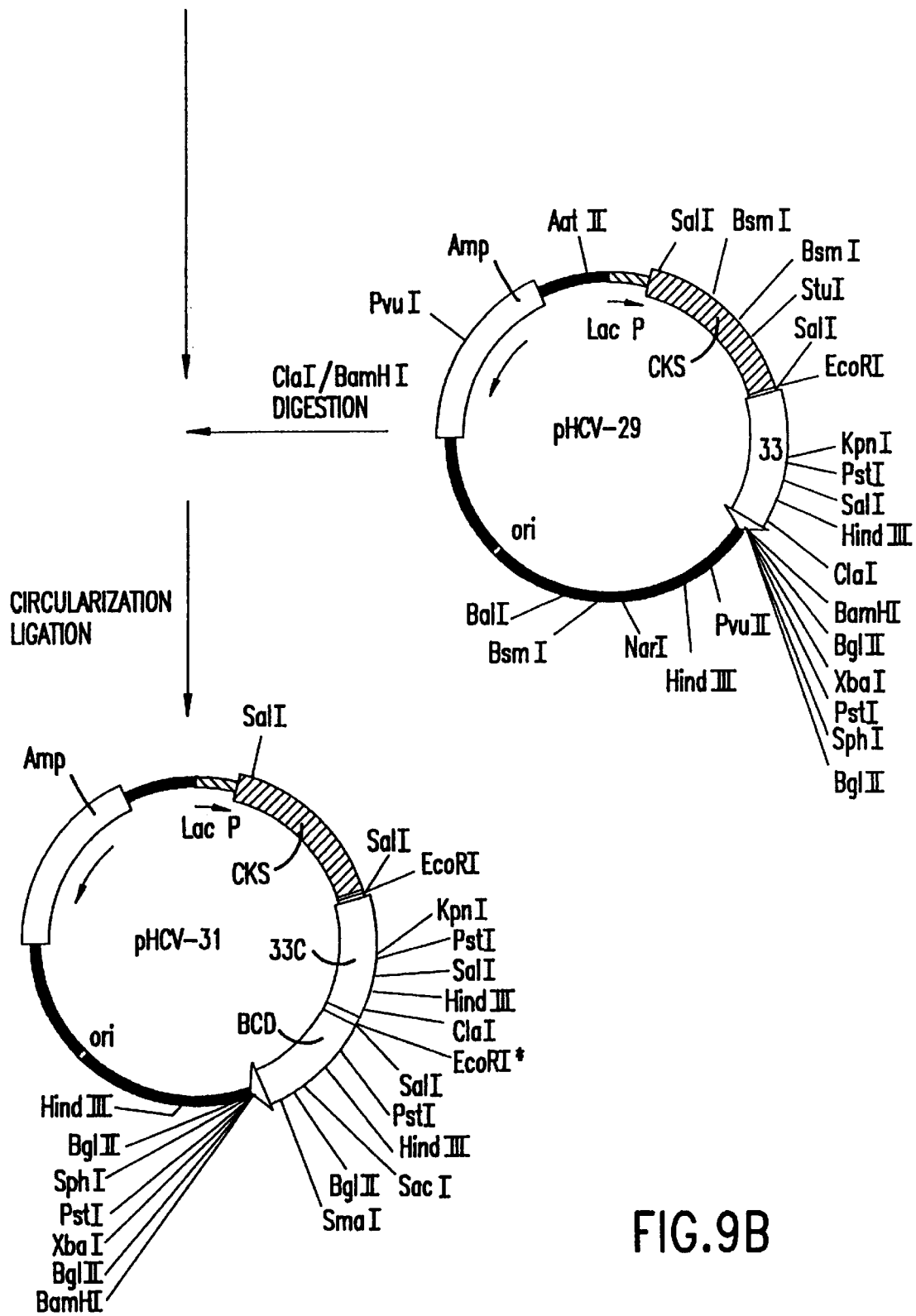
Figure 10:
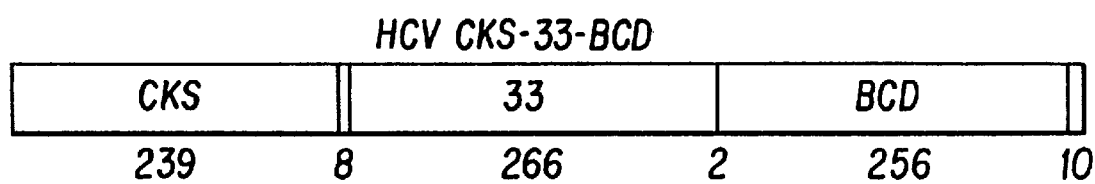
FIG. 10 illustrates the fusion protein pHCV-31.
Figure 12:
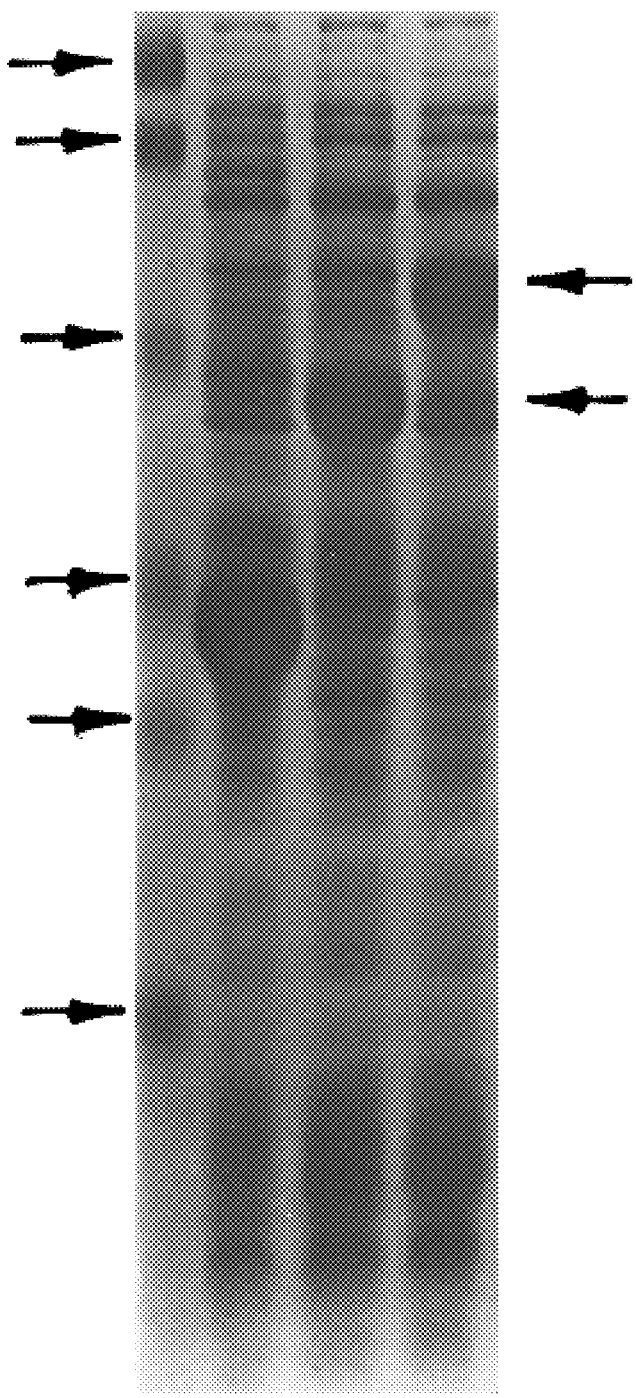
FIG. 12 illustrates the expression of pHCV-23 in *E.coli*.

To construct the plasmid pHCV-31, the 781 base pair EcoRl-BamHl fragment from pHCV-23 representing the HCV-BCD region was linker-adapted to produce a Clal-BamHl fragment which was then gel purified and ligated into pHCV-29 at the Clal-BamHl sites as illustrated in FIG. 9. The resulting plasmid, designated pHCV-31, expresses the pHCV-31 antigen under control of the lac promoter. The complete DNA sequence of pHCV-31 and the entire amino acid sequence of the HCV CKS-33-BCD recombinant antigen produced is presented in SEQ. ID. NOS. 3 and 4. The HCV CKS-33-BCD antigen consists of 239 amino acids of CKS, eight amino acids contributed by linker DNA sequences, 266 amino acids of the HCV NS3 region (amino acids 1192–1457), 2 amino acids contributed by linker DNA sequences, 256 amino acids of the HCV NS4 region (amino acids 1676–1931), and 10 additional amino acids contributed by linker DNA sequences. FIG. 12 presents a schematic representation of the pHCV-31 antigen.

The pHCV-31 plasmid was transformed into E.coli K-12 strain XL-1 in a manner similar to the pHCV-34 and CKS-pTB210 plasmids of Example 1.

B. Characterization of Recombinant HCV CKS-33-BCD

Figure 11:
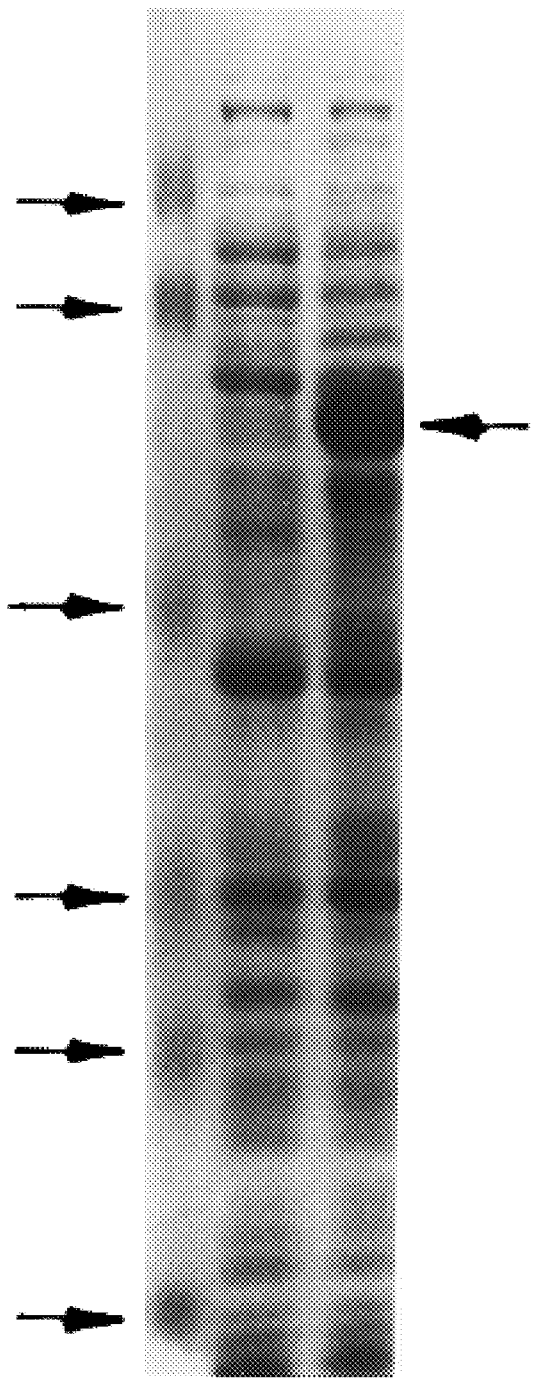
FIG. 11 illustrates the expression of pHCV-29 in *E.coli*.

Characterization of pHCV CKS-33-BCD was carried out in a manner similar to pHCV CKS-Core of Example 1. pHCV-23, pHCV SDS/PAGE gels were run for *E.coli* lysates containing the plasmids pHCV-29 (FIG. 11), pHCV-23 (FIG. 12, and pHCV-31 (FIG. 13) expressing the recombinant fusion proteins CKS-33c, CKS-BCD, and CKS-33-BCD, respectively. For all three figures, molecular weight standards were run in Lane M, with the arrows on the left indicating mobilities of the molecular weight markers the from top to bottom: 110,000; 84,000; 47,000; 33,000; 24,000; and 16,000 daltons. In FIG. 11, Lane 1 contained the *E.coli.* lysate containing pHCV-29 expressing HCV CKS-33c (amino acids 1192 to 1457) prior to induction and lane 2 after 4 hours induction. These results show that the recombinant pHCV-29 fusion protein has an apparent mobility corresponding to a molecular size of 60,000 daltons. This compares acceptably to the predicted molecular mass of 54,911.

In FIG. 12, Lane 1 contained the *E.coli* lysate containing pJO200—the CKS vector without the HCV sequence. Lane 2, contained pHCV-20 expressing the HCV CKS-B (amino acids 1676 to 1790). Lane 3, contained the fusion protein pHCV-23 (amino acids 1676–1931). These results show that the recombinant pHCV-23 fusion protein has an apparent mobility corresponding to a molecular size of 55,000 daltons. This compares acceptably to the predicted molecular mass of 55,070 daltons.

Figure 13:
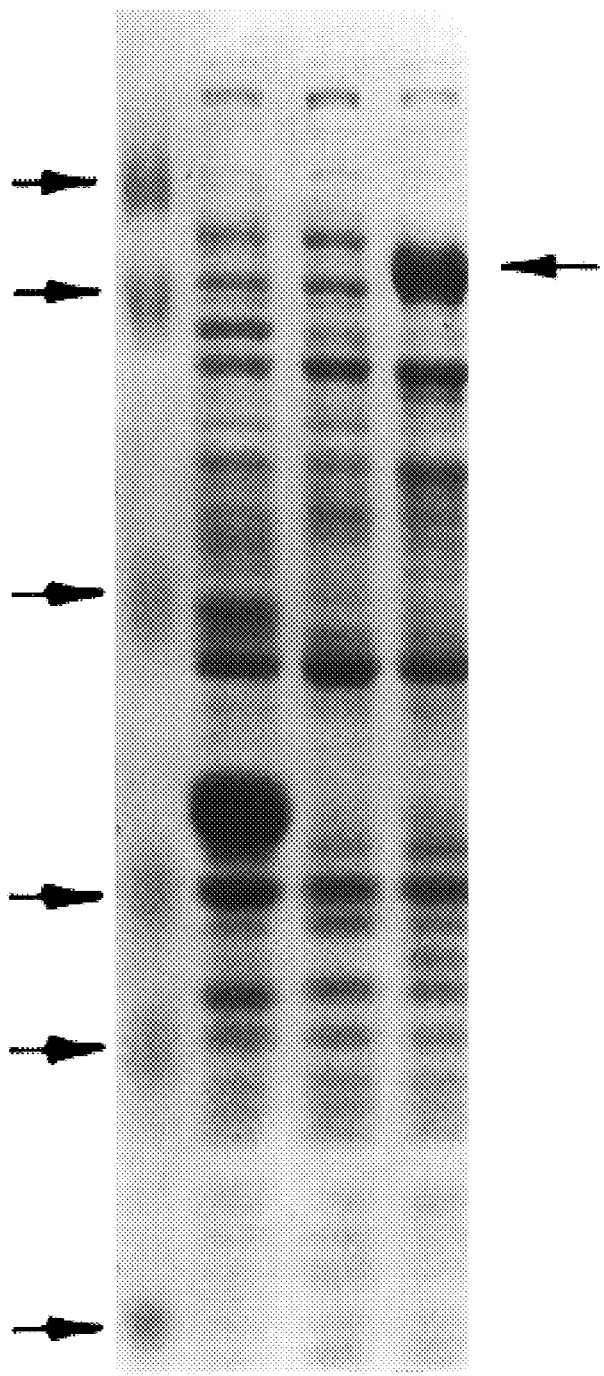
FIG. 13 illustrates the expression of pHCV-31 in *E.coli*.

In FIG. 13, Lane 1 contained the *E.coli* lysate containing pJO200 the CKS vector without the HCV sequences. Lane 2 contained pHCV-31 expressing the CKS-33c-BCD fusion protein (amino acids 1192 to 1447 and 1676 to 1931) prior to induction and lane 3 after 2 hours induction. These results show that the recombinant pHCV-31 (CKS-33c-BCD) fusion protein has an apparent mobility corresponding to a molecular size of 90,000 daltons. This compares acceptably to the predicted molecular mass of 82,995 daltons.

An immunoblot was also run on one of the SDS/PAGE gels derived from the pHCV-31/Xl-1 culture. Human serum from an HCV exposed individual reacted strongly with the major pHCV-31 band at 90,000 daltons. Normal human serum did not react with any component of the pHCV-31 (CKS-33-BCD) preparations.

EXAMPLE 3

Screening Assay

The use of recombinant polypeptides which contain epitopes within c100-3 as well as epitopes from other antigenic regions from the HCV genome, provide immunological assays which have increased sensitivity and may be more specific than HCV immunological assays using epitopes within c100-3 alone.

In the presently preferred screening assay, the procedure uses two *E.coli* expressed recombinant proteins, CKS-Core (pHCV-34; SEQ. ID. NO. 2) and CKS-33-BCD (pHCV-31; SEQ. ID. NO. 4), representing three distinct regions of the HCV genome. These recombinant polypeptides were prepared following procedures described above. In the screening assay, both recombinant antigens are coated onto the same polystyrene bead. In a modification of the screening assay the polystyrene bead may also be coated with the SOD-fusion polypeptide c100-3.

The polystyrene beads are first washed with distilled water and propanol and then incubated with a solution containing recombinant pHCV-31 diluted to 0.5 to 2.0 ug/ml and pHCV-34 diluted to 0.1 to 0.5 ug/ml in 0.1 M $NaH_2PO_4.H20$ with 0.4M NaCl and 0.0022% Triton X-100®, pH 6.5. The beads are incubated in the antigen solution for 2 hours (plus or minus 10 minutes) at 38–42° C., washed in PBS and soaked in 0.1% (w/v) Triton X-100 in PBS for 60 minutes at 38–42° C. The beads are then washed two times in phosphate buffered saline (PBS), overcoated with a solution of 5.0% (w/v) bovine serum albumin (BSA) in PBS for 60 minutes at 38–42° C. and washed one time in PBS. Finally, the beads are overcoated with 5% (w/v) sucrose in PBS, and dried under nitrogen or air.

The polystyrene beads coated with pHCV-31 and pHCV-34 are used in an antibody capture format. Ten microliters of sample are added to the wells of the reaction tray along with 400 ul of a sample diluent and the recombinant coated bead. The sample diluent consists of 10% (v/v) bovine serum and 20% (v/v) goat serum in 20 mM Tris phosphate buffer containing 0.15% (v/v) Triton X-100, 1%(w/v) BSA, 1% *E.coli* lysate and 500 ug/ml or less CKS lysate. When the recombinant yeast c100-3 polypeptide is used, antibodies to yeast antigens which may be present in a sample are reacted with yeast extracts which are added to the sample diluent (typically about 200 ug/ml). The addition of yeast extracts to the sample diluent is used to prevent false positive results. The final material is sterile filtered and filled in plastic bottles, and preserved with 0.1% sodium azide.

After one hour of incubation at 40° C., the beads are washed and 200 ul of conjugate is added to the wells of the reaction tray.

The preferred conjugate is goat anti-human IgG horseradish peroxidase conjugate. Concentrated conjugate is titered to determine a working concentration. A twenty-fold concentrate of the working conjugate solution is then prepared by diluting the concentrate in diluent. The 20× concentrate is sterile filtered and stored in plastic bottles.

The conjugate diluent includes 10% (v/v) bovine serum, 10% (v/v) goat serum and 0.15% Triton-X100 in 20 mM Tris buffer, pH 7.5 with 0.01% gentamicin sulfate, 0.01% thimerosal and red dye. The conjugate is sterile filtered and filled in plastic bottles.

Anti-HCV positive control is prepared from plasma units positive for antibodies to HCV. The pool of units used includes plasma with antibodies reactive to pHCV-31 and pHCV-34. The units are recalcified and heat inactivated at 59–61° C. for 12 hours with constant stirring. The pool is aliquoted and stored at −20° C. or at 2–8° C. For each lot of positive control, the stock solution is diluted with negative control containing 0.1% sodium azide as a preservative. The final material is sterile filtered and filled in plastic bottles.

Anti-HCV negative control is prepared from recalcified human plasma, negative for antibodies to pHCV-31 and pHCV-34 proteins of HCV. The plasma is also negative for antibodies to human immunodeficiency virus (HIV) and negative for hepatitis B surface antigen (HBsAg). The units are pooled, and 0.1% sodium azide is added as a preservative. The final material is sterile filtered and filled in plastic bottles.

After one hour of incubation with the conjugate at 40° C., the beads are washed, exposed to the OPD substrate for thirty minutes at room temperature and the reaction terminated by the addition of 1 N $H_2SO_4$. The absorbance is read at 492 nm.

In order to maintain acceptable specificity, the cutoff for the assay should be at least 5–7 standard deviations above the absorbance value of the normal population mean. In addition, it has generally been observed that acceptable specificity is obtained when the population mean runs at a sample to cutoff (S/CO) value of 0.25 or less. Consistent with these criteria, a "preclinical" cutoff for the screening assay was selected which clearly separated most of the presumed "true negative" from "true positive" specimens. The cutoff value was calculated as the sum of the positive control mean absorbance value multiplied by 0.25 and the negative control mean absorbance value. The cutoff may be expressed algebraically as:

Cutoff value=0.25 PCx+NCx.

Testing may be performed by two methods which differ primarily in the degree of automation and the mechanism for reading the resulting color development in the assay. One method is referred to as the manual or Quantumttm method because Quantum or Quantumatic is used to read absorbance at 492 nm. It is also called the manual method because sample pipetting, washing and reagent additions are generally done manually by the technician, using appropriately calibrated pipettes, dispensers and wash instruments. The second method is referred to as the PPC method and utilizes the automated Abbott Commander® system. This system employs a pipetting device referred to as the Sample Management Center (SMC) and a wash/dispense/read device referred to as the Parallel Processing Center (PPC) disclosed in co-pending patent application U.S. Ser. No. 07/574,821 entitled "Simultaneous Assay for Detecting One Or More Analytes." The optical reader used in the PPC has dual wavelength capabilities that can measure differential absorbencies (peak band and side band) from the sample wells. These readings are converted into results by the processor's Control Center.

Screening Assay Performance

1. Serum/Plasma From Inoculated Chimpanzees

As previously described, FIG. 2 summarizes the results of a study which followed the course of HCV infection in seven chimpanzees using a screening assay which utilized the c100-3 polypeptide, and the screening assay which utilized pHCV-31 (SEQ. ID. NO. 4) and pHCV-34 (SEQ. ID. NO. 2). Both assays gave negative results before inoculation and both assays detected the presence of antibodies after the animal had been infected with HCV. However, in the comparison of the two assays, the assay utilizing pHCV-31 and pHCV-34 detected seroconversion to HCV antigens at an earlier or equivalent bleed date in six of the seven chimpanzees. Data from these chimpanzee studies clearly demonstrate that overall detection of HCV antibodies is greatly increased with the assay utilizing the pHCV-31 and pHCV-34 proteins. This test is sufficiently sensitive to detect seroconversion during the acute phase of this disease, as defined as an elevation in ALT levels, in most animals. Equally important is the high degree of specificity of the test as no pre-inoculation specimens were reactive.

2. Non-A. Non-B Panel II (H. Alter. NIH)

A panel of highly pedigreed human sera from Dr. H. Alter, NIH, Bethesda, Md., containing infectious HCV sera, negative sera and other disease controls were tested. A total of 44 specimens were present in the panel.

Six of seven sera which were "proven infectious" in chimpanzees were positive in both the screening assay using c100-3 as well as in the screening assay utilizing the recombinant proteins pHCV-31 and pHCV-34. These six reactive specimens were obtained from individuals with chronic hepatitis. All six of the reactive specimens were confirmed positive using synthetic peptide sp67. One specimen obtained during the acute phase of NANB post-transfusion hepatitis was non-reactive in both screening assays.

In the group labeled "probable infectious" were three samples taken from the same post transfusion hepatitis patient. The first two acute phase samples were negative in both assays, but the third sample was reactive in both assay. The disease control samples and pedigreed negative controls were uniformly negative.

All sixteen specimens detected as positive by both screening assays were confirmed by the spl17 confirmatory assay (FIG. 14). In addition, specimens 10 and 29 were newly detected in the screening assay utilizing the recombinant pHCV-31 and pHCV-34 antigens and were reactive by the sp75 confirmatory assay. Specimen 39 was initially reactive in the screening test utilizing pHCV-34 and pHCV-31, but upon retesting was negative and could not be confirmed by the confirmatory assays.

In summary, both screening tests identified 6 of 6 chronic NANBH carriers and one of four acute NANBH samples. Paired specimens from an implicated donor were non-reactive in the screening test utilizing c100-3 but were reactive in the screening test with pHCV-31 and pHCV-34. Thus, the screening test utilizing the recombinant antigens pHCV-31 and pHCV-34 appears to be more sensitive than the screening assay utilizing c100-3. None of the disease control specimens or pedigreed negative control specimens were reactive in either screening assay.

3. CBER Reference Panel

A reference panel for antibody to Hepatitis C was received from the Center for Biologics Evaluation and Research (CBER). This 10 member panel consists of eight reactive samples diluted in normal human sera negative for antibody to HCV and two sera that contain no detectable antibody to HCV. This panel was run on the Ortho first generation HCV EIA assay, the screening assay utilizing clOO-3 and the screening assay utilizing pHCV-31 and pHCV-34. The assay results are presented in FIG. 15.

The screening assay utilizing pHCV-31 and pHCV-34 detected all six of the HCV positive or borderline sample dilutions. The two non-reactive sample dilutions (709 and 710) appear to be diluted well beyond endpoint of antibody detectability for both screening assays. A marked increase was observed in the sample to cutoff values for three of the members on the screening assay utilizing pHCV-31 and pHCV-34 compared to the screening assay utilizing c100-3 or the Ortho first generation test. All repeatably reactive specimens were confirmed.

EXAMPLE 4

Confirmatory Assay

The confirmatory assay provides a means for unequivocally identifying the presence of an antibody that is immunologically reactive with an HCV antigen. The confirmatory assay includes synthetic peptides or recombinant antigens representing major epitopes contained within the thee distinct regions of the HCV genome, which are the same regions represented by the two recombinant antigens described in the screening assay. Recombinant proteins used in the confirmatory assay should have a heterologous source of antigen to that used in the primary screening assay (i.e. should not be an *E.coli*-derived recombinant antigen nor a recombinant antigen composed in part, of CKS sequences). Specimens repeatedly reactive in the primary screening assay are retested in the confirmatory assay. Aliquots containing identical amounts of specimen are contacted with a synthetic peptide or recombinant antigen individually coated onto a polystyrene bead. Seroreactivity for epitopes within the c100-3 region of the HCV genome are confirmed by use of the synthetic peptides sp67 and sp65. The synthetic peptide sp117 can also be used to confirm seroreactivity with the c100-3 region. Seroreactivity for HCV epitopes within the putative core region of HCV are confirmed by the use of the synthetic peptide sp75. In order to confirm seroreactivity for HCV epitopes within the 33c region of HCV, a recombinant antigen expressed as a chimeric protein with superoxide dismutase (SOD) in yeast is used. Finally, the antibody-antigen complex is detected.

The assay protocols were similar to those described in Example 3 above. The peptides are each individually coated onto polystyrene beads and used in an antibody capture format similar to that described for the screening assay. Ten microliters (10 μl) of specimen are added to the wells of a reaction tray along with 400 μl of a specimen diluent and a peptide coated bead. After one hour of incubation at 40° C., the beads are washed and 200 μl of conjugate (identical to that described in Example 3) is added to the wells of the reaction tray. After one hour of incubation at 40° C., the beads are washed, exposed to the OPD substrate for 30 minutes at room temperature and the reaction terminated by the addition of 1 N $H_2SO_4$. The absorbance is read at 492 nm. The cutoff value for the peptide assay is four times the mean of the negative control absorbance value.

1. Panels containing Specimens "At Risk" for HCV Infection.

A group of 233 specimens representing 23 hemodialysis patients all with clinically diagnosed NANBH were supplied by Gary Gitnick, M.D. at the University of California, Los Angeles Center for the Health Sciences. These samples which were tested in by the screening assay utilizing c100-3 were subsequently tested in the screening assay which uses pHCV-31 and pHCV-34. A total of 7/23 patients (30.44%) were reactive in the c100-3 screening assay, with a total of 36 repeat reactive specimens. Ten of 23 patients (43.48%) were reactive by the screening assay utilizing pHCV-31 and pHCV-34, with a total of 70 repeatable reactives among the available specimens (FIG. 18). Two specimens were unavailable for testing. All of the 36 repeatedly reactive specimens detected in the c100-3 screening assay were confirmed by synthetic peptide confirmatory assays. A total of 34 of these 36 were repeatedly reactive on HCV EIA utilizing pHCV-34 and pHCV-31: two specimens were not available for testing. Of the 36 specimens additionally detected by the screening assay utilizing pHCV-34 and pHCV-31, nine were confirmed by the core peptide confirmatory assay (sp75) and 27 were confirmed by the SOD-33c confirmatory assay.

Figure 17:
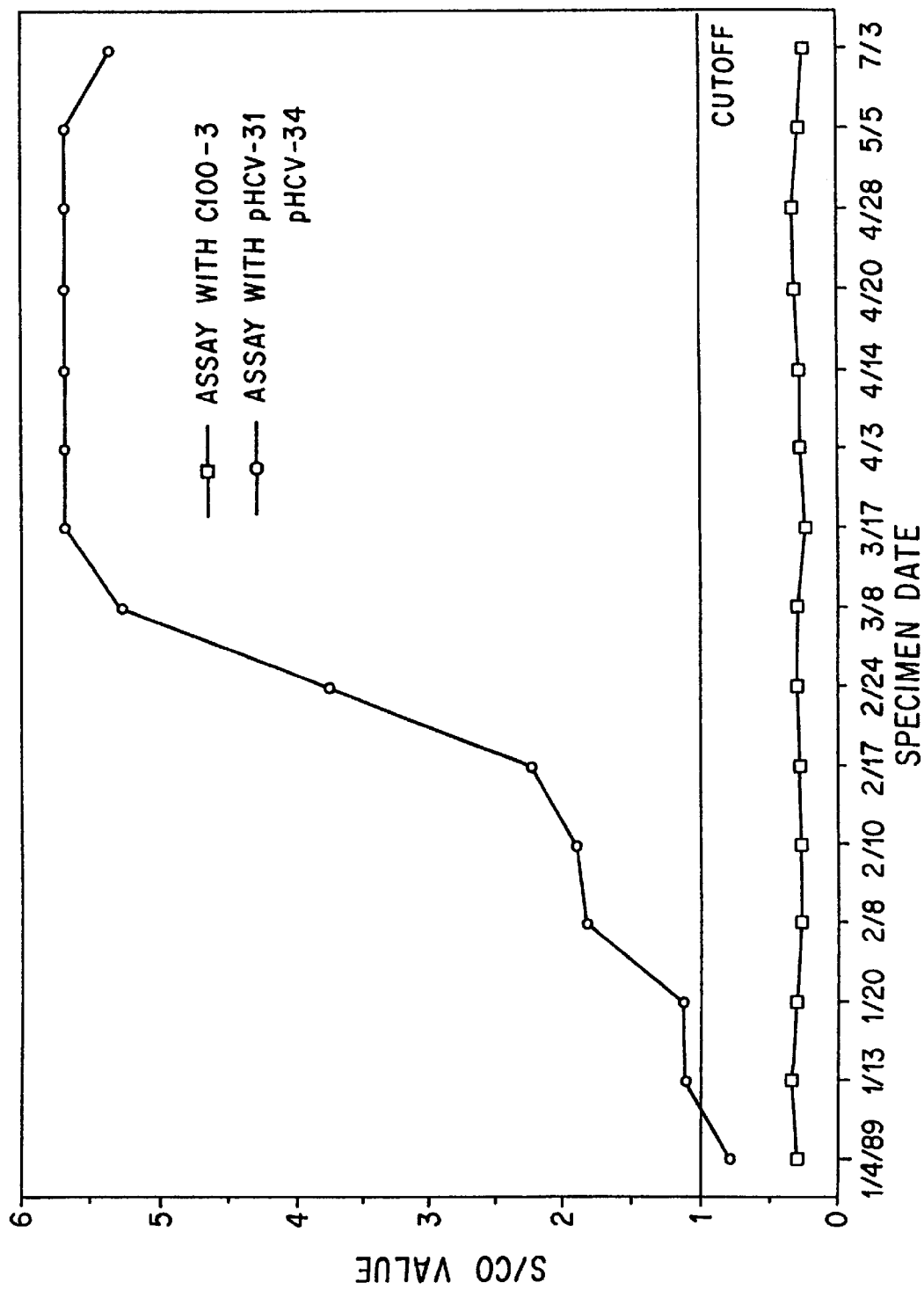
FIG. 17 illustrates earlier detection of HCV in a hemodialysis patient using the screening assay.

In summary these data indicate that detection of anti-HCV by the screening assay utilizing pHCV-31 and pHCV-34 may occur at an equivalent bleed date or as many as nine months earlier, when compared to the c100-3 screening assay. FIG. 17 depicts earlier detection by the screening assay utilizing pHCV-34 and pHCV-31 in a hemodialysis patient 2. Acute/Chronic Non-A. Non-B Hepatitis A population of specimens was identified from individuals diagnosed as having acute or chronic NANBH. Specimens from individuals with acute cases of NANBH were received from Gary Gitnick, M.D. at the University of California, Los Angeles Center for Health Sciences. The diagnosis of acute hepatitis was based on the presence of a cytolytic syndrome (ALT levels greater than 2× the upper normal limit) on at least two serum samples for a duration of less than six months with or without other biological abnormalities and clinical symptoms. All specimens were also negative for IgM antibodies to Hepatitis A Virus (HAV) and were negative for Hepatitis B surface Ag when tested with commercially available tests. Specimens from cases of chronic NANBH were obtained from two clinical sites. Individuals were diagnosed as having chronic NANBH based on the following criteria: persistently elevated ALT levels, liver biopsy results, and/or the absence of detectable HBsAg. Specimens with biopsy results were further categorized as either chronic active NANBH, chronic persistent NANBH, or chronic NANBH with cirrhosis.

These specimens were tested by both the c100-3 screening assay and the screening assay utilizing pHCV-34 and pHCV-31. The latter testing was performed in replicates of two by both the Quantum and PPC methods.

Community Acquired NANBH (Acute)

The c100-3 screening assay detected two of ten specimens (20.00%) as repeatedly reactive, both of which were confirmed. The screening assay utilizing pHCV-34 and pHCV-31 detected both of these specimens plus and additional 2 specimens (FIG. 18). These two specimens were confirmed by sp75 (see FIG. 19).

Acute Post-Transfusion NANBH

The c100-3 assay detected 4 of 32 specimens (12.50%) as repeatedly reactive, all of which was confirmed. The screening assay utilizing pHCV-34 and pHCV-3 1 detected three out of these four specimens (75%) as reactive. The one sample that was missed had an S/CO of 0.95 by the latter screening test. This sample was confirmed by the sp67 peptide (FIG. 18). In addition, the screening assay utilizing pHCV-34 and pHCV-31 detected 11 specimens not reactive in the c100-3 screening assay. Of the nine specimens available for confirmation, eight were confirmed by sp75 and one could not be confirmed but had an S/CO of 0.90 in the sp65 confinatory test. (see FIG. 19).

Chronic NANBH

A summary of the results on these populations is shown in FIG. 20. Overall, 155 of 164 (94.5%) chronic NANBH samples were detected by the screening test utilizing pHCV-31 and pHCV-34 using either Quantum or PPC. The 155 reactive samples were all confirmed in alternate assays using synthetic peptides based on sequences from either the c100, 33c or core regions of the HCV genome. In contrast, only 138 of 164 (84.1%) specimens were positive by the c100-3 assay. All but one of the 138 c100-3 samples were detected as positive by the screening assay utilizing pHCV-31 and pHCV-34. The one discordant specimen was not confirmed by either synthetic or neutralization assays. Conversely, there were 17 confirmed specimens which were positive only by the screening assay utilizing pHCV-34 and pHCV-31.

The results indicate that the screening assay utilizing pHCV-34 and pHCV-31 is more sensitive than the current test in detecting HCV positive individuals within chronically infected NANBH populations.

EXAMPLE 5

Competition Assay

The recombinant polypeptides containing antigenic HCV epitopes are useful for competition assays. To perform a neutralization assay, a recombinant polypeptide representing epitopes within the c100-3 region such as CKS-BCD (pHCV-23) is solubilized and mixed with a sample diluent to a final concentration of 0.5–50 ug/ml. Ten microliters of specimen or diluted specimen is added to a reaction well followed by 400 ul of the sample diluent containing the recombinant polypeptide and if desired, the mixture may be preincubated for about fifteen minutes to two hours. A bead coated with c100-3 antigen is then added to the reaction well and incubated for one hour at 40° C. After washing, 200 ul of a peroxidase labeled goat anti-human IgG in conjugate diluent is added and incubated for one hour at 40° C. After washing, OPD substrate is added and incubated at room temperature for thirty minutes. The reaction is terminated by the addition of 1 N sulfuric acid and the absorbance read at 492 nm.

Samples containing antibodies to the c100-3 antigen generate a reduced signal caused by the competitive binding of the peptides to these antibodies in solution. The percentage of competitive binding may be calculated by comparing the absorbance value of the sample in the presence of a recombinant polypeptide to the absorbance value of the sample assayed in the absence of a recombinant polypeptide at the same dilution.

EXAMPLE 6

Immunodot Assay

The immunodot assay system uses a panel of purified recombinant polypeptides placed in an array on a nitrocellulose solid support. The prepared solid support is contacted with a sample and captures specific antibodies to HCV antigens. The captured antibodies are detected by a conjugate-specific reaction. Preferably, the conjugate specific reaction is quantified using a reflectance optics assembly within an instrument which has been described in U.S. patent applications Ser. No. 07/227,408 filed Aug. 2, 1988. The related U.S. patent applications Ser. Nos. 07/227,272, 07/227,586 and 07/227,590 further describe specific methods and apparatus useful to perform an immunodot assay. The assay has also been described in U.S. application Ser. No. 07/532,489 filed Jun. 6, 1990. Briefly, a nitrocellulose-base test cartridge is treated with multiple antigenic polypeptides. Each polypeptide is contained within a specific reaction zone on the test cartridge. After all the antigenic polypeptides have been placed on the nitrocellulose, excess binding sites on the nitrocellulose are blocked. The test cartridge is then contacted with a sample such that each antigenic polypeptide in each reaction zone will react if the sample contains the appropriate antibody. After reaction, the test cartridge is washed and any antigen-antibody reactions are identified using suitable well known reagents.

As described in the patent applications listed above, the entire process is amenable to automation. The specifications of these applications related to the method and apparatus for performing an immunodot assay are incorporated by reference herein.

In a preferred immunodot assay, the recombinant polypeptides pHCV-23, pHCV-29, pHCV-34, and c100-3 were diluted in the preferred buffers, pH conditions, and spotting concentrations as summarized in FIG. 21 and applied to a preassembled nitrocellulose test cartridge. After drying the cartridge overnight at room temperature 37° C., the non-specific binding capacity of the nitro-cellulose phase was blocked. The blocking solution contained 1% porcine gelatin, 1% casein enzymatic hydrolysate, 5% Tween-20, 0.1% sodium azide, 0.5 M sodium chloride and 20 mM Tris, pH 7.5.

Forty normal donors were assayed by following the method described above. The mean reflectance density value then was determined for each of the recombinant proteins. A cutoff value was calculated as the negative mean plus six standard deviations. Test cartridges were incubated with samples A00642 and 423 (see FIG. 22). Sample A00642 was from a convalescent non-A, non-B hepatitis patient, diluted in negative human plasma from 1:100 to 1:12800. The other sample, 423, was from a paid plasma donor which tested positive in an assay using a recombinant c100-3 polypeptide, diluted in negative human plasma from 1:40 to 1:2560. After sample incubation, sequential incubations with a biotin-conjugated goat anti-human immunoglobulin-specific antibody, an alkaline phosphatase-conjugated rabbit anti-biotin specific antibody, and 5-bromo-4-chloro-3-indolyl phosphate produced a colored product at the site of the reaction. Sample to cutoff values (S/CO) were determined for all HCV recombinant proteins. Those S/CO values greater than or equal to 1.0 were considered reactive. The limiting dilution was defined as the lowest dilution at which the S/CO was greater than or equal to 1.0. As seen in FIG. 22, each sample tested positive for all HCV recombinant proteins. The data demonstrate that reactivity for sample A00642 was greatest with pHCV-29, and decreased for the remaining antigens pHCV-23, c100-3, and pHCV-34. Sample 423-most strongly reacted with the recombinant proteins expressing pHCV-29 and pHCV-34, and to a lesser extent with pHCV-23 and c100-3.

EXAMPLE 7

HCV CKS-NS5 Expression Vectors

A. Preparation of HCV CKS-NS5E

Figure 23:
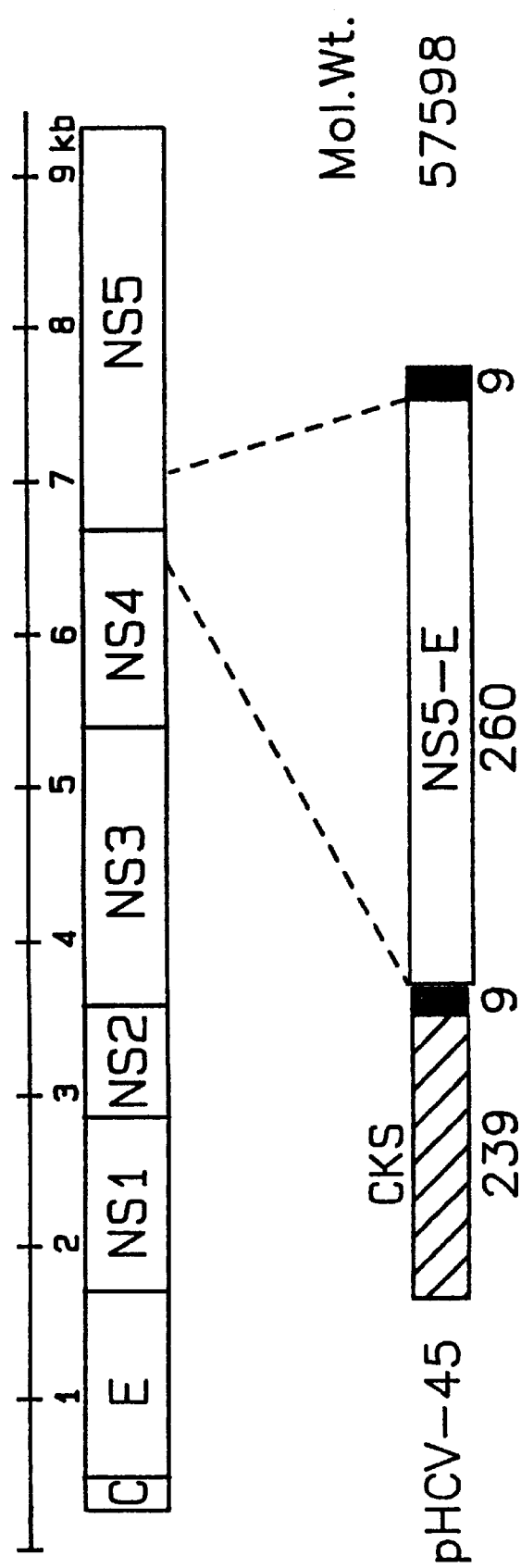
FIG. 23 illustrates the fusion protein pHCV-45.
Figure 24:
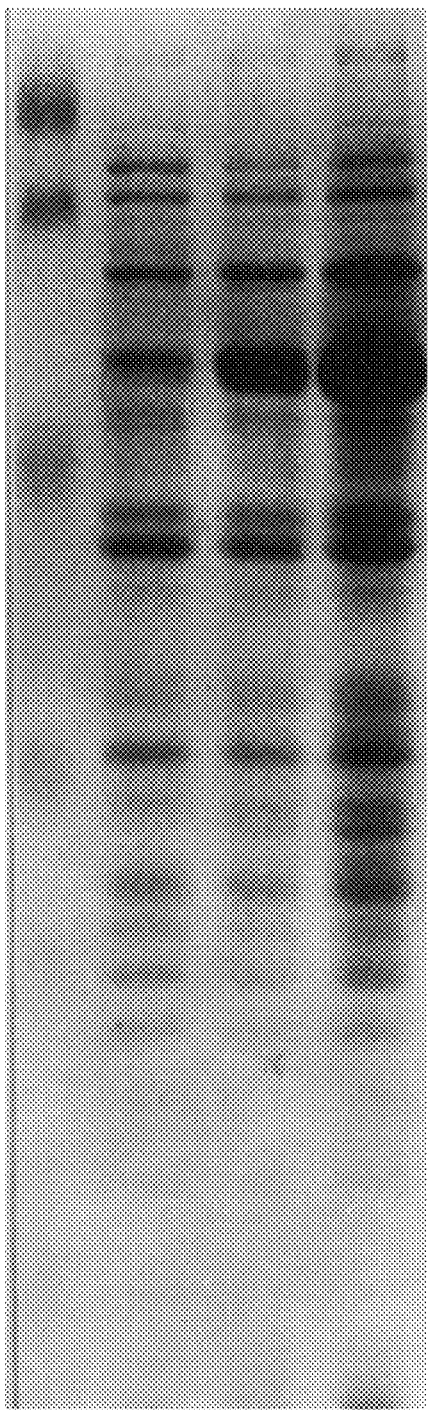
FIG. 24 illustrates the expression of pHCV-45 in *E.coli*.

Eight individual oligonucleotides representing amino acids 1932–2191 of the HCV genome were ligated together and cloned as a 793 base pair EcoRl-BamHl fragment into the CKS fusion vector pJ0200. The resulting plasmid, designated pHCV-45, expresses the HCV CKS-NS5E antigen under control of the lac promoter. The HCV CKS-NS5E antigen consists of 239 amino acids of CKS, nine amino acids contributed by linker DNA sequences, and 260 amino acids from the HCV NS4INS5 region (amino acids 1932–2191). FIG. 23 presents a schematic representation of the recombinant antigen expressed by pHCV-45. SEQ. ID. NOS. 5 and 6 present the DNA and amino acid sequence of the HCV CKS-NS5E recombinant antigen produced by pHCV-45. FIG. 24 presents the expression of pHCV-45 proteins in *E.coli*. Lane 1 contained the *E.coli* lysate containing pHCV-45 expressing the HCV CKS-NS5E antigen (amino acids 1932–2191) prior to induction and lanes 2 and 3 after 2 and 4 hours post induction, respectively. These results show that the pHCV-45 fusion protein has an apparent mobility corresponding to a molecular size of 55,000 daltons. This compares acceptably to the predicted molecular mass of 57,597 daltons.

B. Preparation of HCV CKS-NS5F

Figure 25:
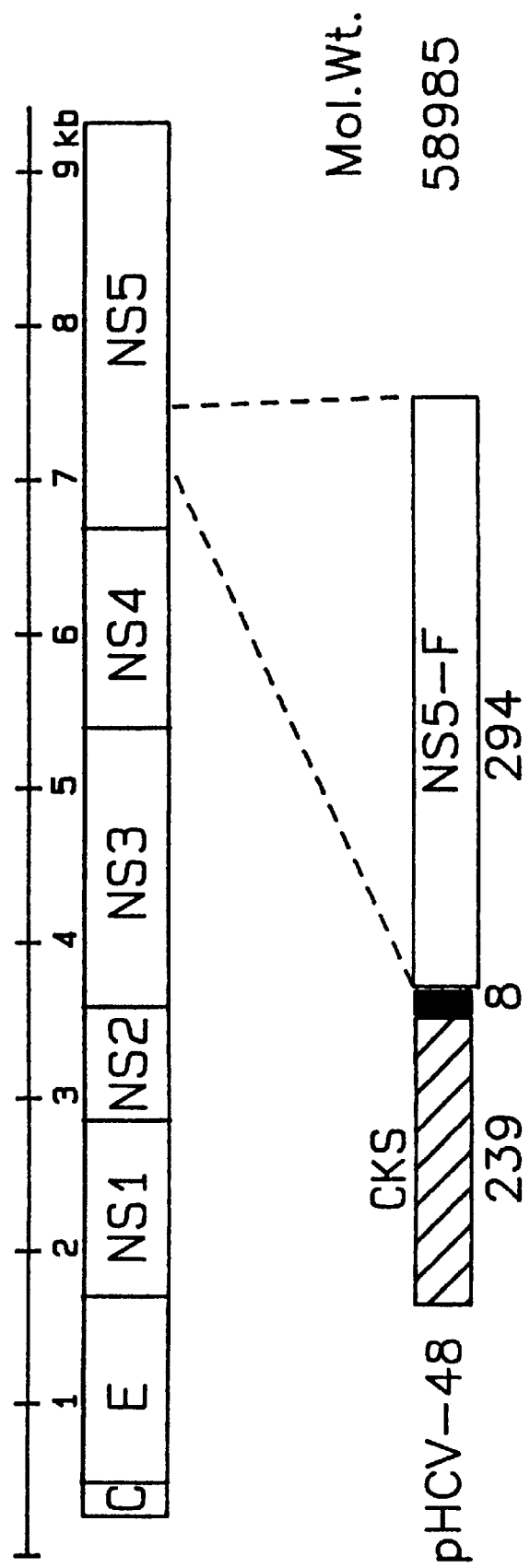
FIG. 25 illustrates the fusion protein pHCV-48.
Figure 26:
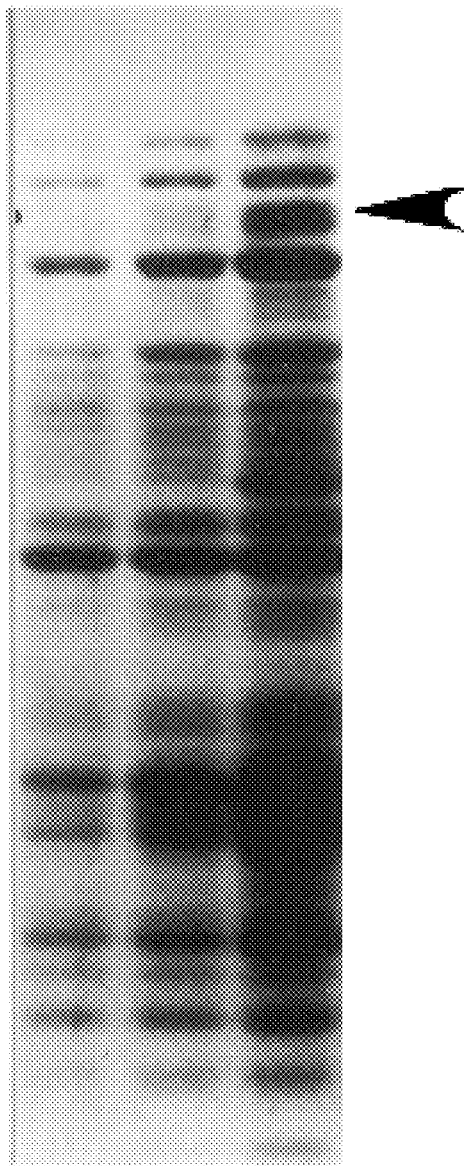
FIG. 26 illustrates the expression of pHCV-48 in *E.coli*.

Eleven individual oligonucleotides representing amino acids 2188–2481 of the HCV genome were ligated together and cloned as a 895 base pair EcoRl-BamHl fragment into the CKS fusion vector pJ0200. The resulting plasmid, designated pHCV-48, expresses the HCV CKS-NS5F antigen under control of the lac promoter. The HCV CKS-NS5F antigen consists of 239 amino acids of CKS, eight amino acids contributed by linker DNA sequences, and 294 amino acids from the HCV NS5 region (amino acids 2188–2481). FIG. 25 presents a schematic representation of the recombinant antigen expressed by pHCV-48. SEQ. ID. NOS. 7 and 8 present the DNA and amino acid sequence of the HCV CKS-NS5F recombinant antigen produced by pHCV-48. FIG. 26 presents the expression of pHCV48 proteins in *E.coli*. Lane 1 contained the *E.coli* lysate containing pHCV-48 expressing the HCV CKS-NS5F antigen (amino acids 2188–2481) prior to induction and lanes 2 and 3 after 2 and 4 hours post induction, respectively. These results show that the pHCV-48 fusion protein has an apparent mobility corresponding to a molecular size of 65,000 daltons.: This compares acceptably to the predicted molecular mass of 58,985 daltons.

C. Preparation of HCV CKS-NS5G

Figure 27:
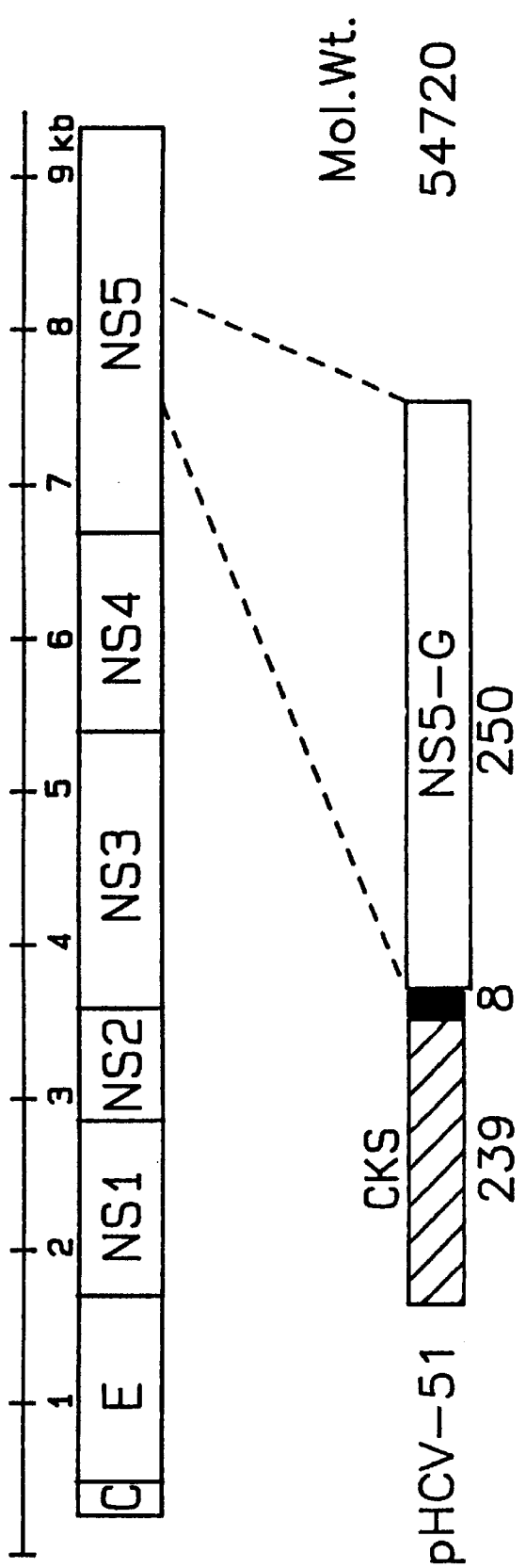
FIG. 27 illustrates the fusion protein pHCV-51.
Figure 28:
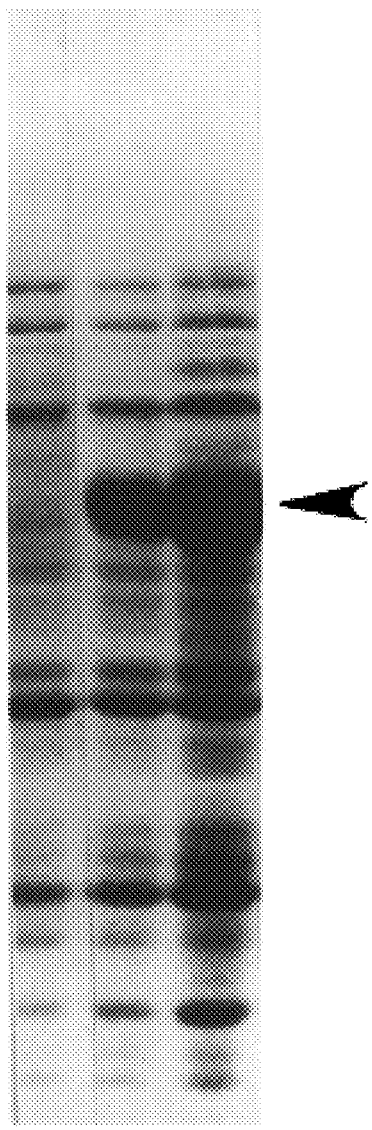
FIG. 28 illustrates the expression of pHCV-51 in *E.coli*.

Seven individual oligonucleotides representing amino acids 2480–2729 of the HCV genome were ligated together and cloned as a 769 base pair EcoRl-BamHl fragment into the CKS fusion vector pJO200. The resulting plasmid, designated pHCV-51, expresses the HCV CKS-NS5G antigen under control of the lac promoter. The HCV CKS-NS5G antigen consists of 239 amino acids of CKS, eight amino acids contributed by linker DNA sequences, and 250 amino acids from the HCV NS5 region (amino acids 2480–2729). FIG. 27 presents a schematic representation of the recombinant antigen expressed by pHCV-51. SEQ. ID. NOS. 9 and 10 present the DNA and amino acid sequence of the HCV CKS-NS5G recombinant antigen produced by pHCV-51. FIG. 28 presents the expression of pHCV-51 proteins in E.coli. Lane 1 contained the E.coli lysate containing pHCV-51 expressing the HCV CKS-NS5G antigen (amino acids 2480–2729) prior to induction and lanes 2 and 3 after 2 and 4 hours post induction, respectively. These results show that the pHCV-51 fusion protein has an apparent mobility corresponding to a molecular size of 55,000 daltons. This compares acceptably to the predicted molecular mass of 54,720 daltons.

D. Preparation of HCV CKS-NS5H

Figure 29:
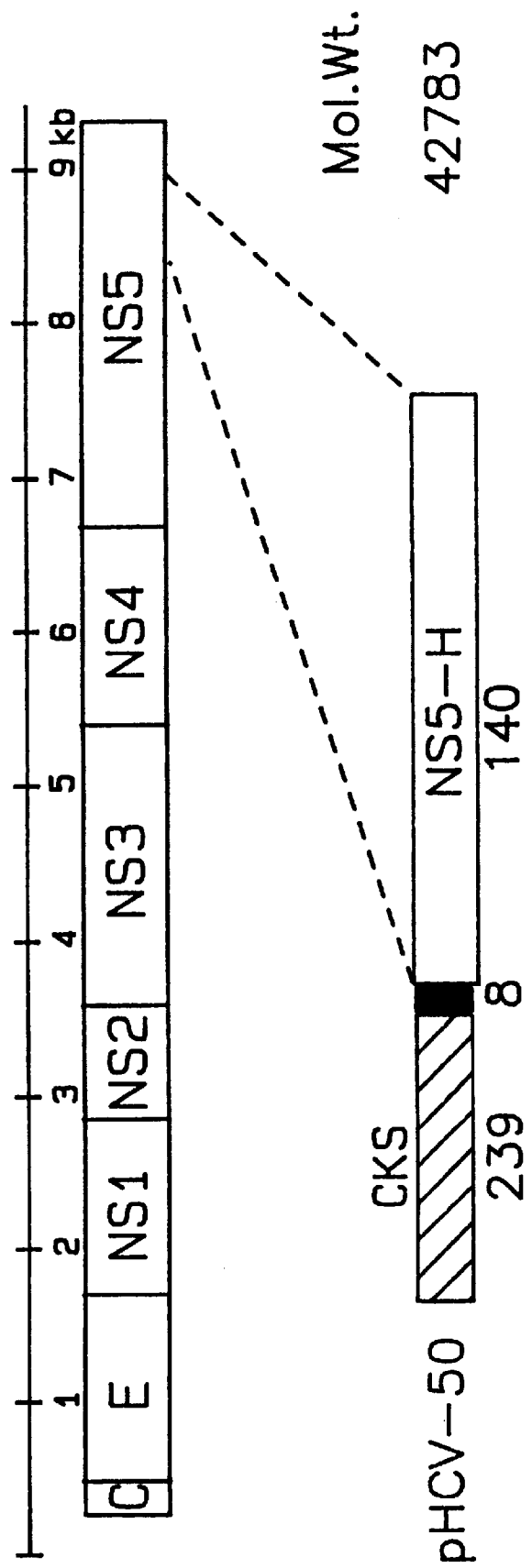
FIG. 29 illustrates the fusion protein pHCV-50.
Figure 30:
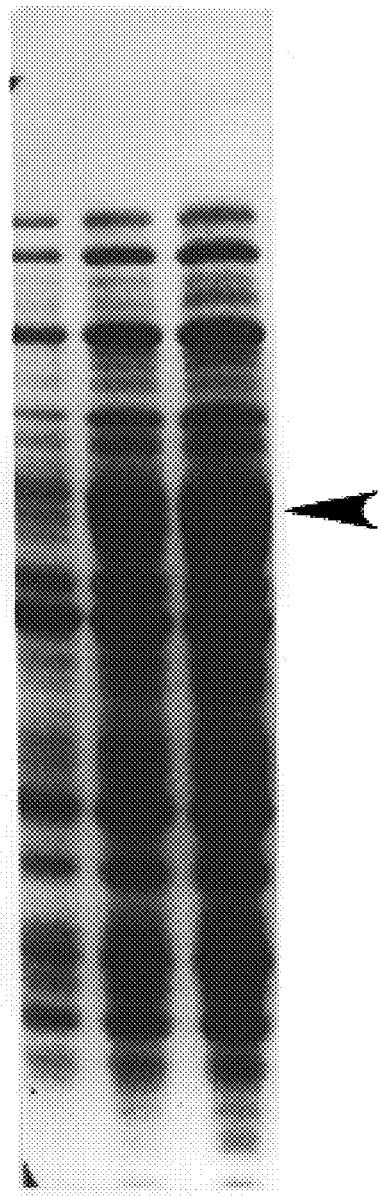
FIG. 30 illustrates the expression of pHCV-50 in *E.coli*.

Six individual oligonucleotides representing amino acids 2728–2867 of the HCV genome were ligated together and cloned as a 439 base pair EcoRl-BamHl fragment into the CKS fusion vector pJO200. The resulting plasmid, designated pHCV-50, expresses the HCV CKS-NS5H antigen under control of the lac promoter. The HCV CKS-NS5H antigen consists of 239 amino acids of CKS, eight amino acids contributed by linker DNA sequences, and 140 amino acids from the HCV NS5 region (amino acids 2728–2867). FIG. 29 presents a schematic representation of the recombinant antigen expressed by pHCV-50. SEQ. ID. NOS. 11 and 12 present the DNA and amino acid sequence of the HCV CKS-NS5H recombinant antigen produced by pHCV-50. FIG. 30 presents the expression of pHCV-50 proteins in E.coli. Lane 1 contained the E.coli lysate containing pHCV-50 expressing the HCV CKS-NS5H antigen (amino acids 2728–2867) prior to induction and lanes 2 and 3 after 2 and 4 hours post induction, respectively. These results show that the pHCV-50 fusion protein has an apparent mobility corresponding to a molecular size of 45,000 daltons. This compares acceptably to the predicted molecular mass of 42,783 daltons.

E. Preparation of HCV CKS-NS5I

Figure 31:
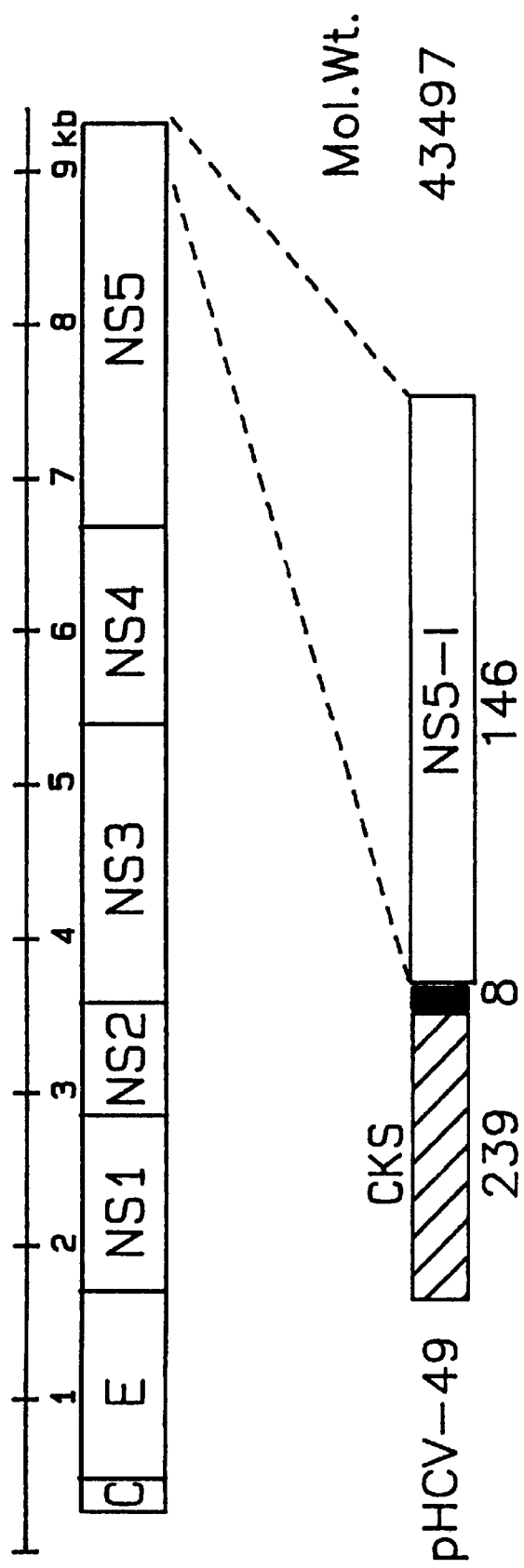
FIG. 31 illustrates the fusion protein pHCV-49.
Figure 32:
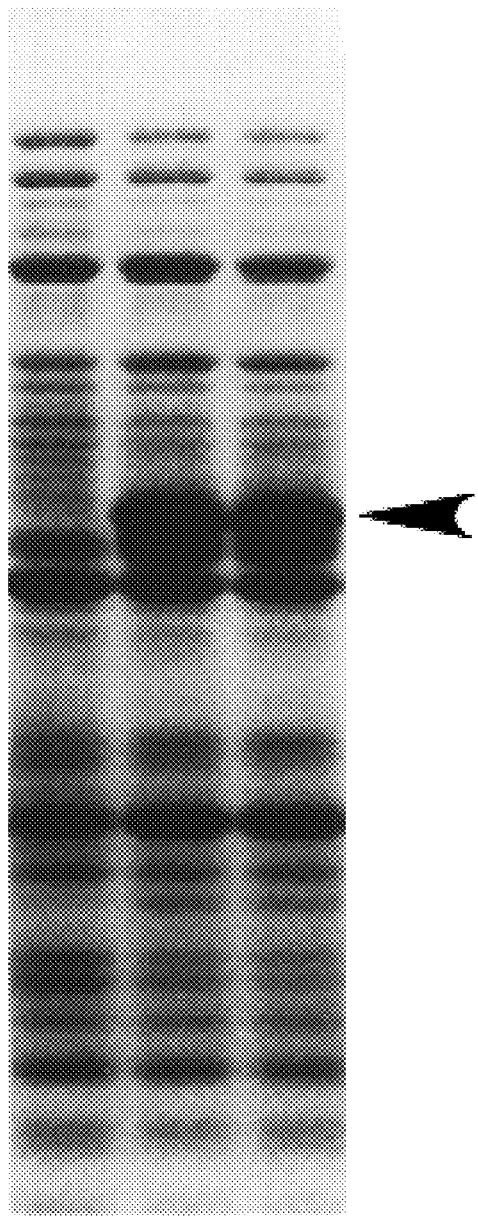
FIG. 32 illustrates the expression of pHCV-49 in *E.coli*.

Six individual oligonucleotides representing amino acids 28663011 of the HCV genome were ligated together and cloned as a 460 base pair EcoRI-BamHI fragment into the CKS fusion vector pJO200. The resulting plasmid, designated pHCV-49, expresses the HCV CKS-NS5I antigen under control of the lac promoter. The HCV CKS-NS5I antigen consists of 239 amino acids of CKS, eight amino acids contributed by linker DNA sequences, and 146 amino acids from the HCV NS5 region (amino acids 2866–3011). FIG. 31 presents a schematic representation of the recombinant antigen expressed by pHCV-49. SEQ. ID. NOS. 13 and 14 present the DNA and amino acid sequence of the HCV CKS-NS5I recombinant antigen produced by pHCV-49. FIG. 32 presents the expression of pHCV-49 proteins in E.coli. Lane 1 contained the E.coli lysate containing pHCV-49 expressing HCV CKS-NS5I antigen (amino acids 2866–3011) prior to induction and lanes 2 and 3 after 2 and 4 hours post induction, respectively. These results show that the pHCV-49 fusion protein has an apparent mobility corresponding to a molecular size of 42,000 daltons. This compares acceptably to the predicted molecular mass of 43,497 daltons.

F. Immunoblot of HCV CKS-NS5 Antigens

Figure 33:
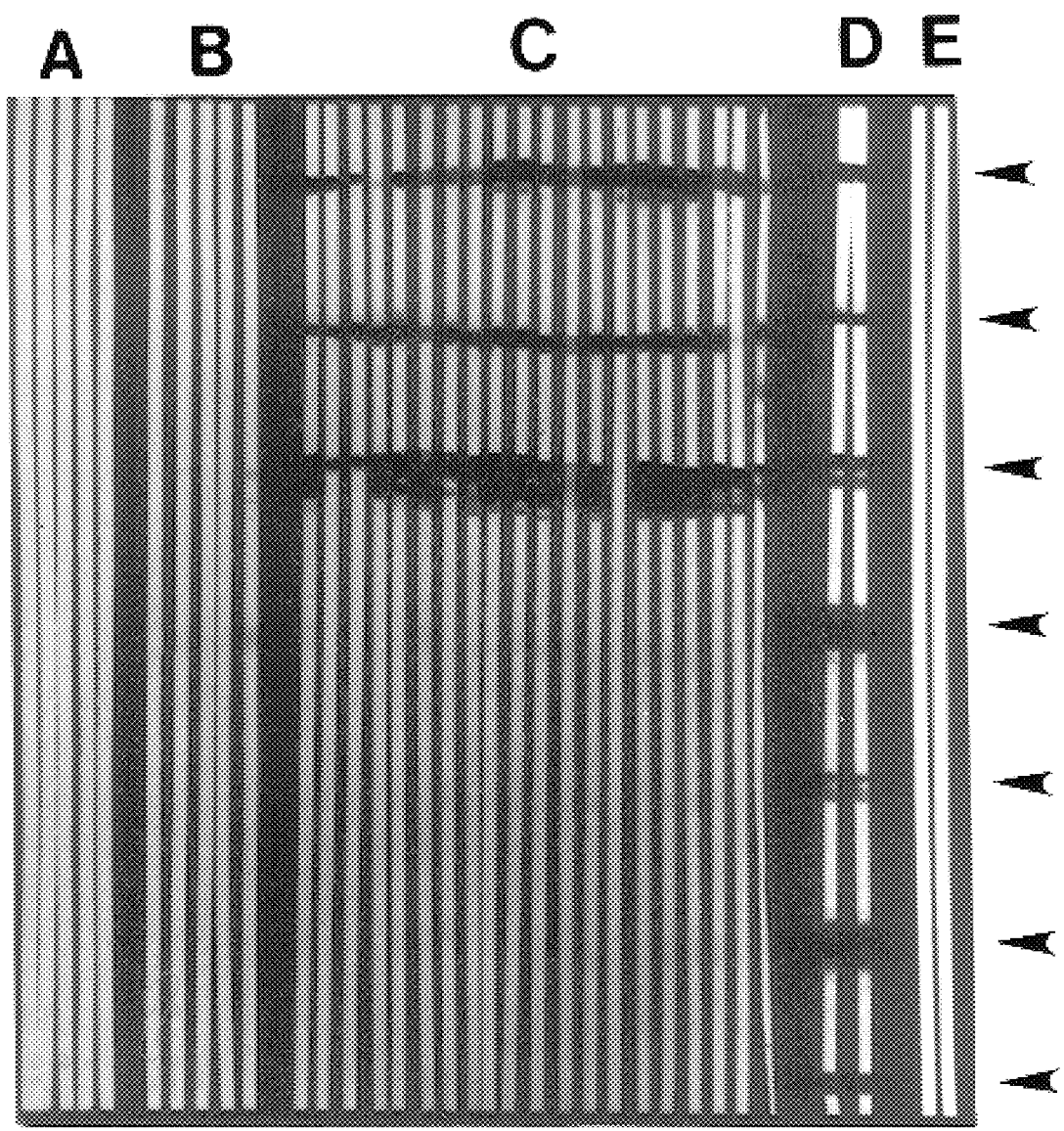
FIG. 33 illustrates an immunoblot of pHCV-23, pHCV-45, pHCV-48, pHCV-51, pHCV-50 and pHCV-49.

Induced E.coli lysates containing pHCV-23, pHCV45, pHCV-48, pHCV-51, pHCV-50, or pHCV-49 were individually run on preparative SDS/PAGE gels to separate the various HCV CKS-NS5 or HCV CKS-BCD recombinant antigens assay from the majority of other E.coli proteins. Gel slices containing the separated individual HCV CKS-NS5 or HCV CKS-BCD recombinant antigens were then electrophoretically transferred to nitrocellulose, and the nitrocellulose sheet cut into strips. FIG. 33 presents the results of a Western Blot analysis of various serum or plasma samples using these nitrocellulose strips. The arrows on the right indicate the position of each HCV CKS-BCD or HCV CKS-NS5 recombinant antigen, from top to bottom pHCV-23 (HCV CKS-BCD), pHCV-45 (HCV CKS-NS5E), pHCV-48 (HCV CKS-NS5F), pHCV-51 (HCV CKS-NS5G), pHCV-50 (HCV CKS-NS5H), pHCV-49 (HCV CKS-NS5I), and pJO200 (CKS). Panel A contained five normal human plasma, panel B contained five normal human sera, panel C contained twenty human sera positive in the Abbott HCV EIA test, panel D contained two mouse sera directed against CKS, and panel E contained two normal mouse sera. Both the HCV CKS-NS 5E antigen expressed by pHCV-45 and the HCV CKS-NS5F antigen expressed by pHCV48 were immunoreactive when screened with human serum samples containing HCV antibodies.

EXAMPLE 8

HCV CKS-C100

A. Preparation of HCV CKS-C100 Vectors Eighteen individual oligonucleotides representing amino acids 1569–1931 of the HCV genome were ligated together and cloned as four separate EcoRI-BamHI subfragments into the CKS fusion vector pJO200. After subsequent DNA sequences confirmation, the four subfragments were digested with the appropriate restriction enzymes, gel purified, ligated together, and cloned as an 1102 base pair EcoRI-BamHI fragment in the CKS fusion vector pJO200. The resulting plasmid, designated pHCV-24, expresses the HCV CKS-C100 antigen under control of the lac promoter. The HCV CKS-c100 antigen consists of 239 amino acids of CKS, eight amino acids contributed by linker DNA sequences, 363 amino acids from the HCV NS4 region (amino acids 1569–1931) and 10 additional amino acids contributed by linker DNA sequences. The HCV CKS-c100 antigen was expressed at very low levels by pHCV-24.

Figure 34:
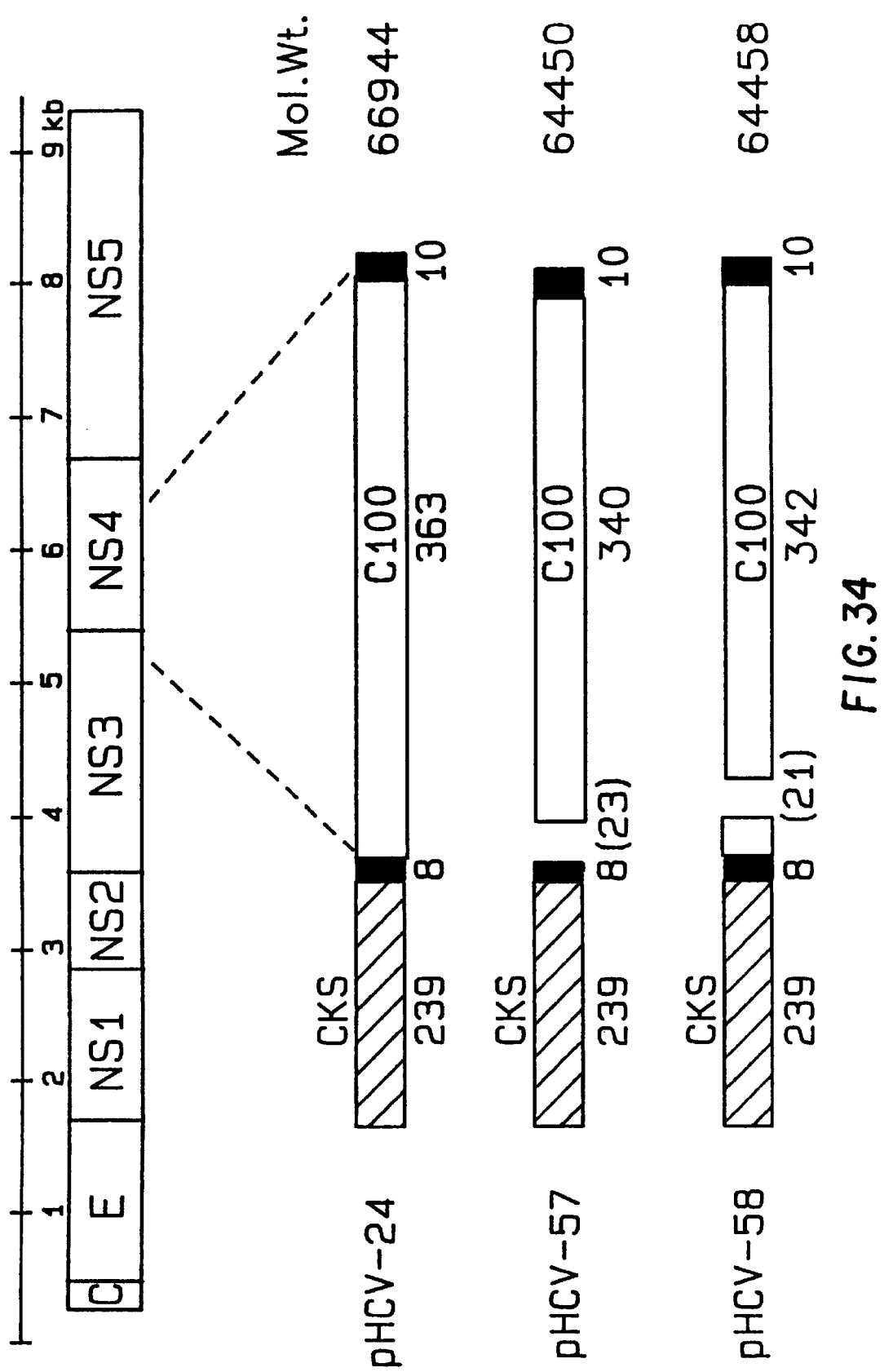
FIG. 34 illustrates the fusion proteins pHCV-24, pHCV-57, pHCV-58.
Figure 35:
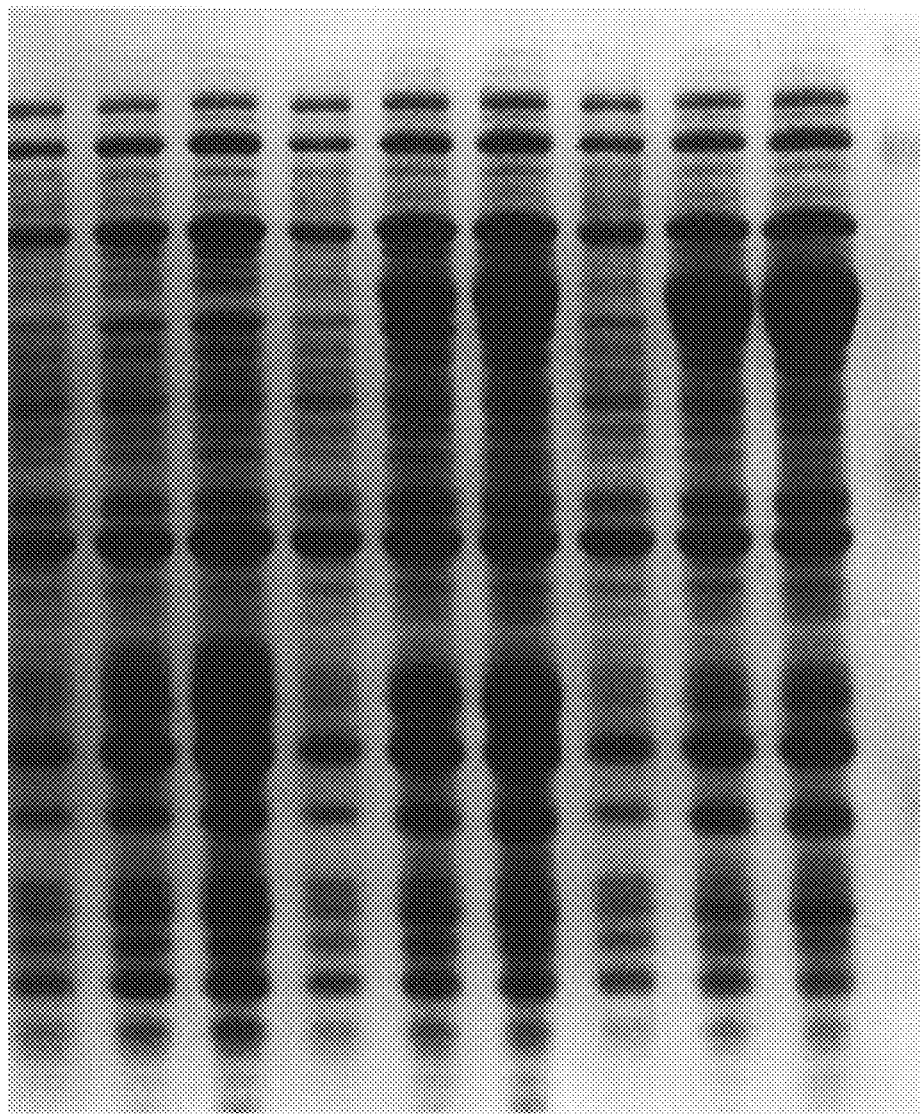
FIG. 35 illustrates the expression of pHCV-24, pHCV-57, and pHCV-58 in *E.coli.*

Poor expression levels of this HCV CKS-c100 recombinant antigen were overcome by constructing two additional clones containing deletions in the extreme amino terminal portion of the HCV c100 region. The first of these clones, designated pHCV-57, contains a 23 amino acid deletion (HCV amino acids 1575–1597) and was constructed by deleting a 69 base pair Ddel restriction fragment. The second of these clones, designated pHCV-58, contains a 21 amino acid deletion (HCV amino acids 1600–1620) and was constructed by deleting a 63 base pair NlalV-Haeml restriction fragment. FIG. 34 presents a schematic representation of the recombinant antigens expressed by pHCV-24, pHCV-57, and pHCV-58. SEQ. ID. NOS. 15 and 16 present the DNA and amino acid sequence of the HCV-C100D1 recombinant antigen produced by pHCV-57. SEQ. ID. NOS. 17 and 18 present the DNA and amino acid sequence of the HCV-C100D2 recombinant antigen produced by pHCV-58. FIG.

35 presents the expression of pHCV-24, pHCV-57, and pHCV-58 proteins in *E.coli*. Lane 1 contained the *E.coli* lysate containing pHCV-24 expressing the HCV CKS-c100 antigen (amino acids 1569–1931) prior to induction and lanes 2 and 3 after 2 and 4 hours post induction, respectively. Lane 4 contained the *E.coli* lysate containing pHCV-57 expressing the HCV-CKS-C100D1 antigen (amino acids 1569–1574 and 1598–1931) prior to induction and lanes 5 and 6 after 2 and 4 hours induction, respectively. Lane 7 contained the *E.coli* lysate containing pHCV-58 expressing the HCV CKS-C100D2 antigen (amino acids 1569–1599 and 1621–1931) prior to induction, and lanes 8 and 9 after 2 and 4 hours induction, respectively. These results show that both the pHCV-57 and pHCV-58 fusion proteins express at significantly higher levels than the pHCV-24 fusion protein and that both the pHCV-57 and pHCV-58 fusion proteins have an apparent mobility corresponding to a molecular size of 65,000 daltons. This compares acceptably to the predicted molecular mass of 64,450 daltons for pHCV-57 and 64,458 daltons for pHCV-58.

EXAMPLE 9

HCV PCR Derived Expression Vectors

A. Preparation of HCV DNA Fragments

RNA was extracted from the serum of various chimpanzees or humans infected with HCV by first subjecting the samples to digestion with Proteinase K and SDS for 1 hour at 37° C. followed by numerous phenol:chloroform extractions. The RNA was then concentrated by several ethanol precipitations and resuspended in water. RNA samples were then reverse transcribed according to supplier's instructions using a specific primer. A second primer was then added and PCR amplification was performed according to supplier's instructions. An aliquot of this PCR reaction was then subjected to an additional round of PCR using nested primers located internal to the first set of primers. In general, these primers also contained restriction endonuclease recognition sequences to be used for subsequent cloning. An aliquot of this second round nested PCR reaction was then subjected to agarose gel electrophoresis and Southern blot analysis to confirm the specificity of the PCR reaction. The remainder of the PCR reaction was then digested with the appropriate restriction enzymes, the HCV DNA fragment of interest gel purified, and ligated to an appropriate cloning vector. This ligation was then transformed into E coli and single colonies were isolated and plasmid DNA prepared for DNA sequences analysis. The DNA sequences was then evaluated to confirm that the specific HCV coding region of interest was intact. HCV DNA fragments obtained in this manner were then cloned into appropriate vectors for expression analysis.

B. Preparation of HCV CKS-NS3

Figure 36:
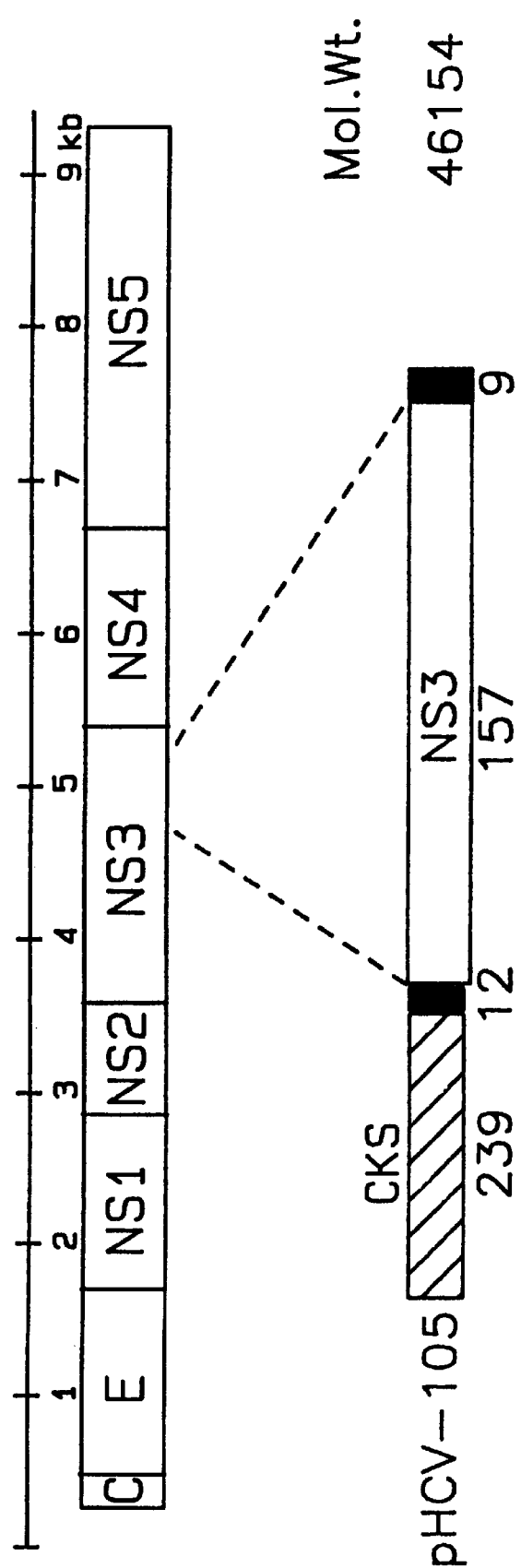
FIG. 36 illustrates the fusion protein pHCV-105.
Figure 37:
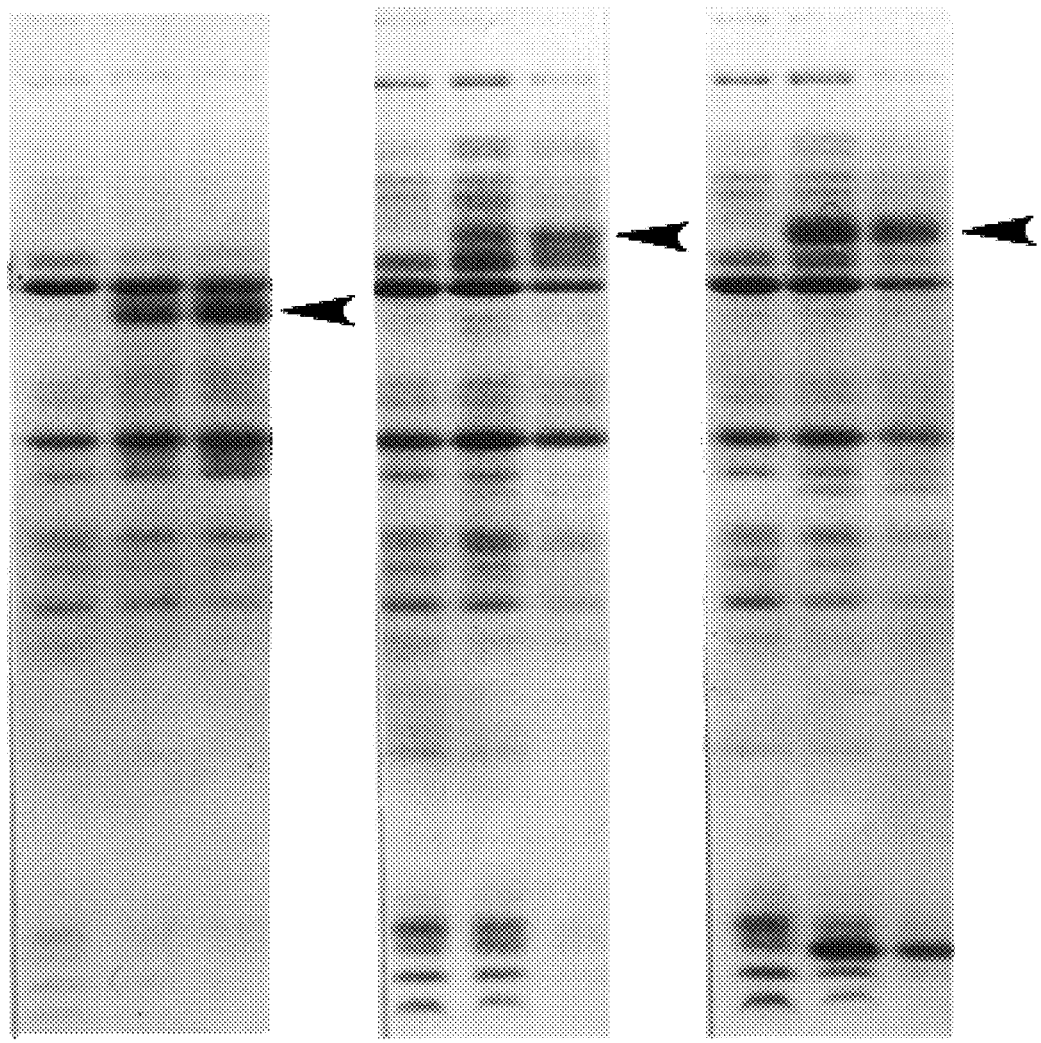
FIG. 37 illustrates the expression of pHCV-105 in *E.coli.*

Using the methods detailed above, a 474 base pair DNA fragment from the putative NS3 region of HCV was generated by PCR. This fragment represents HCV amino acids #1473–1629 and was cloned into the CKS expression vector pJ0201 by blunt-end ligation. The resulting clone, designated pHCV-105, expresses the HCV CKS-NS3 antigen under control of the lac promoter. The HCV CKS-NS3 antigen consists of 239 amino acids of CKS, 12 amino acids contributed by linker DNA sequences, 157 amino acids from the HCV NS3 region (amino acids 1473–1629), and 9 additional amino acids contributed by linker DNA sequences. FIG. 36 presents a schematic representation of the pHCV-105 antigen. SEQ. ID. NOS. 19 and 20 present the DNA and amino acid sequence of the HCV CKS-NS3 recombinant antigen produced by pHCV-105. FIG. 37 presents the expression of pHCV-105 proteins in *E.coli*. Lane 1 contained the *E.coli* lysate containing pHCV-105 expressing the HCV CKS-NS3 antigen (amino acids 1472–1629) prior to induction and lanes 2 and 3 after 2 and 4 hours induction, respectively. These results show that the pHCV-105 fusion protein has an apparent mobility corresponding to a molecular mass of 43,000 daltons. This compares acceptably to the predicted molecular mass of 46,454 daltons.

C. Preparation of HCV CKS-5'ENV

Figure 38:
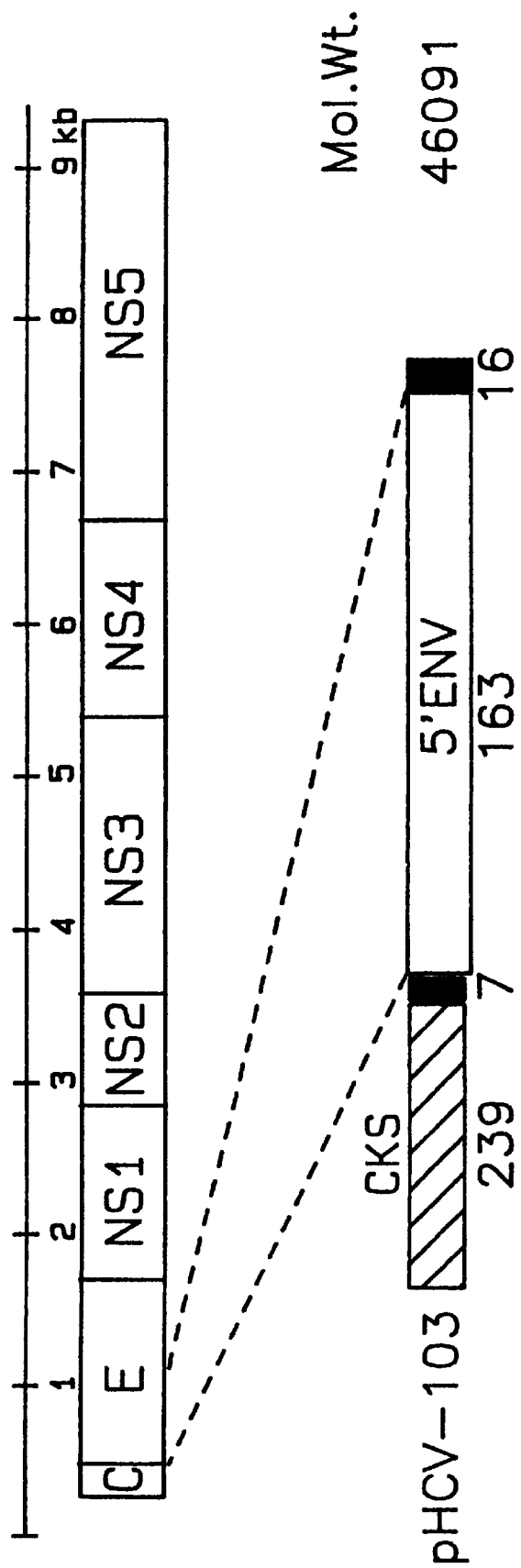
FIG. 38 illustrates the fusion protein pHCV-103.

Using the methods detailed above, a 489 base pair DNA fragment from the putative envelope region of HCV was generated by PCR. This fragment represents the HCV amino acids 114–276 and was cloned into the CKS expression vector pJ0202 using EcoRI-BamHI restriction sites. The resulting clone, designated pHCV-103, expresses the HCV CKS-5'ENV antigen under control of the lac promoter. The HCV CKS-5'ENV antigen consists of 239 amino acids of CKS, 7 amino acids contributed by linker DNA sequences, 163 amino acids from the HCV envelope region (amino acids 114–276), and 16 additional amino acids contributed by linker DNA sequences. FIG. 38 presents a schematic representation of the pHCV-103 antigen. SEQ. ID. NOS. 21 and 22 present the DNA and amino acid sequence of the HCV CKS-5'ENV recombinant antigen produced by pHCV-103. FIG. 37 presents the expression of pHCV-103 proteins in *E.coli*. Lane 1 contained the *E.coli* lysate containing pHCV-103 expressing the HCV CKS-5'ENV antigen (amino acids 114–276) prior to induction and lanes 5 and 6 after 2 and 4 hours induction, respectively. These results show that the pHCV-103 fusion protein has an apparent mobility corresponding to a molecular mass of 47,000 daltons. This compares acceptably to the predicted molecular mass of 46,091 daltons.

D. Preparation of HCV CKS-3'ENV

Figure 39:
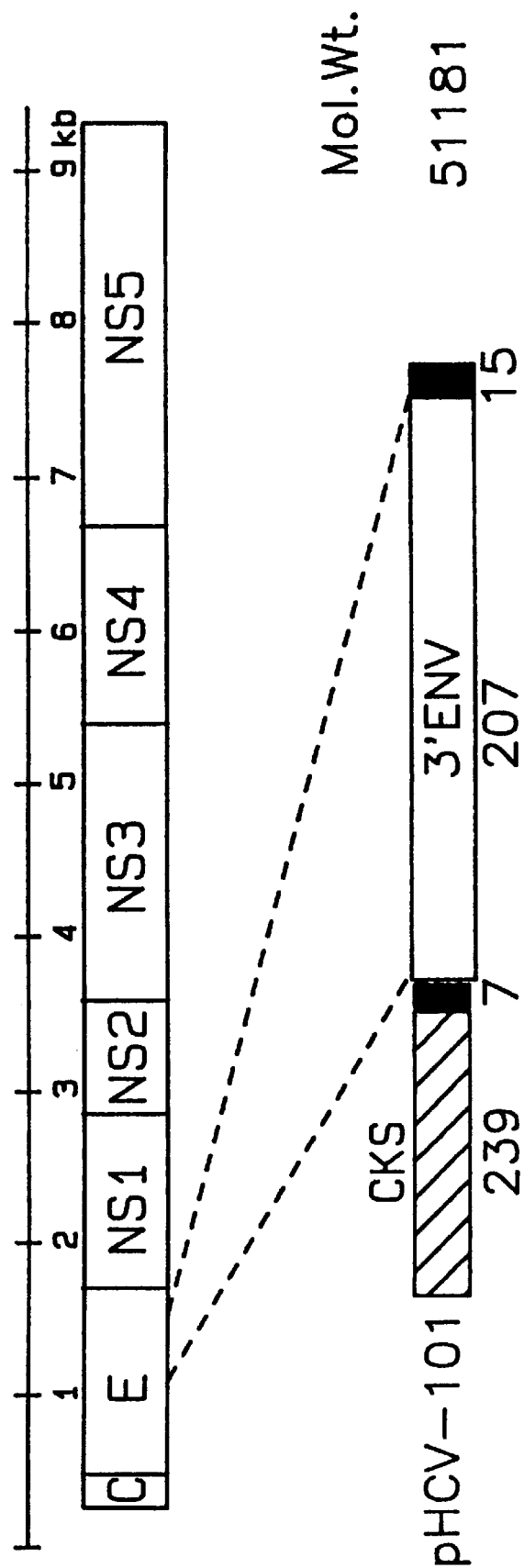
FIG. 39 illustrates the fusion protein pHCV-101.

Using the methods detailed above, a 621 base pair DNA fragment form the putative envelope region of HCV was generated by PCR. This fragment represents HCV amino acids 263–469 and was cloned into the CKS expression vector pJ0202 using EcoRI restriction sites. The resulting clone, designated pHCV-101, expresses the HCV CKS-3'ENV antigen under control of the lac promoter. The HCV CKS-3'ENV antigen consists of 239 amino acids of CKS, 7 amino acids contributed by linker DNA sequences, 207 amino acids from the HCV envelope region (amino acids 263–469), and 15 additional amino acids contributed by linker DNA sequences. FIG. 39 presents a schematic representation of the pHCV-101 antigen. SEQ. ID. NOS. 23 and 24 present the DNA and amino acid sequence of the HCV CKS-3'ENV recombinant antigen produced by pHCV-101. FIG. 37 presents the expression of pHCV-101 proteins in *E.coli*. Lane 7 contained the *E.coli* lysate containing pHCV-101 expressing the HCV CKS-3'ENV antigen (amino acids 263–469) prior to induction and lanes 8 and 9 after 2 and 4 hours induction, respectively. These resulting show that the pHCV-101 fusion protein has an apparent mobility corresponding to a molecular mass of 47,000 daltons. This compares acceptably to the predicted molecular mass of 51,181 daltons.

E. Preparation of HCV CKS-NS2

Figure 40:
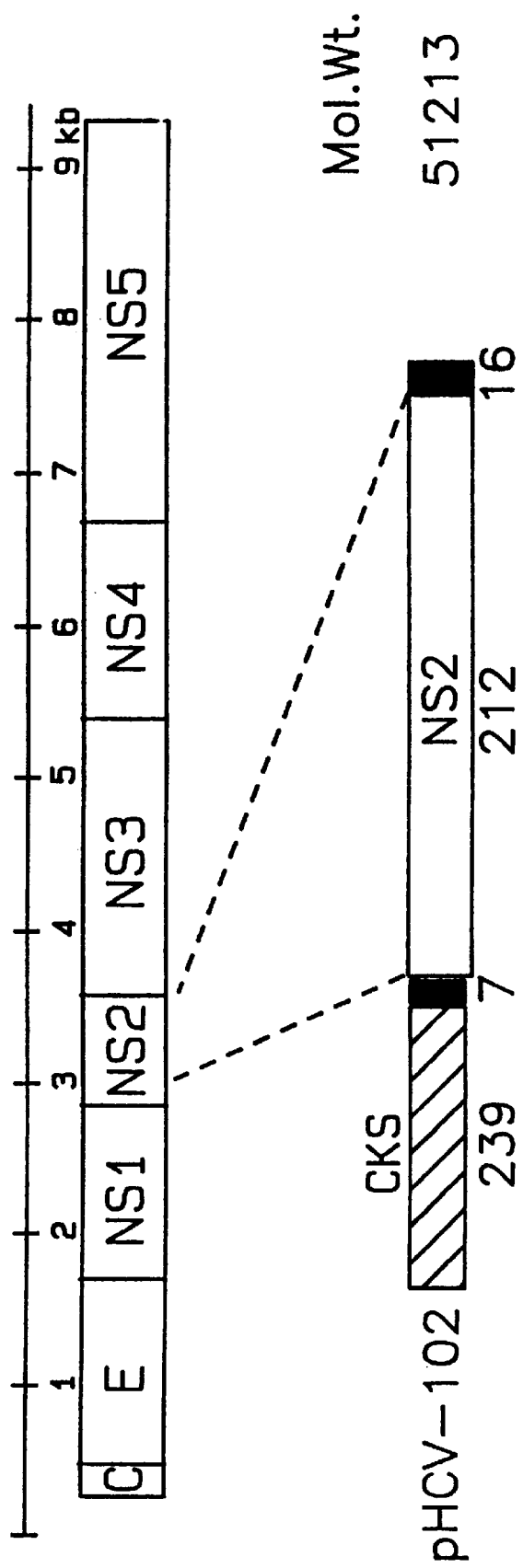
FIG. 40 illustrates the fusion protein pHCV-102.
Figure 41:
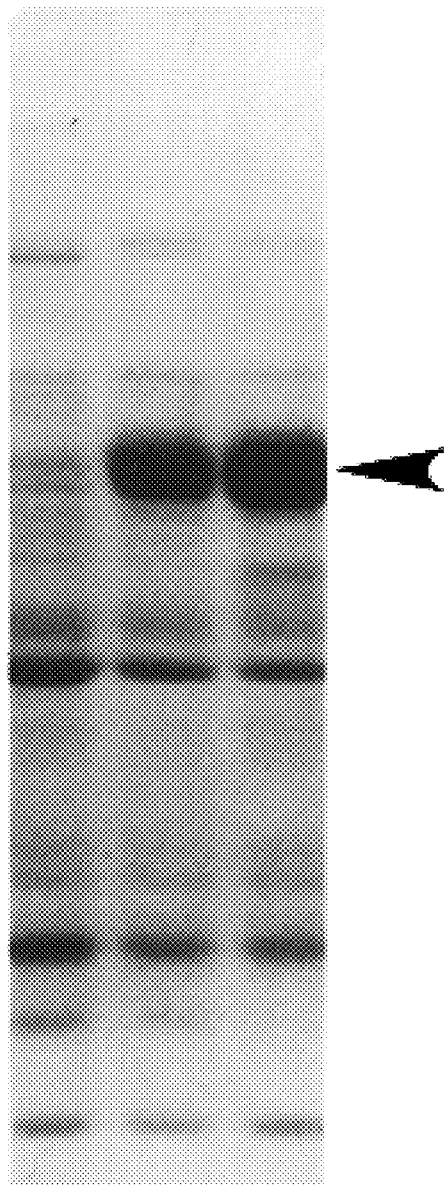
FIG. 41 illustrates the expression of pHCV-102 in *E.coli.*

Using the methods detailed above, a 636 base pair DNA fragment from the putative NS2 region of HCV was generated by PCR. This fragment represents the HCV amino acids 994–1205 and was cloned into the CKS expression vector pJ0201 using EcoRI restriction sites. The resulting clone, designated pHCV-102, expresses the HCV CKS-NS2 antigen under control of the lac promoter. The HCV CKS-NS2 antigen consists of 239 amino acids of CKS, 7 amino acids contributed by linker DNA sequences, 212 amino acids from the HCV NS2 region (amino acids 994–1205), and 16 additional amino acids contributed by linker DNA sequences. FIG. 40 presents a schematic representation of the pHCV-102 antigen. SEQ. ID. NOS. 25 and 26 present the DNA and amino acid sequence of the HCV CKS-NS2 recombinant antigen produced by pHCV-102. FIG. 54 presents the expression of pHCV-102 proteins in *E.coli.* Lane 1 contained the *E.coli* lysate containing pHCV-102 expressing the HCV CKS-NS2 antigen (amino acids 994–1205) prior to induction and lanes 2 and 3 after 2 and 4 hours induction, respectively. These results show that the pHCV-102 fusion protein has an apparent mobility corresponding to a molecular mass of 53,000 daltons. This compares acceptably to the predicted molecular mass of 51,213 daltons.

F. Preparation of HCV CKS-NS 1

Figure 42:
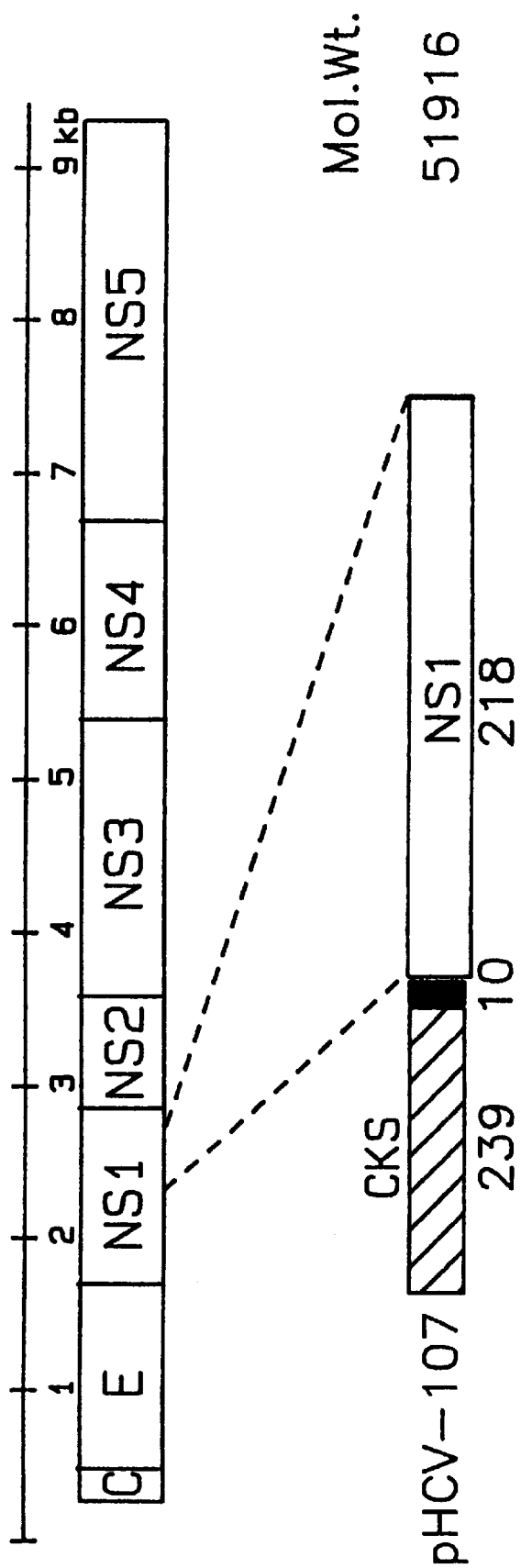
FIG. 42 illustrates the fusion protein pHCV-107.

Using the methods detailed above, a 654 base pair DNA fragment from the putative NS1 region of HCV was generated by PCR. This fragment represents HCV amino acids 617–834 and was cloned into the CKS expression vector pJO200 using EcoRI-BamHI restriction sites. The resulting clone, designated pHCV-107, expresses the HCV CKS-NS1 antigen under control of the lac promoter. The HCV CKS-NS1 antigen consists of 239 amino acids of CKS, 10 amino acids contributed by linker DNA sequences, and 218 amino acids from the HCV NS1 region (amino acids 617–834). FIG. 42 presents a schematic representation of the pHCV-107 antigen. SEQ. ID. NOS. 27 and 28 presents the DNA and amino acid sequence of the HCV CKS-NS1 recombinant antigen produced by pHCV-107.

G. Preparation of HCV CKS-ENV

Figure 43:
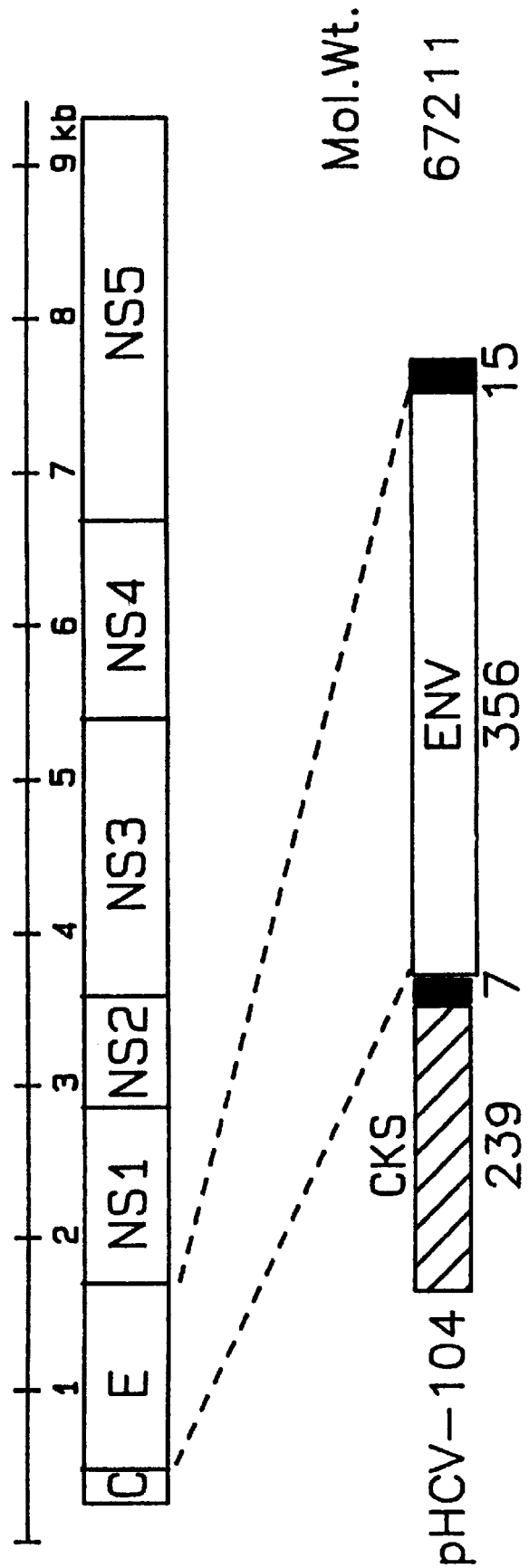
FIG. 43 illustrates the fusion protein pHCV-104.

Using the methods detailed above, a 1068 base pair DNA fragment from the putative envelope region of HCV was generated by PCR. This fragment represents HCV amino acids #114–469 and was cloned into the CKS expression vector pJ0202 using EcoRI restriction sites. The resulting clone, designated pHCV-104, expresses the HCV CKS-ENV antigen under control of the lac promoter. The HCV CKS-ENV antigen consists of 239 amino acids of CKS, 7 amino acids contributed by linker DNA sequences, 356 amino acids from the HCV envelope region (amino acids 114–469), and 15 additional amino acids contributed by linker DNA sequences. FIG. 43 presents a schematic representation of the pHCV-104 antigen. SEQ. ID. NOS. 29 and 30 presents the DNA and amino acid sequence of the HCV CKS-ENV recombinant antigen produced by pHCV-104.

EXAMPLE 10

HCV CKS-NS1S1

A. Construction of the HCV CKS-NS1S1 Expression Vector

Eight individual oligonucleotides representing amino acids 365–579 of the HCV genome were ligated together and cloned as a 645 base pair EcoRuBamffl fragment into the CKS fusion vector pJ0200. The amino acid sequence of this antigen is designated as pHCV-77 (SEQ. ID. NO. 31). The resultant fusion protein HCV CKS-NS1S1 consists of 239 amino acids of CKS, seven amino acids contributed by linked DNA sequences, and 215 amino acids from the NS1 region of the HCV genome.

Figures 47A, 47B:
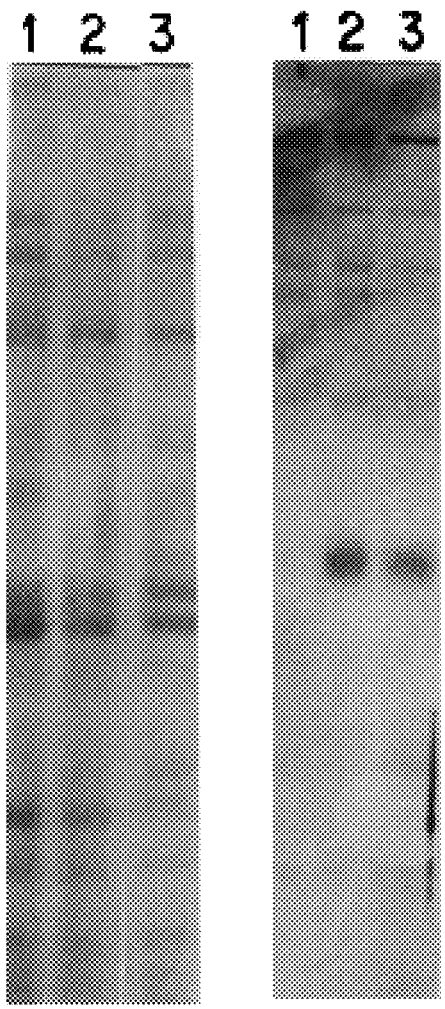
FIG. 47A ilustrates the expression of pHCV-77 in *E. coli.
* and FIG. 47B illustrates an immunblot of pHCV-77 in *E. coli.*

B. Production and Characterization of the Recombinant Antigen HCV-NS1S1 pHCV-77 was transformed into *E.coli* K-12 strain XL-1 (recA1, endA1, gyrA96, thi-1, hsdR17, SupE44, relA1, lac/f1, p10AB, lacl1ADM15, TN10) cells. Expression analysis and characterization of the recombinant protein was done using polyacrylamide gel electrophoresis as described in Example 1. The apparent molecular weight of the pHCV-77 antigen was the same as the expected molecular weight of 50,228 as visualized on a coumassie stained gel. The immunoreactivity as determined by Western blot analysis using human sera indicated that this recombinant antigen was indeed immunoreactive. FIG. 47A presents the expression of pHCV-77 in *E. coli.* FIG. 47B presents an immunoblot of the pHCV-77 antigen expressed in *E. coli.* Lane 1 contained the *E. coli* lysate containing pHCV-77 expressing the HCV CKS-NS1S1 antigen prior to induction and Lanes 2 and 3 are 2 and 4 hours post-induction, respectfully.

EXAMPLE 11

HCV CKS-NS1S2

A. Construction of the HCV CKS-NS1S2 Expression Vector

Six individual oligonucleotides representing amino acids 565–731 of the HCV genome was ligated together and cloned as a 501 base pair EcoRI/BamHIl fragment into the CKS fusion vector pJO200. The complete amino acid sequence of this antigen is designated as pHCV-65 (SEQ. ID. NO. 32). The resultant fusion protein HCV CKS-NS1S2 consists of 239 amino acids of CKS, eight amino acids contributed by linker DNA sequences, and 167 amino acids from the NS1 region of the HCV genome.

Figures 48A, 48B:
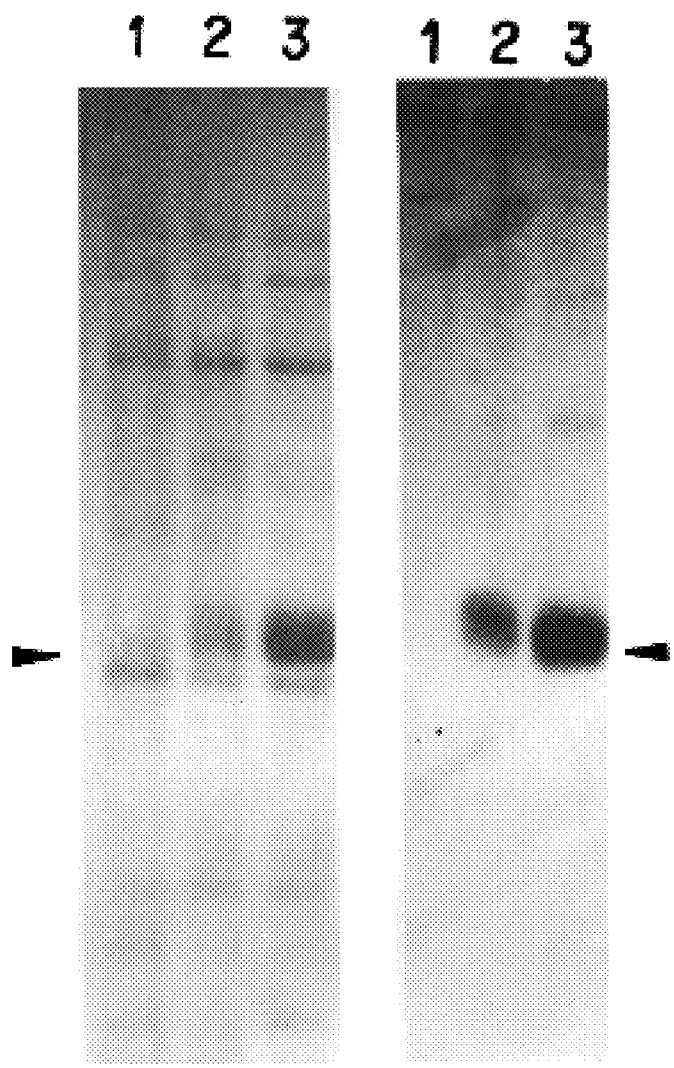
FIG. 48A illustrates the expression of pHCV-65 in *E. coli.
* and FIG. 48B illustrates an immunoblot of pHCV-65 in *E. coli.*

B. Production and Characterization of the Recombinant Antigen HCV-NS1S2 pHCV-65 was transformed into *E.coli* K-12 strain XL-1 (recA1, endA1, gyrA96, thi-1, hsdRl7, SupE44, relA1, lac/f1, p10AB, laclqAMD15, TN10) cells. Expression analysis and characterization of the recombinant protein was done using polyacrylamide gel electrophoresis as described in Example 1. The apparent molecular weight of the pHCV-65 antigen was the same as the expected molecular weight of 46,223 as visualized on a coumassie stained gel. The immunoreactivity as determined by Western blot analyis using human sera indicated that this recombinant antigen was indeed immunoreactive. FIG. 48A presents the expression of pHCV-65 in *E. coli.* FIG. 48B presents an immunoblot of the pHCV-65 antigen expressed in *E. coli.* Lane 1 contained the *E. coli* lysate containing pHCV-65 expressing the HCV CKS-NS1S2 antigen prior to induction and Lanes 2 and 3 are 2 and 4 hours post-induction, respectively.

EXAMPLE 12

CKS-NS1S3

A. Construction of the HCV CKS-NS1S3 Expression Vector

Six individual oligonucleotides representing amino acids 717–847 of the HCV genome were ligated together and cloned as a 393 base pair EcoRI/BamHI fragment into the CKS fusion vector pJO200. The complete amino acid sequence of this antigen is designated as pHCV-78 (SEQ. ID. NO. 33). The resultant fusion protein HCV CKS-NS1S3 consists of 239 amino acids of CKS, eight amino acids contributed by linker DNA sequences, and 131 amino acids from the NS1 region of the HCV genome.

B. Production and Characterization of the Recombinant Antigen HCV-NS1S3 pHCV-78 was transformed into *E.coli* K-12 strain XL-1 (recA1, endA1, gyrA96, thi-1, hsdR17, SupE44, relA1, lac/f1, p10AB, laclqADM15, TN10) cells. Expression analysis and characterization of the recombinant protein was done using polyacrylamide gel electrophoresis as described in Example 1. Analysis of the coumassie stained gel indicated very low levels of expression of the protein with an expected molecular weight of 42,1141. Western blot analysis also failed to show any immunoreactivity and we are continuing to identify human sera that is specific to this region of NS1.

EXAMPLE 13

CKS-NS1S1-NS1S2

A. Construction of the HCV CKS-NS1S1-NS1S2 Expression Vector

The construction of pHCV-80 (NS1S1-NS1S2) involved using the SACI/BamHI insert from pHCV-65 and ligating that into the SacI/BamHI vector backbone of pHCV-77. The resultant HCV gene represents amino acids 365–731 of the HCV genome. This resulted in a 1101 base pair EcoRI/Bamwl fragment of HCV cloned into the CKS fusion vector pJO200. The complete amino acid sequence of this antigen is designated as pHCV-80 (SEQ. ID. NO. 34). The resultant fusion protein HCV CKS NS1S1-NS1S2 consists of 239 amino acids of CKS, seven amino acids contributed by linker DNA sequences, and 367 amino acids from the NS1 region of the HCV genome.

Figures 49A, 49B:
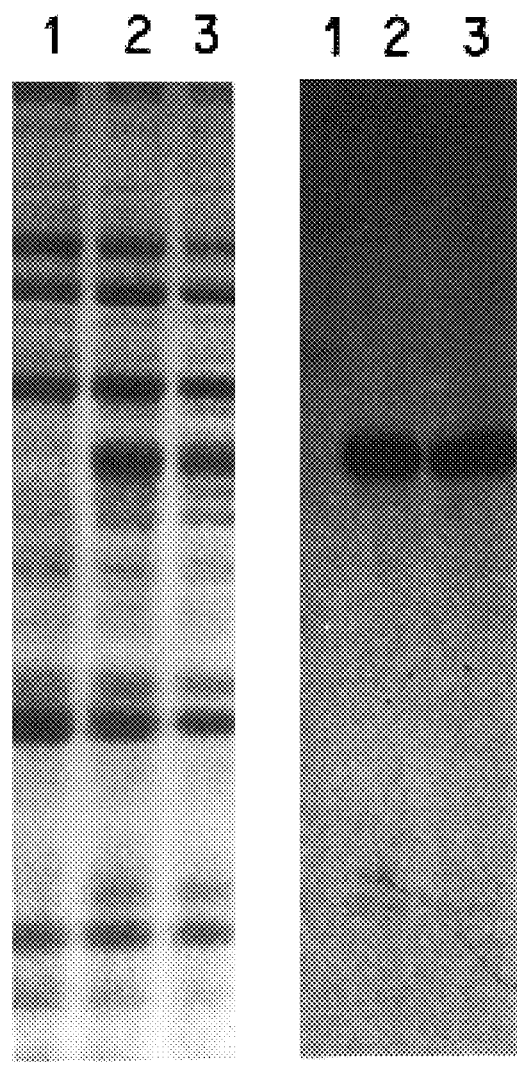
FIG. 49A illustrates the expression of pHCV-80 in *E. coli.
* and FIG. 49B illustrates an immunoblot of pHCV-80 in *E. coli.*

B. Production and Characterization of the Recombinant Antigen HCV-NS1S1-NS1S2 pHCV-80 was transformed into *E.coli* K-12 strain XL-1 (recA1, endA1, gyrA96, thi-1, hsdR17, SupE44, relA1, lac/f1, p10AB, laclqADM15, TN10) cells. Expression analysis and characterization of the recombinant protein was done using polyacrylamide gel electrophoresis as described in Example 1. The apparent molecular weight of the pHCV-80 antigen was the same as the expected molecular weight of 68,454 as visualized on a coumassie stained gel. The immunoreactivity as determined by Western blot analysis using human sera indicated that this recombinant antigen was very immunoreactive. FIG. 49A presents the expression of pHCV-80 in *E. coli*. FIG. 49B presents an immunoblot of pHCV-80 antigen expressed in *E. coli*. Lane 1 contained the *E.coli* lysate containing pHCV-80 expressing the HCV CKS-NS1S1-NS1S2 antigen prior to induction and Lanes 2 and 3 are 2 and 4 hours post-induction, respectively.

EXAMPLE 14

HCV CKS-FULL LENGTH NS1

A. Construction of the HCV CKS-full length NS1 Expression Vector The construction of pHCV-92 (SEQ. ID. NO. 35) full length NS1) involved using the Xhol/BamHI insert from pHCV-78 (SEQ. ID. NO. 33) and ligating that into the Xhol/BamHI vector backbone of pHCV-80 (SEQ. ID. NO. 34). The resultant HCV gene represents amino acids 365–847 of the HCV genome. This resulted in a 1449 base pair EcoRI/BamHI fragment of HCV cloned into CKS fusion vector pJO200. The complete amino acid sequence of this antigen is designated as pHCV-92 (SEQ. ID. NO. 35). The resultant fusion protein HCV CKS-full length NS1 consists of 239 amino acids of CKS, seven amino acids contributed by linker DNA sequences, and 483 amino acids from the NS1 region of the HCV genome.

B. Production and Characterization of the Recombinant Antigen pHCV-92 pHCV-92 was transformed into *E.coli* K-12 strain XL-1 (recA1, endA1, gyrA96, thi-1, hsdR17, SupE44, relA1, lac/f1, p10AB, laclqADM15, TN10) cells. Expression analysis and characterization of the recombinant protein was done using polyacrylameide gel electrophoresis as described in Example 1. The expression levels as seen by counassie stained gel were virtually undectable and the Western blot indicated no immunoreactivity. We are still in the process of identifying sera that will recognize this region of HCV NS1.

The present invention thus provides unique recombinant antigens representing distinct antigenic regions of the HCV genome which can be used as reagents for the detection and/or confirmation of antibodies and antigens in test samples from individuals exposed to HCV. The NS1 protein is considered to be a non-structural membrane glycoprotein and to be able to elicit a protective immune response of the host against lethal viral infection.

EXAMPLE 15

HCV CKS-NS5EF

A. Construction of the HCV CKS-NS5EF Expression Vector

The construction of pHCV-59 (NS5 EF, SEQ. ID. NO. 36) involved using the SaII/BamHI insert from pHCV-48 (SEQ.ID.NO. 8 and 9) and ligating that into the SaII/BamHI vector backbone of pHCV-45, previously described in Example 7A and 7B. The resultant HCV gene represents amino acids 1932–2491 of the HCV genome. This resulted in a 1650 base pair EcoRI/BamHI fragment of HCV cloned into the CKS fusion vector pJO200. The amino acid sequence of this antigen is designated as pHCV-59 (SEQ. ID. NO. 36). The resultant fusion protein HCV CKS-NS5 EF consists of 239 amino acids of CKS, nine amino acids contributed by linker DNA sequences, and 550 amino acids from the NS5 region of the HCV genome.

Figures 51A, 51B:
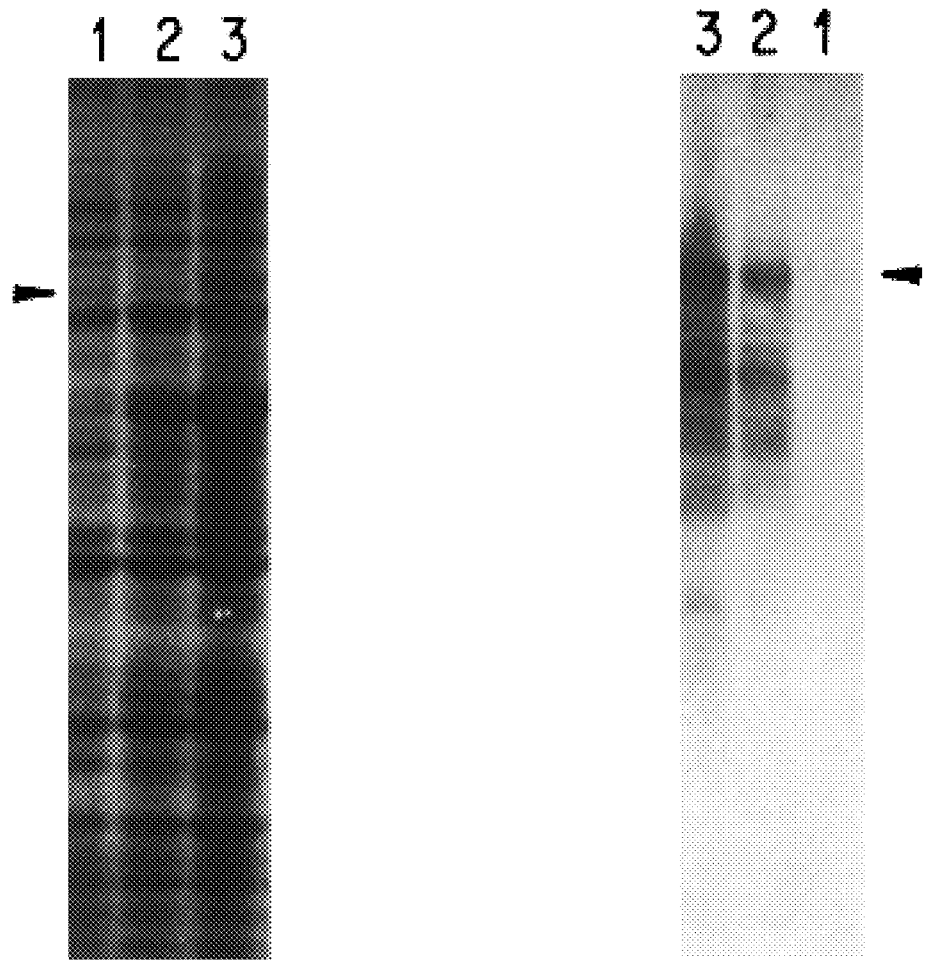
FIG. 51A illustrates the expression of pHCV-59 in *E. coli.
* and FIG. 51B illustrates an immunoblot of pHCV-59 antigen in *E. coli.*

B. Production and Characterization of the Recombinant Antigen HCV-NS5 EF pHCV-59 was transformed into *E. coli* K-12 strain XL-1 (recA1, endA1, gyrA96, thi-1, hsdR17, SupE44, relA1, lac/f1, p10AB, laclqADM15, TN10) cells. Expression analysis and characterization of the recombinant protein was done using polyacrylamide gel electrophoresis and was carried out as described in Example 1. The apparent molecular weight of the pHCV-59 antigen was the same as the expected molecular weight of 87,910 as visualized on a coomassie stained gel. The immunoreactivity as determined by Western blot analysis using human sera indicated that this recombinant antigen was very immunoreactive. FIG. 51A presents the expression of pHCV-59 in *E. coli*. FIG. 51B presents an immunoblot of pHCV-59 antigen in *E. coli*. Lane 1 contained the *E. coli* lysate containing pHCV-59 expressing the HCV CKS-NS5EF antigen prior to induction and Lanes 2 and 3 are 2 and 4 hours post-induction, respectively.

EXAMPLE 16

HCV CKS-C100A

A. Construction of HCV CKS-C100A Deletion Clones

Figure 52A:
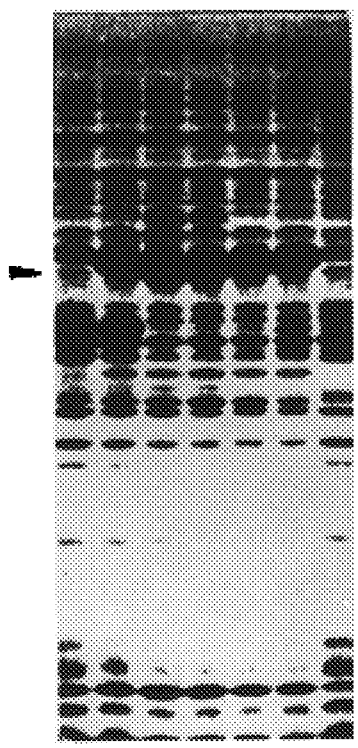
FIG. 52A illustrates the expression of pHCV-19 (lane 1), pHCV-54 (lane 2), pHCV-55 (lane 3), pHCV-94 (lane 4), pHCV-95 (lane 6), pHCV-96 (lane 7) and pHCV-97 (lane 8) in E. coli.
Figure 52B:
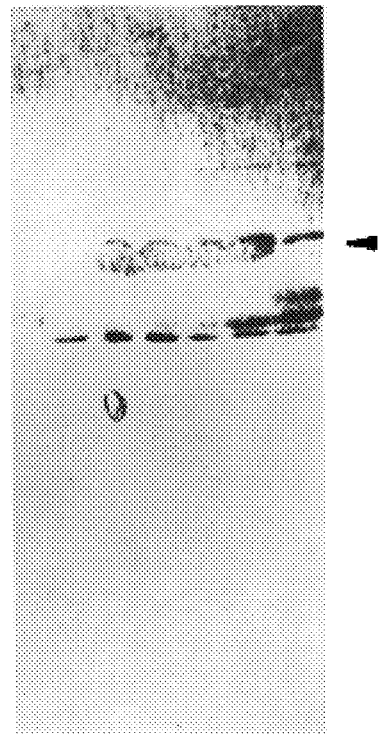
FIG. 52B illustrates an immunoblot of pHCV-19 (lane 1), pHCV-54 (lane 2), pHCV-55 (lane 3), pHCV-94 (lane 4), pHCV-95 (lane 6), pHCV-96 (lane 7) and pHCV-97 (lane 8) in *E. coli.*

Example 8 described the construction of a synthetic gene encoding HCV a.a. 1569–1931. Expression of this synthetic gene as a CKS fusion protein in *E. coli* was at very low levels. In order to define the region(s) that were deleterious to the expression of the HCV CKS-C100 antigen in *E. coli*, the expression levels of four separate subfragments of HCV C100 were examined as fusions to CKS. One such clone, designated pHCV-19, contained HCV a.a. 1569–1677 and did not express the HCV CKS-C100A protein for which it was designed. Two internal deletions located in the amino terminal portion of C100 (HCV a.a. 1575–1620) were constructed. The first of these, pHCV-54, was an internal deletion of 23 amino acids (HCV a.a. 1575–1597) using the restriction site Ddel. This deletion expressed well as a CKS fusion in *E. coli*. SEQ.ID.NO. 37 presents the amino acid sequence of the antigen produced by pHCV-54. FIG. 52A presents the expression of this HCV CKS-C100A protein in *E. coli*. FIG. 52B presents an immunoblot of the antigen produced by pHCV-54. Lane 2 contained the *E. coli* lysate from pHCV-54 expressing the HCV CKS-C100A antigen four hours post induction. The second of these deletion clones, pHCV-55, deleted 21 amino acids (HCV a.a. 1600–1620) and utilized the restriction sites NlalV/HaeIII.

This internal deletion also expressed well in E. coli as a CKS fusion. SEQ.ID.NO. 38 presents the amino acid sequence of the antigen produced by pHCV-55. FIG. 52A presents the expression of this HCV CKS-C100A protein in *E. coli*. FIG. 52B presents an immunoblot of the antigen produced by pHCV-55. Lane 3 contained the *E. coli* lysate from pHCV-55 expressing the HCV CKS-C100A antigen four hours post induction.

Figure 53A:
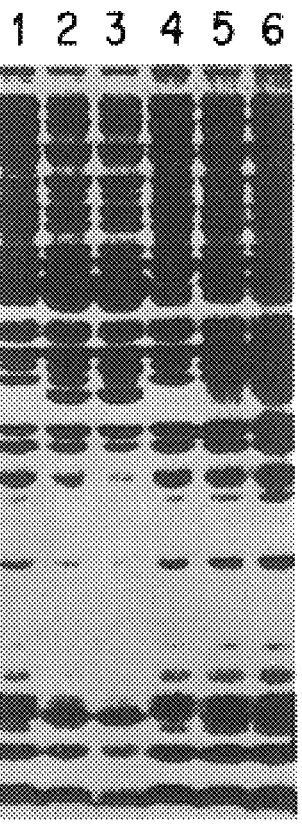
FIG. 53A illustrates the expression of pHCV-202 (lanes 1, 2 and 3) and pHCV-203 (lanes 4, 5 and 6) in *E. coli
Figure 53B:
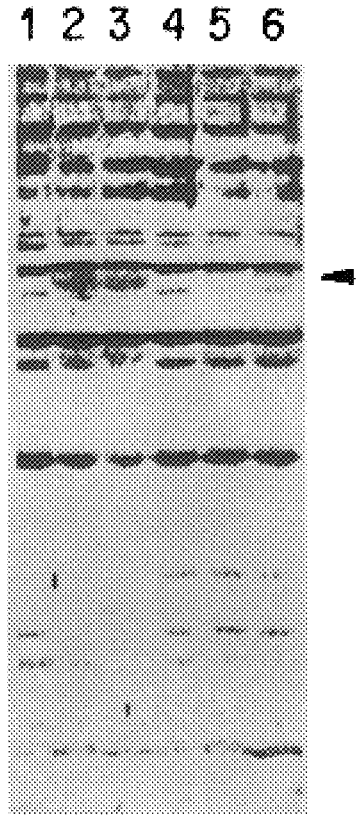
* and FIG. 53B illustrates an immunoblot of pHCV-202 (lanes 1, 2 and 3) and pHCV-203 (lanes 4, 5 and 6) in *E. coli.*

The HCV amino acids deleted in pHCV-55 (HCV aa. 1600–1620) were sequentially replaced from the carboxy-terminal -end using a fragment replacement method. The DNA fragments that were inserted were synthesized as complimentary pairs of single-stranded oligonucleotides. The oligonucleotide pairs were kinased, annealed, and ligated to the remainder of the C100A fragment from pHCV-19 using the restriction enzymes Bsp12861/Sau961. The resulting new C-100A fragments were cloned into the CKS fusion expression vector pJO200 and expressed in *E. coli*. Table 2 summarizes both the HCV amino acids that were manipulated as well as the expression levels of the various HCV CKS-C100A antigens in *E. coli*. SEQ. ID. NO.39 presents the amino acid sequence of the antigen produced by pHCV-94. FIG. 52A presents the expression of this HCV CKS-C100A protein in *E. coli*. FIG. 52B presents an immunoblot of the antigen produced by pHCV-94. Lane 4 contained the *E. coli* lysate from pHCV-94 expressing the HCV CKS-C100A antigen four hours post induction. SEQ.ID.NO. 40 presents the amino acid sequence of the antigen produced by pHCV-95. FIG. 52A presents the expression of the HCV CKS-C100A protein in *E. coli*. FIG. 52B presents an immunoblot of the antigen produced by pHCV-95. Lane 5 contained the *E. coli* lysate from pHCV-95 expressing the HCV CKS-C100A antigen four hours post induction. SEQ.ID.NO. 41 presents the amino acid sequence of the antigen produced by pHCV-96. FIG. 52A presents the expression of this HCV CKS-C100A protein in *E. coli*. FIG. 52B presents an immunoblot of the antigen produced by pHCV-96. Lane 6 contained the *E. coli* lysate from pHCV-96 expressing the HCV CKS-C100A antigen four hours post induction. SEQ.ID.NO. 42 presents the amino acid sequence of the antigen produced by pHCV-97. FIG. 52A presents the expression of this HCV CKS-C100A protein in *E. coli*. FIG. 52B presents an immunoblot of the antigen produced by pHCV-97. Lane 7 contained the E. coli lysate from pHCV-97 expressing the HCV CKS-C100A antigen four hours post induction. SEQ.ID.NO. 43 presents the amino acid sequence of the antigen produced by pHCV-202. FIG. 53A presents the expression of this HCV CKS-C100A in *E. coli*. FIG. 53B presents an immunoblot of the antigen produced by pHCV-202. Lanes 1, 2, and 3 contained the *E. coli* lysate from pHCV-202 expressing the HCV CKS-C100A antigen before induction and two and four hours post induction, respectively. SEQ.ID.NO. 44 presents the amino acid sequence of the antigen produced by pHCV-203. FIG. 53A presents the expression of this HCV CKS-C100A protein in *E. coli*. FIG. 53B presents an immunoblot of the antigen produced by pHCV-203. Lanes 1, 2, and 3 contained the *E. coli* lysate from pHCV-203 expressing the HCV CKS-C100A antigen before induction and two and four hours post induction, respectively. SEQ.ID.NO. 55 delineates the amino acids that were manipulated in the fragment replacements described above. The results summarized in Table 2 indicated that the deletion of three proline residues at HCV a.a. 1600–1602 (pHCV-96) (SEQ.ID.NO. 41) permitted expresion of the HCV CKS-C100A antigen at high levels in *E. coli*. Further analysis showed that the deletion of two proline residues at HCV a.a. 1600–1601 (pHCV-202) also maintained expression of this antigen at high levels. However, when only one of these proline residues was deleted (pHCV-203) (SEQ.ID.NO. 44), the expression level of this antigen was reduced to that of pHCV-19, the original HCV CKS-C100A clone. Therefore, the deletion of two prolines at HCV a.a. 1600–1601 contributes to high level expression of the HCV CKS-C100A antigen in *E. coli* as determined by SDS-PAGE analysis. Western blot analysis of these deletion clones indicated a high degree of immunoreactivity when probed with human sera containing antibodies to HCV C100.

TABLE 2

| Plasmid | HCV a.a. Deleted | Expression Level |
| --- | --- | --- |
| pHCV-19 |  | +/− |
| pHCV-55 | 1600–1620 | +++ |
| pHCV-94 | 1600–1612 | +++ |
| pHCV-95 | 1600–1607 | +++ |
| pHCV-96 | 1600–1602 | +++ |
| pHCV-97 | * | +/− |
| pHCV-202 | 1600–1601 | +++ |
| pHCV-203 | 1600 | +/− |

Figures 54A, 54B:
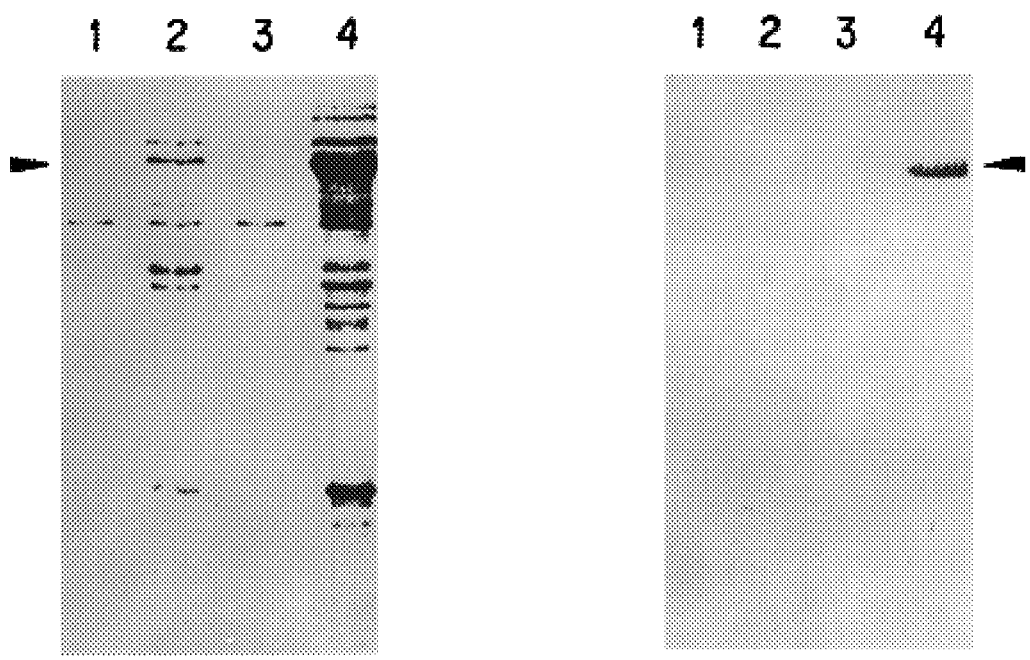
FIG. 54A illustrates the amino acid sequence of the recombinant antigen expressed by pHCV-62 (lanes 1 and 2) and pHCV-63 (lanes 3 and 4) and FIG. 54B illustrates an immunoblot of pHCV-62 (lanes 1 and 2) and pHCV-63 (lanes 3 and 4).
Figure 55A:
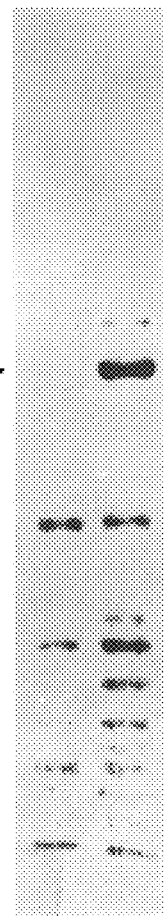
FIG. 55A illustrates the expression of pHCV-204 in *E. coli
Figure 55B:
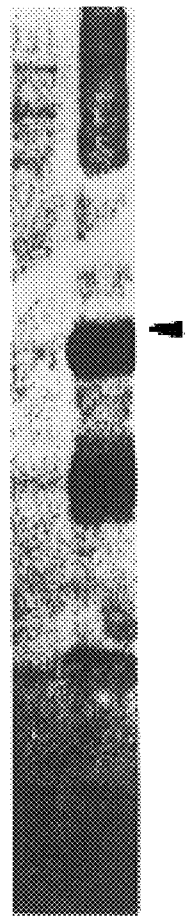
* and FIG. 55B illustrates an immunoblot of pHCV-204 in *E. coli.*

+/− = expression detectable by Western blot only.
+++ = expression level > 10% of total cell protein by coomassie stained gel
*indicates the use of alternate codons optimized for *E. coli* expression B. Construction of HCV CKS-C100 Expression Clones In order to construct a vector which expressed the various HCV CKS-C100 deletion antigens at high levels in *E. coli*, we replaced the EcoRl/Sall fragment from pHCV-24 with the various corresponding EcoRl/Sall fragments from the deletion clones described above. The EcoRl/Sall fragments from pHCV-54 and pHCV-55 were used to replace the EcoRl/Sall fragment of pHCV-24 to create the plasmids pHCV-57 and pHCV-58 as described in Example 8. The HCV CKS-C100 antigens encoded by pHCV-57 and pHCV-58 expressed well in *E. coli*. The 3' end of these clones were altered by PCR changing the linker associated amino acid sequence from WDPLDCRHAK (SEQ. ID. NO. 45) to VHHKR (SEQ. ID. NO. 46). The resulting plasmids were designated pHCV-62 and pHCV-63, respectively. SEQ.ID.NO. 47 presents the amino acid sequence of the antigen produced by pHCV-62. SEQ.ID.NO. 48 presents the amino acid sequence of the antigen produced by pHCV-63. The HCV CKS-C100 antigens encoded by pHCV-62 and pHCV-63 expressed well in *E. coli*. FIG. 54A presents the expression of these HCV CKS-C100 antigens in *E. coli*. FIG. 54B presents an immunoblot of the antigens produced by pHCV-62 and pHCV-63. Lanes 1 and 2 contained the *E. coli* lysate from pHCV-62 expressing the HCV CKS-C100 antigen prior to induction and four hours post induction, respectively. Lanes 3 and 4 contained the *E. coli* lysate from pHCV-63 expressing the HCV CKS-C100 antigen proir to induction and four hours post induction, respectively. The EcoRl/Sall fragment from pHCV-202 was used to replace the EcoRl/Sall fragment of pHCV-63 to create the plasmid pHCV-204. SEQ.ID.NO. 49 presents the amino acid sequence of the antigen produced by pHCV-204. Table 3 summarizes the deletion analysis conducted on the HCV CKS-C100 antigens and their expression levels in *E. coli*. The expression levels of the HCV CKS-C100 deletion clones corresponded with the expression levels of the HCV CKS-C100A deletion clones from which they were derived. FIG. 55A presents the expression of pHCV-204 protein in *E. coli*. FIG. 55B presents an immunoblot of the antigen produced by pHCV-204. Lanes 1 and 2 25 contained the *E. coli* lysate from pHCV-204 expressing the HCV CKS-C100 antigen prior to induction and four hours post induction, respectively.

TABLE 3

| PLASMID | HCV a.a. DELETED | EXPRESSION LEVEL |
| --- | --- | --- |
| HCV-57 | 1575–1597 | +++ |
| pHCV-58 | 1600–1620 | +++ |
| pHCV-62 | 1575–1597 | +++ |
| pHCV-63 | 1600–1620 | +++ |
| pHCV-204 | 1600–1601 | +++ |

+/− = expression detectable by Western blot only
+++ = expression level > 10% of total cell protein by coomassie stained gel

EXAMPLE 17

HCV CKS-C200
Construction of HCV CKS-C200 Expression Clones

Figure 56:
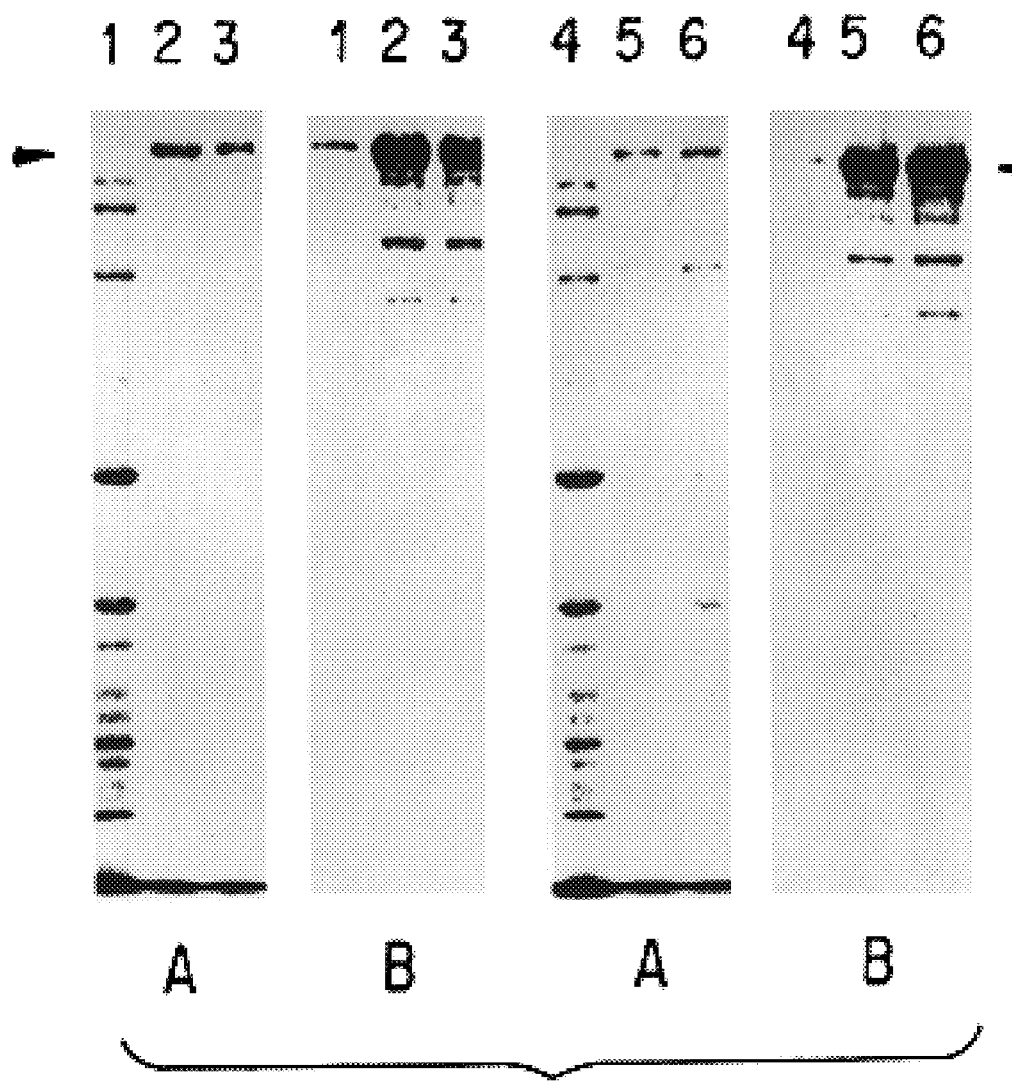
FIG. 56 illustrates the expression of pHCV-72 (lanes 1, 2 and 3) and pHCV-73 (lanes 4, 5 and 6) in *E. coli* and illustrates an immunoblot of pHCV-72 (lanes 1, 2 and 3) and pHCV-73 (lanes 4, 5 and 6) in E. coli.
Figures 57A, 57B:
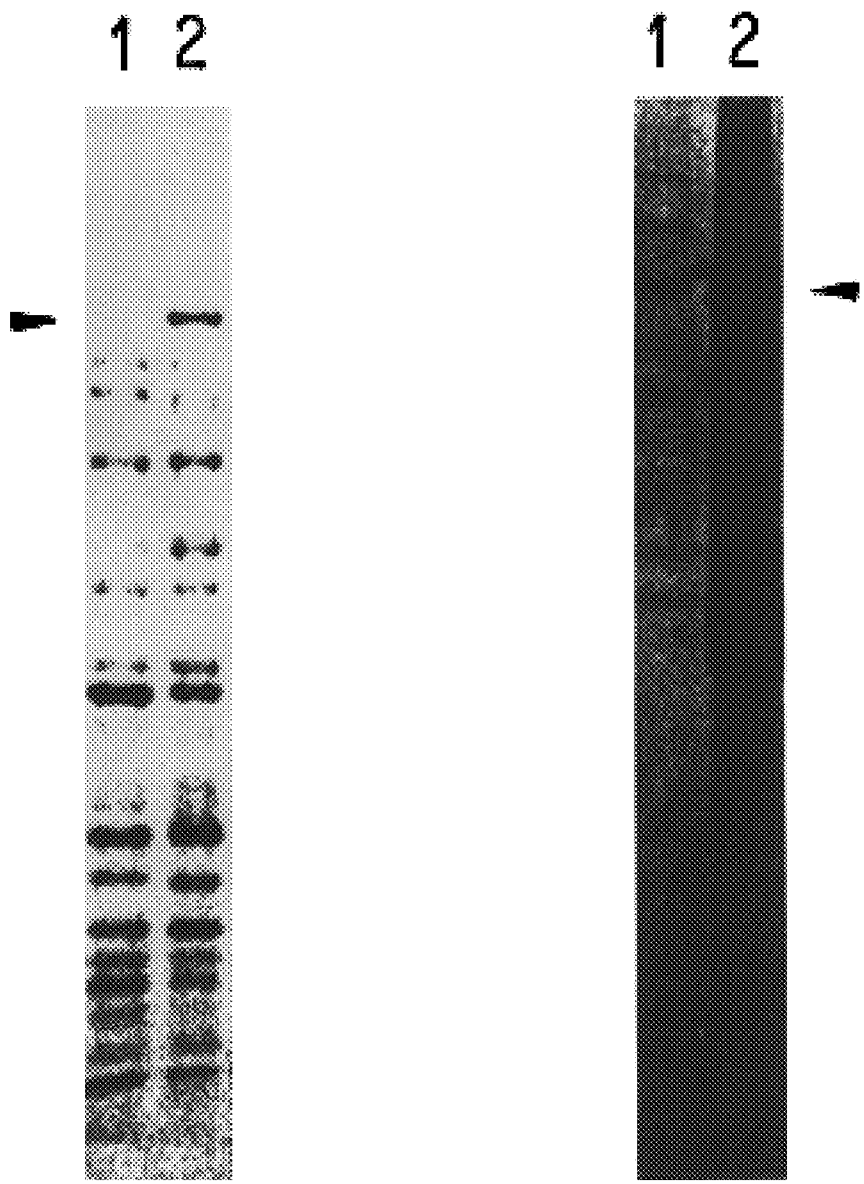
FIG. 57A illustrates the expression of pHCV-205 in *E. coli
* and FIG. 57B illustrates an immunoblot of pHCV-205 in *E. coli.*

The construction of a clone which expressed the HCV CKS-C200 antigen (HCV a.a. 1192–1931) at high levels of E. coli required the steps described hereinbelow. First, a clone expressing the HCV CKS-33C antigen (HCV a.a. 1192–1457) was constructed as described in Example 2, designated pHCV-29. Second, a clone containing the DNA sequence encoding HCV aa. 1454–1569 was constructed using a PCR methodology as described in Example 9, designated as pHCV-108 (SEQ. ID. NO. 56). This DNA sequence was later cloned as an in-frame fusion to CKS in order to express the HCV CKS-NS3-1 antigen (HCV a.a. 1454–1568), designated pHCV-112 (SEQ. ID. 50). Third, a clone expressing the HCV CKS-C100 deletion antigen (HCV a.a. 1569–1574 and 1598–1931) was constructed, designated pHCV-62 described above. Fourth, the NcoI fragment containing the C100 coding region was excised from pHCV-62 and inserted into the NcoI site of pHCV-108 to create pHCV-68 (SEQ. ID. 51). Lastly, the ClaI/BamHI fragment containing the HCV NS3/C100 coding region (HCV a.a. 1454–1574 and 1598–1931) was excised from pHCV-68 and inserted into the Cla/BamHl sites of pHCV-29. The resultant clone, designated pHCV-72, expresses the HCV CKS C200 antigen (HCV a.a. 1192–1574 and 1598–1931). SEQ.ID.NO. 52 presents the amino acid sequence of the antigen produced by pHCV-72. In a similar manner, the C100 coding region of pHCV-63 was substituted for that of pHCV-62 to generate pHCV-69 (SEQ. ID. 57). The ClaI/BamHI fragment containing the HCV NS3/C100 coding region (HCV a.a. 1454–1599 and 1621–1931) was excised frompHCV-69 and inserted into the ClaI/BamHI sites of pHCV-29. The resultant clone, designated pHCV-73, expresses the HCV CKS-C200 antigen (HCV a.a. 1192–1599 and 1621–1931). SEQ.ID.NO. 53 presents the amino acid sequence of the antigen produced by pHCV-73. FIG. 56A presents the expression of these HCV CKS-C200 antigens in E. coli. FIG. 56B presents an immunoblot of the antigen produced from pHCV-73. Lanes 1, 2, and 3 contained the E. coli lysate from pHCV-72 expressing the HCV CKS-C200 antigen before induction and two and four hours post induction, respectively. Lanes 4, 5, and 6 contained the E. coli lysate from pHCV-73 expressing the HCV CKS-C200 antigen before induction and two and four hours post induction, respectively. A different HCV CKS-C200 construct (HCV a.a. 1192–1599 and 1602–1931) was assembled by first obtaining the HCV C100A region (HCV a.a. 1569–1599 and 1602–1677) as a ClaI/NcoI 352 base pair fragment from pHCV-202. The NS3-1 antigen (HCV a.a. 1454–1568) was obtained as a ClaI/NcoI 352 base pair fragment from pHCV-72. The last fragment used was the 792 base pair fragment from pHCV-72 which contained C100 BCD (HCV a.a. 1678–1931). These three fragments were ligated to each other ClaI/NcoI/SalI/BamHI and ligated into the vector backbone pHCV-29 ClaI/BamHI, which contributed the HCV CKS-33C antigen (HCV a.a 1192–1453). The HCV CKS-C200 construct, designated pHCV-205, was expressed as a CKS fusion in pJO200 and expressed at high levels as determined by coosmasie stained gel and Western blot analysis. SEQ.ID.NO. 54 presents the amino acid sequence of the antigen produced by pHCV-205. FIG. 57A presents the expression of the HCV CKS-C200 antigen in E. coli. FIG. 57B presents an immunoblot of the antigen produced by pHCV-205. Lane 1 contained the E. coli lysate from pHCV-205 expressing the HCV CKS-C200 antigen before induction and lane 2 presents two hours post induction. The present invention provides unique antigens corresponding to a distinct antigenic region of the HCV genome which can be utilized as a reagent for the detection and/or confirmation of antibodies and antigen in test samples from individuals exposed to HCV. Although the exact function of the NS4 region is unknown, the antigens described herein are located in the putative immunodominant region of the HCV genome.

The recombinant antigens, either alone or in combination, can be used in the assay formats provided herein and exemplified in the Examples. It also is contemplated that these recombinant antigens can be used to develop specific inhibitors of viral replication and used for therapeutic purposes, such as for vaccines. Other applications and modifications of the use of these antigens and the specific embodiments of this inventions as set forth herein, will be apparent to those skilled in the art. Accordingly, the invention is intended to be limited only in accordance with the appended claims.

What is claimed is:
1. A polypeptide which is SEQ ID NO:49.
2. A polypeptide selected from the group consisting of SEQ ID NO:18 and SEQ ID NO:48.
3. A polypeptide selected from the group consisting of SEQ ID NO:4, SEQ ID NO:53 and SEQ ID NO:54.
4. A polypeptide which is SEQ ID NO:58.

* * * * *

SEQUENCE LISTING (1) GENERAL INFORMATION:

(iii) NUMBER OF SEQUENCES: 59

(2) INFORMATION FOR SEQ ID NO:1:

(i) SEQUENCE CHARACTERISTICS:
       (A) LENGTH: 4481 base pairs
       (B) TYPE: nucleic acid
       (C) STRANDEDNESS: single
       (D) TOPOLOGY: circular (ii) MOLECULE TYPE: DNA (genomic)

(ix) FEATURE:
    (A) NAME/KEY: CDS
    (B) LOCATION: 130..1317

(xi) SEQUENCE DESCRIPTION: SEQ ID NO:1:

```
GAATTAATTC CCATTAATGT GAGTTAGCTC ACTCATTAGG CACCCCAGGC TTTACACTTT        60

ATGTTCCGGC TCGTATTTTG TGTGGAATTG TGAGCGGATA ACAATTGGGC ATCCAGTAAG       120

GAGGTTTAA ATG AGT TTT GTG GTC ATT ATT CCC GCG CGC TAC GCG TCG          168
          Met Ser Phe Val Val Ile Ile Pro Ala Arg Tyr Ala Ser
            1               5                  10

ACG CGT CTG CCC GGT AAA CCA TTG GTT GAT ATT AAC GGC AAA CCC ATG        216
Thr Arg Leu Pro Gly Lys Pro Leu Val Asp Ile Asn Gly Lys Pro Met
 15                  20                  25

ATT GTT CAT GTT CTT GAA CGC GCG CGT GAA TCA GGT GCC GAG CGC ATC        264
Ile Val His Val Leu Glu Arg Ala Arg Glu Ser Gly Ala Glu Arg Ile
 30                  35                  40                  45

ATC GTG GCA ACC GAT CAT GAG GAT GTT GCC CGC GCC GTT GAA GCC GCT        312
Ile Val Ala Thr Asp His Glu Asp Val Ala Arg Ala Val Glu Ala Ala
                 50                  55                  60

GGC GGT GAA GTA TGT ATG ACG CGC GCC GAT CAT CAG TCA GGA ACA GAA        360
Gly Gly Glu Val Cys Met Thr Arg Ala Asp His Gln Ser Gly Thr Glu
             65                  70                  75

CGT CTG GCG GAA GTT GTC GAA AAA TGC GCA TTC AGC GAC GAC ACG GTG        408
Arg Leu Ala Glu Val Val Glu Lys Cys Ala Phe Ser Asp Asp Thr Val
         80                  85                  90

ATC GTT AAT GTG CAG GGT GAT GAA CCG ATG ATC CCT GCG ACA ATC ATT        456
Ile Val Asn Val Gln Gly Asp Glu Pro Met Ile Pro Ala Thr Ile Ile
     95                 100                 105

CGT CAG GTT GCT GAT AAC CTC GCT CAG CGT CAG GTG GGT ATG GCG ACT        504
Arg Gln Val Ala Asp Asn Leu Ala Gln Arg Gln Val Gly Met Ala Thr
110                 115                 120                 125

CTG GCG GTG CCA ATC CAC AAT GCG GAA GAA GCG TTT AAC CCG AAT GCG        552
Leu Ala Val Pro Ile His Asn Ala Glu Glu Ala Phe Asn Pro Asn Ala
                130                 135                 140

GTG AAA GTG GTT CTC GAC GCT GAA GGG TAT GCA CTG TAC TTC TCT CGC        600
Val Lys Val Val Leu Asp Ala Glu Gly Tyr Ala Leu Tyr Phe Ser Arg
            145                 150                 155

GCC ACC ATT CCT TGG GAT CGT GAT CGT TTT GCA GAA GGC CTT GAA ACC        648
Ala Thr Ile Pro Trp Asp Arg Asp Arg Phe Ala Glu Gly Leu Glu Thr
        160                 165                 170

GTT GGC GAT AAC TTC CTG CGT CAT CTT GGT ATT TAT GGC TAC CGT GCA        696
Val Gly Asp Asn Phe Leu Arg His Leu Gly Ile Tyr Gly Tyr Arg Ala
    175                 180                 185

GGC TTT ATC CGT CGT TAC GTC AAC TGG CAG CCA AGT CCG TTA GAA CAC        744
Gly Phe Ile Arg Arg Tyr Val Asn Trp Gln Pro Ser Pro Leu Glu His
190                 195                 200                 205

ATC GAA ATG TTA GAG CAG CTT CGT GTT CTG TGG TAC GGC GAA AAA ATC        792
Ile Glu Met Leu Glu Gln Leu Arg Val Leu Trp Tyr Gly Glu Lys Ile
                210                 215                 220

CAT GTT GCT GTT GCT CAG GAA GTT CCT GGC ACA GGT GTG GAT ACC CCT        840
His Val Ala Val Ala Gln Glu Val Pro Gly Thr Gly Val Asp Thr Pro
            225                 230                 235

GAA GAT CTC GAC CCG TCG ACG AAT TCC ATG TCT ACC AAC CCG AAA CCG        888
Glu Asp Leu Asp Pro Ser Thr Asn Ser Met Ser Thr Asn Pro Lys Pro
        240                 245                 250

CAG AAA AAA AAC AAA CGT AAC ACC AAC CGT CGT CCG CAG GAC GTT AAA        936
Gln Lys Lys Asn Lys Arg Asn Thr Asn Arg Arg Pro Gln Asp Val Lys
```

|     |     |     |     |     |     |     |     |     |     |     |     |     |     |     |      |
| --- | --- | --- | --- | --- | --- | --- | --- | --- | --- | --- | --- | --- | --- | --- | ---- |
|     |     |     | 255 |     |     |     |     | 260 |     |     |     |     | 265 |     |      |
| TTC | CCG | GGT | GGT | GGT | CAG | ATC | GTT | GGT | GGT | GTT | TAC | CTG | CTG | CCG | CGT  | 984 |
| Phe | Pro | Gly | Gly | Gly | Gln | Ile | Val | Gly | Gly | Val | Tyr | Leu | Leu | Pro | Arg  |
| 270 |     |     |     | 275 |     |     |     |     | 280 |     |     |     |     | 285 |      |
| CGT | GGT | CCG | CGT | CTG | GGT | GTT | CGT | GCT | ACG | CGT | AAA | ACC | TCT | GAA | CGT  | 1032 |
| Arg | Gly | Pro | Arg | Leu | Gly | Val | Arg | Ala | Thr | Arg | Lys | Thr | Ser | Glu | Arg  |
|     |     |     | 290 |     |     |     |     | 295 |     |     |     |     | 300 |     |      |
| TCT | CAG | CCG | CGT | GGG | CGT | CGT | CAG | CCG | ATC | CCG | AAA | GCT | CGT | CGT | CCG  | 1080 |
| Ser | Gln | Pro | Arg | Gly | Arg | Arg | Gln | Pro | Ile | Pro | Lys | Ala | Arg | Arg | Pro  |
|     |     | 305 |     |     |     |     | 310 |     |     |     |     | 315 |     |     |      |
| GAA | GGT | CGT | ACC | TGG | GCT | CAG | CCG | GGT | TAC | CCG | TGG | CCG | CTG | TAC | GGT  | 1128 |
| Glu | Gly | Arg | Thr | Trp | Ala | Gln | Pro | Gly | Tyr | Pro | Trp | Pro | Leu | Tyr | Gly  |
|     |     | 320 |     |     |     |     | 325 |     |     |     |     | 330 |     |     |      |
| AAC | GAA | GGT | TGC | GGT | TGG | GCT | GGT | TGG | CTG | CTG | TCT | CCG | CGT | GGA | TCT  | 1176 |
| Asn | Glu | Gly | Cys | Gly | Trp | Ala | Gly | Trp | Leu | Leu | Ser | Pro | Arg | Gly | Ser  |
|     | 335 |     |     |     |     | 340 |     |     |     |     | 345 |     |     |     |      |
| CGT | CCG | TCT | TGG | GGT | CCG | ACC | GAC | CCG | CGT | CGT | CGT | TCT | CGT | AAC | CTT  | 1224 |
| Arg | Pro | Ser | Trp | Gly | Pro | Thr | Asp | Pro | Arg | Arg | Arg | Ser | Arg | Asn | Leu  |
| 350 |     |     |     |     | 355 |     |     |     |     | 360 |     |     |     |     | 365  |
| GGT | AAA | GTT | ATC | GAT | ACC | CTG | ACC | TGC | GGT | TTC | GCT | GAC | CTG | ATG | GGT  | 1272 |
| Gly | Lys | Val | Ile | Asp | Thr | Leu | Thr | Cys | Gly | Phe | Ala | Asp | Leu | Met | Gly  |
|     |     |     | 370 |     |     |     |     | 375 |     |     |     |     | 380 |     |      |
| TAC | ATA | CCG | CTG | GTT | GGA | GCT | CCG | CTG | GGT | GGT | GCT | GCT | CGT | GCT |      | 1317 |
| Tyr | Ile | Pro | Leu | Val | Gly | Ala | Pro | Leu | Gly | Gly | Ala | Ala | Arg | Ala |      |
|     |     |     | 385 |     |     |     |     | 390 |     |     |     |     | 395 |     |      |

```
TAACCCATGG ATCCTCTAGA CTGCAGGCAT GCTAAGTAAG TAGATCTTGA GCGCGTTCGC    1377
GCTGAAATGC GCTAATTTCA CTTCACGACA CTTCAGCCAA TTTTGGGAGG AGTGTCGTAC    1437
CGTTACGATT TTCCTCAATT TTTCTTTTCA ACAATTGATC TCATTCAGGT GACATCTTTT    1497
ATATTGGCGC TCATTATGAA AGCAGTAGCT TTTATGAGGG TAATCTGAAT GGAACAGCTG    1557
CGTGCCGAAT TAAGCCATTT ACTGGGCGAA AAACTCAGTC GTATTGAGTG CGTCAATGAA    1617
AAAGCGGATA CGGCGTTGTG GGCTTTGTAT GACAGCCAGG GAAACCCAAT GCCGTTAATG    1677
GCAAGAAGCT TAGCCCGCCT AATGAGCGGG CTTTTTTTTC GACGCGAGGC TGGATGGCCT    1737
TCCCCATTAT GATTCTTCTC GCTTCCGGCG GCATCGGGAT GCCCGCGTTG CAGGCCATGC    1797
TGTCCAGGCA GGTAGATGAC GACCATCAGG GACAGCTTCA AGGATCGCTC GCGGCTCTTA    1857
CCAGCCTAAC TTCGATCACT GGACCGCTGA TCGTCACGGC GATTTATGCC GCCTCGGCGA    1917
GCACATGGAA CGGGTTGGCA TGGATTGTAG GCGCCGCCCT ATACCTTGTC TGCCTCCCCG    1977
CGTTGCGTCG CGGTGCATGG AGCCGGGCCA CCTCGACCTG AATGGAAGCC GGCGGCACCT    2037
CGCTAACGGA TTCACCACTC CAAGAATTGG AGCCAATCAA TTCTTGCGGA GAACTGTGAA    2097
TGCGCAAACC AACCCTTGGC AGAACATATC CATCGCGTCC GCCATCTCCA GCAGCCGCAC    2157
GCGGCGCATC TCGGGCAGCG TTGGGTCCTG GCCACGGGTG CGCATGATCG TGCTCCTGTC    2217
GTTGAGGACC CGGCTAGGCT GGCGGGGTTG CCTTACTGGT TAGCAGAATG AATCACCGAT    2277
ACGCGAGCGA ACGTGAAGCG ACTGCTGCTG CAAAACGTCT GCGACCTGAG CAACAACATG    2337
AATGGTCTTC GGTTTCCGTG TTTCGTAAAG TCTGGAAACG CGGAAGTCAG CGCCCTGCAC    2397
CATTATGTTC CGGATCTGCA TCGCAGGATG CTGCTGGCTA CCCTGTGGAA CACCTACATC    2457
TGTATTAACG AAGCGCTTCT TCCGCTTCCT CGCTCACTGA CTCGCTGCGC TCGGTCGTTC    2517
GGCTGCGGCG AGCGGTATCA GCTCACTCAA AGGCGGTAAT ACGGTTATCC ACAGAATCAG    2577
GGGATAACGC AGGAAAGAAC ATGTGAGCAA AAGGCCAGCA AAAGGCCAGG AACCGTAAAA    2637
AGGCCGCGTT GCTGGCGTTT TTCCATAGGC TCCGCCCCCC TGACGAGCAT CACAAAAATC    2697
```

-continued

```
GACGCTCAAG TCAGAGGTGG CGAAACCCGA CAGGACTATA AAGATACCAG GCGTTTCCCC    2757

CTGGAAGCTC CCTCGTGCGC TCTCCTGTTC CGACCCTGCC GCTTACCGGA TACCTGTCCG    2817

CCTTTCTCCC TTCGGGAAGC GTGGCGCTTT CTCAATGCTC ACGCTGTAGG TATCTCAGTT    2877

CGGTGTAGGT CGTTCGCTCC AAGCTGGGCT GTGTGCACGA ACCCCCGTT CAGCCCGACC     2937

GCTGCGCCTT ATCCGGTAAC TATCGTCTTG AGTCCAACCC GGTAAGACAC GACTTATCGC    2997

CACTGGCAGC AGCCACTGGT AACAGGATTA GCAGAGCGAG GTATGTAGGC GGTGCTACAG    3057

AGTTCTTGAA GTGGTGGCCT AACTACGGCT ACACTAGAAG GACAGTATTT GGTATCTGCG    3117

CTCTGCTGAA GCCAGTTACC TTCGGAAAAA GAGTTGGTAG CTCTTGATCC GGCAAACAAA    3177

CCACCGCTGG TAGCGGTGGT TTTTTTGTTT GCAAGCAGCA GATTACGCGC AGAAAAAAAG    3237

GATCTCAAGA AGATCCTTTG ATCTTTTCTA CGGGGTCTGA CGCTCAGTGG AACGAAAACT    3297

CACGTTAAGG GATTTTGGTC ATGAGATTAT CAAAAAGGAT CTTCACCTAG ATCCTTTTAA    3357

ATTAAAAATG AAGTTTTAAA TCAATCTAAA GTATATATGA GTAAACTTGG TCTGACAGTT    3417

ACCAATGCTT AATCAGTGAG GCACCTATCT CAGCGATCTG TCTATTTCGT TCATCCATAG    3477

TTGCCTGACT CCCCGTCGTG TAGATAACTA CGATACGGGA GGGCTTACCA TCTGGCCCCA    3537

GTGCTGCAAT GATACCGCGA GACCCACGCT CACCGGCTCC AGATTTATCA GCAATAAACC    3597

AGCCAGCCGG AAGGGCCGAG CGCAGAAGTG GTCCTGCAAC TTTATCCGCC TCCATCCAGT    3657

CTATTAATTG TTGCCGGGAA GCTAGAGTAA GTAGTTCGCC AGTTAATAGT TTGCGCAACG    3717

TTGTTGCCAT TGCTACAGGC ATCGTGGTGT CACGCTCGTC GTTTGGTATG GCTTCATTCA    3777

GCTCCGGTTC CCAACGATCA AGGCGAGTTA CATGATCCCC CATGTTGTGC AAAAAAGCGG    3837

TTAGCTCCTT CGGTCCTCCG ATCGTTGTCA GAAGTAAGTT GGCCGCAGTG TTATCACTCA    3897

TGGTTATGGC AGCACTGCAT AATTCTCTTA CTGTCATGCC ATCCGTAAGA TGCTTTTCTG    3957

TGACTGGTGA GTACTCAACC AAGTCATTCT GAGAATAGTG TATGCGGCGA CCGAGTTGCT    4017

CTTGCCCGGC GTCAACACGG GATAATACCG CGCCACATAG CAGAACTTTA AAAGTGCTCA    4077

TCATTGGAAA ACGTTCTTCG GGGCGAAAAC TCTCAAGGAT CTTACCGCTG TTGAGATCCA    4137

GTTCGATGTA ACCCACTCGT GCACCCAACT GATCTTCAGC ATCTTTTACT TTCACCAGCG    4197

TTTCTGGGTG AGCAAAAACA GGAAGGCAAA ATGCCGCAAA AAAGGGAATA AGGGCGACAC    4257

GGAAATGTTG AATACTCATA CTCTTCCTTT TTCAATATTA TTGAAGCATT TATCAGGGTT    4317

ATTGTCTCAT GAGCGGATAC ATATTTGAAT GTATTTAGAA AAATAAACAA ATAGGGGTTC    4377

CGCGCACATT TCCCCGAAAA GTGCCACCTG ACGTCTAAGA AACCATTATT ATCATGACAT    4437

TAACCTATAA AAATAGGCGT ATCACGAGGC CCTTTCGTCT TCAA                     4481
```

(2) INFORMATION FOR SEQ ID NO:2:

(i) SEQUENCE CHARACTERISTICS:
        (A) LENGTH: 396 amino acids
        (B) TYPE: amino acid
        (D) TOPOLOGY: linear (ii) MOLECULE TYPE: protein (xi) SEQUENCE DESCRIPTION: SEQ ID NO:2:

```
Met Ser Phe Val Val Ile Ile Pro Ala Arg Tyr Ala Ser Thr Arg Leu
 1               5                  10                  15

Pro Gly Lys Pro Leu Val Asp Ile Asn Gly Lys Pro Met Ile Val His
             20                  25                  30
```

```
Val Leu Glu Arg Ala Arg Glu Ser Gly Ala Glu Arg Ile Ile Val Ala
         35                  40                  45

Thr Asp His Glu Asp Val Ala Arg Ala Val Glu Ala Ala Gly Gly Glu
     50                  55                  60

Val Cys Met Thr Arg Ala Asp His Gln Ser Gly Thr Glu Arg Leu Ala
 65                  70                  75                  80

Glu Val Val Glu Lys Cys Ala Phe Ser Asp Asp Thr Val Ile Val Asn
                 85                  90                  95

Val Gln Gly Asp Glu Pro Met Ile Pro Ala Thr Ile Ile Arg Gln Val
                100                 105                 110

Ala Asp Asn Leu Ala Gln Arg Gln Val Gly Met Ala Thr Leu Ala Val
            115                 120                 125

Pro Ile His Asn Ala Glu Glu Ala Phe Asn Pro Asn Ala Val Lys Val
        130                 135                 140

Val Leu Asp Ala Glu Gly Tyr Ala Leu Tyr Phe Ser Arg Ala Thr Ile
145                 150                 155                 160

Pro Trp Asp Arg Asp Arg Phe Ala Glu Gly Leu Glu Thr Val Gly Asp
                165                 170                 175

Asn Phe Leu Arg His Leu Gly Ile Tyr Gly Tyr Arg Ala Gly Phe Ile
            180                 185                 190

Arg Arg Tyr Val Asn Trp Gln Pro Ser Pro Leu Glu His Ile Glu Met
        195                 200                 205

Leu Glu Gln Leu Arg Val Leu Trp Tyr Gly Glu Lys Ile His Val Ala
    210                 215                 220

Val Ala Gln Glu Val Pro Gly Thr Gly Val Asp Thr Pro Glu Asp Leu
225                 230                 235                 240

Asp Pro Ser Thr Asn Ser Met Ser Thr Asn Pro Lys Pro Gln Lys Lys
                245                 250                 255

Asn Lys Arg Asn Thr Asn Arg Arg Pro Gln Asp Val Lys Phe Pro Gly
            260                 265                 270

Gly Gly Gln Ile Val Gly Gly Val Tyr Leu Leu Pro Arg Arg Gly Pro
        275                 280                 285

Arg Leu Gly Val Arg Ala Thr Arg Lys Thr Ser Glu Arg Ser Gln Pro
    290                 295                 300

Arg Gly Arg Arg Gln Pro Ile Pro Lys Ala Arg Arg Pro Glu Gly Arg
305                 310                 315                 320

Thr Trp Ala Gln Pro Gly Tyr Pro Trp Pro Leu Tyr Gly Asn Glu Gly
                325                 330                 335

Cys Gly Trp Ala Gly Trp Leu Leu Ser Pro Arg Gly Ser Arg Pro Ser
            340                 345                 350

Trp Gly Pro Thr Asp Pro Arg Arg Ser Arg Asn Leu Gly Lys Val
        355                 360                 365

Ile Asp Thr Leu Thr Cys Gly Phe Ala Asp Leu Met Gly Tyr Ile Pro
        370                 375                 380

Leu Val Gly Ala Pro Leu Gly Gly Ala Ala Arg Ala
385                 390                 395

(2) INFORMATION FOR SEQ ID NO:3:

(i) SEQUENCE CHARACTERISTICS:
        (A) LENGTH: 5600 base pairs
        (B) TYPE: nucleic acid
        (C) STRANDEDNESS: single
        (D) TOPOLOGY: circular (ii) MOLECULE TYPE: DNA (genomic)
```

```
    (ix) FEATURE:
        (A) NAME/KEY: CDS
        (B) LOCATION: 130..2472

(xi) SEQUENCE DESCRIPTION: SEQ ID NO:3:

GAATTAATTC CCATTAATGT GAGTTAGCTC ACTCATTAGG CACCCCAGGC TTTACACTTT        60

ATGTTCCGGC TCGTATTTTG TGTGGAATTG TGAGCGGATA ACAATTGGGC ATCCAGTAAG       120

GAGGTTTAA ATG AGT TTT GTG GTC ATT ATT CCC GCG CGC TAC GCG TCG          168
          Met Ser Phe Val Val Ile Ile Pro Ala Arg Tyr Ala Ser
           1               5                  10

ACG CGT CTG CCC GGT AAA CCA TTG GTT GAT ATT AAC GGC AAA CCC ATG        216
Thr Arg Leu Pro Gly Lys Pro Leu Val Asp Ile Asn Gly Lys Pro Met
 15                  20                  25

ATT GTT CAT GTT CTT GAA CGC GCG CGT GAA TCA GGT GCC GAG CGC ATC        264
Ile Val His Val Leu Glu Arg Ala Arg Glu Ser Gly Ala Glu Arg Ile
 30                  35                  40                  45

ATC GTG GCA ACC GAT CAT GAG GAT GTT GCC CGC GCC GTT GAA GCC GCT        312
Ile Val Ala Thr Asp His Glu Asp Val Ala Arg Ala Val Glu Ala Ala
                 50                  55                  60

GGC GGT GAA GTA TGT ATG ACG CGC GCC GAT CAT CAG TCA GGA ACA GAA        360
Gly Gly Glu Val Cys Met Thr Arg Ala Asp His Gln Ser Gly Thr Glu
 65                  70                  75

CGT CTG GCG GAA GTT GTC GAA AAA TGC GCA TTC AGC GAC GAC ACG GTG        408
Arg Leu Ala Glu Val Val Glu Lys Cys Ala Phe Ser Asp Asp Thr Val
 80                  85                  90

ATC GTT AAT GTG CAG GGT GAT GAA CCG ATG ATC CCT GCG ACA ATC ATT        456
Ile Val Asn Val Gln Gly Asp Glu Pro Met Ile Pro Ala Thr Ile Ile
 95                 100                 105

CGT CAG GTT GCT GAT AAC CTC GCT CAG CGT CAG GTG GGT ATG GCG ACT        504
Arg Gln Val Ala Asp Asn Leu Ala Gln Arg Gln Val Gly Met Ala Thr
110                 115                 120                 125

CTG GCG GTG CCA ATC CAC AAT GCG GAA GAA GCG TTT AAC CCG AAT GCG        552
Leu Ala Val Pro Ile His Asn Ala Glu Glu Ala Phe Asn Pro Asn Ala
                130                 135                 140

GTG AAA GTG GTT CTC GAC GCT GAA GGG TAT GCA CTG TAC TTC TCT CGC        600
Val Lys Val Val Leu Asp Ala Glu Gly Tyr Ala Leu Tyr Phe Ser Arg
                145                 150                 155

GCC ACC ATT CCT TGG GAT CGT GAT CGT TTT GCA GAA GGC CTT GAA ACC        648
Ala Thr Ile Pro Trp Asp Arg Asp Arg Phe Ala Glu Gly Leu Glu Thr
            160                 165                 170

GTT GGC GAT AAC TTC CTG CGT CAT CTT GGT ATT TAT GGC TAC CGT GCA        696
Val Gly Asp Asn Phe Leu Arg His Leu Gly Ile Tyr Gly Tyr Arg Ala
        175                 180                 185

GGC TTT ATC CGT CGT TAC GTC AAC TGG CAG CCA AGT CCG TTA GAA CAC        744
Gly Phe Ile Arg Arg Tyr Val Asn Trp Gln Pro Ser Pro Leu Glu His
190                 195                 200                 205

ATC GAA ATG TTA GAG CAG CTT CGT GTT CTG TGG TAC GGC GAA AAA ATC        792
Ile Glu Met Leu Glu Gln Leu Arg Val Leu Trp Tyr Gly Glu Lys Ile
                210                 215                 220

CAT GTT GCT GTT GCT CAG GAA GTT CCT GGC ACA GGT GTG GAT ACC CCT        840
His Val Ala Val Ala Gln Glu Val Pro Gly Thr Gly Val Asp Thr Pro
                225                 230                 235

GAA GAT CTC GAC CCG TCG ACG AAT TCC ATG GCT GTT GAC TTT ATC CCG        888
Glu Asp Leu Asp Pro Ser Thr Asn Ser Met Ala Val Asp Phe Ile Pro
            240                 245                 250

GTT GAA AAT CTC GAG ACT ACT ATG CGT TCT CCG GTT TTC ACT GAC AAC        936
Val Glu Asn Leu Glu Thr Thr Met Arg Ser Pro Val Phe Thr Asp Asn
        255                 260                 265
```

```
TCT TCT CCG CCG GTT GTT CCG CAG TCT TTC CAG GTT GCT CAC CTG CAT      984
Ser Ser Pro Pro Val Val Pro Gln Ser Phe Gln Val Ala His Leu His
270             275                 280                 285

GCT CCG ACT GGT TCT GGT AAA TCT ACT AAA GTT CCA GCT GCT TAC GCT     1032
Ala Pro Thr Gly Ser Gly Lys Ser Thr Lys Val Pro Ala Ala Tyr Ala
                290                 295                 300

GCT CAG GGT TAC AAA GTT CTG GTT CTG AAC CCG TCT GTT GCT GCT ACT     1080
Ala Gln Gly Tyr Lys Val Leu Val Leu Asn Pro Ser Val Ala Ala Thr
            305                 310                 315

CTG GGT TTC GGC GCC TAC ATG TCT AAA GCT CAC GGT ATC GAC CCG AAC     1128
Leu Gly Phe Gly Ala Tyr Met Ser Lys Ala His Gly Ile Asp Pro Asn
        320                 325                 330

ATT CGT ACT GGT GTA CGT ACT ATC ACT ACT GGT TCT CCG ATC ACT TAC     1176
Ile Arg Thr Gly Val Arg Thr Ile Thr Thr Gly Ser Pro Ile Thr Tyr
335                 340                 345

TCT ACT TAC GGT AAA TTC CTG GCT GAC GGT GGT TGC TCT GGT GGT GCT     1224
Ser Thr Tyr Gly Lys Phe Leu Ala Asp Gly Gly Cys Ser Gly Gly Ala
350                 355                 360                 365

TAC GAT ATC ATC ATC TGC GAC GAA TGC CAC TCT ACT GAC GCT ACT TCT     1272
Tyr Asp Ile Ile Ile Cys Asp Glu Cys His Ser Thr Asp Ala Thr Ser
                370                 375                 380

ATC CTG GGT ATC GGT ACC GTT CTG GAC CAG GCT GAA ACT GCA GGT GCT     1320
Ile Leu Gly Ile Gly Thr Val Leu Asp Gln Ala Glu Thr Ala Gly Ala
            385                 390                 395

CGT CTG GTT GTT CTG GCT ACT GCT ACT CCG CCG GGT TCT GTT ACT GTT     1368
Arg Leu Val Val Leu Ala Thr Ala Thr Pro Pro Gly Ser Val Thr Val
        400                 405                 410

CCG CAC CCG AAC ATC GAA GAA GTT GCT CTG TCG ACT ACT GGT GAA ATC     1416
Pro His Pro Asn Ile Glu Glu Val Ala Leu Ser Thr Thr Gly Glu Ile
    415                 420                 425

CCG TTC TAC GGT AAA GCT ATC CCG CTC GAG GTT ATC AAA GGT GGT CGT     1464
Pro Phe Tyr Gly Lys Ala Ile Pro Leu Glu Val Ile Lys Gly Gly Arg
430                 435                 440                 445

CAC CTG ATT TTC TGC CAC TCT AAA AAA AAA TGC GAC GAA CTG GCT GCT     1512
His Leu Ile Phe Cys His Ser Lys Lys Lys Cys Asp Glu Leu Ala Ala
                450                 455                 460

AAG CTT GTT GCT CTG GGT ATC AAC GCT GTT GCT TAC TAC CGT GGT CTG     1560
Lys Leu Val Ala Leu Gly Ile Asn Ala Val Ala Tyr Tyr Arg Gly Leu
            465                 470                 475

GAC GTT TCT GTT ATC CCG ACT TCT GGT GAC GTT GTT GTG GCC ACT         1608
Asp Val Ser Val Ile Pro Thr Ser Gly Asp Val Val Val Ala Thr
        480                 485                 490

GAC GCT CTG ATG ACT GGT TAC ACT GGT GAC TTC GAC TCT GTT ATC GAT     1656
Asp Ala Leu Met Thr Gly Tyr Thr Gly Asp Phe Asp Ser Val Ile Asp
    495                 500                 505

TGC AAC ACT TGC AAT TCG TCG ACC GGT TGC GTT GTT ATC GTT GGT CGT     1704
Cys Asn Thr Cys Asn Ser Ser Thr Gly Cys Val Val Ile Val Gly Arg
510                 515                 520                 525

GTT GTT CTG TCT GGT AAA CCG GCC ATT ATC CCG GAC CGT GAA GTT CTG     1752
Val Val Leu Ser Gly Lys Pro Ala Ile Ile Pro Asp Arg Glu Val Leu
                530                 535                 540

TAC CGT GAG TTC GAC GAA ATG GAA GAA TGC TCT CAG CAC CTG CCG TAC     1800
Tyr Arg Glu Phe Asp Glu Met Glu Glu Cys Ser Gln His Leu Pro Tyr
            545                 550                 555

ATC GAA CAG GGT ATG ATG CTG GCT GAA CAG TTC AAA CAG AAA GCT CTG     1848
Ile Glu Gln Gly Met Met Leu Ala Glu Gln Phe Lys Gln Lys Ala Leu
        560                 565                 570

GGT CTG CTG CAG ACC GCT TCT CGT CAG GCT GAA GTT ATC GCT CCG GCT     1896
Gly Leu Leu Gln Thr Ala Ser Arg Gln Ala Glu Val Ile Ala Pro Ala
575                 580                 585
```

```
GTT CAG ACC AAC TGG CAG AAA CTC GAG ACC TTC TGG GCT AAA CAC ATG      1944
Val Gln Thr Asn Trp Gln Lys Leu Glu Thr Phe Trp Ala Lys His Met
590             595                 600                 605

TGG AAC TTC ATC TCT GGT ATC CAG TAC CTG GCT GGT CTG TCT ACC CTG      1992
Trp Asn Phe Ile Ser Gly Ile Gln Tyr Leu Ala Gly Leu Ser Thr Leu
                610                 615                 620

CCG GGT AAC CCG GCT ATC GCA AGC TTG ATG GCT TTC ACC GCT GCT GTT      2040
Pro Gly Asn Pro Ala Ile Ala Ser Leu Met Ala Phe Thr Ala Ala Val
            625                 630                 635

ACC TCT CCG CTG ACC ACC TCT CAG ACC CTG CTG TTC AAC ATT CTG GGT      2088
Thr Ser Pro Leu Thr Thr Ser Gln Thr Leu Leu Phe Asn Ile Leu Gly
        640                 645                 650

GGT TGG GTT GCT GCT CAG CTG GCT GCT CCG GGT GCT GCT ACC GCT TTC      2136
Gly Trp Val Ala Ala Gln Leu Ala Ala Pro Gly Ala Ala Thr Ala Phe
    655                 660                 665

GTT GGT GCT GGT CTG GCT GGT GCT GCT ATC GGT TCT GTA GGC CTG GGT      2184
Val Gly Ala Gly Leu Ala Gly Ala Ala Ile Gly Ser Val Gly Leu Gly
670                 675                 680                 685

AAA GTT CTG ATC GAC ATT CTG GCT GGT TAC GGT GCT GGT GTT GCT GGA      2232
Lys Val Leu Ile Asp Ile Leu Ala Gly Tyr Gly Ala Gly Val Ala Gly
                690                 695                 700

GCT CTG GTT GCT TTC AAA ATC ATG TCT GGT GAA GTT CCG TCT ACC GAA      2280
Ala Leu Val Ala Phe Lys Ile Met Ser Gly Glu Val Pro Ser Thr Glu
            705                 710                 715

GAT CTG GTT AAC CTG CTG CCG GCT ATC CTG TCT CCG GGT GCT CTG GTT      2328
Asp Leu Val Asn Leu Leu Pro Ala Ile Leu Ser Pro Gly Ala Leu Val
        720                 725                 730

GTT GGT GTT GTT TGC GCT GCT ATC CTG CGT CGT CAC GTT GGC CCG GGT      2376
Val Gly Val Val Cys Ala Ala Ile Leu Arg Arg His Val Gly Pro Gly
    735                 740                 745

GAA GGT GCT GTT CAG TGG ATG AAC CGT CTG ATC GCT TTC GCT TCT CGT      2424
Glu Gly Ala Val Gln Trp Met Asn Arg Leu Ile Ala Phe Ala Ser Arg
750                 755                 760                 765

GGT AAC CAC GTT TCT CCA TGG GAT CCT CTA GAC TGC AGG CAT GCT AAG      2472
Gly Asn His Val Ser Pro Trp Asp Pro Leu Asp Cys Arg His Ala Lys
                770                 775                 780

TAAGTAGATC TTGAGCGCGT TCGCGCTGAA ATGCGCTAAT TTCACTTCAC GACACTTCAG    2532

CCAATTTTGG GAGGAGTGTC GTACCGTTAC GATTTTCCTC AATTTTTCTT TTCAACAATT    2592

GATCTCATTC AGGTGACATC TTTTATATTG GCGCTCATTA TGAAAGCAGT AGCTTTTATG    2652

AGGGTAATCT GAATGGAACA GCTGCGTGCC GAATTAAGCC ATTTACTGGG CGAAAAACTC    2712

AGTCGTATTG AGTGCGTCAA TGAAAAAGCG GATACGGCGT TGTGGGCTTT GTATGACAGC    2772

CAGGGAAACC CAATGCCGTT AATGGCAAGA AGCTTAGCCC GCCTAATGAG CGGGCTTTTT    2832

TTTCGACGCG AGGCTGGATG GCCTTCCCCA TTATGATTCT TCTCGCTTCC GGCGGCATCG    2892

GGATGCCCGC GTTGCAGGCC ATGCTGTCCA GGCAGGTAGA TGACGACCAT CAGGGACAGC    2952

TTCAAGGATC GCTCGCGGCT CTTACCAGCC TAACTTCGAT CACTGGACCG CTGATCGTCA    3012

CGGCGATTTA TGCCGCCTCG GCGAGCACAT GGAACGGGTT GGCATGGATT GTAGGCGCCG    3072

CCCTATACCT TGTCTGCCTC CCCGCGTTGC GTCGCGGTGC ATGGAGCCGG GCCACCTCGA    3132

CCTGAATGGA AGCCGGCGGC ACCTCGCTAA CGGATTCACC ACTCCAAGAA TTGGAGCCAA    3192

TCAATTCTTG CGGAGAACTG TGAATGCGCA AACCAACCCT TGGCAGAACA TATCCATCGC    3252

GTCCGCCATC TCCAGCAGCC GCACGCGGCG CATCTCGGGC AGCGTTGGGT CCTGGCCACG    3312

GGTGCGCATG ATCGTGCTCC TGTCGTTGAG GACCCGGCTA GGCTGGCGGG GTTGCCTTAC    3372
```

```
TGGTTAGCAG AATGAATCAC CGATACGCGA GCGAACGTGA AGCGACTGCT GCTGCAAAAC    3432

GTCTGCGACC TGAGCAACAA CATGAATGGT CTTCGGTTTC CGTGTTTCGT AAAGTCTGGA    3492

AACGCGGAAG TCAGCGCCCT GCACCATTAT GTTCCGGATC TGCATCGCAG GATGCTGCTG    3552

GCTACCCTGT GGAACACCTA CATCTGTATT AACGAAGCGC TTCTTCCGCT TCCTCGCTCA    3612

CTGACTCGCT GCGCTCGGTC GTTCGGCTGC GGCGAGCGGT ATCAGCTCAC TCAAAGGCGG    3672

TAATACGGTT ATCCACAGAA TCAGGGGATA ACGCAGGAAA GAACATGTGA GCAAAAGGCC    3732

AGCAAAAGGC CAGGAACCGT AAAAAGGCCG CGTTGCTGGC GTTTTTCCAT AGGCTCCGCC    3792

CCCCTGACGA GCATCACAAA AATCGACGCT CAAGTCAGAG GTGGCGAAAC CCGACAGGAC    3852

TATAAAGATA CCAGGCGTTT CCCCCTGGAA GCTCCCTCGT GCGCTCTCCT GTTCCGACCC    3912

TGCCGCTTAC CGGATACCTG TCCGCCTTTC TCCCTTCGGG AAGCGTGGCG CTTTCTCAAT    3972

GCTCACGCTG TAGGTATCTC AGTTCGGTGT AGGTCGTTCG CTCCAAGCTG GGCTGTGTGC    4032

ACGAACCCCC CGTTCAGCCC GACCGCTGCG CCTTATCCGG TAACTATCGT CTTGAGTCCA    4092

ACCCGGTAAG ACACGACTTA TCGCCACTGG CAGCAGCCAC TGGTAACAGG ATTAGCAGAG    4152

CGAGGTATGT AGGCGGTGCT ACAGAGTTCT TGAAGTGGTG GCCTAACTAC GGCTACACTA    4212

GAAGGACAGT ATTTGGTATC TGCGCTCTGC TGAAGCCAGT TACCTTCGGA AAAAGAGTTG    4272

GTAGCTCTTG ATCCGGCAAA CAAACCACCG CTGGTAGCGG TGGTTTTTTT GTTTGCAAGC    4332

AGCAGATTAC GCGCAGAAAA AAAGGATCTC AAGAAGATCC TTTGATCTTT TCTACGGGGT    4392

CTGACGCTCA GTGGAACGAA AACTCACGTT AAGGGATTTT GGTCATGAGA TTATCAAAAA    4452

GGATCTTCAC CTAGATCCTT TTAAATTAAA AATGAAGTTT TAAATCAATC TAAAGTATAT    4512

ATGAGTAAAC TTGGTCTGAC AGTTACCAAT GCTTAATCAG TGAGGCACCT ATCTCAGCGA    4572

TCTGTCTATT TCGTTCATCC ATAGTTGCCT GACTCCCCGT CGTGTAGATA ACTACGATAC    4632

GGGAGGGCTT ACCATCTGGC CCCAGTGCTG CAATGATACC GCGAGACCCA CGCTCACCGG    4692

CTCCAGATTT ATCAGCAATA AACCAGCCAG CCGGAAGGGC CGAGCGCAGA AGTGGTCCTG    4752

CAACTTTATC CGCCTCCATC CAGTCTATTA ATTGTTGCCG GGAAGCTAGA GTAAGTAGTT    4812

CGCCAGTTAA TAGTTTGCGC AACGTTGTTG CCATTGCTAC AGGCATCGTG GTGTCACGCT    4872

CGTCGTTTGG TATGGCTTCA TTCAGCTCCG GTTCCCAACG ATCAAGGCGA GTTACATGAT    4932

CCCCCATGTT GTGCAAAAAA GCGGTTAGCT CCTTCGGTCC TCCGATCGTT GTCAGAAGTA    4992

AGTTGGCCGC AGTGTTATCA CTCATGGTTA TGGCAGCACT GCATAATTCT CTTACTGTCA    5052

TGCCATCCGT AAGATGCTTT TCTGTGACTG GTGAGTACTC AACCAAGTCA TTCTGAGAAT    5112

AGTGTATGCG GCGACCGAGT TGCTCTTGCC CGGCGTCAAC ACGGGATAAT ACCGCGCCAC    5172

ATAGCAGAAC TTTAAAAGTG CTCATCATTG GAAAACGTTC TTCGGGGCGA AAACTCTCAA    5232

GGATCTTACC GCTGTTGAGA TCCAGTTCGA TGTAACCCAC TCGTGCACCC AACTGATCTT    5292

CAGCATCTTT TACTTTCACC AGCGTTTCTG GGTGAGCAAA AACAGGAAGG CAAAATGCCG    5352

CAAAAAAGGG AATAAGGGCG ACACGGAAAT GTTGAATACT CATACTCTTC CTTTTTCAAT    5412

ATTATTGAAG CATTTATCAG GGTTATTGTC TCATGAGCGG ATACATATTT GAATGTATTT    5472

AGAAAAATAA ACAAATAGGG GTTCCGCGCA CATTTCCCCG AAAAGTGCCA CCTGACGTCT    5532

AAGAAACCAT TATTATCATG ACATTAACCT ATAAAAATAG GCGTATCACG AGGCCCTTTC    5592

GTCTTCAA                                                            5600
```

(2) INFORMATION FOR SEQ ID NO:4:

(i) SEQUENCE CHARACTERISTICS:
    (A) LENGTH: 781 amino acids
    (B) TYPE: amino acid
    (D) TOPOLOGY: linear (ii) MOLECULE TYPE: protein (xi) SEQUENCE DESCRIPTION: SEQ ID NO:4:

```
Met Ser Phe Val Val Ile Ile Pro Ala Arg Tyr Ala Ser Thr Arg Leu
 1               5                  10                  15

Pro Gly Lys Pro Leu Val Asp Ile Asn Gly Lys Pro Met Ile Val His
            20                  25                  30

Val Leu Glu Arg Ala Arg Glu Ser Gly Ala Glu Arg Ile Ile Val Ala
        35                  40                  45

Thr Asp His Glu Asp Val Ala Arg Ala Val Glu Ala Ala Gly Gly Glu
    50                  55                  60

Val Cys Met Thr Arg Ala Asp His Gln Ser Gly Thr Glu Arg Leu Ala
65                  70                  75                  80

Glu Val Val Glu Lys Cys Ala Phe Ser Asp Asp Thr Val Ile Val Asn
                85                  90                  95

Val Gln Gly Asp Glu Pro Met Ile Pro Ala Thr Ile Ile Arg Gln Val
            100                 105                 110

Ala Asp Asn Leu Ala Gln Arg Gln Val Gly Met Ala Thr Leu Ala Val
        115                 120                 125

Pro Ile His Asn Ala Glu Glu Ala Phe Asn Pro Asn Ala Val Lys Val
    130                 135                 140

Val Leu Asp Ala Glu Gly Tyr Ala Leu Tyr Phe Ser Arg Ala Thr Ile
145                 150                 155                 160

Pro Trp Asp Arg Asp Arg Phe Ala Glu Gly Leu Glu Thr Val Gly Asp
                165                 170                 175

Asn Phe Leu Arg His Leu Gly Ile Tyr Gly Tyr Arg Ala Gly Phe Ile
            180                 185                 190

Arg Arg Tyr Val Asn Trp Gln Pro Ser Pro Leu Glu His Ile Glu Met
        195                 200                 205

Leu Glu Gln Leu Arg Val Leu Trp Tyr Gly Glu Lys Ile His Val Ala
    210                 215                 220

Val Ala Gln Glu Val Pro Gly Thr Gly Val Asp Thr Pro Glu Asp Leu
225                 230                 235                 240

Asp Pro Ser Thr Asn Ser Met Ala Val Asp Phe Ile Pro Val Glu Asn
                245                 250                 255

Leu Glu Thr Thr Met Arg Ser Pro Val Phe Thr Asp Asn Ser Ser Pro
            260                 265                 270

Pro Val Val Pro Gln Ser Phe Gln Val Ala His Leu His Ala Pro Thr
        275                 280                 285

Gly Ser Gly Lys Ser Thr Lys Val Pro Ala Ala Tyr Ala Ala Gln Gly
    290                 295                 300

Tyr Lys Val Leu Val Leu Asn Pro Ser Val Ala Ala Thr Leu Gly Phe
305                 310                 315                 320

Gly Ala Tyr Met Ser Lys Ala His Gly Ile Asp Pro Asn Ile Arg Thr
                325                 330                 335

Gly Val Arg Thr Ile Thr Thr Gly Ser Pro Ile Thr Tyr Ser Thr Tyr
            340                 345                 350

Gly Lys Phe Leu Ala Asp Gly Gly Cys Ser Gly Gly Ala Tyr Asp Ile
        355                 360                 365

Ile Ile Cys Asp Glu Cys His Ser Thr Asp Ala Thr Ser Ile Leu Gly
```

```
            370                 375                 380
Ile Gly Thr Val Leu Asp Gln Ala Glu Thr Ala Gly Ala Arg Leu Val
385                 390                 395                 400
Val Leu Ala Thr Ala Thr Pro Pro Gly Ser Val Thr Val Pro His Pro
                    405                 410                 415
Asn Ile Glu Glu Val Ala Leu Ser Thr Thr Gly Glu Ile Pro Phe Tyr
                420                 425                 430
Gly Lys Ala Ile Pro Leu Glu Val Ile Lys Gly Arg His Leu Ile
            435                 440                 445
Phe Cys His Ser Lys Lys Cys Asp Glu Leu Ala Ala Lys Leu Val
        450                 455                 460
Ala Leu Gly Ile Asn Ala Val Ala Tyr Tyr Arg Gly Leu Asp Val Ser
465                 470                 475                 480
Val Ile Pro Thr Ser Gly Asp Val Val Val Ala Thr Asp Ala Leu
                485                 490                 495
Met Thr Gly Tyr Thr Gly Asp Phe Asp Ser Val Ile Asp Cys Asn Thr
                500                 505                 510
Cys Asn Ser Ser Thr Gly Cys Val Val Ile Val Gly Arg Val Val Leu
            515                 520                 525
Ser Gly Lys Pro Ala Ile Ile Pro Asp Arg Glu Val Leu Tyr Arg Glu
            530                 535                 540
Phe Asp Glu Met Glu Glu Cys Ser Gln His Leu Pro Tyr Ile Glu Gln
545                 550                 555                 560
Gly Met Met Leu Ala Glu Gln Phe Lys Gln Lys Ala Leu Gly Leu Leu
                565                 570                 575
Gln Thr Ala Ser Arg Gln Ala Glu Val Ile Ala Pro Ala Val Gln Thr
            580                 585                 590
Asn Trp Gln Lys Leu Glu Thr Phe Trp Ala Lys His Met Trp Asn Phe
            595                 600                 605
Ile Ser Gly Ile Gln Tyr Leu Ala Gly Leu Ser Thr Leu Pro Gly Asn
            610                 615                 620
Pro Ala Ile Ala Ser Leu Met Ala Phe Thr Ala Ala Val Thr Ser Pro
625                 630                 635                 640
Leu Thr Thr Ser Gln Thr Leu Leu Phe Asn Ile Leu Gly Gly Trp Val
                645                 650                 655
Ala Ala Gln Leu Ala Ala Pro Gly Ala Ala Thr Ala Phe Val Gly Ala
                660                 665                 670
Gly Leu Ala Gly Ala Ala Ile Gly Ser Val Gly Leu Gly Lys Val Leu
            675                 680                 685
Ile Asp Ile Leu Ala Gly Tyr Gly Ala Gly Val Ala Gly Ala Leu Val
            690                 695                 700
Ala Phe Lys Ile Met Ser Gly Glu Val Pro Ser Thr Glu Asp Leu Val
705                 710                 715                 720
Asn Leu Leu Pro Ala Ile Leu Ser Pro Gly Ala Leu Val Val Gly Val
                725                 730                 735
Val Cys Ala Ala Ile Leu Arg Arg His Val Gly Pro Gly Glu Gly Ala
                740                 745                 750
Val Gln Trp Met Asn Arg Leu Ile Ala Phe Ala Ser Arg Gly Asn His
            755                 760                 765
Val Ser Pro Trp Asp Pro Leu Asp Cys Arg His Ala Lys
        770                 775                 780

(2) INFORMATION FOR SEQ ID NO:5:
```

```
    (i) SEQUENCE CHARACTERISTICS:
        (A) LENGTH: 1548 base pairs
        (B) TYPE: nucleic acid
        (C) STRANDEDNESS: single
        (D) TOPOLOGY: circular (ii) MOLECULE TYPE: DNA (genomic)

(ix) FEATURE:
        (A) NAME/KEY: CDS
        (B) LOCATION: 1..1548

(xi) SEQUENCE DESCRIPTION: SEQ ID NO:5:

ATG AGT TTT GTG GTC ATT ATT CCC GCG CGC TAC GCG TCG ACG CGT CTG        48
Met Ser Phe Val Val Ile Ile Pro Ala Arg Tyr Ala Ser Thr Arg Leu
 1               5                  10                  15

CCC GGT AAA CCA TTG GTT GAT ATT AAC GGC AAA CCC ATG ATT GTT CAT        96
Pro Gly Lys Pro Leu Val Asp Ile Asn Gly Lys Pro Met Ile Val His
             20                  25                  30

GTT CTT GAA CGC GCG CGT GAA TCA GGT GCC GAG CGC ATC ATC GTG GCA       144
Val Leu Glu Arg Ala Arg Glu Ser Gly Ala Glu Arg Ile Ile Val Ala
         35                  40                  45

ACC GAT CAT GAG GAT GTT GCC CGC GCC GTT GAA GCC GCT GGC GGT GAA       192
Thr Asp His Glu Asp Val Ala Arg Ala Val Glu Ala Ala Gly Gly Glu
     50                  55                  60

GTA TGT ATG ACG CGC GCC GAT CAT CAG TCA GGA ACA GAA CGT CTG GCG       240
Val Cys Met Thr Arg Ala Asp His Gln Ser Gly Thr Glu Arg Leu Ala
 65                  70                  75                  80

GAA GTT GTC GAA AAA TGC GCA TTC AGC GAC GAC ACG GTG ATC GTT AAT       288
Glu Val Val Glu Lys Cys Ala Phe Ser Asp Asp Thr Val Ile Val Asn
                 85                  90                  95

GTG CAG GGT GAT GAA CCG ATG ATC CCT GCG ACA ATC ATT CGT CAG GTT       336
Val Gln Gly Asp Glu Pro Met Ile Pro Ala Thr Ile Ile Arg Gln Val
            100                 105                 110

GCT GAT AAC CTC GCT CAG CGT CAG GTG GGT ATG GCG ACT CTG GCG GTG       384
Ala Asp Asn Leu Ala Gln Arg Gln Val Gly Met Ala Thr Leu Ala Val
        115                 120                 125

CCA ATC CAC AAT GCG GAA GAA GCG TTT AAC CCG AAT GCG GTG AAA GTG       432
Pro Ile His Asn Ala Glu Glu Ala Phe Asn Pro Asn Ala Val Lys Val
    130                 135                 140

GTT CTC GAC GCT GAA GGG TAT GCA CTG TAC TTC TCT CGC GCC ACC ATT       480
Val Leu Asp Ala Glu Gly Tyr Ala Leu Tyr Phe Ser Arg Ala Thr Ile
145                 150                 155                 160

CCT TGG GAT CGT GAT CGT TTT GCA GAA GGC CTT GAA ACC GTT GGC GAT       528
Pro Trp Asp Arg Asp Arg Phe Ala Glu Gly Leu Glu Thr Val Gly Asp
                165                 170                 175

AAC TTC CTG CGT CAT CTT GGT ATT TAT GGC TAC CGT GCA GGC TTT ATC       576
Asn Phe Leu Arg His Leu Gly Ile Tyr Gly Tyr Arg Ala Gly Phe Ile
            180                 185                 190

CGT CGT TAC GTC AAC TGG CAG CCA AGT CCG TTA GAA CAC ATC GAA ATG       624
Arg Arg Tyr Val Asn Trp Gln Pro Ser Pro Leu Glu His Ile Glu Met
        195                 200                 205

TTA GAG CAG CTT CGT GTT CTG TGG TAC GGC GAA AAA ATC CAT GTT GCT       672
Leu Glu Gln Leu Arg Val Leu Trp Tyr Gly Glu Lys Ile His Val Ala
    210                 215                 220

GTT GCT CAG GAA GTT CCT GGC ACA GGT GTG GAT ACC CCT GAA GAT CTC       720
Val Ala Gln Glu Val Pro Gly Thr Gly Val Asp Thr Pro Glu Asp Leu
225                 230                 235                 240

GAC CCG TCG ACG AAT TCC CCA TGG ACC CAC TAC GTT CCG GAA TCT GAC       768
Asp Pro Ser Thr Asn Ser Pro Trp Thr His Tyr Val Pro Glu Ser Asp
                245                 250                 255
```

```
GCT GCT GCT CGA GTT ACC GCT ATC CTG TCT TCT CTG ACC GTT ACC CAG    816
Ala Ala Ala Arg Val Thr Ala Ile Leu Ser Ser Leu Thr Val Thr Gln
            260                 265                 270

CTT CTG CGT CGT CTG CAC CAG TGG ATC TCT TCT GAA TGC ACC ACC CCG    864
Leu Leu Arg Arg Leu His Gln Trp Ile Ser Ser Glu Cys Thr Thr Pro
        275                 280                 285

TGC TCT GGT TCT TGG CTG CGT GAC ATC TGG GAC TGG ATC TGC GAA GTT    912
Cys Ser Gly Ser Trp Leu Arg Asp Ile Trp Asp Trp Ile Cys Glu Val
290                 295                 300

CTG TCT GAC TTC AAA ACC TGG CTG AAA GCT AAA CTG ATG CCG CAG CTG    960
Leu Ser Asp Phe Lys Thr Trp Leu Lys Ala Lys Leu Met Pro Gln Leu
305                 310                 315                 320

CCG GGT ATC CCG TTC GTT TCT TGC CAG CGT GGT TAC AAA GGT GTT TGG   1008
Pro Gly Ile Pro Phe Val Ser Cys Gln Arg Gly Tyr Lys Gly Val Trp
                325                 330                 335

CGT GTT GAC GGT ATC ATG CAC ACC CGT TGC CAC TGC GGT GCT GAA ATC   1056
Arg Val Asp Gly Ile Met His Thr Arg Cys His Cys Gly Ala Glu Ile
            340                 345                 350

ACC GGT CAC GTT AAA AAC GGT ACC ATG CGT ATC GTT GGT CCG CGT ACC   1104
Thr Gly His Val Lys Asn Gly Thr Met Arg Ile Val Gly Pro Arg Thr
        355                 360                 365

TGC CGT AAC ATG TGG TCT GGC ACC TTC CCG ATC AAC GCT TAC ACC ACC   1152
Cys Arg Asn Met Trp Ser Gly Thr Phe Pro Ile Asn Ala Tyr Thr Thr
370                 375                 380

GGT CCG TGC ACC CCG CTG CCG GCT CCG AAC TAC ACC TTC GCT CTG TGG   1200
Gly Pro Cys Thr Pro Leu Pro Ala Pro Asn Tyr Thr Phe Ala Leu Trp
385                 390                 395                 400

CGT GTT TCT GCT GAA GAA TAC GTT GAA ATC CGT CAG GTT GGT GAC TTC   1248
Arg Val Ser Ala Glu Glu Tyr Val Glu Ile Arg Gln Val Gly Asp Phe
                405                 410                 415

CAC TAC GTT ACC GGT ATG ACC ACC GAC AAC CTG AAA TGC CCG TGC CAG   1296
His Tyr Val Thr Gly Met Thr Thr Asp Asn Leu Lys Cys Pro Cys Gln
            420                 425                 430

GTT CCG TCT CCG GAG TTC TTC ACC GAA CTG GAC GGT GTT CGT CTG CAC   1344
Val Pro Ser Pro Glu Phe Phe Thr Glu Leu Asp Gly Val Arg Leu His
        435                 440                 445

CGT TTC GCT CCG CCG TGC AAA CCG CTG CTG CGT GAA GAA GTT TCT TTC   1392
Arg Phe Ala Pro Pro Cys Lys Pro Leu Leu Arg Glu Glu Val Ser Phe
450                 455                 460

CGT GTT GGT CTG CAC GAA TAC CCG GTT GGT TCT CAG CTG CCG TGC GAA   1440
Arg Val Gly Leu His Glu Tyr Pro Val Gly Ser Gln Leu Pro Cys Glu
465                 470                 475                 480

CCG GAA CCG GAC GTT GCT GTT CTG ACC TCT ATG CTG ACC GAC CCG TCT   1488
Pro Glu Pro Asp Val Ala Val Leu Thr Ser Met Leu Thr Asp Pro Ser
                485                 490                 495

CAC ATC ACC GCT GAA GCT GCT GGT CGT CGA CTG GAT CCT CTA GAC TGC   1536
His Ile Thr Ala Glu Ala Ala Gly Arg Arg Leu Asp Pro Leu Asp Cys
            500                 505                 510

AGG CAT GCT AAG                                                   1548
Arg His Ala Lys
        515
```

(2) INFORMATION FOR SEQ ID NO:6:

(i) SEQUENCE CHARACTERISTICS:
        (A) LENGTH: 516 amino acids
        (B) TYPE: amino acid
        (D) TOPOLOGY: linear (ii) MOLECULE TYPE: protein (xi) SEQUENCE DESCRIPTION: SEQ ID NO:6:

-continued

```
Met Ser Phe Val Val Ile Ile Pro Ala Arg Tyr Ala Ser Thr Arg Leu
 1               5                   10                  15

Pro Gly Lys Pro Leu Val Asp Ile Asn Gly Lys Pro Met Ile Val His
             20                  25                  30

Val Leu Glu Arg Ala Arg Glu Ser Gly Ala Glu Arg Ile Ile Val Ala
             35                  40                  45

Thr Asp His Glu Asp Val Ala Arg Ala Val Glu Ala Ala Gly Gly Glu
 50                  55                  60

Val Cys Met Thr Arg Ala Asp His Gln Ser Gly Thr Glu Arg Leu Ala
 65              70                  75                  80

Glu Val Val Glu Lys Cys Ala Phe Ser Asp Asp Thr Val Ile Val Asn
                 85                  90                  95

Val Gln Gly Asp Glu Pro Met Ile Pro Ala Thr Ile Ile Arg Gln Val
                100                 105                 110

Ala Asp Asn Leu Ala Gln Arg Gln Val Gly Met Ala Thr Leu Ala Val
             115                 120                 125

Pro Ile His Asn Ala Glu Glu Ala Phe Asn Pro Asn Ala Val Lys Val
         130                 135                 140

Val Leu Asp Ala Glu Gly Tyr Ala Leu Tyr Phe Ser Arg Ala Thr Ile
145                 150                 155                 160

Pro Trp Asp Arg Asp Arg Phe Ala Glu Gly Leu Glu Thr Val Gly Asp
                165                 170                 175

Asn Phe Leu Arg His Leu Gly Ile Tyr Gly Tyr Arg Ala Gly Phe Ile
             180                 185                 190

Arg Arg Tyr Val Asn Trp Gln Pro Ser Pro Leu Glu His Ile Glu Met
         195                 200                 205

Leu Glu Gln Leu Arg Val Leu Trp Tyr Gly Glu Lys Ile His Val Ala
         210                 215                 220

Val Ala Gln Glu Val Pro Gly Thr Gly Val Asp Thr Pro Glu Asp Leu
225                 230                 235                 240

Asp Pro Ser Thr Asn Ser Pro Trp Thr His Tyr Val Pro Glu Ser Asp
                245                 250                 255

Ala Ala Ala Arg Val Thr Ala Ile Leu Ser Ser Leu Thr Val Thr Gln
             260                 265                 270

Leu Leu Arg Arg Leu His Gln Trp Ile Ser Ser Glu Cys Thr Thr Pro
         275                 280                 285

Cys Ser Gly Ser Trp Leu Arg Asp Ile Trp Asp Trp Ile Cys Glu Val
         290                 295                 300

Leu Ser Asp Phe Lys Thr Trp Leu Lys Ala Lys Leu Met Pro Gln Leu
305                 310                 315                 320

Pro Gly Ile Pro Phe Val Ser Cys Gln Arg Gly Tyr Lys Gly Val Trp
                325                 330                 335

Arg Val Asp Gly Ile Met His Thr Arg Cys His Cys Gly Ala Glu Ile
             340                 345                 350

Thr Gly His Val Lys Asn Gly Thr Met Arg Ile Val Gly Pro Arg Thr
         355                 360                 365

Cys Arg Asn Met Trp Ser Gly Thr Phe Pro Ile Asn Ala Tyr Thr Thr
370                 375                 380

Gly Pro Cys Thr Pro Leu Pro Ala Pro Asn Tyr Thr Phe Ala Leu Trp
385                 390                 395                 400

Arg Val Ser Ala Glu Glu Tyr Val Glu Ile Arg Gln Val Gly Asp Phe
             405                 410                 415
```

-continued

```
His Tyr Val Thr Gly Met Thr Thr Asp Asn Leu Lys Cys Pro Cys Gln
            420                 425                 430

Val Pro Ser Pro Glu Phe Phe Thr Glu Leu Asp Gly Val Arg Leu His
        435                 440                 445

Arg Phe Ala Pro Pro Cys Lys Pro Leu Leu Arg Glu Glu Val Ser Phe
    450                 455                 460

Arg Val Gly Leu His Glu Tyr Pro Val Gly Ser Gln Leu Pro Cys Glu
465                 470                 475                 480

Pro Glu Pro Asp Val Ala Val Leu Thr Ser Met Leu Thr Asp Pro Ser
                485                 490                 495

His Ile Thr Ala Glu Ala Ala Gly Arg Arg Leu Asp Pro Leu Asp Cys
            500                 505                 510

Arg His Ala Lys
            515
```

(2) INFORMATION FOR SEQ ID NO:7:

(i) SEQUENCE CHARACTERISTICS:
       (A) LENGTH: 1623 base pairs
       (B) TYPE: nucleic acid
       (C) STRANDEDNESS: single
       (D) TOPOLOGY: circular (ii) MOLECULE TYPE: DNA (genomic)

(ix) FEATURE:
       (A) NAME/KEY: CDS
       (B) LOCATION: 1..1623

(xi) SEQUENCE DESCRIPTION: SEQ ID NO:7:

```
ATG AGT TTT GTG GTC ATT ATT CCC GCG CGC TAC GCG TCG ACG CGT CTG      48
Met Ser Phe Val Val Ile Ile Pro Ala Arg Tyr Ala Ser Thr Arg Leu
 1               5                  10                  15

CCC GGT AAA CCA TTG GTT GAT ATT AAC GGC AAA CCC ATG ATT GTT CAT      96
Pro Gly Lys Pro Leu Val Asp Ile Asn Gly Lys Pro Met Ile Val His
                20                  25                  30

GTT CTT GAA CGC GCG CGT GAA TCA GGT GCC GAG CGC ATC ATC GTG GCA     144
Val Leu Glu Arg Ala Arg Glu Ser Gly Ala Glu Arg Ile Ile Val Ala
            35                  40                  45

ACC GAT CAT GAG GAT GTT GCC CGC GCC GTT GAA GCC GCT GGC GGT GAA     192
Thr Asp His Glu Asp Val Ala Arg Ala Val Glu Ala Ala Gly Gly Glu
        50                  55                  60

GTA TGT ATG ACG CGC GCC GAT CAT CAG TCA GGA ACA GAA CGT CTG GCG     240
Val Cys Met Thr Arg Ala Asp His Gln Ser Gly Thr Glu Arg Leu Ala
65                  70                  75                  80

GAA GTT GTC GAA AAA TGC GCA TTC AGC GAC GAC ACG GTG ATC GTT AAT     288
Glu Val Val Glu Lys Cys Ala Phe Ser Asp Asp Thr Val Ile Val Asn
                85                  90                  95

GTG CAG GGT GAT GAA CCG ATG ATC CCT GCG ACA ATC ATT CGT CAG GTT     336
Val Gln Gly Asp Glu Pro Met Ile Pro Ala Thr Ile Ile Arg Gln Val
                100                 105                 110

GCT GAT AAC CTC GCT CAG CGT CAG GTG GGT ATG GCG ACT CTG GCG GTG     384
Ala Asp Asn Leu Ala Gln Arg Gln Val Gly Met Ala Thr Leu Ala Val
            115                 120                 125

CCA ATC CAC AAT GCG GAA GAA GCG TTT AAC CCG AAT GCG GTG AAA GTG     432
Pro Ile His Asn Ala Glu Glu Ala Phe Asn Pro Asn Ala Val Lys Val
        130                 135                 140

GTT CTC GAC GCT GAA GGG TAT GCA CTG TAC TTC TCT CGC GCC ACC ATT     480
Val Leu Asp Ala Glu Gly Tyr Ala Leu Tyr Phe Ser Arg Ala Thr Ile
145                 150                 155                 160

CCT TGG GAT CGT GAT CGT TTT GCA GAA GGC CTT GAA ACC GTT GGC GAT     528
```

```
              Pro Trp Asp Arg Asp Arg Phe Ala Glu Gly Leu Glu Thr Val Gly Asp
                              165                 170                 175

AAC TTC CTG CGT CAT CTT GGT ATT TAT GGC TAC CGT GCA GGC TTT ATC            576
Asn Phe Leu Arg His Leu Gly Ile Tyr Gly Tyr Arg Ala Gly Phe Ile
              180                 185                 190

CGT CGT TAC GTC AAC TGG CAG CCA AGT CCG TTA GAA CAC ATC GAA ATG            624
Arg Arg Tyr Val Asn Trp Gln Pro Ser Pro Leu Glu His Ile Glu Met
              195                 200                 205

TTA GAG CAG CTT CGT GTT CTG TGG TAC GGC GAA AAA ATC CAT GTT GCT            672
Leu Glu Gln Leu Arg Val Leu Trp Tyr Gly Glu Lys Ile His Val Ala
              210                 215                 220

GTT GCT CAG GAA GTT CCT GGC ACA GGT GTG GAT ACC CCT GAA GAT CTC            720
Val Ala Gln Glu Val Pro Gly Thr Gly Val Asp Thr Pro Glu Asp Leu
225                   230                 235                 240

GAC CCG TCG ACG AAT TCT ATG CGT CGA CTG GCT CGT GGT TCT CCG CCG            768
Asp Pro Ser Thr Asn Ser Met Arg Arg Leu Ala Arg Gly Ser Pro Pro
                  245                 250                 255

TCT GTT GCT TCT TCT TCT GCT TCT CAA CTG TCT GCT CCG TCT CTG AAA            816
Ser Val Ala Ser Ser Ser Ala Ser Gln Leu Ser Ala Pro Ser Leu Lys
                  260                 265                 270

GCT ACC TGC ACC GCT AAC CAC GAC TCT CCG GAC GCT GAA CTG ATC GAA            864
Ala Thr Cys Thr Ala Asn His Asp Ser Pro Asp Ala Glu Leu Ile Glu
              275                 280                 285

GCT AAC CTG CTG TGG CGT CAG GAA ATG GGT GGT AAC ATC ACC CGT GTT            912
Ala Asn Leu Leu Trp Arg Gln Glu Met Gly Gly Asn Ile Thr Arg Val
              290                 295                 300

GAA TCT GAA AAC AAA GTT GTT ATC CTG GAC TCT TTC GAC CCG CTG GTT            960
Glu Ser Glu Asn Lys Val Val Ile Leu Asp Ser Phe Asp Pro Leu Val
305                   310                 315                 320

GCT GAA GAA GAC GAA CGT GAG ATC TCT GTT CCG GCT GAA ATC CTG CGT           1008
Ala Glu Glu Asp Glu Arg Glu Ile Ser Val Pro Ala Glu Ile Leu Arg
                  325                 330                 335

AAA TCT CGT CGT TTC GCT CAG GCT CTG CCG GTT TGG GCT CGT CCG GAC           1056
Lys Ser Arg Arg Phe Ala Gln Ala Leu Pro Val Trp Ala Arg Pro Asp
              340                 345                 350

TAC AAC CCG CCG CTG GTT GAA ACC TGG AAA AAA CCG GAC TAC GAA CCG           1104
Tyr Asn Pro Pro Leu Val Glu Thr Trp Lys Lys Pro Asp Tyr Glu Pro
              355                 360                 365

CCG GTT GTT CAC GGT TGC CCG CTG CCG CCG CCG AAA TCT CCG CCG GTT           1152
Pro Val Val His Gly Cys Pro Leu Pro Pro Pro Lys Ser Pro Pro Val
              370                 375                 380

CCG CCG CCG CGT AAA AAA CGT ACC GTT GTT CTG ACC GAA TCT ACC CTG           1200
Pro Pro Pro Arg Lys Lys Arg Thr Val Val Leu Thr Glu Ser Thr Leu
385                   390                 395                 400

TCT ACC GCT CTG GCT GAA CTG GCT ACC CGT TCT TTC GGT TCT TCT TCT           1248
Ser Thr Ala Leu Ala Glu Leu Ala Thr Arg Ser Phe Gly Ser Ser Ser
                  405                 410                 415

ACC TCG GGT ATC ACC GGT GAC AAC ACC ACC ACC TCT TCT GAA CCG GCT           1296
Thr Ser Gly Ile Thr Gly Asp Asn Thr Thr Thr Ser Ser Glu Pro Ala
              420                 425                 430

CCG TCT GGT TGC CCG CCG GAC TCT GAC GCT GAA TCT TAC TCT TCT ATG           1344
Pro Ser Gly Cys Pro Pro Asp Ser Asp Ala Glu Ser Tyr Ser Ser Met
              435                 440                 445

CCG CCG CTG GAA GGT GAA CCG GGT GAC CCG GAT CTG TCT GAC GGT TCT           1392
Pro Pro Leu Glu Gly Glu Pro Gly Asp Pro Asp Leu Ser Asp Gly Ser
              450                 455                 460

TGG TCT ACC GTT TCT TCT GAA GCT AAC GCT GAA GAC GTT GTT TGC TGC           1440
Trp Ser Thr Val Ser Ser Glu Ala Asn Ala Glu Asp Val Val Cys Cys
465                   470                 475                 480
```

```
TCT ATG TCT TAC TCT TGG ACC GGT GCT CTG GTT ACT CCG TGC GCT GCT    1488
Ser Met Ser Tyr Ser Trp Thr Gly Ala Leu Val Thr Pro Cys Ala Ala
            485                 490                 495

GAA GAA CAG AAA CTG CCG ATC AAC GCT CTG TCT AAC TCT CTG CTG CGT    1536
Glu Glu Gln Lys Leu Pro Ile Asn Ala Leu Ser Asn Ser Leu Leu Arg
            500                 505                 510

CAC CAC AAC CTG GTT TAC TCT ACC ACC TCT CGT TCT GCT TGC CAG CGT    1584
His His Asn Leu Val Tyr Ser Thr Thr Ser Arg Ser Ala Cys Gln Arg
            515                 520                 525

CAG AAA AAA GTT ACC TTC GAC CGT CTG CAA GTT CTA GAC                1623
Gln Lys Lys Val Thr Phe Asp Arg Leu Gln Val Leu Asp
            530                 535                 540
```

(2) INFORMATION FOR SEQ ID NO:8:

(i) SEQUENCE CHARACTERISTICS:
        (A) LENGTH: 541 amino acids
        (B) TYPE: amino acid
        (D) TOPOLOGY: linear (ii) MOLECULE TYPE: protein (xi) SEQUENCE DESCRIPTION: SEQ ID NO:8:

```
Met Ser Phe Val Val Ile Ile Pro Ala Arg Tyr Ala Ser Thr Arg Leu
 1               5                  10                  15

Pro Gly Lys Pro Leu Val Asp Ile Asn Gly Lys Pro Met Ile Val His
                20                  25                  30

Val Leu Glu Arg Ala Arg Glu Ser Gly Ala Glu Arg Ile Ile Val Ala
            35                  40                  45

Thr Asp His Glu Asp Val Ala Arg Ala Val Glu Ala Ala Gly Gly Glu
        50                  55                  60

Val Cys Met Thr Arg Ala Asp His Gln Ser Gly Thr Glu Arg Leu Ala
65                  70                  75                  80

Glu Val Val Glu Lys Cys Ala Phe Ser Asp Asp Thr Val Ile Val Asn
                85                  90                  95

Val Gln Gly Asp Glu Pro Met Ile Pro Ala Thr Ile Ile Arg Gln Val
            100                 105                 110

Ala Asp Asn Leu Ala Gln Arg Gln Val Gly Met Ala Thr Leu Ala Val
        115                 120                 125

Pro Ile His Asn Ala Glu Glu Ala Phe Asn Pro Asn Ala Val Lys Val
    130                 135                 140

Val Leu Asp Ala Glu Gly Tyr Ala Leu Tyr Phe Ser Arg Ala Thr Ile
145                 150                 155                 160

Pro Trp Asp Arg Asp Arg Phe Ala Glu Gly Leu Glu Thr Val Gly Asp
                165                 170                 175

Asn Phe Leu Arg His Leu Gly Ile Tyr Gly Tyr Arg Ala Gly Phe Ile
            180                 185                 190

Arg Arg Tyr Val Asn Trp Gln Pro Ser Pro Leu Glu His Ile Glu Met
        195                 200                 205

Leu Glu Gln Leu Arg Val Leu Trp Tyr Gly Glu Lys Ile His Val Ala
    210                 215                 220

Val Ala Gln Glu Val Pro Gly Thr Gly Val Asp Thr Pro Glu Asp Leu
225                 230                 235                 240

Asp Pro Ser Thr Asn Ser Met Arg Arg Leu Ala Arg Gly Ser Pro Pro
                245                 250                 255

Ser Val Ala Ser Ser Ala Ser Gln Leu Ser Ala Pro Ser Leu Lys
            260                 265                 270
```

```
Ala Thr Cys Thr Ala Asn His Asp Ser Pro Asp Ala Glu Leu Ile Glu
        275                 280                 285

Ala Asn Leu Leu Trp Arg Gln Glu Met Gly Gly Asn Ile Thr Arg Val
    290                 295                 300

Glu Ser Glu Asn Lys Val Val Ile Leu Asp Ser Phe Asp Pro Leu Val
305                 310                 315                 320

Ala Glu Glu Asp Glu Arg Glu Ile Ser Val Pro Ala Glu Ile Leu Arg
                325                 330                 335

Lys Ser Arg Arg Phe Ala Gln Ala Leu Pro Val Trp Ala Arg Pro Asp
                340                 345                 350

Tyr Asn Pro Pro Leu Val Glu Thr Trp Lys Lys Pro Asp Tyr Glu Pro
        355                 360                 365

Pro Val His Gly Cys Pro Leu Pro Pro Lys Ser Pro Pro Val
    370                 375                 380

Pro Pro Pro Arg Lys Lys Arg Thr Val Val Leu Thr Glu Ser Thr Leu
385                 390                 395                 400

Ser Thr Ala Leu Ala Glu Leu Ala Thr Arg Ser Phe Gly Ser Ser Ser
                405                 410                 415

Thr Ser Gly Ile Thr Gly Asp Asn Thr Thr Thr Ser Ser Glu Pro Ala
        420                 425                 430

Pro Ser Gly Cys Pro Pro Asp Ser Asp Ala Glu Ser Tyr Ser Ser Met
        435                 440                 445

Pro Pro Leu Glu Gly Glu Pro Gly Asp Pro Asp Leu Ser Asp Gly Ser
        450                 455                 460

Trp Ser Thr Val Ser Ser Glu Ala Asn Ala Glu Asp Val Val Cys Cys
465                 470                 475                 480

Ser Met Ser Tyr Ser Trp Thr Gly Ala Leu Val Thr Pro Cys Ala Ala
                485                 490                 495

Glu Glu Gln Lys Leu Pro Ile Asn Ala Leu Ser Asn Ser Leu Leu Arg
                500                 505                 510

His His Asn Leu Val Tyr Ser Thr Thr Ser Arg Ser Ala Cys Gln Arg
        515                 520                 525

Gln Lys Lys Val Thr Phe Asp Arg Leu Gln Val Leu Asp
530                 535                 540

(2) INFORMATION FOR SEQ ID NO:9:

(i) SEQUENCE CHARACTERISTICS:
        (A) LENGTH: 1488 base pairs
        (B) TYPE: nucleic acid
        (C) STRANDEDNESS: single
        (D) TOPOLOGY: circular (ii) MOLECULE TYPE: DNA (genomic)

(ix) FEATURE:
        (A) NAME/KEY: CDS
        (B) LOCATION: 1..1488

(xi) SEQUENCE DESCRIPTION: SEQ ID NO:9:

ATG AGT TTT GTG GTC ATT ATT CCC GCG CGC TAC GCG TCG ACG CGT CTG      48
Met Ser Phe Val Val Ile Ile Pro Ala Arg Tyr Ala Ser Thr Arg Leu
  1               5                  10                  15

CCC GGT AAA CCA TTG GTT GAT ATT AAC GGC AAA CCC ATG ATT GTT CAT      96
Pro Gly Lys Pro Leu Val Asp Ile Asn Gly Lys Pro Met Ile Val His
                 20                  25                  30

GTT CTT GAA CGC GCG CGT GAA TCA GGT GCC GAG CGC ATC ATC GTG GCA     144
Val Leu Glu Arg Ala Arg Glu Ser Gly Ala Glu Arg Ile Ile Val Ala
             35                  40                  45
```

```
ACC GAT CAT GAG GAT GTT GCC CGC GCC GTT GAA GCC GCT GGC GGT GAA      192
Thr Asp His Glu Asp Val Ala Arg Ala Val Glu Ala Ala Gly Gly Glu
     50                  55                  60

GTA TGT ATG ACG CGC GCC GAT CAT CAG TCA GGA ACA GAA CGT CTG GCG      240
Val Cys Met Thr Arg Ala Asp His Gln Ser Gly Thr Glu Arg Leu Ala
 65                  70                  75                  80

GAA GTT GTC GAA AAA TGC GCA TTC AGC GAC GAC ACG GTG ATC GTT AAT      288
Glu Val Val Glu Lys Cys Ala Phe Ser Asp Asp Thr Val Ile Val Asn
                 85                  90                  95

GTG CAG GGT GAT GAA CCG ATG ATC CCT GCG ACA ATC ATT CGT CAG GTT      336
Val Gln Gly Asp Glu Pro Met Ile Pro Ala Thr Ile Ile Arg Gln Val
            100                 105                 110

GCT GAT AAC CTC GCT CAG CGT CAG GTG GGT ATG GCG ACT CTG GCG GTG      384
Ala Asp Asn Leu Ala Gln Arg Gln Val Gly Met Ala Thr Leu Ala Val
        115                 120                 125

CCA ATC CAC AAT GCG GAA GAA GCG TTT AAC CCG AAT GCG GTG AAA GTG      432
Pro Ile His Asn Ala Glu Glu Ala Phe Asn Pro Asn Ala Val Lys Val
    130                 135                 140

GTT CTC GAC GCT GAA GGG TAT GCA CTG TAC TTC TCT CGC GCC ACC ATT      480
Val Leu Asp Ala Glu Gly Tyr Ala Leu Tyr Phe Ser Arg Ala Thr Ile
145                 150                 155                 160

CCT TGG GAT CGT GAT CGT TTT GCA GAA GGC CTT GAA ACC GTT GGC GAT      528
Pro Trp Asp Arg Asp Arg Phe Ala Glu Gly Leu Glu Thr Val Gly Asp
                165                 170                 175

AAC TTC CTG CGT CAT CTT GGT ATT TAT GGC TAC CGT GCA GGC TTT ATC      576
Asn Phe Leu Arg His Leu Gly Ile Tyr Gly Tyr Arg Ala Gly Phe Ile
            180                 185                 190

CGT CGT TAC GTC AAC TGG CAG CCA AGT CCG TTA GAA CAC ATC GAA ATG      624
Arg Arg Tyr Val Asn Trp Gln Pro Ser Pro Leu Glu His Ile Glu Met
        195                 200                 205

TTA GAG CAG CTT CGT GTT CTG TGG TAC GGC GAA AAA ATC CAT GTT GCT      672
Leu Glu Gln Leu Arg Val Leu Trp Tyr Gly Glu Lys Ile His Val Ala
    210                 215                 220

GTT GCT CAG GAA GTT CCT GGC ACA GGT GTG GAT ACC CCT GAA GAT CTC      720
Val Ala Gln Glu Val Pro Gly Thr Gly Val Asp Thr Pro Glu Asp Leu
225                 230                 235                 240

GAC CCG TCG ACG AAT TCT CTA GAC TCC CAC TAC CAG GAC GTT CTG AAA      768
Asp Pro Ser Thr Asn Ser Leu Asp Ser His Tyr Gln Asp Val Leu Lys
                245                 250                 255

GAA GTT AAA GCT GCT GCT TCT AAA GTT AAA GCT AAC CTG CTG TCT GTT      816
Glu Val Lys Ala Ala Ala Ser Lys Val Lys Ala Asn Leu Leu Ser Val
            260                 265                 270

GAA GAA GCA TGC TCT CTG ACC CCG CCG CAC TCT GCT AAA TCT AAA TTC      864
Glu Glu Ala Cys Ser Leu Thr Pro Pro His Ser Ala Lys Ser Lys Phe
        275                 280                 285

GGT TAC GGT GCT AAA GAC GTT CGT TGC CAC GCT CGT AAA GCT GTT ACC      912
Gly Tyr Gly Ala Lys Asp Val Arg Cys His Ala Arg Lys Ala Val Thr
    290                 295                 300

CAC ATC AAC TCT GTT TGG AAA GAT CTG CTG GAA GAC AAC GTT ACC CCG      960
His Ile Asn Ser Val Trp Lys Asp Leu Leu Glu Asp Asn Val Thr Pro
305                 310                 315                 320

ATC GAC ACC ACC ATC ATG GCT AAA AAC GAA GTT TTC TGC GTT CAG CCG     1008
Ile Asp Thr Thr Ile Met Ala Lys Asn Glu Val Phe Cys Val Gln Pro
                325                 330                 335

GAA AAA GGT GGT CGT AAA CCG GCT CGT CTG ATC GTT TTC CCG GAC CTG     1056
Glu Lys Gly Gly Arg Lys Pro Ala Arg Leu Ile Val Phe Pro Asp Leu
            340                 345                 350

GGT GTT CGT GTT TGC GAA AAA ATG GCT CTG TAC GAC GTT GTT ACC AAA     1104
Gly Val Arg Val Cys Glu Lys Met Ala Leu Tyr Asp Val Val Thr Lys
```

```
                 355                  360                      365
CTG CCG CTG GCT GTT ATG GGT TCT TCT TAC GGT TTC CAG TAC TCT CCG    1152
Leu Pro Leu Ala Val Met Gly Ser Ser Tyr Gly Phe Gln Tyr Ser Pro
    370                 375                 380

GGT CAG CGT GTT GAG TTC CTG GTT CAG GCT TGG AAA TCT AAA AAA ACC    1200
Gly Gln Arg Val Glu Phe Leu Val Gln Ala Trp Lys Ser Lys Lys Thr
385                 390                 395                 400

CCG ATG GGT TTC TCT TAC GAC ACC CGT TGC TTC GAC TCT ACC GTT ACC    1248
Pro Met Gly Phe Ser Tyr Asp Thr Arg Cys Phe Asp Ser Thr Val Thr
                405                 410                 415

GAA TCT GAC ATT CGT ACC GAA GAA GCT ATC TAC CAG TGC TGC GAC CTG    1296
Glu Ser Asp Ile Arg Thr Glu Glu Ala Ile Tyr Gln Cys Cys Asp Leu
            420                 425                 430

GAC CCG CAG GCT CGT GTT GCT ATC AAA TCT CTG ACC GAA CGT CTG TAC    1344
Asp Pro Gln Ala Arg Val Ala Ile Lys Ser Leu Thr Glu Arg Leu Tyr
        435                 440                 445

GTT GGT GGT CCG CTG ACC AAC TCT CGG GGT GAA AAC TGC GGT TAC CGT    1392
Val Gly Gly Pro Leu Thr Asn Ser Arg Gly Glu Asn Cys Gly Tyr Arg
    450                 455                 460

CGT TGC CGT GCT TCT GGT GTT CTG ACC ACC TCT TGC GGT AAC ACC CTG    1440
Arg Cys Arg Ala Ser Gly Val Leu Thr Thr Ser Cys Gly Asn Thr Leu
465                 470                 475                 480

ACC TGC TAC ATC AAA GCT CGT GCT GCT TGC CGT GCT GCT GGT CTG CAG    1488
Thr Cys Tyr Ile Lys Ala Arg Ala Ala Cys Arg Ala Ala Gly Leu Gln
                485                 490                 495
```

(2) INFORMATION FOR SEQ ID NO:10:

(i) SEQUENCE CHARACTERISTICS:
        (A) LENGTH: 496 amino acids
        (B) TYPE: amino acid
        (D) TOPOLOGY: linear (ii) MOLECULE TYPE: protein (xi) SEQUENCE DESCRIPTION: SEQ ID NO:10:

```
Met Ser Phe Val Val Ile Ile Pro Ala Arg Tyr Ala Ser Thr Arg Leu
 1               5                  10                  15

Pro Gly Lys Pro Leu Val Asp Ile Asn Gly Lys Pro Met Ile Val His
                20                  25                  30

Val Leu Glu Arg Ala Arg Glu Ser Gly Ala Glu Arg Ile Ile Val Ala
            35                  40                  45

Thr Asp His Glu Asp Val Ala Arg Ala Val Glu Ala Ala Gly Gly Glu
        50                  55                  60

Val Cys Met Thr Arg Ala Asp His Gln Ser Gly Thr Glu Arg Leu Ala
65                  70                  75                  80

Glu Val Val Glu Lys Cys Ala Phe Ser Asp Asp Thr Val Ile Val Asn
                85                  90                  95

Val Gln Gly Asp Glu Pro Met Ile Pro Ala Thr Ile Ile Arg Gln Val
            100                 105                 110

Ala Asp Asn Leu Ala Gln Arg Gln Val Gly Met Ala Thr Leu Ala Val
        115                 120                 125

Pro Ile His Asn Ala Glu Glu Ala Phe Asn Pro Asn Ala Val Lys Val
    130                 135                 140

Val Leu Asp Ala Glu Gly Tyr Ala Leu Tyr Phe Ser Arg Ala Thr Ile
145                 150                 155                 160

Pro Trp Asp Arg Asp Arg Phe Ala Glu Gly Leu Glu Thr Val Gly Asp
                165                 170                 175
```

```
Asn Phe Leu Arg His Leu Gly Ile Tyr Gly Tyr Arg Ala Gly Phe Ile
            180                 185                 190

Arg Arg Tyr Val Asn Trp Gln Pro Ser Pro Leu Glu His Ile Glu Met
        195                 200                 205

Leu Glu Gln Leu Arg Val Leu Trp Tyr Gly Glu Lys Ile His Val Ala
    210                 215                 220

Val Ala Gln Glu Val Pro Gly Thr Gly Val Asp Thr Pro Glu Asp Leu
225                 230                 235                 240

Asp Pro Ser Thr Asn Ser Leu Asp Ser His Tyr Gln Asp Val Leu Lys
                245                 250                 255

Glu Val Lys Ala Ala Ser Lys Val Lys Ala Asn Leu Leu Ser Val
            260                 265                 270

Glu Glu Ala Cys Ser Leu Thr Pro Pro His Ser Ala Lys Ser Lys Phe
        275                 280                 285

Gly Tyr Gly Ala Lys Asp Val Arg Cys His Ala Arg Lys Ala Val Thr
    290                 295                 300

His Ile Asn Ser Val Trp Lys Asp Leu Leu Glu Asp Asn Val Thr Pro
305                 310                 315                 320

Ile Asp Thr Thr Ile Met Ala Lys Asn Glu Val Phe Cys Val Gln Pro
                325                 330                 335

Glu Lys Gly Gly Arg Lys Pro Ala Arg Leu Ile Val Phe Pro Asp Leu
            340                 345                 350

Gly Val Arg Val Cys Glu Lys Met Ala Leu Tyr Asp Val Val Thr Lys
        355                 360                 365

Leu Pro Leu Ala Val Met Gly Ser Ser Tyr Gly Phe Gln Tyr Ser Pro
    370                 375                 380

Gly Gln Arg Val Glu Phe Leu Val Gln Ala Trp Lys Ser Lys Lys Thr
385                 390                 395                 400

Pro Met Gly Phe Ser Tyr Asp Thr Arg Cys Phe Asp Ser Thr Val Thr
                405                 410                 415

Glu Ser Asp Ile Arg Thr Glu Glu Ala Ile Tyr Gln Cys Cys Asp Leu
            420                 425                 430

Asp Pro Gln Ala Arg Val Ala Ile Lys Ser Leu Thr Glu Arg Leu Tyr
        435                 440                 445

Val Gly Gly Pro Leu Thr Asn Ser Arg Gly Glu Asn Cys Gly Tyr Arg
    450                 455                 460

Arg Cys Arg Ala Ser Gly Val Leu Thr Thr Ser Cys Gly Asn Thr Leu
465                 470                 475                 480

Thr Cys Tyr Ile Lys Ala Arg Ala Ala Cys Arg Ala Ala Gly Leu Gln
                485                 490                 495

(2) INFORMATION FOR SEQ ID NO:11:

(i) SEQUENCE CHARACTERISTICS:
        (A) LENGTH: 1161 base pairs
        (B) TYPE: nucleic acid
        (C) STRANDEDNESS: single
        (D) TOPOLOGY: circular (ii) MOLECULE TYPE: DNA (genomic)

(ix) FEATURE:
        (A) NAME/KEY: CDS
        (B) LOCATION: 1..1161

(xi) SEQUENCE DESCRIPTION: SEQ ID NO:11:

ATG AGT TTT GTG GTC ATT ATT CCC GCG CGC TAC GCG TCG ACG CGT CTG      48
Met Ser Phe Val Val Ile Ile Pro Ala Arg Tyr Ala Ser Thr Arg Leu
```

|  |  |  |  |  |  |  |  |  |  |  |  |  |  |  |  |
|---|---|---|---|---|---|---|---|---|---|---|---|---|---|---|---|
| 1 |  |  |  | 5 |  |  |  |  | 10 |  |  |  |  | 15 |  |

```
CCC GGT AAA CCA TTG GTT GAT ATT AAC GGC AAA CCC ATG ATT GTT CAT        96
Pro Gly Lys Pro Leu Val Asp Ile Asn Gly Lys Pro Met Ile Val His
             20                  25                  30

GTT CTT GAA CGC GCG CGT GAA TCA GGT GCC GAG CGC ATC ATC GTG GCA       144
Val Leu Glu Arg Ala Arg Glu Ser Gly Ala Glu Arg Ile Ile Val Ala
         35                  40                  45

ACC GAT CAT GAG GAT GTT GCC CGC GCC GTT GAA GCC GCT GGC GGT GAA       192
Thr Asp His Glu Asp Val Ala Arg Ala Val Glu Ala Ala Gly Gly Glu
     50                  55                  60

GTA TGT ATG ACG CGC GCC GAT CAT CAG TCA GGA ACA GAA CGT CTG GCG       240
Val Cys Met Thr Arg Ala Asp His Gln Ser Gly Thr Glu Arg Leu Ala
 65                  70                  75                  80

GAA GTT GTC GAA AAA TGC GCA TTC AGC GAC GAC ACG GTG ATC GTT AAT       288
Glu Val Val Glu Lys Cys Ala Phe Ser Asp Asp Thr Val Ile Val Asn
                 85                  90                  95

GTG CAG GGT GAT GAA CCG ATG ATC CCT GCG ACA ATC ATT CGT CAG GTT       336
Val Gln Gly Asp Glu Pro Met Ile Pro Ala Thr Ile Ile Arg Gln Val
             100                 105                 110

GCT GAT AAC CTC GCT CAG CGT CAG GTG GGT ATG GCG ACT CTG GCG GTG       384
Ala Asp Asn Leu Ala Gln Arg Gln Val Gly Met Ala Thr Leu Ala Val
         115                 120                 125

CCA ATC CAC AAT GCG GAA GAA GCG TTT AAC CCG AAT GCG GTG AAA GTG       432
Pro Ile His Asn Ala Glu Glu Ala Phe Asn Pro Asn Ala Val Lys Val
     130                 135                 140

GTT CTC GAC GCT GAA GGG TAT GCA CTG TAC TTC TCT CGC GCC ACC ATT       480
Val Leu Asp Ala Glu Gly Tyr Ala Leu Tyr Phe Ser Arg Ala Thr Ile
145                 150                 155                 160

CCT TGG GAT CGT GAT CGT TTT GCA GAA GGC CTT GAA ACC GTT GGC GAT       528
Pro Trp Asp Arg Asp Arg Phe Ala Glu Gly Leu Glu Thr Val Gly Asp
                 165                 170                 175

AAC TTC CTG CGT CAT CTT GGT ATT TAT GGC TAC CGT GCA GGC TTT ATC       576
Asn Phe Leu Arg His Leu Gly Ile Tyr Gly Tyr Arg Ala Gly Phe Ile
             180                 185                 190

CGT CGT TAC GTC AAC TGG CAG CCA AGT CCG TTA GAA CAC ATC GAA ATG       624
Arg Arg Tyr Val Asn Trp Gln Pro Ser Pro Leu Glu His Ile Glu Met
         195                 200                 205

TTA GAG CAG CTT CGT GTT CTG TGG TAC GGC GAA AAA ATC CAT GTT GCT       672
Leu Glu Gln Leu Arg Val Leu Trp Tyr Gly Glu Lys Ile His Val Ala
     210                 215                 220

GTT GCT CAG GAA GTT CCT GGC ACA GGT GTG GAT ACC CCT GAA GAT CTC       720
Val Ala Gln Glu Val Pro Gly Thr Gly Val Asp Thr Pro Glu Asp Leu
225                 230                 235                 240

GAC CCG TCG ACG AAT TGC ATG CTG CAG GAC TGC ACC ATG CTG GTT TGC       768
Asp Pro Ser Thr Asn Cys Met Leu Gln Asp Cys Thr Met Leu Val Cys
                 245                 250                 255

GGT GAC GAC CTG GTT GTT ATC TGC GAA TCT GCT GGT GTT CAG GAA GAC       816
Gly Asp Asp Leu Val Val Ile Cys Glu Ser Ala Gly Val Gln Glu Asp
             260                 265                 270

GCT GCT TCT CTG CGT GCT TTC ACC GAA GCT ATG ACC CGT TAC TCT GCT       864
Ala Ala Ser Leu Arg Ala Phe Thr Glu Ala Met Thr Arg Tyr Ser Ala
         275                 280                 285

CCC CCG GGT GAC CCG CCG CAG CCG GAA TAC GAC CTG GAA CTG ATC ACC       912
Pro Pro Gly Asp Pro Pro Gln Pro Glu Tyr Asp Leu Glu Leu Ile Thr
     290                 295                 300

TCT TGC TCT TCT AAC GTT TCT GTT GCT CAC GAC GGT GCT GGT AAA CGT       960
Ser Cys Ser Ser Asn Val Ser Val Ala His Asp Gly Ala Gly Lys Arg
305                 310                 315                 320

GTT TAC TAC CTG ACC CGT GAC CCG ACC ACC CCG CTG GCT CGT GCT GCT      1008
```

```
Val Tyr Tyr Leu Thr Arg Asp Pro Thr Thr Pro Leu Ala Arg Ala Ala
                325                 330                 335

TGG GAA ACC GCT CGT CAC ACC CCG GTA AAC TCT TGG CTG GGT AAC ATC    1056
Trp Glu Thr Ala Arg His Thr Pro Val Asn Ser Trp Leu Gly Asn Ile
                340                 345                 350

ATC ATG TTC GCT CCG ACC CTG TGG GCC CGT ATG ATC CTG ATG ACC CAC    1104
Ile Met Phe Ala Pro Thr Leu Trp Ala Arg Met Ile Leu Met Thr His
            355                 360                 365

TTC TTC TCT GTT CTG ATC GCT CGT GAC CAG CTG GAA CAG GCT CTG GAC    1152
Phe Phe Ser Val Leu Ile Ala Arg Asp Gln Leu Glu Gln Ala Leu Asp
370                 375                 380

TGC GAG ATC                                                         1161
Cys Glu Ile
385
```

(2) INFORMATION FOR SEQ ID NO:12:

(i) SEQUENCE CHARACTERISTICS:
        (A) LENGTH: 387 amino acids
        (B) TYPE: amino acid
        (D) TOPOLOGY: linear (ii) MOLECULE TYPE: protein (xi) SEQUENCE DESCRIPTION: SEQ ID NO:12:

```
Met Ser Phe Val Val Ile Ile Pro Ala Arg Tyr Ala Ser Thr Arg Leu
 1               5                  10                  15

Pro Gly Lys Pro Leu Val Asp Ile Asn Gly Lys Pro Met Ile Val His
                20                  25                  30

Val Leu Glu Arg Ala Arg Glu Ser Gly Ala Glu Arg Ile Ile Val Ala
            35                  40                  45

Thr Asp His Glu Asp Val Ala Arg Ala Val Glu Ala Ala Gly Gly Glu
        50                  55                  60

Val Cys Met Thr Arg Ala Asp His Gln Ser Gly Thr Glu Arg Leu Ala
65                  70                  75                  80

Glu Val Val Glu Lys Cys Ala Phe Ser Asp Asp Thr Val Ile Val Asn
                85                  90                  95

Val Gln Gly Asp Glu Pro Met Ile Pro Ala Thr Ile Ile Arg Gln Val
                100                 105                 110

Ala Asp Asn Leu Ala Gln Arg Gln Val Gly Met Ala Thr Leu Ala Val
            115                 120                 125

Pro Ile His Asn Ala Glu Glu Ala Phe Asn Pro Asn Ala Val Lys Val
        130                 135                 140

Val Leu Asp Ala Glu Gly Tyr Ala Leu Tyr Phe Ser Arg Ala Thr Ile
145                 150                 155                 160

Pro Trp Asp Arg Asp Arg Phe Ala Glu Gly Leu Glu Thr Val Gly Asp
                165                 170                 175

Asn Phe Leu Arg His Leu Gly Ile Tyr Gly Tyr Arg Ala Gly Phe Ile
                180                 185                 190

Arg Arg Tyr Val Asn Trp Gln Pro Ser Pro Leu Glu His Ile Glu Met
            195                 200                 205

Leu Glu Gln Leu Arg Val Leu Trp Tyr Gly Glu Lys Ile His Val Ala
        210                 215                 220

Val Ala Gln Glu Val Pro Gly Thr Gly Val Asp Thr Pro Glu Asp Leu
225                 230                 235                 240

Asp Pro Ser Thr Asn Cys Met Leu Gln Asp Cys Thr Met Leu Val Cys
                245                 250                 255
```

```
Gly Asp Asp Leu Val Val Ile Cys Glu Ser Ala Gly Val Gln Glu Asp
            260                 265                 270

Ala Ala Ser Leu Arg Ala Phe Thr Glu Ala Met Thr Arg Tyr Ser Ala
            275                 280                 285

Pro Pro Gly Asp Pro Pro Gln Pro Glu Tyr Asp Leu Glu Leu Ile Thr
    290                 295                 300

Ser Cys Ser Ser Asn Val Ser Val Ala His Asp Gly Ala Gly Lys Arg
305                 310                 315                 320

Val Tyr Tyr Leu Thr Arg Asp Pro Thr Thr Pro Leu Ala Arg Ala Ala
                325                 330                 335

Trp Glu Thr Ala Arg His Thr Pro Val Asn Ser Trp Leu Gly Asn Ile
            340                 345                 350

Ile Met Phe Ala Pro Thr Leu Trp Ala Arg Met Ile Leu Met Thr His
            355                 360                 365

Phe Phe Ser Val Leu Ile Ala Arg Asp Gln Leu Glu Gln Ala Leu Asp
    370                 375                 380

Cys Glu Ile
385
```

(2) INFORMATION FOR SEQ ID NO:13:

(i) SEQUENCE CHARACTERISTICS:
       (A) LENGTH: 1179 base pairs
       (B) TYPE: nucleic acid
       (C) STRANDEDNESS: single
       (D) TOPOLOGY: circular (ii) MOLECULE TYPE: DNA (genomic)

(ix) FEATURE:
       (A) NAME/KEY: CDS
       (B) LOCATION: 1..1179

(xi) SEQUENCE DESCRIPTION: SEQ ID NO:13:

```
ATG AGT TTT GTG GTC ATT ATT CCC GCG CGC TAC GCG TCG ACG CGT CTG        48
Met Ser Phe Val Val Ile Ile Pro Ala Arg Tyr Ala Ser Thr Arg Leu
  1               5                  10                  15

CCC GGT AAA CCA TTG GTT GAT ATT AAC GGC AAA CCC ATG ATT GTT CAT        96
Pro Gly Lys Pro Leu Val Asp Ile Asn Gly Lys Pro Met Ile Val His
                 20                  25                  30

GTT CTT GAA CGC GCG CGT GAA TCA GGT GCC GAG CGC ATC ATC GTG GCA       144
Val Leu Glu Arg Ala Arg Glu Ser Gly Ala Glu Arg Ile Ile Val Ala
             35                  40                  45

ACC GAT CAT GAG GAT GTT GCC CGC GCC GTT GAA GCC GCT GGC GGT GAA       192
Thr Asp His Glu Asp Val Ala Arg Ala Val Glu Ala Ala Gly Gly Glu
         50                  55                  60

GTA TGT ATG ACG CGC GCC GAT CAT CAG TCA GGA ACA GAA CGT CTG GCG       240
Val Cys Met Thr Arg Ala Asp His Gln Ser Gly Thr Glu Arg Leu Ala
 65                  70                  75                  80

GAA GTT GTC GAA AAA TGC GCA TTC AGC GAC GAC ACG GTG ATC GTT AAT       288
Glu Val Val Glu Lys Cys Ala Phe Ser Asp Asp Thr Val Ile Val Asn
                 85                  90                  95

GTG CAG GGT GAT GAA CCG ATG ATC CCT GCG ACA ATC ATT CGT CAG GTT       336
Val Gln Gly Asp Glu Pro Met Ile Pro Ala Thr Ile Ile Arg Gln Val
            100                 105                 110

GCT GAT AAC CTC GCT CAG CGT CAG GTG GGT ATG GCG ACT CTG GCG GTG       384
Ala Asp Asn Leu Ala Gln Arg Gln Val Gly Met Ala Thr Leu Ala Val
        115                 120                 125

CCA ATC CAC AAT GCG GAA GAA GCG TTT AAC CCG AAT GCG GTG AAA GTG       432
Pro Ile His Asn Ala Glu Glu Ala Phe Asn Pro Asn Ala Val Lys Val
    130                 135                 140
```

```
GTT CTC GAC GCT GAA GGG TAT GCA CTG TAC TTC TCT CGC GCC ACC ATT      480
Val Leu Asp Ala Glu Gly Tyr Ala Leu Tyr Phe Ser Arg Ala Thr Ile
145                 150                 155                 160

CCT TGG GAT CGT GAT CGT TTT GCA GAA GGC CTT GAA ACC GTT GGC GAT      528
Pro Trp Asp Arg Asp Arg Phe Ala Glu Gly Leu Glu Thr Val Gly Asp
                165                 170                 175

AAC TTC CTG CGT CAT CTT GGT ATT TAT GGC TAC CGT GCA GGC TTT ATC      576
Asn Phe Leu Arg His Leu Gly Ile Tyr Gly Tyr Arg Ala Gly Phe Ile
            180                 185                 190

CGT CGT TAC GTC AAC TGG CAG CCA AGT CCG TTA GAA CAC ATC GAA ATG      624
Arg Arg Tyr Val Asn Trp Gln Pro Ser Pro Leu Glu His Ile Glu Met
        195                 200                 205

TTA GAG CAG CTT CGT GTT CTG TGG TAC GGC GAA AAA ATC CAT GTT GCT      672
Leu Glu Gln Leu Arg Val Leu Trp Tyr Gly Glu Lys Ile His Val Ala
    210                 215                 220

GTT GCT CAG GAA GTT CCT GGC ACA GGT GTG GAT ACC CCT GAA GAT CTC      720
Val Ala Gln Glu Val Pro Gly Thr Gly Val Asp Thr Pro Glu Asp Leu
225                 230                 235                 240

GAC CCG TCG ACG AAT TCC ATG GAG ATC TAC GGT GCT TGC TAC TCT ATC      768
Asp Pro Ser Thr Asn Ser Met Glu Ile Tyr Gly Ala Cys Tyr Ser Ile
                245                 250                 255

GAA CCG CTG GAC CTG CCG CCG ATC ATT CAG CGT CTG CAC GGT CTG TCT      816
Glu Pro Leu Asp Leu Pro Pro Ile Ile Gln Arg Leu His Gly Leu Ser
            260                 265                 270

GCT TTC TCT CTG CAC TCT TAC TCC CCG GGT GAA ATC AAC CGT GTT GCT      864
Ala Phe Ser Leu His Ser Tyr Ser Pro Gly Glu Ile Asn Arg Val Ala
        275                 280                 285

GCT TGC CTG CGT AAA CTG GGT GTT CCG CCG CTG CGT GCT TGG CGT CAC      912
Ala Cys Leu Arg Lys Leu Gly Val Pro Pro Leu Arg Ala Trp Arg His
    290                 295                 300

CGT GCT CGT TCT GTT CGT GCT CGT CTG CTG GCT CGT GGT GGC CGT GCT      960
Arg Ala Arg Ser Val Arg Ala Arg Leu Leu Ala Arg Gly Gly Arg Ala
305                 310                 315                 320

GCT ATC TGC GGT AAA TAC CTG TTC AAC TGG GCT GTT CGT ACC AAA CTG     1008
Ala Ile Cys Gly Lys Tyr Leu Phe Asn Trp Ala Val Arg Thr Lys Leu
                325                 330                 335

AAA CTG ACC CCG ATC GCT GCT GCT GGT CAG CTG GAC CTG TCT GGT TGG     1056
Lys Leu Thr Pro Ile Ala Ala Ala Gly Gln Leu Asp Leu Ser Gly Trp
            340                 345                 350

TTC ACC GCT GGT TAC TCT GGT GGT GAC ATC TAC CAC TCT GTT TCT CAC     1104
Phe Thr Ala Gly Tyr Ser Gly Gly Asp Ile Tyr His Ser Val Ser His
        355                 360                 365

GCT CGT CCG CGT TGG ATC TGG TTC TGC CTG CTG CTG CTG GCT GCT GGT     1152
Ala Arg Pro Arg Trp Ile Trp Phe Cys Leu Leu Leu Leu Ala Ala Gly
    370                 375                 380

GTT GGT ATC TAC CTG CTG CCG AAC CGT                                  1179
Val Gly Ile Tyr Leu Leu Pro Asn Arg
385                 390

(2) INFORMATION FOR SEQ ID NO:14:

(i) SEQUENCE CHARACTERISTICS:
        (A) LENGTH: 393 amino acids
        (B) TYPE: amino acid
        (D) TOPOLOGY: linear (ii) MOLECULE TYPE: protein (xi) SEQUENCE DESCRIPTION: SEQ ID NO:14:

Met Ser Phe Val Val Ile Ile Pro Ala Arg Tyr Ala Ser Thr Arg Leu
  1               5                  10                  15
```

```
Pro Gly Lys Pro Leu Val Asp Ile Asn Gly Lys Pro Met Ile Val His
         20                  25                  30
Val Leu Glu Arg Ala Arg Glu Ser Gly Ala Glu Arg Ile Ile Val Ala
         35                  40                  45
Thr Asp His Glu Asp Val Ala Arg Ala Val Glu Ala Ala Gly Gly Glu
     50                  55                  60
Val Cys Met Thr Arg Ala Asp His Gln Ser Gly Thr Glu Arg Leu Ala
65                  70                  75                  80
Glu Val Val Glu Lys Cys Ala Phe Ser Asp Asp Thr Val Ile Val Asn
                 85                  90                  95
Val Gln Gly Asp Glu Pro Met Ile Pro Ala Thr Ile Ile Arg Gln Val
             100                 105                 110
Ala Asp Asn Leu Ala Gln Arg Gln Val Gly Met Ala Thr Leu Ala Val
         115                 120                 125
Pro Ile His Asn Ala Glu Glu Ala Phe Asn Pro Asn Ala Val Lys Val
     130                 135                 140
Val Leu Asp Ala Glu Gly Tyr Ala Leu Tyr Phe Ser Arg Ala Thr Ile
145                 150                 155                 160
Pro Trp Asp Arg Asp Arg Phe Ala Glu Gly Leu Glu Thr Val Gly Asp
                 165                 170                 175
Asn Phe Leu Arg His Leu Gly Ile Tyr Gly Tyr Arg Ala Gly Phe Ile
             180                 185                 190
Arg Arg Tyr Val Asn Trp Gln Pro Ser Pro Leu Glu His Ile Glu Met
         195                 200                 205
Leu Glu Gln Leu Arg Val Leu Trp Tyr Gly Glu Lys Ile His Val Ala
     210                 215                 220
Val Ala Gln Glu Val Pro Gly Thr Gly Val Asp Thr Pro Glu Asp Leu
225                 230                 235                 240
Asp Pro Ser Thr Asn Ser Met Glu Ile Tyr Gly Ala Cys Tyr Ser Ile
                 245                 250                 255
Glu Pro Leu Asp Leu Pro Pro Ile Ile Gln Arg Leu His Gly Leu Ser
             260                 265                 270
Ala Phe Ser Leu His Ser Tyr Ser Pro Gly Glu Ile Asn Arg Val Ala
         275                 280                 285
Ala Cys Leu Arg Lys Leu Gly Val Pro Pro Leu Arg Ala Trp Arg His
     290                 295                 300
Arg Ala Arg Ser Val Arg Ala Arg Leu Leu Ala Arg Gly Gly Arg Ala
305                 310                 315                 320
Ala Ile Cys Gly Lys Tyr Leu Phe Asn Trp Ala Val Arg Thr Lys Leu
                 325                 330                 335
Lys Leu Thr Pro Ile Ala Ala Gly Gln Leu Asp Leu Ser Gly Trp
             340                 345                 350
Phe Thr Ala Gly Tyr Ser Gly Gly Asp Ile Tyr His Ser Val Ser His
         355                 360                 365
Ala Arg Pro Arg Trp Ile Trp Phe Cys Leu Leu Leu Ala Ala Gly
     370                 375                 380
Val Gly Ile Tyr Leu Leu Pro Asn Arg
385                 390

(2) INFORMATION FOR SEQ ID NO:15:

(i) SEQUENCE CHARACTERISTICS:
        (A) LENGTH: 1791 base pairs
        (B) TYPE: nucleic acid
```

(C) STRANDEDNESS: single
            (D) TOPOLOGY: circular (ii) MOLECULE TYPE: DNA (genomic)

(ix) FEATURE:
            (A) NAME/KEY: CDS
            (B) LOCATION: 1..1791

(xi) SEQUENCE DESCRIPTION: SEQ ID NO:15:

```
ATG AGT TTT GTG GTC ATT ATT CCC GCG CGC TAC GCG TCG ACG CGT CTG       48
Met Ser Phe Val Val Ile Ile Pro Ala Arg Tyr Ala Ser Thr Arg Leu
  1               5                  10                  15

CCC GGT AAA CCA TTG GTT GAT ATT AAC GGC AAA CCC ATG ATT GTT CAT       96
Pro Gly Lys Pro Leu Val Asp Ile Asn Gly Lys Pro Met Ile Val His
             20                  25                  30

GTT CTT GAA CGC GCG CGT GAA TCA GGT GCC GAG CGC ATC ATC GTG GCA      144
Val Leu Glu Arg Ala Arg Glu Ser Gly Ala Glu Arg Ile Ile Val Ala
         35                  40                  45

ACC GAT CAT GAG GAT GTT GCC CGC GCC GTT GAA GCC GCT GGC GGT GAA      192
Thr Asp His Glu Asp Val Ala Arg Ala Val Glu Ala Ala Gly Gly Glu
     50                  55                  60

GTA TGT ATG ACG CGC GCC GAT CAT CAG TCA GGA ACA GAA CGT CTG GCG      240
Val Cys Met Thr Arg Ala Asp His Gln Ser Gly Thr Glu Arg Leu Ala
 65                  70                  75                  80

GAA GTT GTC GAA AAA TGC GCA TTC AGC GAC GAC ACG GTG ATC GTT AAT      288
Glu Val Val Glu Lys Cys Ala Phe Ser Asp Asp Thr Val Ile Val Asn
                 85                  90                  95

GTG CAG GGT GAT GAA CCG ATG ATC CCT GCG ACA ATC ATT CGT CAG GTT      336
Val Gln Gly Asp Glu Pro Met Ile Pro Ala Thr Ile Ile Arg Gln Val
            100                 105                 110

GCT GAT AAC CTC GCT CAG CGT CAG GTG GGT ATG GCG ACT CTG GCG GTG      384
Ala Asp Asn Leu Ala Gln Arg Gln Val Gly Met Ala Thr Leu Ala Val
        115                 120                 125

CCA ATC CAC AAT GCG GAA GAA GCG TTT AAC CCG AAT GCG GTG AAA GTG      432
Pro Ile His Asn Ala Glu Glu Ala Phe Asn Pro Asn Ala Val Lys Val
    130                 135                 140

GTT CTC GAC GCT GAA GGG TAT GCA CTG TAC TTC TCT CGC GCC ACC ATT      480
Val Leu Asp Ala Glu Gly Tyr Ala Leu Tyr Phe Ser Arg Ala Thr Ile
145                 150                 155                 160

CCT TGG GAT CGT GAT CGT TTT GCA GAA GGC CTT GAA ACC GTT GGC GAT      528
Pro Trp Asp Arg Asp Arg Phe Ala Glu Gly Leu Glu Thr Val Gly Asp
                165                 170                 175

AAC TTC CTG CGT CAT CTT GGT ATT TAT GGC TAC CGT GCA GGC TTT ATC      576
Asn Phe Leu Arg His Leu Gly Ile Tyr Gly Tyr Arg Ala Gly Phe Ile
            180                 185                 190

CGT CGT TAC GTC AAC TGG CAG CCA AGT CCG TTA GAA CAC ATC GAA ATG      624
Arg Arg Tyr Val Asn Trp Gln Pro Ser Pro Leu Glu His Ile Glu Met
        195                 200                 205

TTA GAG CAG CTT CGT GTT CTG TGG TAC GGC GAA AAA ATC CAT GTT GCT      672
Leu Glu Gln Leu Arg Val Leu Trp Tyr Gly Glu Lys Ile His Val Ala
    210                 215                 220

GTT GCT CAG GAA GTT CCT GGC ACA GGT GTG GAT ACC CCT GAA GAT CTC      720
Val Ala Gln Glu Val Pro Gly Thr Gly Val Asp Thr Pro Glu Asp Leu
225                 230                 235                 240

GAC CCG TCG ACG AAT TCC ATG GAC GCT CAC TTC CTG TCT CAG GCG CCG      768
Asp Pro Ser Thr Asn Ser Met Asp Ala His Phe Leu Ser Gln Ala Pro
                245                 250                 255

CCG CCG TCT TGG GAT CAG ATG TGG AAA TGC CTG ATC CGT CTG AAA CCG      816
Pro Pro Ser Trp Asp Gln Met Trp Lys Cys Leu Ile Arg Leu Lys Pro
            260                 265                 270
```

```
ACC CTG CAC GGC CCG ACC CCG CTG CTG TAC CGT CTG GGT GCT GTT CAG      864
Thr Leu His Gly Pro Thr Pro Leu Leu Tyr Arg Leu Gly Ala Val Gln
        275                 280                 285

AAC GAA ATC ACC CTG ACC CAC CCG GTT ACC AAA TAC ATC ATG ACC TGC      912
Asn Glu Ile Thr Leu Thr His Pro Val Thr Lys Tyr Ile Met Thr Cys
    290                 295                 300

ATG TCT GCT GAT CTA GAA GTT GTT ACC TCT ACC TGG GTT CTG GTT GGT      960
Met Ser Ala Asp Leu Glu Val Val Thr Ser Thr Trp Val Leu Val Gly
305                 310                 315                 320

GGT GTT CTG GCT GCT CTG GCT GCT TAC TGC CTG TCG ACC GGT TGC GTT     1008
Gly Val Leu Ala Ala Leu Ala Ala Tyr Cys Leu Ser Thr Gly Cys Val
                325                 330                 335

GTT ATC GTT GGT CGT GTT GTT CTG TCT GGT AAA CCG GCC ATT ATC CCG     1056
Val Ile Val Gly Arg Val Val Leu Ser Gly Lys Pro Ala Ile Ile Pro
            340                 345                 350

GAC CGT GAA GTT CTG TAC CGT GAG TTC GAC GAA ATG GAA GAA TGC TCT     1104
Asp Arg Glu Val Leu Tyr Arg Glu Phe Asp Glu Met Glu Glu Cys Ser
        355                 360                 365

CAG CAC CTG CCG TAC ATC GAA CAG GGT ATG ATG CTG GCT GAA CAG TTC     1152
Gln His Leu Pro Tyr Ile Glu Gln Gly Met Met Leu Ala Glu Gln Phe
    370                 375                 380

AAA CAG AAA GCT CTG GGT CTG CTG CAG ACC GCT TCT CGT CAG GCT GAA     1200
Lys Gln Lys Ala Leu Gly Leu Leu Gln Thr Ala Ser Arg Gln Ala Glu
385                 390                 395                 400

GTT ATC GCT CCG GCT GTT CAG ACC AAC TGG CAG AAA CTC GAG ACC TTC     1248
Val Ile Ala Pro Ala Val Gln Thr Asn Trp Gln Lys Leu Glu Thr Phe
                405                 410                 415

TGG GCT AAA CAC ATG TGG AAC TTC ATC TCT GGT ATC CAG TAC CTG GCT     1296
Trp Ala Lys His Met Trp Asn Phe Ile Ser Gly Ile Gln Tyr Leu Ala
            420                 425                 430

GGT CTG TCT ACC CTG CCG GGT AAC CCG GCT ATC GCA AGC TTG ATG GCT     1344
Gly Leu Ser Thr Leu Pro Gly Asn Pro Ala Ile Ala Ser Leu Met Ala
        435                 440                 445

TTC ACC GCT GCT GTT ACC TCT CCG CTG ACC ACC TCT CAG ACC CTG CTG     1392
Phe Thr Ala Ala Val Thr Ser Pro Leu Thr Thr Ser Gln Thr Leu Leu
    450                 455                 460

TTC AAC ATT CTG GGT GGT TGG GTT GCT GCT CAG CTG GCT GCT CCG GGT     1440
Phe Asn Ile Leu Gly Gly Trp Val Ala Ala Gln Leu Ala Ala Pro Gly
465                 470                 475                 480

GCT GCT ACC GCT TTC GTT GGT GCT GGT CTG GCT GGT GCT GCT ATC GGT     1488
Ala Ala Thr Ala Phe Val Gly Ala Gly Leu Ala Gly Ala Ala Ile Gly
                485                 490                 495

TCT GTA GGC CTG GGT AAA GTT CTG ATC GAC ATT CTG GCT GGT TAC GGT     1536
Ser Val Gly Leu Gly Lys Val Leu Ile Asp Ile Leu Ala Gly Tyr Gly
            500                 505                 510

GCT GGT GTT GCT GGA GCT CTG GTT GCT TTC AAA ATC ATG TCT GGT GAA     1584
Ala Gly Val Ala Gly Ala Leu Val Ala Phe Lys Ile Met Ser Gly Glu
        515                 520                 525

GTT CCG TCT ACC GAA GAT CTG GTT AAC CTG CTG CCG GCT ATC CTG TCT     1632
Val Pro Ser Thr Glu Asp Leu Val Asn Leu Leu Pro Ala Ile Leu Ser
    530                 535                 540

CCG GGT GCT CTG GTT GTT GGT GTT GTT TGC GCT GCT ATC CTG CGT CGT     1680
Pro Gly Ala Leu Val Val Gly Val Val Cys Ala Ala Ile Leu Arg Arg
545                 550                 555                 560

CAC GTT GGC CCG GGT GAA GGT GCT GTT CAG TGG ATG AAC CGT CTG ATC     1728
His Val Gly Pro Gly Glu Gly Ala Val Gln Trp Met Asn Arg Leu Ile
                565                 570                 575

GCT TTC GCT TCT CGT GGT AAC CAC GTT TCT CCA TGG GAT CCT CTA GAC     1776
Ala Phe Ala Ser Arg Gly Asn His Val Ser Pro Trp Asp Pro Leu Asp
            580                 585                 590
```

```
TGC AGG CAT GCT AAG                                                    1791
Cys Arg His Ala Lys
        595
```

(2) INFORMATION FOR SEQ ID NO:16:

(i) SEQUENCE CHARACTERISTICS:
        (A) LENGTH: 597 amino acids
        (B) TYPE: amino acid
        (D) TOPOLOGY: linear (ii) MOLECULE TYPE: protein (xi) SEQUENCE DESCRIPTION: SEQ ID NO:16:

```
Met Ser Phe Val Val Ile Ile Pro Ala Arg Tyr Ala Ser Thr Arg Leu
 1               5                  10                  15

Pro Gly Lys Pro Leu Val Asp Ile Asn Gly Lys Pro Met Ile Val His
                20                  25                  30

Val Leu Glu Arg Ala Arg Glu Ser Gly Ala Glu Arg Ile Ile Val Ala
            35                  40                  45

Thr Asp His Glu Asp Val Ala Arg Ala Val Glu Ala Ala Gly Gly Glu
    50                  55                  60

Val Cys Met Thr Arg Ala Asp His Gln Ser Gly Thr Glu Arg Leu Ala
65                  70                  75                  80

Glu Val Val Glu Lys Cys Ala Phe Ser Asp Asp Thr Val Ile Val Asn
                85                  90                  95

Val Gln Gly Asp Glu Pro Met Ile Pro Ala Thr Ile Ile Arg Gln Val
                100                 105                 110

Ala Asp Asn Leu Ala Gln Arg Gln Val Gly Met Ala Thr Leu Ala Val
            115                 120                 125

Pro Ile His Asn Ala Glu Glu Ala Phe Asn Pro Asn Ala Val Lys Val
    130                 135                 140

Val Leu Asp Ala Glu Gly Tyr Ala Leu Tyr Phe Ser Arg Ala Thr Ile
145                 150                 155                 160

Pro Trp Asp Arg Asp Arg Phe Ala Glu Gly Leu Glu Thr Val Gly Asp
                165                 170                 175

Asn Phe Leu Arg His Leu Gly Ile Tyr Gly Tyr Arg Ala Gly Phe Ile
            180                 185                 190

Arg Arg Tyr Val Asn Trp Gln Pro Ser Pro Leu Glu His Ile Glu Met
    195                 200                 205

Leu Glu Gln Leu Arg Val Leu Trp Tyr Gly Glu Lys Ile His Val Ala
    210                 215                 220

Val Ala Gln Glu Val Pro Gly Thr Gly Val Asp Thr Pro Glu Asp Leu
225                 230                 235                 240

Asp Pro Ser Thr Asn Ser Met Asp Ala His Phe Leu Ser Gln Ala Pro
                245                 250                 255

Pro Pro Ser Trp Asp Gln Met Trp Lys Cys Leu Ile Arg Leu Lys Pro
                260                 265                 270

Thr Leu His Gly Pro Thr Pro Leu Leu Tyr Arg Leu Gly Ala Val Gln
            275                 280                 285

Asn Glu Ile Thr Leu Thr His Pro Val Thr Lys Tyr Ile Met Thr Cys
    290                 295                 300

Met Ser Ala Asp Leu Glu Val Val Thr Ser Thr Trp Val Leu Val Gly
305                 310                 315                 320

Gly Val Leu Ala Ala Leu Ala Ala Tyr Cys Leu Ser Thr Gly Cys Val
                325                 330                 335
```

```
Val Ile Val Gly Arg Val Val Leu Ser Gly Lys Pro Ala Ile Ile Pro
            340                 345                 350

Asp Arg Glu Val Leu Tyr Arg Glu Phe Asp Glu Met Glu Glu Cys Ser
        355                 360                 365

Gln His Leu Pro Tyr Ile Glu Gln Gly Met Met Leu Ala Glu Gln Phe
    370                 375                 380

Lys Gln Lys Ala Leu Gly Leu Leu Gln Thr Ala Ser Arg Gln Ala Glu
385                 390                 395                 400

Val Ile Ala Pro Ala Val Gln Thr Asn Trp Gln Lys Leu Glu Thr Phe
                405                 410                 415

Trp Ala Lys His Met Trp Asn Phe Ile Ser Gly Ile Gln Tyr Leu Ala
            420                 425                 430

Gly Leu Ser Thr Leu Pro Gly Asn Pro Ala Ile Ala Ser Leu Met Ala
        435                 440                 445

Phe Thr Ala Ala Val Thr Ser Pro Leu Thr Thr Ser Gln Thr Leu Leu
    450                 455                 460

Phe Asn Ile Leu Gly Gly Trp Val Ala Ala Gln Leu Ala Ala Pro Gly
465                 470                 475                 480

Ala Ala Thr Ala Phe Val Gly Ala Gly Leu Ala Gly Ala Ala Ile Gly
                485                 490                 495

Ser Val Gly Leu Gly Lys Val Leu Ile Asp Ile Leu Ala Gly Tyr Gly
            500                 505                 510

Ala Gly Val Ala Gly Ala Leu Val Ala Phe Lys Ile Met Ser Gly Glu
        515                 520                 525

Val Pro Ser Thr Glu Asp Leu Val Asn Leu Leu Pro Ala Ile Leu Ser
    530                 535                 540

Pro Gly Ala Leu Val Val Gly Val Val Cys Ala Ala Ile Leu Arg Arg
545                 550                 555                 560

His Val Gly Pro Gly Glu Gly Ala Val Gln Trp Met Asn Arg Leu Ile
                565                 570                 575

Ala Phe Ala Ser Arg Gly Asn His Val Ser Pro Trp Asp Pro Leu Asp
            580                 585                 590

Cys Arg His Ala Lys
        595

(2) INFORMATION FOR SEQ ID NO:17:

(i) SEQUENCE CHARACTERISTICS:
        (A) LENGTH: 1797 base pairs
        (B) TYPE: nucleic acid
        (C) STRANDEDNESS: single
        (D) TOPOLOGY: circular (ii) MOLECULE TYPE: DNA (genomic)

(ix) FEATURE:
        (A) NAME/KEY: CDS
        (B) LOCATION: 1..1797

(xi) SEQUENCE DESCRIPTION: SEQ ID NO:17:

ATG AGT TTT GTG GTC ATT ATT CCC GCG CGC TAC GCG TCG ACG CGT CTG        48
Met Ser Phe Val Val Ile Ile Pro Ala Arg Tyr Ala Ser Thr Arg Leu
  1               5                  10                  15

CCC GGT AAA CCA TTG GTT GAT ATT AAC GGC AAA CCC ATG ATT GTT CAT        96
Pro Gly Lys Pro Leu Val Asp Ile Asn Gly Lys Pro Met Ile Val His
                 20                  25                  30

GTT CTT GAA CGC GCG CGT GAA TCA GGT GCC GAG CGC ATC ATC GTG GCA       144
Val Leu Glu Arg Ala Arg Glu Ser Gly Ala Glu Arg Ile Ile Val Ala
```

```
              35                      40                      45
ACC GAT CAT GAG GAT GTT GCC CGC GCC GTT GAA GCC GCT GGC GGT GAA        192
Thr Asp His Glu Asp Val Ala Arg Ala Val Glu Ala Ala Gly Gly Glu
         50                      55                      60

GTA TGT ATG ACG CGC GCC GAT CAT CAG TCA GGA ACA GAA CGT CTG GCG        240
Val Cys Met Thr Arg Ala Asp His Gln Ser Gly Thr Glu Arg Leu Ala
 65                      70                      75                  80

GAA GTT GTC GAA AAA TGC GCA TTC AGC GAC GAC ACG GTG ATC GTT AAT        288
Glu Val Val Glu Lys Cys Ala Phe Ser Asp Asp Thr Val Ile Val Asn
                 85                      90                      95

GTG CAG GGT GAT GAA CCG ATG ATC CCT GCG ACA ATC ATT CGT CAG GTT        336
Val Gln Gly Asp Glu Pro Met Ile Pro Ala Thr Ile Ile Arg Gln Val
                    100                     105                     110

GCT GAT AAC CTC GCT CAG CGT CAG GTG GGT ATG GCG ACT CTG GCG GTG        384
Ala Asp Asn Leu Ala Gln Arg Gln Val Gly Met Ala Thr Leu Ala Val
            115                     120                     125

CCA ATC CAC AAT GCG GAA GAA GCG TTT AAC CCG AAT GCG GTG AAA GTG        432
Pro Ile His Asn Ala Glu Glu Ala Phe Asn Pro Asn Ala Val Lys Val
        130                     135                     140

GTT CTC GAC GCT GAA GGG TAT GCA CTG TAC TTC TCT CGC GCC ACC ATT        480
Val Leu Asp Ala Glu Gly Tyr Ala Leu Tyr Phe Ser Arg Ala Thr Ile
145                     150                     155                     160

CCT TGG GAT CGT GAT CGT TTT GCA GAA GGC CTT GAA ACC GTT GGC GAT        528
Pro Trp Asp Arg Asp Arg Phe Ala Glu Gly Leu Glu Thr Val Gly Asp
                    165                     170                     175

AAC TTC CTG CGT CAT CTT GGT ATT TAT GGC TAC CGT GCA GGC TTT ATC        576
Asn Phe Leu Arg His Leu Gly Ile Tyr Gly Tyr Arg Ala Gly Phe Ile
                180                     185                     190

CGT CGT TAC GTC AAC TGG CAG CCA AGT CCG TTA GAA CAC ATC GAA ATG        624
Arg Arg Tyr Val Asn Trp Gln Pro Ser Pro Leu Glu His Ile Glu Met
            195                     200                     205

TTA GAG CAG CTT CGT GTT CTG TGG TAC GGC GAA AAA ATC CAT GTT GCT        672
Leu Glu Gln Leu Arg Val Leu Trp Tyr Gly Glu Lys Ile His Val Ala
        210                     215                     220

GTT GCT CAG GAA GTT CCT GGC ACA GGT GTG GAT ACC CCT GAA GAT CTC        720
Val Ala Gln Glu Val Pro Gly Thr Gly Val Asp Thr Pro Glu Asp Leu
225                     230                     235                     240

GAC CCG TCG ACG AAT TCC ATG GAC GCT CAC TTC CTG TCT CAG ACC AAA        768
Asp Pro Ser Thr Asn Ser Met Asp Ala His Phe Leu Ser Gln Thr Lys
                    245                     250                     255

CAG TCT GGT GAA AAC CTT CCG TAC CTG GTT GCT TAC CAG GCT ACC GTT        816
Gln Ser Gly Glu Asn Leu Pro Tyr Leu Val Ala Tyr Gln Ala Thr Val
                260                     265                     270

TGC GCT CGT GCT CAG GCC CCG ACC CCG CTG CTG TAC CGT CTG GGT GCT        864
Cys Ala Arg Ala Gln Ala Pro Thr Pro Leu Leu Tyr Arg Leu Gly Ala
            275                     280                     285

GTT CAG AAC GAA ATC ACC CTG ACC CAC CCG GTT ACC AAA TAC ATC ATG        912
Val Gln Asn Glu Ile Thr Leu Thr His Pro Val Thr Lys Tyr Ile Met
        290                     295                     300

ACC TGC ATG TCT GCT GAT CTA GAA GTT GTT ACC TCT ACC TGG GTT CTG        960
Thr Cys Met Ser Ala Asp Leu Glu Val Val Thr Ser Thr Trp Val Leu
305                     310                     315                     320

GTT GGT GGT GTT CTG GCT GCT CTG GCT GCT TAC TGC CTG TCG ACC GGT       1008
Val Gly Gly Val Leu Ala Ala Leu Ala Ala Tyr Cys Leu Ser Thr Gly
                    325                     330                     335

TGC GTT GTT ATC GTT GGT CGT GTT GTT CTG TCT GGT AAA CCG GCC ATT       1056
Cys Val Val Ile Val Gly Arg Val Val Leu Ser Gly Lys Pro Ala Ile
                340                     345                     350

ATC CCG GAC CGT GAA GTT CTG TAC CGT GAG TTC GAC GAA ATG GAA GAA       1104
```

```
Ile Pro Asp Arg Glu Val Leu Tyr Arg Glu Phe Asp Glu Met Glu Glu
        355                 360                 365

TGC TCT CAG CAC CTG CCG TAC ATC GAA CAG GGT ATG ATG CTG GCT GAA      1152
Cys Ser Gln His Leu Pro Tyr Ile Glu Gln Gly Met Met Leu Ala Glu
    370                 375                 380

CAG TTC AAA CAG AAA GCT CTG GGT CTG CTG CAG ACC GCT TCT CGT CAG      1200
Gln Phe Lys Gln Lys Ala Leu Gly Leu Leu Gln Thr Ala Ser Arg Gln
385                 390                 395                 400

GCT GAA GTT ATC GCT CCG GCT GTT CAG ACC AAC TGG CAG AAA CTC GAG      1248
Ala Glu Val Ile Ala Pro Ala Val Gln Thr Asn Trp Gln Lys Leu Glu
                405                 410                 415

ACC TTC TGG GCT AAA CAC ATG TGG AAC TTC ATC TCT GGT ATC CAG TAC      1296
Thr Phe Trp Ala Lys His Met Trp Asn Phe Ile Ser Gly Ile Gln Tyr
            420                 425                 430

CTG GCT GGT CTG TCT ACC CTG CCG GGT AAC CCG GCT ATC GCA AGC TTG      1344
Leu Ala Gly Leu Ser Thr Leu Pro Gly Asn Pro Ala Ile Ala Ser Leu
        435                 440                 445

ATG GCT TTC ACC GCT GCT GTT ACC TCT CCG CTG ACC ACC TCT CAG ACC      1392
Met Ala Phe Thr Ala Ala Val Thr Ser Pro Leu Thr Thr Ser Gln Thr
    450                 455                 460

CTG CTG TTC AAC ATT CTG GGT GGT TGG GTT GCT GCT CAG CTG GCT GCT      1440
Leu Leu Phe Asn Ile Leu Gly Gly Trp Val Ala Ala Gln Leu Ala Ala
465                 470                 475                 480

CCG GGT GCT GCT ACC GCT TTC GTT GGT GCT GGT CTG GCT GGT GCT GCT      1488
Pro Gly Ala Ala Thr Ala Phe Val Gly Ala Gly Leu Ala Gly Ala Ala
                485                 490                 495

ATC GGT TCT GTA GGC CTG GGT AAA GTT CTG ATC GAC ATT CTG GCT GGT      1536
Ile Gly Ser Val Gly Leu Gly Lys Val Leu Ile Asp Ile Leu Ala Gly
            500                 505                 510

TAC GGT GCT GGT GTT GCT GGA GCT CTG GTT GCT TTC AAA ATC ATG TCT      1584
Tyr Gly Ala Gly Val Ala Gly Ala Leu Val Ala Phe Lys Ile Met Ser
        515                 520                 525

GGT GAA GTT CCG TCT ACC GAA GAT CTG GTT AAC CTG CTG CCG GCT ATC      1632
Gly Glu Val Pro Ser Thr Glu Asp Leu Val Asn Leu Leu Pro Ala Ile
    530                 535                 540

CTG TCT CCG GGT GCT CTG GTT GTT GGT GTT GTT TGC GCT GCT ATC CTG      1680
Leu Ser Pro Gly Ala Leu Val Val Gly Val Val Cys Ala Ala Ile Leu
545                 550                 555                 560

CGT CGT CAC GTT GGC CCG GGT GAA GGT GCT GTT CAG TGG ATG AAC CGT      1728
Arg Arg His Val Gly Pro Gly Glu Gly Ala Val Gln Trp Met Asn Arg
                565                 570                 575

CTG ATC GCT TTC GCT TCT CGT GGT AAC CAC GTT TCT CCA TGG GAT CCT      1776
Leu Ile Ala Phe Ala Ser Arg Gly Asn His Val Ser Pro Trp Asp Pro
            580                 585                 590

CTA GAC TGC AGG CAT GCT AAG                                          1797
Leu Asp Cys Arg His Ala Lys
        595

(2) INFORMATION FOR SEQ ID NO:18:

(i) SEQUENCE CHARACTERISTICS:
        (A) LENGTH: 599 amino acids
        (B) TYPE: amino acid
        (D) TOPOLOGY: linear (ii) MOLECULE TYPE: protein (xi) SEQUENCE DESCRIPTION: SEQ ID NO:18:

Met Ser Phe Val Val Ile Ile Pro Ala Arg Tyr Ala Ser Thr Arg Leu
  1               5                  10                  15

Pro Gly Lys Pro Leu Val Asp Ile Asn Gly Lys Pro Met Ile Val His
```

-continued

```
                20                  25                  30
Val Leu Glu Arg Ala Arg Ser Gly Ala Glu Arg Ile Ile Val Ala
            35                  40                  45
Thr Asp His Glu Asp Val Ala Arg Ala Val Glu Ala Ala Gly Gly Glu
        50                  55                  60
Val Cys Met Thr Arg Ala Asp His Gln Ser Gly Thr Glu Arg Leu Ala
 65                  70                  75                  80
Glu Val Val Glu Lys Cys Ala Phe Ser Asp Asp Thr Val Ile Val Asn
                85                  90                  95
Val Gln Gly Asp Glu Pro Met Ile Pro Ala Thr Ile Ile Arg Gln Val
            100                 105                 110
Ala Asp Asn Leu Ala Gln Arg Gln Val Gly Met Ala Thr Leu Ala Val
            115                 120                 125
Pro Ile His Asn Ala Glu Glu Ala Phe Asn Pro Asn Ala Val Lys Val
        130                 135                 140
Val Leu Asp Ala Glu Gly Tyr Ala Leu Tyr Phe Ser Arg Ala Thr Ile
145                 150                 155                 160
Pro Trp Asp Arg Asp Arg Phe Ala Glu Gly Leu Glu Thr Val Gly Asp
                165                 170                 175
Asn Phe Leu Arg His Leu Gly Ile Tyr Gly Tyr Arg Ala Gly Phe Ile
            180                 185                 190
Arg Arg Tyr Val Asn Trp Gln Pro Ser Pro Leu Glu His Ile Glu Met
        195                 200                 205
Leu Glu Gln Leu Arg Val Leu Trp Tyr Gly Glu Lys Ile His Val Ala
        210                 215                 220
Val Ala Gln Glu Val Pro Gly Thr Gly Val Asp Thr Pro Glu Asp Leu
225                 230                 235                 240
Asp Pro Ser Thr Asn Ser Met Asp Ala His Phe Leu Ser Gln Thr Lys
                245                 250                 255
Gln Ser Gly Glu Asn Leu Pro Tyr Leu Val Ala Tyr Gln Ala Thr Val
            260                 265                 270
Cys Ala Arg Ala Gln Ala Pro Thr Pro Leu Leu Tyr Arg Leu Gly Ala
        275                 280                 285
Val Gln Asn Glu Ile Thr Leu Thr His Pro Val Thr Lys Tyr Ile Met
        290                 295                 300
Thr Cys Met Ser Ala Asp Leu Glu Val Val Thr Ser Thr Trp Val Leu
305                 310                 315                 320
Val Gly Gly Val Leu Ala Ala Leu Ala Ala Tyr Cys Leu Ser Thr Gly
                325                 330                 335
Cys Val Val Ile Val Gly Arg Val Val Leu Ser Gly Lys Pro Ala Ile
            340                 345                 350
Ile Pro Asp Arg Glu Val Leu Tyr Arg Glu Phe Asp Glu Met Glu Glu
        355                 360                 365
Cys Ser Gln His Leu Pro Tyr Ile Glu Gln Gly Met Met Leu Ala Glu
        370                 375                 380
Gln Phe Lys Gln Lys Ala Leu Gly Leu Leu Gln Thr Ala Ser Arg Gln
385                 390                 395                 400
Ala Glu Val Ile Ala Pro Ala Val Gln Thr Asn Trp Gln Lys Leu Glu
                405                 410                 415
Thr Phe Trp Ala Lys His Met Trp Asn Phe Ile Ser Gly Ile Gln Tyr
            420                 425                 430
Leu Ala Gly Leu Ser Thr Leu Pro Gly Asn Pro Ala Ile Ala Ser Leu
        435                 440                 445
```

```
Met Ala Phe Thr Ala Ala Val Thr Ser Pro Leu Thr Thr Ser Gln Thr
        450                     455                     460

Leu Leu Phe Asn Ile Leu Gly Gly Trp Val Ala Ala Gln Leu Ala Ala
465                     470                     475                     480

Pro Gly Ala Ala Thr Ala Phe Val Gly Ala Gly Leu Ala Gly Ala Ala
                    485                     490                     495

Ile Gly Ser Val Gly Leu Gly Lys Val Leu Ile Asp Ile Leu Ala Gly
                500                     505                     510

Tyr Gly Ala Gly Val Ala Gly Ala Leu Val Ala Phe Lys Ile Met Ser
            515                     520                     525

Gly Glu Val Pro Ser Thr Glu Asp Leu Val Asn Leu Leu Pro Ala Ile
        530                     535                     540

Leu Ser Pro Gly Ala Leu Val Val Gly Val Val Cys Ala Ala Ile Leu
545                     550                     555                     560

Arg Arg His Val Gly Pro Gly Glu Gly Ala Val Gln Trp Met Asn Arg
                565                     570                     575

Leu Ile Ala Phe Ala Ser Arg Gly Asn His Val Ser Pro Trp Asp Pro
                580                     585                     590

Leu Asp Cys Arg His Ala Lys
        595
```

(2) INFORMATION FOR SEQ ID NO:19:

(i) SEQUENCE CHARACTERISTICS:
        (A) LENGTH: 1251 base pairs
        (B) TYPE: nucleic acid
        (C) STRANDEDNESS: single
        (D) TOPOLOGY: circular (ii) MOLECULE TYPE: DNA (genomic)

(ix) FEATURE:
        (A) NAME/KEY: CDS
        (B) LOCATION: 1..1251

(xi) SEQUENCE DESCRIPTION: SEQ ID NO:19:

```
ATG AGT TTT GTG GTC ATT ATT CCC GCG CGC TAC GCG TCG ACG CGT CTG      48
Met Ser Phe Val Val Ile Ile Pro Ala Arg Tyr Ala Ser Thr Arg Leu
 1               5                  10                  15

CCC GGT AAA CCA TTG GTT GAT ATT AAC GGC AAA CCC ATG ATT GTT CAT      96
Pro Gly Lys Pro Leu Val Asp Ile Asn Gly Lys Pro Met Ile Val His
                20                  25                  30

GTT CTT GAA CGC GCG CGT GAA TCA GGT GCC GAG CGC ATC ATC GTG GCA     144
Val Leu Glu Arg Ala Arg Glu Ser Gly Ala Glu Arg Ile Ile Val Ala
         35                  40                  45

ACC GAT CAT GAG GAT GTT GCC CGC GCC GTT GAA GCC GCT GGC GGT GAA     192
Thr Asp His Glu Asp Val Ala Arg Ala Val Glu Ala Ala Gly Gly Glu
 50                  55                  60

GTA TGT ATG ACG CGC GCC GAT CAT CAG TCA GGA ACA GAA CGT CTG GCG     240
Val Cys Met Thr Arg Ala Asp His Gln Ser Gly Thr Glu Arg Leu Ala
 65                  70                  75                  80

GAA GTT GTC GAA AAA TGC GCA TTC AGC GAC GAC ACG GTG ATC GTT AAT     288
Glu Val Val Glu Lys Cys Ala Phe Ser Asp Asp Thr Val Ile Val Asn
                 85                  90                  95

GTG CAG GGT GAT GAA CCG ATG ATC CCT GCG ACA ATC ATT CGT CAG GTT     336
Val Gln Gly Asp Glu Pro Met Ile Pro Ala Thr Ile Ile Arg Gln Val
            100                 105                 110

GCT GAT AAC CTC GCT CAG CGT CAG GTG GGT ATG GCG ACT CTG GCG GTG     384
Ala Asp Asn Leu Ala Gln Arg Gln Val Gly Met Ala Thr Leu Ala Val
        115                 120                 125
```

-continued

```
CCA ATC CAC AAT GCG GAA GAA GCG TTT AAC CCG AAT GCG GTG AAA GTG       432
Pro Ile His Asn Ala Glu Glu Ala Phe Asn Pro Asn Ala Val Lys Val
    130                 135                 140

GTT CTC GAC GCT GAA GGG TAT GCA CTG TAC TTC TCT CGC GCC ACC ATT       480
Val Leu Asp Ala Glu Gly Tyr Ala Leu Tyr Phe Ser Arg Ala Thr Ile
145                 150                 155                 160

CCT TGG GAT CGT GAT CGT TTT GCA GAA GGC CTT GAA ACC GTT GGC GAT       528
Pro Trp Asp Arg Asp Arg Phe Ala Glu Gly Leu Glu Thr Val Gly Asp
                165                 170                 175

AAC TTC CTG CGT CAT CTT GGT ATT TAT GGC TAC CGT GCA GGC TTT ATC       576
Asn Phe Leu Arg His Leu Gly Ile Tyr Gly Tyr Arg Ala Gly Phe Ile
            180                 185                 190

CGT CGT TAC GTC AAC TGG CAG CCA AGT CCG TTA GAA CAC ATC GAA ATG       624
Arg Arg Tyr Val Asn Trp Gln Pro Ser Pro Leu Glu His Ile Glu Met
        195                 200                 205

TTA GAG CAG CTT CGT GTT CTG TGG TAC GGC GAA AAA ATC CAT GTT GCT       672
Leu Glu Gln Leu Arg Val Leu Trp Tyr Gly Glu Lys Ile His Val Ala
    210                 215                 220

GTT GCT CAG GAA GTT CCT GGC ACA GGT GTG GAT ACC CCT GAA GAT CTC       720
Val Ala Gln Glu Val Pro Gly Thr Gly Val Asp Thr Pro Glu Asp Leu
225                 230                 235                 240

GAC CCG TCG ACT CGA ATT CGA GCT CGG TAC CCT GAG ACA ATC ACG CTT       768
Asp Pro Ser Thr Arg Ile Arg Ala Arg Tyr Pro Glu Thr Ile Thr Leu
                245                 250                 255

CCC CAG GAT GCT GTC TCC CGC ACC CAG CGT CGG GGC AGG ACT GGC AGG       816
Pro Gln Asp Ala Val Ser Arg Thr Gln Arg Arg Gly Arg Thr Gly Arg
            260                 265                 270

GGG AAG CCA GGC ATC TAC AGA TTT GTG GCA CCG GGG GAG CGC CCT TCC       864
Gly Lys Pro Gly Ile Tyr Arg Phe Val Ala Pro Gly Glu Arg Pro Ser
        275                 280                 285

GGC ATG TTC GAC TCG TCC GTC CTC TGC GAG TGC TAT GAC GCG GGC TGG       912
Gly Met Phe Asp Ser Ser Val Leu Cys Glu Cys Tyr Asp Ala Gly Trp
    290                 295                 300

CCT TGG TAT GAG CTC ACA CCC GCC GAG ACC ACA GTT AGG CTA CGA GCG       960
Pro Trp Tyr Glu Leu Thr Pro Ala Glu Thr Thr Val Arg Leu Arg Ala
305                 310                 315                 320

TAC ATG AAC ACC CCG GGA CTC CCC GTG TGC CAA GAC CAT CTT GAA TTT      1008
Tyr Met Asn Thr Pro Gly Leu Pro Val Cys Gln Asp His Leu Glu Phe
                325                 330                 335

TGG GAG GGC GTC TTC ACG GGT CTC ACC CAT ATA GAC GCC CAC TTT CTA      1056
Trp Glu Gly Val Phe Thr Gly Leu Thr His Ile Asp Ala His Phe Leu
            340                 345                 350

TCC CAG ACA AAG CAG AGT GGG GAA AAC CTT CCT TAC CTG GTA GCG TAC      1104
Ser Gln Thr Lys Gln Ser Gly Glu Asn Leu Pro Tyr Leu Val Ala Tyr
        355                 360                 365

CAA GCC ACC GTG TGC GCT AGA GCT CAA GCC CCT CCC CCA TCG TGG GAC      1152
Gln Ala Thr Val Cys Ala Arg Ala Gln Ala Pro Pro Pro Ser Trp Asp
    370                 375                 380

CAG ATG TGG AAG TGC TTG ATC CGC CTC AAG CCT ACC CTT CAT GGG CCG      1200
Gln Met Trp Lys Cys Leu Ile Arg Leu Lys Pro Thr Leu His Gly Pro
385                 390                 395                 400

ACC CCC CTG CTA TAC AGA CTG GGC GGG GGA TCC TCT AGA CTG CAG GCA      1248
Thr Pro Leu Leu Tyr Arg Leu Gly Gly Gly Ser Ser Arg Leu Gln Ala
                405                 410                 415

TGC                                                                   1251
Cys
```

(2) INFORMATION FOR SEQ ID NO:20:

```
    (i) SEQUENCE CHARACTERISTICS:
         (A) LENGTH: 417 amino acids
         (B) TYPE: amino acid
         (D) TOPOLOGY: linear (ii) MOLECULE TYPE: protein (xi) SEQUENCE DESCRIPTION: SEQ ID NO:20:

Met Ser Phe Val Val Ile Ile Pro Ala Arg Tyr Ala Ser Thr Arg Leu
 1               5                  10                  15

Pro Gly Lys Pro Leu Val Asp Ile Asn Gly Lys Pro Met Ile Val His
            20                  25                  30

Val Leu Glu Arg Ala Arg Glu Ser Gly Ala Glu Arg Ile Ile Val Ala
        35                  40                  45

Thr Asp His Glu Asp Val Ala Arg Ala Val Glu Ala Ala Gly Gly Glu
    50                  55                  60

Val Cys Met Thr Arg Ala Asp His Gln Ser Gly Thr Glu Arg Leu Ala
65                  70                  75                  80

Glu Val Val Glu Lys Cys Ala Phe Ser Asp Asp Thr Val Ile Val Asn
                85                  90                  95

Val Gln Gly Asp Glu Pro Met Ile Pro Ala Thr Ile Ile Arg Gln Val
            100                 105                 110

Ala Asp Asn Leu Ala Gln Arg Gln Val Gly Met Ala Thr Leu Ala Val
        115                 120                 125

Pro Ile His Asn Ala Glu Glu Ala Phe Asn Pro Asn Ala Val Lys Val
    130                 135                 140

Val Leu Asp Ala Glu Gly Tyr Ala Leu Tyr Phe Ser Arg Ala Thr Ile
145                 150                 155                 160

Pro Trp Asp Arg Asp Arg Phe Ala Glu Gly Leu Glu Thr Val Gly Asp
                165                 170                 175

Asn Phe Leu Arg His Leu Gly Ile Tyr Gly Tyr Arg Ala Gly Phe Ile
            180                 185                 190

Arg Arg Tyr Val Asn Trp Gln Pro Ser Pro Leu Glu His Ile Glu Met
        195                 200                 205

Leu Glu Gln Leu Arg Val Leu Trp Tyr Gly Glu Lys Ile His Val Ala
    210                 215                 220

Val Ala Gln Glu Val Pro Gly Thr Gly Val Asp Thr Pro Glu Asp Leu
225                 230                 235                 240

Asp Pro Ser Thr Arg Ile Arg Ala Arg Tyr Pro Glu Thr Ile Thr Leu
                245                 250                 255

Pro Gln Asp Ala Val Ser Arg Thr Gln Arg Arg Gly Arg Thr Gly Arg
            260                 265                 270

Gly Lys Pro Gly Ile Tyr Arg Phe Val Ala Pro Gly Glu Arg Pro Ser
        275                 280                 285

Gly Met Phe Asp Ser Ser Val Leu Cys Glu Cys Tyr Asp Ala Gly Trp
    290                 295                 300

Pro Trp Tyr Glu Leu Thr Pro Ala Glu Thr Thr Val Arg Leu Arg Ala
305                 310                 315                 320

Tyr Met Asn Thr Pro Gly Leu Pro Val Cys Gln Asp His Leu Glu Phe
                325                 330                 335

Trp Glu Gly Val Phe Thr Gly Leu Thr His Ile Asp Ala His Phe Leu
            340                 345                 350

Ser Gln Thr Lys Gln Ser Gly Glu Asn Leu Pro Tyr Leu Val Ala Tyr
        355                 360                 365

Gln Ala Thr Val Cys Ala Arg Ala Gln Ala Pro Pro Pro Ser Trp Asp
```

```
                    370                 375                 380
Gln Met Trp Lys Cys Leu Ile Arg Leu Lys Pro Thr Leu His Gly Pro
385                 390                 395                 400

Thr Pro Leu Leu Tyr Arg Leu Gly Gly Gly Ser Ser Arg Leu Gln Ala
                405                 410                 415

Cys (2) INFORMATION FOR SEQ ID NO:21:

(i) SEQUENCE CHARACTERISTICS:
        (A) LENGTH: 1275 base pairs
        (B) TYPE: nucleic acid
        (C) STRANDEDNESS: single
        (D) TOPOLOGY: circular (ii) MOLECULE TYPE: DNA (genomic)

(ix) FEATURE:
        (A) NAME/KEY: CDS
        (B) LOCATION: 1..1275

(xi) SEQUENCE DESCRIPTION: SEQ ID NO:21:

ATG AGT TTT GTG GTC ATT ATT CCC GCG CGC TAC GCG TCG ACG CGT CTG         48
Met Ser Phe Val Val Ile Ile Pro Ala Arg Tyr Ala Ser Thr Arg Leu
 1               5                  10                  15

CCC GGT AAA CCA TTG GTT GAT ATT AAC GGC AAA CCC ATG ATT GTT CAT         96
Pro Gly Lys Pro Leu Val Asp Ile Asn Gly Lys Pro Met Ile Val His
            20                  25                  30

GTT CTT GAA CGC GCG CGT GAA TCA GGT GCC GAG CGC ATC ATC GTG GCA        144
Val Leu Glu Arg Ala Arg Glu Ser Gly Ala Glu Arg Ile Ile Val Ala
         35                  40                  45

ACC GAT CAT GAG GAT GTT GCC CGC GCC GTT GAA GCC GCT GGC GGT GAA        192
Thr Asp His Glu Asp Val Ala Arg Ala Val Glu Ala Ala Gly Gly Glu
     50                  55                  60

GTA TGT ATG ACG CGC GCC GAT CAT CAG TCA GGA ACA GAA CGT CTG GCG        240
Val Cys Met Thr Arg Ala Asp His Gln Ser Gly Thr Glu Arg Leu Ala
 65                  70                  75                  80

GAA GTT GTC GAA AAA TGC GCA TTC AGC GAC GAC ACG GTG ATC GTT AAT        288
Glu Val Val Glu Lys Cys Ala Phe Ser Asp Asp Thr Val Ile Val Asn
                 85                  90                  95

GTG CAG GGT GAT GAA CCG ATG ATC CCT GCG ACA ATC ATT CGT CAG GTT        336
Val Gln Gly Asp Glu Pro Met Ile Pro Ala Thr Ile Ile Arg Gln Val
            100                 105                 110

GCT GAT AAC CTC GCT CAG CGT CAG GTG GGT ATG GCG ACT CTG GCG GTG        384
Ala Asp Asn Leu Ala Gln Arg Gln Val Gly Met Ala Thr Leu Ala Val
        115                 120                 125

CCA ATC CAC AAT GCG GAA GAA GCG TTT AAC CCG AAT GCG GTG AAA GTG        432
Pro Ile His Asn Ala Glu Glu Ala Phe Asn Pro Asn Ala Val Lys Val
    130                 135                 140

GTT CTC GAC GCT GAA GGG TAT GCA CTG TAC TTC TCT CGC GCC ACC ATT        480
Val Leu Asp Ala Glu Gly Tyr Ala Leu Tyr Phe Ser Arg Ala Thr Ile
145                 150                 155                 160

CCT TGG GAT CGT GAT CGT TTT GCA GAA GGC CTT GAA ACC GTT GGC GAT        528
Pro Trp Asp Arg Asp Arg Phe Ala Glu Gly Leu Glu Thr Val Gly Asp
                165                 170                 175

AAC TTC CTG CGT CAT CTT GGT ATT TAT GGC TAC CGT GCA GGC TTT ATC        576
Asn Phe Leu Arg His Leu Gly Ile Tyr Gly Tyr Arg Ala Gly Phe Ile
            180                 185                 190

CGT CGT TAC GTC AAC TGG CAG CCA AGT CCG TTA GAA CAC ATC GAA ATG        624
Arg Arg Tyr Val Asn Trp Gln Pro Ser Pro Leu Glu His Ile Glu Met
        195                 200                 205
```

```
TTA GAG CAG CTT CGT GTT CTG TGG TAC GGC GAA AAA ATC CAT GTT GCT      672
Leu Glu Gln Leu Arg Val Leu Trp Tyr Gly Glu Lys Ile His Val Ala
    210                 215                 220

GTT GCT CAG GAA GTT CCT GGC ACA GGT GTG GAT ACC CCT GAA GAT CTC      720
Val Ala Gln Glu Val Pro Gly Thr Gly Val Asp Thr Pro Glu Asp Leu
225                 230                 235                 240

GAC CCG TCG ACT CGA ATT CGT AGG TCG CGC AAT TTG GGT AAG GTC ATC      768
Asp Pro Ser Thr Arg Ile Arg Arg Ser Arg Asn Leu Gly Lys Val Ile
                245                 250                 255

GAC ACC CTC ACG TGC GGC TTC GCC GAC CTC ATG GGG TAT ATT CCG CTC      816
Asp Thr Leu Thr Cys Gly Phe Ala Asp Leu Met Gly Tyr Ile Pro Leu
            260                 265                 270

GTC GGC GCC CCT CTT GGA GGC GCT GCC AGG GCC CTG GGC CAT GGC GTC      864
Val Gly Ala Pro Leu Gly Gly Ala Ala Arg Ala Leu Gly His Gly Val
        275                 280                 285

CGG GTT CTG GAA GAC GGC GTG AAC TAT GCG ACA GGG AAT CTT CCT GGT      912
Arg Val Leu Glu Asp Gly Val Asn Tyr Ala Thr Gly Asn Leu Pro Gly
    290                 295                 300

TGC TCT TTC TCT ATC TTC CTT CTG GCC CTG CTC TCT TGC CTG ACC GTG      960
Cys Ser Phe Ser Ile Phe Leu Leu Ala Leu Leu Ser Cys Leu Thr Val
305                 310                 315                 320

CCC GCA TCA GCC TAC CAA GTA CGC AAC TCC TCG GGC CTT TAC CAT GTC     1008
Pro Ala Ser Ala Tyr Gln Val Arg Asn Ser Ser Gly Leu Tyr His Val
                325                 330                 335

ACC AAT GAT TGC CCC AAC TCG AGT ATT GTG TAC GAG ACG GCC GAT GCC     1056
Thr Asn Asp Cys Pro Asn Ser Ser Ile Val Tyr Glu Thr Ala Asp Ala
            340                 345                 350

ATC CTG CAC ACT CCG GGG TGC GTC CCT TGC GTT CGT GAG GGC AAC GCC     1104
Ile Leu His Thr Pro Gly Cys Val Pro Cys Val Arg Glu Gly Asn Ala
        355                 360                 365

TCG AGA TGT TGG GTG GCG GTG GCC CCC ACA GTG GCC ACC AGG GAT GGA     1152
Ser Arg Cys Trp Val Ala Val Ala Pro Thr Val Ala Thr Arg Asp Gly
    370                 375                 380

AAA CTC CCC GCA ACG CAG CTT CGA CGT CAC ATT GAT CTG CTT GTC GGG     1200
Lys Leu Pro Ala Thr Gln Leu Arg Arg His Ile Asp Leu Leu Val Gly
385                 390                 395                 400

AGC GCC ACC CTC TGT TCG GCC CTC TAC TTA AGG AGC TCG GTA CCC GGG     1248
Ser Ala Thr Leu Cys Ser Ala Leu Tyr Leu Arg Ser Ser Val Pro Gly
                405                 410                 415

GAT CCT CTA GAC TGC AGG CAT GCT AAG                                 1275
Asp Pro Leu Asp Cys Arg His Ala Lys
            420                 425

(2) INFORMATION FOR SEQ ID NO:22:

(i) SEQUENCE CHARACTERISTICS:
        (A) LENGTH: 425 amino acids
        (B) TYPE: amino acid
        (D) TOPOLOGY: linear (ii) MOLECULE TYPE: protein (xi) SEQUENCE DESCRIPTION: SEQ ID NO:22:

Met Ser Phe Val Val Ile Ile Pro Ala Arg Tyr Ala Ser Thr Arg Leu
1               5                  10                  15

Pro Gly Lys Pro Leu Val Asp Ile Asn Gly Lys Pro Met Ile Val His
                20                  25                  30

Val Leu Glu Arg Ala Arg Glu Ser Gly Ala Glu Arg Ile Ile Val Ala
            35                  40                  45

Thr Asp His Glu Asp Val Ala Arg Ala Val Glu Ala Ala Gly Gly Glu
        50                  55                  60
```

```
Val Cys Met Thr Arg Ala Asp His Gln Ser Gly Thr Glu Arg Leu Ala
 65                  70                  75                  80

Glu Val Val Glu Lys Cys Ala Phe Ser Asp Asp Thr Val Ile Val Asn
                 85                  90                  95

Val Gln Gly Asp Glu Pro Met Ile Pro Ala Thr Ile Ile Arg Gln Val
            100                 105                 110

Ala Asp Asn Leu Ala Gln Arg Gln Val Gly Met Ala Thr Leu Ala Val
            115                 120                 125

Pro Ile His Asn Ala Glu Glu Ala Phe Asn Pro Asn Ala Val Lys Val
            130                 135                 140

Val Leu Asp Ala Glu Gly Tyr Ala Leu Tyr Phe Ser Arg Ala Thr Ile
145                 150                 155                 160

Pro Trp Asp Arg Asp Arg Phe Ala Glu Gly Leu Glu Thr Val Gly Asp
                165                 170                 175

Asn Phe Leu Arg His Leu Gly Ile Tyr Gly Tyr Arg Ala Gly Phe Ile
                180                 185                 190

Arg Arg Tyr Val Asn Trp Gln Pro Ser Pro Leu Glu His Ile Glu Met
            195                 200                 205

Leu Glu Gln Leu Arg Val Leu Trp Tyr Gly Glu Lys Ile His Val Ala
210                 215                 220

Val Ala Gln Glu Val Pro Gly Thr Gly Val Asp Thr Pro Glu Asp Leu
225                 230                 235                 240

Asp Pro Ser Thr Arg Ile Arg Arg Ser Arg Asn Leu Gly Lys Val Ile
                245                 250                 255

Asp Thr Leu Thr Cys Gly Phe Ala Asp Leu Met Gly Tyr Ile Pro Leu
                260                 265                 270

Val Gly Ala Pro Leu Gly Gly Ala Ala Arg Ala Leu Gly His Gly Val
            275                 280                 285

Arg Val Leu Glu Asp Gly Val Asn Tyr Ala Thr Gly Asn Leu Pro Gly
290                 295                 300

Cys Ser Phe Ser Ile Phe Leu Leu Ala Leu Leu Ser Cys Leu Thr Val
305                 310                 315                 320

Pro Ala Ser Ala Tyr Gln Val Arg Asn Ser Ser Gly Leu Tyr His Val
            325                 330                 335

Thr Asn Asp Cys Pro Asn Ser Ser Ile Val Tyr Glu Thr Ala Asp Ala
            340                 345                 350

Ile Leu His Thr Pro Gly Cys Val Pro Cys Val Arg Glu Gly Asn Ala
            355                 360                 365

Ser Arg Cys Trp Val Ala Val Ala Pro Thr Val Ala Thr Arg Asp Gly
370                 375                 380

Lys Leu Pro Ala Thr Gln Leu Arg Arg His Ile Asp Leu Leu Val Gly
385                 390                 395                 400

Ser Ala Thr Leu Cys Ser Ala Leu Tyr Leu Arg Ser Ser Val Pro Gly
                405                 410                 415

Asp Pro Leu Asp Cys Arg His Ala Lys
            420                 425

(2) INFORMATION FOR SEQ ID NO:23:

(i) SEQUENCE CHARACTERISTICS:
        (A) LENGTH: 1401 base pairs
        (B) TYPE: nucleic acid
        (C) STRANDEDNESS: single
        (D) TOPOLOGY: circular
```

(ii) MOLECULE TYPE: DNA (genomic)

(ix) FEATURE:
    (A) NAME/KEY: CDS
    (B) LOCATION: 1..1401

(xi) SEQUENCE DESCRIPTION: SEQ ID NO:23:

```
ATG AGT TTT GTG GTC ATT ATT CCC GCG CGC TAC GCG TCG ACG CGT CTG       48
Met Ser Phe Val Val Ile Ile Pro Ala Arg Tyr Ala Ser Thr Arg Leu
 1               5                  10                  15

CCC GGT AAA CCA TTG GTT GAT ATT AAC GGC AAA CCC ATG ATT GTT CAT       96
Pro Gly Lys Pro Leu Val Asp Ile Asn Gly Lys Pro Met Ile Val His
             20                  25                  30

GTT CTT GAA CGC GCG CGT GAA TCA GGT GCC GAG CGC ATC ATC GTG GCA      144
Val Leu Glu Arg Ala Arg Glu Ser Gly Ala Glu Arg Ile Ile Val Ala
         35                  40                  45

ACC GAT CAT GAG GAT GTT GCC CGC GCC GTT GAA GCC GCT GGC GGT GAA      192
Thr Asp His Glu Asp Val Ala Arg Ala Val Glu Ala Ala Gly Gly Glu
     50                  55                  60

GTA TGT ATG ACG CGC GCC GAT CAT CAG TCA GGA ACA GAA CGT CTG GCG      240
Val Cys Met Thr Arg Ala Asp His Gln Ser Gly Thr Glu Arg Leu Ala
 65                  70                  75                  80

GAA GTT GTC GAA AAA TGC GCA TTC AGC GAC GAC ACG GTG ATC GTT AAT      288
Glu Val Val Glu Lys Cys Ala Phe Ser Asp Asp Thr Val Ile Val Asn
                 85                  90                  95

GTG CAG GGT GAT GAA CCG ATG ATC CCT GCG ACA ATC ATT CGT CAG GTT      336
Val Gln Gly Asp Glu Pro Met Ile Pro Ala Thr Ile Ile Arg Gln Val
            100                 105                 110

GCT GAT AAC CTC GCT CAG CGT CAG GTG GGT ATG GCG ACT CTG GCG GTG      384
Ala Asp Asn Leu Ala Gln Arg Gln Val Gly Met Ala Thr Leu Ala Val
        115                 120                 125

CCA ATC CAC AAT GCG GAA GAA GCG TTT AAC CCG AAT GCG GTG AAA GTG      432
Pro Ile His Asn Ala Glu Glu Ala Phe Asn Pro Asn Ala Val Lys Val
    130                 135                 140

GTT CTC GAC GCT GAA GGG TAT GCA CTG TAC TTC TCT CGC GCC ACC ATT      480
Val Leu Asp Ala Glu Gly Tyr Ala Leu Tyr Phe Ser Arg Ala Thr Ile
145                 150                 155                 160

CCT TGG GAT CGT GAT CGT TTT GCA GAA GGC CTT GAA ACC GTT GGC GAT      528
Pro Trp Asp Arg Asp Arg Phe Ala Glu Gly Leu Glu Thr Val Gly Asp
                165                 170                 175

AAC TTC CTG CGT CAT CTT GGT ATT TAT GGC TAC CGT GCA GGC TTT ATC      576
Asn Phe Leu Arg His Leu Gly Ile Tyr Gly Tyr Arg Ala Gly Phe Ile
            180                 185                 190

CGT CGT TAC GTC AAC TGG CAG CCA AGT CCG TTA GAA CAC ATC GAA ATG      624
Arg Arg Tyr Val Asn Trp Gln Pro Ser Pro Leu Glu His Ile Glu Met
        195                 200                 205

TTA GAG CAG CTT CGT GTT CTG TGG TAC GGC GAA AAA ATC CAT GTT GCT      672
Leu Glu Gln Leu Arg Val Leu Trp Tyr Gly Glu Lys Ile His Val Ala
    210                 215                 220

GTT GCT CAG GAA GTT CCT GGC ACA GGT GTG GAT ACC CCT GAA GAT CTC      720
Val Ala Gln Glu Val Pro Gly Thr Gly Val Asp Thr Pro Glu Asp Leu
225                 230                 235                 240

GAC CCG TCG ACT CGA ATT CTG CTT GTC GGG AGC GCC ACC CTC TGC TCG      768
Asp Pro Ser Thr Arg Ile Leu Leu Val Gly Ser Ala Thr Leu Cys Ser
                245                 250                 255

GCC CTC TAT GTG GGG GAC TTG TGC GGG TCT GTC TTT CTT GTC GGT CAA      816
Ala Leu Tyr Val Gly Asp Leu Cys Gly Ser Val Phe Leu Val Gly Gln
            260                 265                 270

CTG TTC ACT TTC TCC CCC AGG CAG CAC TGG ACA ACG CAA GAC TGC AAC      864
Leu Phe Thr Phe Ser Pro Arg Gln His Trp Thr Thr Gln Asp Cys Asn
        275                 280                 285
```

-continued

```
TGT TCT ATC TAC CCC GGC CAC GTA ACG GGT CAC CGC ATG GCA TGG GAT      912
Cys Ser Ile Tyr Pro Gly His Val Thr Gly His Arg Met Ala Trp Asp
    290                 295                 300

ATG ATG ATG AAC TGG TCC CCT ACG ACA GCG CTG GTA GTA GCT CAG CTG      960
Met Met Met Asn Trp Ser Pro Thr Thr Ala Leu Val Val Ala Gln Leu
305                 310                 315                 320

CTC AGG GTC CCG CAA GCC ATC TTG GAC ATG ATC GCT GGT GCC CAC TGG     1008
Leu Arg Val Pro Gln Ala Ile Leu Asp Met Ile Ala Gly Ala His Trp
                325                 330                 335

GGA GTC CTA GCG GGC ATA GCG TAT TTC TCC ATG GTG GGG AAC TGG GCG     1056
Gly Val Leu Ala Gly Ile Ala Tyr Phe Ser Met Val Gly Asn Trp Ala
            340                 345                 350

AAG GTC CTG GTA GTG CTG CTG CTA TTT GCC GGC GTT GAC GCG GAA ACC     1104
Lys Val Leu Val Val Leu Leu Leu Phe Ala Gly Val Asp Ala Glu Thr
        355                 360                 365

CAC GTC ACC GGG GGA AGT GCC GGC CAC ATT ACG GCT GGG CTT GTT CGT     1152
His Val Thr Gly Gly Ser Ala Gly His Ile Thr Ala Gly Leu Val Arg
    370                 375                 380

CTC CTT TCA CCA GGC GCC AAG CAG AAC ATC CAA CTG ATC AAC ACC AAC     1200
Leu Leu Ser Pro Gly Ala Lys Gln Asn Ile Gln Leu Ile Asn Thr Asn
385                 390                 395                 400

GGC AGT TGG CAC ATC AAT AGC ACG GCC TTG AAC TGC AAT GAA AGC CTT     1248
Gly Ser Trp His Ile Asn Ser Thr Ala Leu Asn Cys Asn Glu Ser Leu
                405                 410                 415

AAC ACC GGC TGG TTA GCA GGG CTC TTC TAT CAC CAC AAA TTC AAC TCT     1296
Asn Thr Gly Trp Leu Ala Gly Leu Phe Tyr His His Lys Phe Asn Ser
            420                 425                 430

TCA GGC TGT CCT GAG AGG GTT GCC AGC TGC CGT CGC CTT ACC GAT TTT     1344
Ser Gly Cys Pro Glu Arg Val Ala Ser Cys Arg Arg Leu Thr Asp Phe
        435                 440                 445

GAC CAG GGC TGG GAA TTC GAG CTC GGT ACC CGG GGA TCC TCT AGA CTG     1392
Asp Gln Gly Trp Glu Phe Glu Leu Gly Thr Arg Gly Ser Ser Arg Leu
    450                 455                 460

CAG GCA TGC                                                         1401
Gln Ala Cys
465
```

(2) INFORMATION FOR SEQ ID NO:24:

(i) SEQUENCE CHARACTERISTICS:
        (A) LENGTH: 467 amino acids
        (B) TYPE: amino acid
        (D) TOPOLOGY: linear (ii) MOLECULE TYPE: protein (xi) SEQUENCE DESCRIPTION: SEQ ID NO:24:

```
Met Ser Phe Val Val Ile Ile Pro Ala Arg Tyr Ala Ser Thr Arg Leu
1               5                   10                  15

Pro Gly Lys Pro Leu Val Asp Ile Asn Gly Lys Pro Met Ile Val His
                20                  25                  30

Val Leu Glu Arg Ala Arg Glu Ser Gly Ala Glu Arg Ile Ile Val Ala
            35                  40                  45

Thr Asp His Glu Asp Val Ala Arg Ala Val Glu Ala Ala Gly Gly Glu
        50                  55                  60

Val Cys Met Thr Arg Ala Asp His Gln Ser Gly Thr Glu Arg Leu Ala
65                  70                  75                  80

Glu Val Val Glu Lys Cys Ala Phe Ser Asp Asp Thr Val Ile Val Asn
                85                  90                  95
```

```
Val Gln Gly Asp Glu Pro Met Ile Pro Ala Thr Ile Ile Arg Gln Val
            100                 105                 110

Ala Asp Asn Leu Ala Gln Arg Gln Val Gly Met Ala Thr Leu Ala Val
        115                 120                 125

Pro Ile His Asn Ala Glu Glu Ala Phe Asn Pro Asn Ala Val Lys Val
    130                 135                 140

Val Leu Asp Ala Glu Gly Tyr Ala Leu Tyr Phe Ser Arg Ala Thr Ile
145                 150                 155                 160

Pro Trp Asp Arg Asp Arg Phe Ala Glu Gly Leu Glu Thr Val Gly Asp
                165                 170                 175

Asn Phe Leu Arg His Leu Gly Ile Tyr Gly Tyr Arg Ala Gly Phe Ile
            180                 185                 190

Arg Arg Tyr Val Asn Trp Gln Pro Ser Pro Leu Glu His Ile Glu Met
        195                 200                 205

Leu Glu Gln Leu Arg Val Leu Trp Tyr Gly Lys Ile His Val Ala
    210                 215                 220

Val Ala Gln Glu Val Pro Gly Thr Gly Val Asp Thr Pro Glu Asp Leu
225                 230                 235                 240

Asp Pro Ser Thr Arg Ile Leu Leu Val Gly Ser Ala Thr Leu Cys Ser
                245                 250                 255

Ala Leu Tyr Val Gly Asp Leu Cys Gly Ser Val Phe Leu Val Gly Gln
            260                 265                 270

Leu Phe Thr Phe Ser Pro Arg Gln His Trp Thr Thr Gln Asp Cys Asn
        275                 280                 285

Cys Ser Ile Tyr Pro Gly His Val Thr Gly His Arg Met Ala Trp Asp
        290                 295                 300

Met Met Met Asn Trp Ser Pro Thr Thr Ala Leu Val Val Ala Gln Leu
305                 310                 315                 320

Leu Arg Val Pro Gln Ala Ile Leu Asp Met Ile Ala Gly Ala His Trp
                325                 330                 335

Gly Val Leu Ala Gly Ile Ala Tyr Phe Ser Met Val Gly Asn Trp Ala
            340                 345                 350

Lys Val Leu Val Val Leu Leu Phe Ala Gly Val Asp Ala Glu Thr
        355                 360                 365

His Val Thr Gly Gly Ser Ala Gly His Ile Thr Ala Gly Leu Val Arg
    370                 375                 380

Leu Leu Ser Pro Gly Ala Lys Gln Asn Ile Gln Leu Ile Asn Thr Asn
385                 390                 395                 400

Gly Ser Trp His Ile Asn Ser Thr Ala Leu Asn Cys Asn Glu Ser Leu
                405                 410                 415

Asn Thr Gly Trp Leu Ala Gly Leu Phe Tyr His His Lys Phe Asn Ser
            420                 425                 430

Ser Gly Cys Pro Glu Arg Val Ala Ser Cys Arg Arg Leu Thr Asp Phe
        435                 440                 445

Asp Gln Gly Trp Glu Phe Glu Leu Gly Thr Arg Gly Ser Ser Arg Leu
    450                 455                 460

Gln Ala Cys
465

(2) INFORMATION FOR SEQ ID NO:25:

(i) SEQUENCE CHARACTERISTICS:
        (A) LENGTH: 1422 base pairs
        (B) TYPE: nucleic acid
        (C) STRANDEDNESS: single
```

(D) TOPOLOGY: circular (ii) MOLECULE TYPE: DNA (genomic)

(ix) FEATURE:
         (A) NAME/KEY: CDS
         (B) LOCATION: 1..1422

(xi) SEQUENCE DESCRIPTION: SEQ ID NO:25:

```
ATG AGT TTT GTG GTC ATT ATT CCC GCG CGC TAC GCG TCG ACG CGT CTG      48
Met Ser Phe Val Val Ile Ile Pro Ala Arg Tyr Ala Ser Thr Arg Leu
 1               5                  10                  15

CCC GGT AAA CCA TTG GTT GAT ATT AAC GGC AAA CCC ATG ATT GTT CAT      96
Pro Gly Lys Pro Leu Val Asp Ile Asn Gly Lys Pro Met Ile Val His
             20                  25                  30

GTT CTT GAA CGC GCG CGT GAA TCA GGT GCC GAG CGC ATC ATC GTG GCA     144
Val Leu Glu Arg Ala Arg Glu Ser Gly Ala Glu Arg Ile Ile Val Ala
         35                  40                  45

ACC GAT CAT GAG GAT GTT GCC CGC GCC GTT GAA GCC GCT GGC GGT GAA     192
Thr Asp His Glu Asp Val Ala Arg Ala Val Glu Ala Ala Gly Gly Glu
     50                  55                  60

GTA TGT ATG ACG CGC GCC GAT CAT CAG TCA GGA ACA GAA CGT CTG GCG     240
Val Cys Met Thr Arg Ala Asp His Gln Ser Gly Thr Glu Arg Leu Ala
 65                  70                  75                  80

GAA GTT GTC GAA AAA TGC GCA TTC AGC GAC GAC ACG GTG ATC GTT AAT     288
Glu Val Val Glu Lys Cys Ala Phe Ser Asp Asp Thr Val Ile Val Asn
                 85                  90                  95

GTG CAG GGT GAT GAA CCG ATG ATC CCT GCG ACA ATC ATT CGT CAG GTT     336
Val Gln Gly Asp Glu Pro Met Ile Pro Ala Thr Ile Ile Arg Gln Val
            100                 105                 110

GCT GAT AAC CTC GCT CAG CGT CAG GTG GGT ATG GCG ACT CTG GCG GTG     384
Ala Asp Asn Leu Ala Gln Arg Gln Val Gly Met Ala Thr Leu Ala Val
        115                 120                 125

CCA ATC CAC AAT GCG GAA GAA GCG TTT AAC CCG AAT GCG GTG AAA GTG     432
Pro Ile His Asn Ala Glu Glu Ala Phe Asn Pro Asn Ala Val Lys Val
    130                 135                 140

GTT CTC GAC GCT GAA GGG TAT GCA CTG TAC TTC TCT CGC GCC ACC ATT     480
Val Leu Asp Ala Glu Gly Tyr Ala Leu Tyr Phe Ser Arg Ala Thr Ile
145                 150                 155                 160

CCT TGG GAT CGT GAT CGT TTT GCA GAA GGC CTT GAA ACC GTT GGC GAT     528
Pro Trp Asp Arg Asp Arg Phe Ala Glu Gly Leu Glu Thr Val Gly Asp
                165                 170                 175

AAC TTC CTG CGT CAT CTT GGT ATT TAT GGC TAC CGT GCA GGC TTT ATC     576
Asn Phe Leu Arg His Leu Gly Ile Tyr Gly Tyr Arg Ala Gly Phe Ile
            180                 185                 190

CGT CGT TAC GTC AAC TGG CAG CCA AGT CCG TTA GAA CAC ATC GAA ATG     624
Arg Arg Tyr Val Asn Trp Gln Pro Ser Pro Leu Glu His Ile Glu Met
        195                 200                 205

TTA GAG CAG CTT CGT GTT CTG TGG TAC GGC GAA AAA ATC CAT GTT GCT     672
Leu Glu Gln Leu Arg Val Leu Trp Tyr Gly Glu Lys Ile His Val Ala
    210                 215                 220

GTT GCT CAG GAA GTT CCT GGC ACA GGT GTG GAT ACC CCT GAA GAT CTC     720
Val Ala Gln Glu Val Pro Gly Thr Gly Val Asp Thr Pro Glu Asp Leu
225                 230                 235                 240

GAC CCG TCG ACC GAA TTC GGT GAC ATC ATC AAC GGC TTG CCC GTC TCC     768
Asp Pro Ser Thr Glu Phe Gly Asp Ile Ile Asn Gly Leu Pro Val Ser
                245                 250                 255

GCC CGT AGG GGC CAG GAG ATA CTG CTC GGA CCA GCC GAC GGA ATG GTC     816
Ala Arg Arg Gly Gln Glu Ile Leu Leu Gly Pro Ala Asp Gly Met Val
            260                 265                 270

TCC AAG GGG TGG AGG TTG CTG GCG CCC ATC ACG GCG TAC GCC CAG CAG     864
```

```
Ser Lys Gly Trp Arg Leu Leu Ala Pro Ile Thr Ala Tyr Ala Gln Gln
        275                 280                 285

ACA AGG GGC CTC CTA GGG TGT ATA ATC ACC AGC CTG ACT GGC CGG GAC      912
Thr Arg Gly Leu Leu Gly Cys Ile Ile Thr Ser Leu Thr Gly Arg Asp
    290                 295                 300

AAA AAC CAA GCG GAG GGT GAG GTC CAG ATT GTG TCA ACT GCT GCC CAA      960
Lys Asn Gln Ala Glu Gly Glu Val Gln Ile Val Ser Thr Ala Ala Gln
305                 310                 315                 320

ACT TTC CTG GCA ACG TGC ATC AAT GGG GTA TGC TGG ACT GTC TAC CAT     1008
Thr Phe Leu Ala Thr Cys Ile Asn Gly Val Cys Trp Thr Val Tyr His
                325                 330                 335

GGG GCC GGA ACG AGG ACC CTC GCA TCA CCC AAG GGT CCT GTT ATC CAG     1056
Gly Ala Gly Thr Arg Thr Leu Ala Ser Pro Lys Gly Pro Val Ile Gln
            340                 345                 350

ATG TAT ACC AAT GTA GAC CAA GAC CTT GTG GGC TGG CCC GCT CCT CAA     1104
Met Tyr Thr Asn Val Asp Gln Asp Leu Val Gly Trp Pro Ala Pro Gln
        355                 360                 365

GGT GCC CGC TCA TTG ACA CCC TGC ACC TGC GGC TCC TCG GAC CTT TAC     1152
Gly Ala Arg Ser Leu Thr Pro Cys Thr Cys Gly Ser Ser Asp Leu Tyr
370                 375                 380

CTG GTT ACG AGG CAC GCC GAT GTC ATT CCC GTG CGC CGG CGG GGT GAT     1200
Leu Val Thr Arg His Ala Asp Val Ile Pro Val Arg Arg Arg Gly Asp
385                 390                 395                 400

AGC AGG GGC AGC CTG CTT TCG CCC CGG CCC ATT TCT TAT TTG AAA GGC     1248
Ser Arg Gly Ser Leu Leu Ser Pro Arg Pro Ile Ser Tyr Leu Lys Gly
                405                 410                 415

TCC TCG GGG GGT CCG CTG TTG TGC CCC GCG GGA CAC GCC GTG GGC ATA     1296
Ser Ser Gly Gly Pro Leu Leu Cys Pro Ala Gly His Ala Val Gly Ile
            420                 425                 430

TTC AGG GCC GCG GTG TGT ACC CGT GGA GTG GCT AAG GCG GTG GAC TTT     1344
Phe Arg Ala Ala Val Cys Thr Arg Gly Val Ala Lys Ala Val Asp Phe
        435                 440                 445

GTC CCC GTG GAG AAC CTC GAG ACA ACC ATG AAT TCG AGC TCG GTA CCC     1392
Val Pro Val Glu Asn Leu Glu Thr Thr Met Asn Ser Ser Ser Val Pro
450                 455                 460

GGG GAT CCT CTA GAC TGC AGG CAT GCT AAG                             1422
Gly Asp Pro Leu Asp Cys Arg His Ala Lys
465                 470

(2) INFORMATION FOR SEQ ID NO:26:

(i) SEQUENCE CHARACTERISTICS:
        (A) LENGTH: 474 amino acids
        (B) TYPE: amino acid
        (D) TOPOLOGY: linear (ii) MOLECULE TYPE: protein (xi) SEQUENCE DESCRIPTION: SEQ ID NO:26:

Met Ser Phe Val Val Ile Ile Pro Ala Arg Tyr Ala Ser Thr Arg Leu
  1               5                  10                  15

Pro Gly Lys Pro Leu Val Asp Ile Asn Gly Lys Pro Met Ile Val His
                 20                  25                  30

Val Leu Glu Arg Ala Arg Glu Ser Gly Ala Glu Arg Ile Ile Val Ala
             35                  40                  45

Thr Asp His Glu Asp Val Ala Arg Ala Val Glu Ala Ala Gly Gly Glu
         50                  55                  60

Val Cys Met Thr Arg Ala Asp His Gln Ser Gly Thr Glu Arg Leu Ala
 65                  70                  75                  80

Glu Val Val Glu Lys Cys Ala Phe Ser Asp Asp Thr Val Ile Val Asn
```

```
                     85                  90                  95
Val Gln Gly Asp Glu Pro Met Ile Pro Ala Thr Ile Ile Arg Gln Val
                100                 105                 110

Ala Asp Asn Leu Ala Gln Arg Gln Val Gly Met Ala Thr Leu Ala Val
                115                 120                 125

Pro Ile His Asn Ala Glu Glu Ala Phe Asn Pro Asn Ala Val Lys Val
            130                 135                 140

Val Leu Asp Ala Glu Gly Tyr Ala Leu Tyr Phe Ser Arg Ala Thr Ile
145                 150                 155                 160

Pro Trp Asp Arg Asp Arg Phe Ala Glu Gly Leu Glu Thr Val Gly Asp
                165                 170                 175

Asn Phe Leu Arg His Leu Gly Ile Tyr Gly Tyr Arg Ala Gly Phe Ile
                180                 185                 190

Arg Arg Tyr Val Asn Trp Gln Pro Ser Pro Leu Glu His Ile Glu Met
            195                 200                 205

Leu Glu Gln Leu Arg Val Leu Trp Tyr Gly Glu Lys Ile His Val Ala
        210                 215                 220

Val Ala Gln Glu Val Pro Gly Thr Gly Val Asp Thr Pro Glu Asp Leu
225                 230                 235                 240

Asp Pro Ser Thr Glu Phe Gly Asp Ile Ile Asn Gly Leu Pro Val Ser
                245                 250                 255

Ala Arg Arg Gly Gln Glu Ile Leu Leu Gly Pro Ala Asp Gly Met Val
            260                 265                 270

Ser Lys Gly Trp Arg Leu Leu Ala Pro Ile Thr Ala Tyr Ala Gln Gln
        275                 280                 285

Thr Arg Gly Leu Leu Gly Cys Ile Ile Thr Ser Leu Thr Gly Arg Asp
    290                 295                 300

Lys Asn Gln Ala Glu Gly Glu Val Gln Ile Val Ser Thr Ala Ala Gln
305                 310                 315                 320

Thr Phe Leu Ala Thr Cys Ile Asn Gly Val Cys Trp Thr Val Tyr His
                325                 330                 335

Gly Ala Gly Thr Arg Thr Leu Ala Ser Pro Lys Gly Pro Val Ile Gln
            340                 345                 350

Met Tyr Thr Asn Val Asp Gln Asp Leu Val Gly Trp Pro Ala Pro Gln
        355                 360                 365

Gly Ala Arg Ser Leu Thr Pro Cys Thr Cys Gly Ser Ser Asp Leu Tyr
    370                 375                 380

Leu Val Thr Arg His Ala Asp Val Ile Pro Val Arg Arg Arg Gly Asp
385                 390                 395                 400

Ser Arg Gly Ser Leu Leu Ser Pro Arg Pro Ile Ser Tyr Leu Lys Gly
                405                 410                 415

Ser Ser Gly Gly Pro Leu Leu Cys Pro Ala Gly His Ala Val Gly Ile
            420                 425                 430

Phe Arg Ala Ala Val Cys Thr Arg Gly Val Ala Lys Ala Val Asp Phe
        435                 440                 445

Val Pro Val Glu Asn Leu Glu Thr Thr Met Asn Ser Ser Ser Val Pro
    450                 455                 460

Gly Asp Pro Leu Asp Cys Arg His Ala Lys
465                 470

(2) INFORMATION FOR SEQ ID NO:27:

(i) SEQUENCE CHARACTERISTICS:
        (A) LENGTH: 1401 base pairs
```

(B) TYPE: nucleic acid
            (C) STRANDEDNESS: single
            (D) TOPOLOGY: circular (ii) MOLECULE TYPE: DNA (genomic)

(ix) FEATURE:
            (A) NAME/KEY: CDS
            (B) LOCATION: 1..1401

(xi) SEQUENCE DESCRIPTION: SEQ ID NO:27:

```
ATG AGT TTT GTG GTC ATT ATT CCC GCG CGC TAC GCG TCG ACG CGT CTG      48
Met Ser Phe Val Val Ile Ile Pro Ala Arg Tyr Ala Ser Thr Arg Leu
 1               5                  10                  15

CCC GGT AAA CCA TTG GTT GAT ATT AAC GGC AAA CCC ATG ATT GTT CAT      96
Pro Gly Lys Pro Leu Val Asp Ile Asn Gly Lys Pro Met Ile Val His
             20                  25                  30

GTT CTT GAA CGC GCG CGT GAA TCA GGT GCC GAG CGC ATC ATC GTG GCA     144
Val Leu Glu Arg Ala Arg Glu Ser Gly Ala Glu Arg Ile Ile Val Ala
         35                  40                  45

ACC GAT CAT GAG GAT GTT GCC CGC GCC GTT GAA GCC GCT GGC GGT GAA     192
Thr Asp His Glu Asp Val Ala Arg Ala Val Glu Ala Ala Gly Gly Glu
     50                  55                  60

GTA TGT ATG ACG CGC GCC GAT CAT CAG TCA GGA ACA GAA CGT CTG GCG     240
Val Cys Met Thr Arg Ala Asp His Gln Ser Gly Thr Glu Arg Leu Ala
 65                  70                  75                  80

GAA GTT GTC GAA AAA TGC GCA TTC AGC GAC GAC ACG GTG ATC GTT AAT     288
Glu Val Val Glu Lys Cys Ala Phe Ser Asp Asp Thr Val Ile Val Asn
                 85                  90                  95

GTG CAG GGT GAT GAA CCG ATG ATC CCT GCG ACA ATC ATT CGT CAG GTT     336
Val Gln Gly Asp Glu Pro Met Ile Pro Ala Thr Ile Ile Arg Gln Val
            100                 105                 110

GCT GAT AAC CTC GCT CAG CGT CAG GTG GGT ATG ACG ACT CTG GCG GTG     384
Ala Asp Asn Leu Ala Gln Arg Gln Val Gly Met Thr Thr Leu Ala Val
        115                 120                 125

CCA ATC CAC AAT GCG GAA GAA GCG TTT AAC CCG AAT GCG GTG AAA GTG     432
Pro Ile His Asn Ala Glu Glu Ala Phe Asn Pro Asn Ala Val Lys Val
    130                 135                 140

GTT CTC GAC GCT GAA GGG TAT GCA CTG TAC TTC TCT CGC GCC ACC ATT     480
Val Leu Asp Ala Glu Gly Tyr Ala Leu Tyr Phe Ser Arg Ala Thr Ile
145                 150                 155                 160

CCT TGG GAT CGT GAT CGT TTT GCA GAA GGC CTT GAA ACC GTT GGC GAT     528
Pro Trp Asp Arg Asp Arg Phe Ala Glu Gly Leu Glu Thr Val Gly Asp
                165                 170                 175

AAC TTC CTG CGT CAT CTT GGT ATT TAT GGC TAC CGT GCA GGC TTT ATC     576
Asn Phe Leu Arg His Leu Gly Ile Tyr Gly Tyr Arg Ala Gly Phe Ile
            180                 185                 190

CGT CGT TAC GTC AAC TGG CAG CCA AGT CCG TTA GAA CAC ATC GAA ATG     624
Arg Arg Tyr Val Asn Trp Gln Pro Ser Pro Leu Glu His Ile Glu Met
        195                 200                 205

TTA GAG CAG CTT CGT GTT CTG TGG TAC GGC GAA AAA ATC CAT GTT GCT     672
Leu Glu Gln Leu Arg Val Leu Trp Tyr Gly Glu Lys Ile His Val Ala
    210                 215                 220

GTT GCT CAG GAA GTT CCT GGC ACA GGT GTG GAT ACC CCT GAA GAT CTC     720
Val Ala Gln Glu Val Pro Gly Thr Gly Val Asp Thr Pro Glu Asp Leu
225                 230                 235                 240

GAC CCG TCG ACG AAT TCC ACC ATG GGG CAT TAT CCT TGT ACC ATC AAC     768
Asp Pro Ser Thr Asn Ser Thr Met Gly His Tyr Pro Cys Thr Ile Asn
                245                 250                 255

TAC ACC CTG TTC AAA GTC AGG ATG TAC GTG GGA GGG GTC GAG CAC AGG     816
Tyr Thr Leu Phe Lys Val Arg Met Tyr Val Gly Gly Val Glu His Arg
            260                 265                 270
```

```
CTG GAA GTT GCT TGC AAC TGG ACG CGG GGC GAA CGT TGT GAT CTG GAC        864
Leu Glu Val Ala Cys Asn Trp Thr Arg Gly Glu Arg Cys Asp Leu Asp
        275                 280                 285

GAC AGG GAC AGG TCC GAG CTC AGC CCG CTG CTG TCC ACC ACT CAG            912
Asp Arg Asp Arg Ser Glu Leu Ser Pro Leu Leu Ser Thr Thr Gln
        290                 295                 300

TGG CAG GTC CTT CCG TGT TCC TTC ACG ACC TTG CCA GCC TTG ACC ACC        960
Trp Gln Val Leu Pro Cys Ser Phe Thr Thr Leu Pro Ala Leu Thr Thr
305                 310                 315                 320

GGC CTC ATC CAC CTC CAC CAG AAC ATC GTG GAC GTG CAA TAC TTG TAC       1008
Gly Leu Ile His Leu His Gln Asn Ile Val Asp Val Gln Tyr Leu Tyr
                325                 330                 335

GGG GTG GGG TCA AGC ATT GTG TCC TGG GCC ATC AAG TGG GAG TAC GTC       1056
Gly Val Gly Ser Ser Ile Val Ser Trp Ala Ile Lys Trp Glu Tyr Val
                340                 345                 350

ATC CTC TTG TTT CTC CTG CTT GCA GAC GCG CGC ATC TGC TCC TGC TTG       1104
Ile Leu Leu Phe Leu Leu Leu Ala Asp Ala Arg Ile Cys Ser Cys Leu
        355                 360                 365

TGG ATG ATG TTA CTC ATA TCC CAA GCG GAG GCA GCC TTG GAA AAC CTT       1152
Trp Met Met Leu Leu Ile Ser Gln Ala Glu Ala Ala Leu Glu Asn Leu
        370                 375                 380

GTG TTA CTC AAT GCG GCG TCT CTG GCC GGG ACG CAC GGT CTT GTG TCC       1200
Val Leu Leu Asn Ala Ala Ser Leu Ala Gly Thr His Gly Leu Val Ser
385                 390                 395                 400

TTC CTC GTG TTT TTC TGC TTT GCA TGG TAT CTG AAG GGT AAG TGG GTG       1248
Phe Leu Val Phe Phe Cys Phe Ala Trp Tyr Leu Lys Gly Lys Trp Val
                405                 410                 415

CCC GGA GTG GCC TAC GCC TTC TAC GGG ATG TGG CCT TTC CTC CTG CTC       1296
Pro Gly Val Ala Tyr Ala Phe Tyr Gly Met Trp Pro Phe Leu Leu Leu
                420                 425                 430

CTG TTA GCG TTG CCC CAA CGG GCA TAC GCG CTG GAC ACG GAG ATG GCC       1344
Leu Leu Ala Leu Pro Gln Arg Ala Tyr Ala Leu Asp Thr Glu Met Ala
        435                 440                 445

GCG TCG TGT GGC GGC GTT GTT CTT GTC GGG TTA ATG GCG CTG ACT CTG       1392
Ala Ser Cys Gly Gly Val Val Leu Val Gly Leu Met Ala Leu Thr Leu
450                 455                 460

TCA CCA TAT                                                           1401
Ser Pro Tyr
465

(2) INFORMATION FOR SEQ ID NO:28:

(i) SEQUENCE CHARACTERISTICS:
        (A) LENGTH: 467 amino acids
        (B) TYPE: amino acid
        (D) TOPOLOGY: linear (ii) MOLECULE TYPE: protein (xi) SEQUENCE DESCRIPTION: SEQ ID NO:28:

Met Ser Phe Val Val Ile Ile Pro Ala Arg Tyr Ala Ser Thr Arg Leu
 1               5                  10                  15

Pro Gly Lys Pro Leu Val Asp Ile Asn Gly Lys Pro Met Ile Val His
            20                  25                  30

Val Leu Glu Arg Ala Arg Glu Ser Gly Ala Glu Arg Ile Ile Val Ala
        35                  40                  45

Thr Asp His Glu Asp Val Ala Arg Ala Val Glu Ala Ala Gly Gly Glu
    50                  55                  60

Val Cys Met Thr Arg Ala Asp His Gln Ser Gly Thr Glu Arg Leu Ala
65                  70                  75                  80
```

```
Glu Val Val Glu Lys Cys Ala Phe Ser Asp Asp Thr Val Ile Val Asn
                85                  90                  95
Val Gln Gly Asp Glu Pro Met Ile Pro Ala Thr Ile Ile Arg Gln Val
            100                 105                 110
Ala Asp Asn Leu Ala Gln Arg Gln Val Gly Met Thr Thr Leu Ala Val
            115                 120                 125
Pro Ile His Asn Ala Glu Glu Ala Phe Asn Pro Asn Ala Val Lys Val
            130                 135                 140
Val Leu Asp Ala Glu Gly Tyr Ala Leu Tyr Phe Ser Arg Ala Thr Ile
145                 150                 155                 160
Pro Trp Asp Arg Asp Arg Phe Ala Glu Gly Leu Glu Thr Val Gly Asp
                165                 170                 175
Asn Phe Leu Arg His Leu Gly Ile Tyr Gly Tyr Arg Ala Gly Phe Ile
                180                 185                 190
Arg Arg Tyr Val Asn Trp Gln Pro Ser Pro Leu Glu His Ile Glu Met
            195                 200                 205
Leu Glu Gln Leu Arg Val Leu Trp Tyr Gly Lys Ile His Val Ala
            210                 215                 220
Val Ala Gln Glu Val Pro Gly Thr Gly Val Asp Thr Pro Glu Asp Leu
225                 230                 235                 240
Asp Pro Ser Thr Asn Ser Thr Met Gly His Tyr Pro Cys Thr Ile Asn
                245                 250                 255
Tyr Thr Leu Phe Lys Val Arg Met Tyr Val Gly Val Glu His Arg
                260                 265                 270
Leu Glu Val Ala Cys Asn Trp Thr Arg Gly Glu Arg Cys Asp Leu Asp
            275                 280                 285
Asp Arg Asp Arg Ser Glu Leu Ser Pro Leu Leu Ser Thr Thr Gln
290                 295                 300
Trp Gln Val Leu Pro Cys Ser Phe Thr Thr Leu Pro Ala Leu Thr Thr
305                 310                 315                 320
Gly Leu Ile His Leu His Gln Asn Ile Val Asp Val Gln Tyr Leu Tyr
                325                 330                 335
Gly Val Gly Ser Ser Ile Val Ser Trp Ala Ile Lys Trp Glu Tyr Val
            340                 345                 350
Ile Leu Leu Phe Leu Leu Leu Ala Asp Ala Arg Ile Cys Ser Cys Leu
            355                 360                 365
Trp Met Met Leu Leu Ile Ser Gln Ala Glu Ala Leu Glu Asn Leu
            370                 375                 380
Val Leu Leu Asn Ala Ala Ser Leu Ala Gly Thr His Gly Leu Val Ser
385                 390                 395                 400
Phe Leu Val Phe Phe Cys Phe Ala Trp Tyr Leu Lys Gly Lys Trp Val
                405                 410                 415
Pro Gly Val Ala Tyr Ala Phe Tyr Gly Met Trp Pro Phe Leu Leu Leu
            420                 425                 430
Leu Leu Ala Leu Pro Gln Arg Ala Tyr Ala Leu Asp Thr Glu Met Ala
            435                 440                 445
Ala Ser Cys Gly Gly Val Val Leu Val Gly Leu Met Ala Leu Thr Leu
450                 455                 460
Ser Pro Tyr
465
```

(2) INFORMATION FOR SEQ ID NO:29:

(i) SEQUENCE CHARACTERISTICS:
    (A) LENGTH: 1851 base pairs
    (B) TYPE: nucleic acid
    (C) STRANDEDNESS: single
    (D) TOPOLOGY: circular (ii) MOLECULE TYPE: DNA (genomic)

(ix) FEATURE:
    (A) NAME/KEY: CDS
    (B) LOCATION: 1..1851

(xi) SEQUENCE DESCRIPTION: SEQ ID NO:29:

```
ATG AGT TTT GTG GTC ATT ATT CCC GCG CGC TAC GCG TCG ACG CGT CTG      48
Met Ser Phe Val Val Ile Ile Pro Ala Arg Tyr Ala Ser Thr Arg Leu
 1               5                  10                  15

CCC GGT AAA CCA TTG GTT GAT ATT AAC GGC AAA CCC ATG ATT GTT CAT      96
Pro Gly Lys Pro Leu Val Asp Ile Asn Gly Lys Pro Met Ile Val His
             20                  25                  30

GTT CTT GAA CGC GCG CGT GAA TCA GGT GCC GAG CGC ATC ATC GTG GCA     144
Val Leu Glu Arg Ala Arg Glu Ser Gly Ala Glu Arg Ile Ile Val Ala
         35                  40                  45

ACC GAT CAT GAG GAT GTT GCC CGC GCC GTT GAA GCC GCT GGC GGT GAA     192
Thr Asp His Glu Asp Val Ala Arg Ala Val Glu Ala Ala Gly Gly Glu
     50                  55                  60

GTA TGT ATG ACG CGC GCC GAT CAT CAG TCA GGA ACA GAA CGT CTG GCG     240
Val Cys Met Thr Arg Ala Asp His Gln Ser Gly Thr Glu Arg Leu Ala
 65                  70                  75                  80

GAA GTT GTC GAA AAA TGC GCA TTC AGC GAC GAC ACG GTG ATC GTT AAT     288
Glu Val Val Glu Lys Cys Ala Phe Ser Asp Asp Thr Val Ile Val Asn
                 85                  90                  95

GTG CAG GGT GAT GAA CCG ATG ATC CCT GCG ACA ATC ATT CGT CAG GTT     336
Val Gln Gly Asp Glu Pro Met Ile Pro Ala Thr Ile Ile Arg Gln Val
            100                 105                 110

GCT GAT AAC CTC GCT CAG CGT CAG GTG GGT ATG GCG ACT CTG GCG GTG     384
Ala Asp Asn Leu Ala Gln Arg Gln Val Gly Met Ala Thr Leu Ala Val
        115                 120                 125

CCA ATC CAC AAT GCG GAA GAA GCG TTT AAC CCG AAT GCG GTG AAA GTG     432
Pro Ile His Asn Ala Glu Glu Ala Phe Asn Pro Asn Ala Val Lys Val
    130                 135                 140

GTT CTC GAC GCT GAA GGG TAT GCA CTG TAC TTC TCT CGC GCC ACC ATT     480
Val Leu Asp Ala Glu Gly Tyr Ala Leu Tyr Phe Ser Arg Ala Thr Ile
145                 150                 155                 160

CCT TGG GAT CGT GAT CGT TTT GCA GAA GGC CTT GAA ACC GTT GGC GAT     528
Pro Trp Asp Arg Asp Arg Phe Ala Glu Gly Leu Glu Thr Val Gly Asp
                165                 170                 175

AAC TTC CTG CGT CAT CTT GGT ATT TAT GGC TAC CGT GCA GGC TTT ATC     576
Asn Phe Leu Arg His Leu Gly Ile Tyr Gly Tyr Arg Ala Gly Phe Ile
            180                 185                 190

CGT CGT TAC GTC AAC TGG CAG CCA AGT CCG TTA GAA CAC ATC GAA ATG     624
Arg Arg Tyr Val Asn Trp Gln Pro Ser Pro Leu Glu His Ile Glu Met
        195                 200                 205

TTA GAG CAG CTT CGT GTT CTG TGG TAC GGC GAA AAA ATC CAT GTT GCT     672
Leu Glu Gln Leu Arg Val Leu Trp Tyr Gly Glu Lys Ile His Val Ala
    210                 215                 220

GTT GCT CAG GAA GTT CCT GGC ACA GGT GTG GAT ACC CCT GAA GAT CTC     720
Val Ala Gln Glu Val Pro Gly Thr Gly Val Asp Thr Pro Glu Asp Leu
225                 230                 235                 240

GAC CCG TCG ACT CGA ATT CGT AGG TCG CGC AAT TTG GGT AAG GTC ATC     768
Asp Pro Ser Thr Arg Ile Arg Arg Ser Arg Asn Leu Gly Lys Val Ile
                245                 250                 255

GAT ACC CTC ACG TGC GGC TTC GCC GAC CTC ATG GGG TAC ATT CCG CTC     816
```

-continued

| | | |
|---|---|---|
| Asp Thr Leu Thr Cys Gly Phe Ala Asp Leu Met Gly Tyr Ile Pro Leu<br>    260                                   265                      270 | | |

```
GTC GGC GCC CCT CTT GGA GGC GCT GCC AGG GCC CTG GCG CAT GGC GTC       864
Val Gly Ala Pro Leu Gly Gly Ala Ala Arg Ala Leu Ala His Gly Val
            275                 280                 285

CGG GTT CTG GAA GAC GGC GTG AAC TAT GCA ACA GGG AAC CTT CCC GGT       912
Arg Val Leu Glu Asp Gly Val Asn Tyr Ala Thr Gly Asn Leu Pro Gly
        290                 295                 300

TGC TCT TTC TCT ATC TTC CTT GCC CTG CTC TCT TGC CTG ACT GTG           960
Cys Ser Phe Ser Ile Phe Leu Ala Leu Leu Ser Cys Leu Thr Val
305                 310                 315                 320

CCC GCG TCA TCC TAC CAA GTA CGC AAC TCC TCG GGC TTT TAT CAT GTC      1008
Pro Ala Ser Ser Tyr Gln Val Arg Asn Ser Ser Gly Leu Tyr His Val
                325                 330                 335

ACC AAT GAT TGC CCC AAC TCG AGC ATT GTG TAC GAG ACG GCC GAT ACC      1056
Thr Asn Asp Cys Pro Asn Ser Ser Ile Val Tyr Glu Thr Ala Asp Thr
            340                 345                 350

ATC CTA CAC TCT CCG GGG TGC GTC CCT TGC GTT CGC GAG GGC AAC ACC      1104
Ile Leu His Ser Pro Gly Cys Val Pro Cys Val Arg Glu Gly Asn Thr
        355                 360                 365

TCG AAA TGT TGG GTG GCG GTG GCC CCC ACA GTG GCC ACC AGG GAC GGC      1152
Ser Lys Cys Trp Val Ala Val Ala Pro Thr Val Ala Thr Arg Asp Gly
370                 375                 380

AAA CTC CCC TCA ACG CAG CTT CGA CGT CAC ATC GAT CTG CTC GTC GGG      1200
Lys Leu Pro Ser Thr Gln Leu Arg Arg His Ile Asp Leu Leu Val Gly
385                 390                 395                 400

AGC GCC ACC CTC TGC TCG GCC CTC TAT GTG GGG GAC TTG TGC GGG TCT      1248
Ser Ala Thr Leu Cys Ser Ala Leu Tyr Val Gly Asp Leu Cys Gly Ser
                405                 410                 415

GTC TTT CTT GTC AGT CAA CTG TTC ACC TTC TCC CCT AGG CGC CAT TGG      1296
Val Phe Leu Val Ser Gln Leu Phe Thr Phe Ser Pro Arg Arg His Trp
            420                 425                 430

ACA ACG CAA GAC TGC AAC TGT TCT ATC TAC CCC GGC CAT ATA ACG GGT      1344
Thr Thr Gln Asp Cys Asn Cys Ser Ile Tyr Pro Gly His Ile Thr Gly
        435                 440                 445

CAC CGC ATG GCA TGG GAT ATG ATG ATG AAC TGG TCC CCT ACA ACG GCG      1392
His Arg Met Ala Trp Asp Met Met Met Asn Trp Ser Pro Thr Thr Ala
450                 455                 460

CTG GTA GTA GCT CAG CTG CTC AGG GTC CCA CAA GCC ATC TTG GAC ATG      1440
Leu Val Val Ala Gln Leu Leu Arg Val Pro Gln Ala Ile Leu Asp Met
465                 470                 475                 480

ATC GCA GGT GCC CAC TGG GGA GTC CTA GCG GGC ATA GCG TAT TTC TCC      1488
Ile Ala Gly Ala His Trp Gly Val Leu Ala Gly Ile Ala Tyr Phe Ser
                485                 490                 495

ATG GTG GGG AAC TGG GCG AAG GTC CTG GTA GTG CTG TTG CTG TTT TCC      1536
Met Val Gly Asn Trp Ala Lys Val Leu Val Val Leu Leu Leu Phe Ser
            500                 505                 510

GGC GTC GAT GCG GCA ACC TAC ACC ACC GGG GGG AGC GTT GCT AGG ACC      1584
Gly Val Asp Ala Ala Thr Tyr Thr Thr Gly Gly Ser Val Ala Arg Thr
        515                 520                 525

ACG CAT GGA TTC TCC AGC TTA TTC AGT CAA GGC GCC AAG CAG AAC ATC      1632
Thr His Gly Phe Ser Ser Leu Phe Ser Gln Gly Ala Lys Gln Asn Ile
    530                 535                 540

CAG CTG ATT AAC ACC AAC GGC AGT TGG CAC ATC AAT CGC ACG GCC TTG      1680
Gln Leu Ile Asn Thr Asn Gly Ser Trp His Ile Asn Arg Thr Ala Leu
545                 550                 555                 560

AAC TGT AAT GCA AGC CTC GAC ACT GGC TGG GTA GCG GGG CTC TTC TAT      1728
Asn Cys Asn Ala Ser Leu Asp Thr Gly Trp Val Ala Gly Leu Phe Tyr
                565                 570                 575
```

```
TAC CAC AAA TTC AAC TCT TCA GGC TGC CCT GAG AGG ATG GCC AGC TGT      1776
Tyr His Lys Phe Asn Ser Ser Gly Cys Pro Glu Arg Met Ala Ser Cys
         580                 585                 590

AGA CCC CTT GCC GAT TTT GAC CAG GGC TGG GAA TTC GAG CTC GGT ACC      1824
Arg Pro Leu Ala Asp Phe Asp Gln Gly Trp Glu Phe Glu Leu Gly Thr
    595                 600                 605

CGG GGA TCC TCT AGA CTG CAG GCA TGC                                  1851
Arg Gly Ser Ser Arg Leu Gln Ala Cys
    610                 615
```

(2) INFORMATION FOR SEQ ID NO:30:

(i) SEQUENCE CHARACTERISTICS:
        (A) LENGTH: 617 amino acids
        (B) TYPE: amino acid
        (D) TOPOLOGY: linear (ii) MOLECULE TYPE: protein (xi) SEQUENCE DESCRIPTION: SEQ ID NO:30:

```
Met Ser Phe Val Val Ile Ile Pro Ala Arg Tyr Ala Ser Thr Arg Leu
 1               5                  10                  15

Pro Gly Lys Pro Leu Val Asp Ile Asn Gly Lys Pro Met Ile Val His
             20                  25                  30

Val Leu Glu Arg Ala Arg Glu Ser Gly Ala Glu Arg Ile Ile Val Ala
         35                  40                  45

Thr Asp His Glu Asp Val Ala Arg Ala Val Glu Ala Ala Gly Gly Glu
     50                  55                  60

Val Cys Met Thr Arg Ala Asp His Gln Ser Gly Thr Glu Arg Leu Ala
 65                  70                  75                  80

Glu Val Val Glu Lys Cys Ala Phe Ser Asp Asp Thr Val Ile Val Asn
                 85                  90                  95

Val Gln Gly Asp Glu Pro Met Ile Pro Ala Thr Ile Ile Arg Gln Val
            100                 105                 110

Ala Asp Asn Leu Ala Gln Arg Gln Val Gly Met Ala Thr Leu Ala Val
        115                 120                 125

Pro Ile His Asn Ala Glu Glu Ala Phe Asn Pro Asn Ala Val Lys Val
    130                 135                 140

Val Leu Asp Ala Glu Gly Tyr Ala Leu Tyr Phe Ser Arg Ala Thr Ile
145                 150                 155                 160

Pro Trp Asp Arg Asp Arg Phe Ala Glu Gly Leu Glu Thr Val Gly Asp
                165                 170                 175

Asn Phe Leu Arg His Leu Gly Ile Tyr Gly Tyr Arg Ala Gly Phe Ile
            180                 185                 190

Arg Arg Tyr Val Asn Trp Gln Pro Ser Pro Leu Glu His Ile Glu Met
        195                 200                 205

Leu Glu Gln Leu Arg Val Leu Trp Tyr Gly Glu Lys Ile His Val Ala
    210                 215                 220

Val Ala Gln Glu Val Pro Gly Thr Gly Val Asp Thr Pro Glu Asp Leu
225                 230                 235                 240

Asp Pro Ser Thr Arg Ile Arg Arg Ser Arg Asn Leu Gly Lys Val Ile
                245                 250                 255

Asp Thr Leu Thr Cys Gly Phe Ala Asp Leu Met Gly Tyr Ile Pro Leu
            260                 265                 270

Val Gly Ala Pro Leu Gly Gly Ala Ala Arg Ala Leu Ala His Gly Val
        275                 280                 285

Arg Val Leu Glu Asp Gly Val Asn Tyr Ala Thr Gly Asn Leu Pro Gly
```

```
                    290                 295                 300
Cys Ser Phe Ser Ile Phe Leu Leu Ala Leu Leu Ser Cys Leu Thr Val
305                 310                 315                 320

Pro Ala Ser Ser Tyr Gln Val Arg Asn Ser Ser Gly Leu Tyr His Val
                    325                 330                 335

Thr Asn Asp Cys Pro Asn Ser Ser Ile Val Tyr Glu Thr Ala Asp Thr
                    340                 345                 350

Ile Leu His Ser Pro Gly Cys Val Pro Cys Val Arg Glu Gly Asn Thr
                    355                 360                 365

Ser Lys Cys Trp Val Ala Val Ala Pro Thr Val Ala Thr Arg Asp Gly
370                 375                 380

Lys Leu Pro Ser Thr Gln Leu Arg Arg His Ile Asp Leu Leu Val Gly
385                 390                 395                 400

Ser Ala Thr Leu Cys Ser Ala Leu Tyr Val Gly Asp Leu Cys Gly Ser
                    405                 410                 415

Val Phe Leu Val Ser Gln Leu Phe Thr Phe Ser Pro Arg Arg His Trp
                    420                 425                 430

Thr Thr Gln Asp Cys Asn Cys Ser Ile Tyr Pro Gly His Ile Thr Gly
                    435                 440                 445

His Arg Met Ala Trp Asp Met Met Met Asn Trp Ser Pro Thr Thr Ala
450                 455                 460

Leu Val Val Ala Gln Leu Leu Arg Val Pro Gln Ala Ile Leu Asp Met
465                 470                 475                 480

Ile Ala Gly Ala His Trp Gly Val Leu Ala Gly Ile Ala Tyr Phe Ser
                    485                 490                 495

Met Val Gly Asn Trp Ala Lys Val Leu Val Val Leu Leu Leu Phe Ser
                    500                 505                 510

Gly Val Asp Ala Ala Thr Tyr Thr Thr Gly Gly Ser Val Ala Arg Thr
                    515                 520                 525

Thr His Gly Phe Ser Ser Leu Phe Ser Gln Gly Ala Lys Gln Asn Ile
                    530                 535                 540

Gln Leu Ile Asn Thr Asn Gly Ser Trp His Ile Asn Arg Thr Ala Leu
545                 550                 555                 560

Asn Cys Asn Ala Ser Leu Asp Thr Gly Trp Val Ala Gly Leu Phe Tyr
                    565                 570                 575

Tyr His Lys Phe Asn Ser Ser Gly Cys Pro Glu Arg Met Ala Ser Cys
                    580                 585                 590

Arg Pro Leu Ala Asp Phe Asp Gln Gly Trp Glu Phe Glu Leu Gly Thr
                    595                 600                 605

Arg Gly Ser Ser Arg Leu Gln Ala Cys
610                 615
```

(2) INFORMATION FOR SEQ ID NO:31:

(i) SEQUENCE CHARACTERISTICS:
        (A) LENGTH: 463 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:31:

```
Met Ser Phe Val Val Ile Ile Pro Ala Arg Tyr Ala Ser Thr Arg Leu
1               5                   10                  15

Pro Gly Lys Pro Leu Val Asp Ile Asn Gly Lys Pro Met Ile Val His
```

```
                    20                  25                  30
Val Leu Glu Arg Ala Arg Glu Ser Gly Ala Glu Arg Ile Ile Val Ala
             35                  40                  45
Thr Asp His Glu Asp Val Ala Arg Ala Val Glu Ala Ala Gly Gly Glu
     50                  55                  60
Val Cys Met Thr Arg Ala Asp His Gln Ser Gly Thr Glu Arg Leu Ala
 65                  70                  75                  80
Glu Val Val Glu Lys Cys Ala Phe Ser Asp Asp Thr Val Ile Val Asn
                 85                  90                  95
Val Gln Gly Asp Glu Pro Met Ile Pro Ala Thr Ile Ile Arg Gln Val
                100                 105                 110
Ala Asp Asn Leu Ala Gln Arg Gln Val Gly Met Thr Thr Leu Ala Val
            115                 120                 125
Pro Ile His Asn Ala Glu Glu Ala Phe Asn Pro Asn Ala Val Lys Val
        130                 135                 140
Val Leu Asp Ala Glu Gly Tyr Ala Leu Tyr Phe Ser Arg Ala Thr Ile
145                 150                 155                 160
Pro Trp Asp Arg Asp Arg Phe Ala Glu Gly Leu Glu Thr Val Gly Asp
                165                 170                 175
Asn Phe Leu Arg His Leu Gly Ile Tyr Gly Tyr Arg Ala Gly Phe Ile
            180                 185                 190
Arg Arg Tyr Val Asn Trp Gln Pro Ser Pro Leu Glu His Ile Glu Met
        195                 200                 205
Leu Glu Gln Leu Arg Val Leu Trp Tyr Gly Glu Lys Ile His Val Ala
    210                 215                 220
Val Ala Gln Glu Val Pro Gly Thr Gly Val Asp Thr Pro Glu Asp Leu
225                 230                 235                 240
Asp Pro Ser Thr Asn Ser Thr Met Val Gly Asn Trp Ala Lys Val Leu
                245                 250                 255
Val Val Leu Leu Leu Phe Ala Gly Val Asp Ala Glu Thr His Val Thr
            260                 265                 270
Gly Gly Ser Ala Gly His Thr Val Ser Gly Phe Val Ser Leu Leu Ala
        275                 280                 285
Pro Gly Ala Lys Gln Asn Val Gln Leu Ile Asn Thr Asn Gly Ser Trp
    290                 295                 300
His Leu Asn Ser Thr Ala Leu Asn Cys Asn Asp Ser Leu Asn Thr Gly
305                 310                 315                 320
Trp Leu Ala Gly Leu Phe Tyr His His Lys Phe Asn Ser Ser Gly Cys
                325                 330                 335
Pro Glu Arg Leu Ala Ser Cys Arg Pro Leu Thr Asp Phe Asp Gln Gly
            340                 345                 350
Trp Gly Gln Ile Ser Tyr Ala Asn Gly Ser Gly Pro Asp Gln Arg Pro
        355                 360                 365
Tyr Cys Trp His Tyr Pro Pro Lys Pro Cys Gly Ile Val Pro Ala Lys
    370                 375                 380
Ser Val Cys Gly Pro Val Tyr Cys Phe Thr Pro Ser Pro Val Val Val
385                 390                 395                 400
Gly Thr Thr Asp Arg Ser Gly Ala Pro Thr Tyr Ser Trp Gly Glu Asn
                405                 410                 415
Asp Thr Asp Val Phe Val Leu Asn Asn Thr Arg Pro Pro Leu Gly Asn
            420                 425                 430
Trp Phe Gly Cys Thr Trp Met Asn Ser Thr Gly Phe Thr Lys Val Cys
        435                 440                 445
```

```
Gly Ala Pro Pro Cys Val Ile Gly Gly Ala Gly Asn Asn Thr Leu
    450                 455                 460
```

(2) INFORMATION FOR SEQ ID NO:32:

(i) SEQUENCE CHARACTERISTICS:
        (A) LENGTH: 414 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:32:

```
Met Ser Phe Val Val Ile Ile Pro Ala Arg Tyr Ala Ser Thr Arg Leu
1               5                   10                  15

Pro Gly Lys Pro Leu Val Asp Ile Asn Gly Lys Pro Met Ile Val His
            20                  25                  30

Val Leu Glu Arg Ala Arg Glu Ser Gly Ala Glu Arg Ile Ile Val Ala
        35                  40                  45

Thr Asp His Glu Asp Val Ala Arg Ala Val Glu Ala Ala Gly Gly Glu
50                  55                  60

Val Cys Met Thr Arg Ala Asp His Gln Ser Gly Thr Glu Arg Leu Ala
65                  70                  75                  80

Glu Val Val Glu Lys Cys Ala Phe Ser Asp Asp Thr Val Ile Val Asn
                85                  90                  95

Val Gln Gly Asp Glu Pro Met Ile Pro Ala Thr Ile Ile Arg Gln Val
            100                 105                 110

Ala Asp Asn Leu Ala Gln Arg Gln Val Gly Met Thr Thr Leu Ala Val
        115                 120                 125

Pro Ile His Asn Ala Glu Glu Ala Phe Asn Pro Asn Ala Val Lys Val
130                 135                 140

Val Leu Asp Ala Glu Gly Tyr Ala Leu Tyr Phe Ser Arg Ala Thr Ile
145                 150                 155                 160

Pro Trp Asp Arg Asp Arg Phe Ala Glu Gly Leu Glu Thr Val Gly Asp
                165                 170                 175

Asn Phe Leu Arg His Leu Gly Ile Tyr Gly Tyr Arg Ala Gly Phe Ile
            180                 185                 190

Arg Arg Tyr Val Asn Trp Gln Pro Ser Pro Leu Glu His Ile Glu Met
        195                 200                 205

Leu Glu Gln Leu Arg Val Leu Trp Tyr Gly Glu Lys Ile His Val Ala
210                 215                 220

Val Ala Gln Glu Val Pro Gly Thr Gly Val Asp Thr Pro Glu Asp Leu
225                 230                 235                 240

Asp Pro Ser Thr Asn Ser Met Gly Ala Pro Pro Cys Val Ile Gly Gly
                245                 250                 255

Ala Gly Asn Asn Thr Leu His Cys Pro Thr Asp Cys Phe Arg Lys His
            260                 265                 270

Pro Asp Ala Thr Tyr Ser Arg Cys Gly Ser Gly Pro Trp Ile Thr Pro
        275                 280                 285

Arg Cys Leu Val Asp Tyr Pro Tyr Arg Leu Trp His Thr Pro Cys Thr
290                 295                 300

Ile Asn Thr Thr Ile Phe Lys Ile Arg Met Tyr Val Gly Gly Val Glu
305                 310                 315                 320

His Arg Leu Glu Ala Ala Cys Asn Trp Thr Arg Gly Glu Arg Cys Asp
                325                 330                 335
```

```
Leu Glu Asp Arg Asp Arg Ser Glu Leu Ser Pro Leu Leu Leu Thr Thr
                340                 345                 350

Thr Gln Trp Gln Val Leu Pro Cys Ser Phe Thr Thr Leu Pro Ala Leu
            355                 360                 365

Ser Thr Gly Leu Ile His Leu Gly Gln Asn Ile Val Asp Val Gln Tyr
        370                 375                 380

Leu Tyr Gly Val Gly Ser Ser Ile Ala Ser Trp Ala Ile Lys Trp Glu
385                 390                 395                 400

Tyr Val Val Leu Leu Phe Leu Leu Leu Ala Asp Ala Arg Val
                405                 410
```

(2) INFORMATION FOR SEQ ID NO:33:

(i) SEQUENCE CHARACTERISTICS:
        (A) LENGTH: 378 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:33:

```
Met Ser Phe Val Ile Ile Pro Ala Arg Tyr Ala Ser Thr Arg Leu Pro
1               5                   10                  15

Gly Lys Pro Leu Val Asp Ile Asn Gly Lys Pro Met Ile Val His Val
                20                  25                  30

Leu Glu Arg Ala Arg Glu Ser Gly Ala Glu Arg Ile Ile Val Ala Thr
            35                  40                  45

Asp His Glu Asp Val Ala Arg Ala Val Glu Ala Ala Gly Gly Glu Val
        50                  55                  60

Cys Met Thr Arg Ala Asp His Gln Ser Gly Thr Glu Arg Leu Ala Glu
65                  70                  75                  80

Val Val Glu Lys Cys Ala Phe Ser Asp Asp Thr Val Ile Val Asn Val
                85                  90                  95

Gln Gly Asp Glu Pro Met Ile Pro Ala Thr Ile Ile Arg Gln Val Ala
                100                 105                 110

Asp Asn Leu Ala Gln Arg Gln Val Gly Met Thr Thr Leu Ala Val Pro
            115                 120                 125

Ile His Asn Ala Glu Glu Ala Phe Asn Pro Asn Ala Val Lys Val Val
        130                 135                 140

Leu Asp Ala Glu Gly Tyr Ala Leu Tyr Phe Ser Arg Ala Thr Ile Pro
145                 150                 155                 160

Trp Asp Arg Asp Arg Phe Ala Glu Gly Leu Glu Thr Val Gly Asp Asn
                165                 170                 175

Phe Leu Arg His Leu Gly Ile Tyr Gly Tyr Arg Ala Gly Phe Ile Arg
            180                 185                 190

Arg Tyr Val Asn Trp Gln Pro Ser Pro Leu Glu His Ile Glu Met Leu
        195                 200                 205

Glu Gln Leu Arg Val Leu Trp Tyr Gly Glu Lys Ile His Val Ala Val
        210                 215                 220

Ala Gln Glu Val Pro Gly Thr Gly Val Asp Thr Pro Glu Asp Leu Asp
225                 230                 235                 240

Pro Ser Thr Asn Ser Thr Met Glu Tyr Val Val Leu Leu Phe Leu Leu
                245                 250                 255

Leu Ala Asp Ala Arg Val Cys Ser Cys Leu Trp Met Met Leu Leu Ile
                260                 265                 270
```

```
Ser Gln Ala Glu Ala Ala Leu Glu Asn Leu Val Ile Leu Asn Ala Ala
        275                 280                 285

Ser Leu Ala Gly Thr His Gly Leu Val Ser Phe Leu Val Phe Phe Cys
        290                 295                 300

Phe Ala Trp Tyr Leu Lys Gly Lys Trp Val Pro Gly Ala Val Tyr Thr
305                 310                 315                 320

Phe Tyr Gly Met Trp Pro Leu Leu Leu Leu Leu Ala Leu Pro Gln
                325                 330                 335

Arg Ala Tyr Ala Leu Asp Thr Glu Val Ala Ala Ser Cys Gly Gly Val
            340                 345                 350

Val Leu Val Gly Leu Met Ala Leu Thr Leu Ser Pro Tyr Tyr Lys Arg
            355                 360                 365

Tyr Ile Ser Trp Cys Leu Trp Trp Leu Gln
370                 375

(2) INFORMATION FOR SEQ ID NO:34:

(i) SEQUENCE CHARACTERISTICS:
        (A) LENGTH: 622 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:34:

Met Ser Phe Val Val Ile Ile Pro Ala Arg Tyr Ala Ser Thr Arg Leu
1               5                   10                  15

Pro Gly Lys Pro Leu Val Asp Ile Asn Gly Lys Pro Met Ile Val His
                20                  25                  30

Val Leu Glu Arg Ala Arg Glu Ser Gly Ala Glu Arg Ile Ile Val Ala
            35                  40                  45

Thr Asp His Glu Asp Val Ala Arg Ala Val Glu Ala Ala Gly Gly Glu
        50                  55                  60

Val Cys Met Thr Arg Ala Asp His Gln Ser Gly Thr Glu Arg Leu Ala
65                  70                  75                  80

Glu Val Val Glu Lys Cys Ala Phe Ser Asp Asp Thr Val Ile Val Asn
                85                  90                  95

Val Gln Gly Asp Glu Pro Met Ile Pro Ala Thr Ile Ile Arg Gln Val
            100                 105                 110

Ala Asp Asn Leu Ala Gln Arg Gln Val Gly Met Thr Thr Leu Ala Val
        115                 120                 125

Pro Ile His Asn Ala Glu Glu Ala Phe Asn Pro Asn Ala Val Lys Val
    130                 135                 140

Val Leu Asp Ala Glu Gly Tyr Ala Leu Tyr Phe Ser Arg Ala Thr Ile
145                 150                 155                 160

Pro Trp Asp Arg Asp Arg Phe Ala Glu Gly Leu Glu Thr Val Gly Asp
                165                 170                 175

Asn Phe Leu Arg His Leu Gly Ile Tyr Gly Tyr Arg Ala Gly Phe Ile
            180                 185                 190

Arg Arg Tyr Val Asn Trp Gln Pro Ser Pro Leu Glu His Ile Glu Met
        195                 200                 205

Leu Glu Gln Leu Arg Val Leu Trp Tyr Gly Glu Lys Ile His Val Ala
    210                 215                 220

Val Ala Gln Glu Val Pro Gly Thr Gly Val Asp Thr Pro Glu Asp Leu
225                 230                 235                 240
```

-continued

```
Asp Pro Ser Thr Asn Ser Thr Met Val Gly Asn Trp Ala Lys Val Leu
            245                 250                 255
Val Val Leu Leu Leu Phe Ala Gly Val Asp Ala Glu Thr His Val Thr
        260                 265                 270
Gly Gly Ser Ala Gly His Thr Val Ser Gly Phe Val Ser Leu Leu Ala
    275                 280                 285
Pro Gly Ala Lys Gln Asn Val Gln Leu Ile Asn Thr Asn Gly Ser Trp
290                 295                 300
His Leu Asn Ser Thr Ala Leu Asn Cys Asn Asp Ser Leu Asn Thr Gly
305                 310                 315                 320
Trp Leu Ala Gly Leu Phe Tyr His His Lys Phe Asn Ser Ser Gly Cys
                325                 330                 335
Pro Glu Arg Leu Ala Ser Cys Arg Pro Leu Thr Asp Phe Asp Gln Gly
            340                 345                 350
Trp Gly Gln Ile Ser Tyr Ala Asn Gly Ser Gly Pro Asp Gln Arg Pro
        355                 360                 365
Tyr Cys Trp His Tyr Pro Pro Lys Pro Cys Gly Ile Val Pro Ala Lys
    370                 375                 380
Ser Val Cys Gly Pro Val Tyr Cys Phe Thr Pro Ser Pro Val Val Val
385                 390                 395                 400
Gly Thr Thr Asp Arg Ser Gly Ala Pro Thr Tyr Ser Trp Gly Glu Asn
                405                 410                 415
Asp Thr Asp Val Phe Val Leu Asn Asn Thr Arg Pro Pro Leu Gly Asn
            420                 425                 430
Trp Phe Gly Cys Thr Trp Met Asn Ser Thr Gly Phe Thr Lys Val Cys
        435                 440                 445
Gly Ala Pro Pro Cys Val Ile Gly Pro Pro Cys Val Ile Gly Gly Ala
    450                 455                 460
Gly Asn Asn Thr Leu His Cys Pro Thr Asp Cys Phe Arg Lys His Pro
465                 470                 475                 480
Asp Ala Thr Tyr Ser Arg Cys Gly Ser Gly Pro Trp Ile Thr Pro Arg
                485                 490                 495
Cys Leu Val Asp Tyr Pro Tyr Arg Leu Trp His Tyr Pro Cys Thr Ile
            500                 505                 510
Asn Tyr Thr Ile Phe Lys Ile Arg Met Tyr Val Gly Gly Val Glu His
        515                 520                 525
Arg Leu Glu Ala Ala Cys Asn Trp Thr Arg Gly Glu Arg Cys Asp Leu
    530                 535                 540
Glu Asp Arg Asp Arg Ser Glu Leu Ser Pro Leu Leu Leu Thr Thr Thr
545                 550                 555                 560
Gln Trp Gln Val Leu Pro Cys Ser Phe Thr Thr Leu Pro Ala Leu Ser
                565                 570                 575
Thr Gly Leu Ile His Leu His Gln Asn Ile Val Asp Val Gln Tyr Leu
            580                 585                 590
Tyr Gly Val Gly Ser Ser Ile Ala Ser Trp Ala Ile Lys Trp Glu Tyr
        595                 600                 605
Val Val Leu Leu Phe Leu Leu Leu Ala Asp Ala Arg Val Xaa
    610                 615                 620
```

(2) INFORMATION FOR SEQ ID NO:35:

(i) SEQUENCE CHARACTERISTICS:
        (A) LENGTH: 738 amino acids
        (B) TYPE: amino acid

```
        (C) STRANDEDNESS: single
        (D) TOPOLOGY: linear (ii) MOLECULE TYPE: peptide (xi) SEQUENCE DESCRIPTION: SEQ ID NO:35:

Met Ser Phe Val Val Ile Ile Pro Ala Arg Tyr Ala Ser Thr Arg Leu
1               5                   10                  15

Pro Gly Lys Pro Leu Val Asp Ile Asn Gly Lys Pro Met Ile Val His
                20                  25                  30

Val Leu Glu Arg Ala Arg Glu Ser Gly Ala Glu Arg Ile Ile Val Ala
            35                  40                  45

Thr Asp His Glu Asp Val Ala Arg Ala Val Glu Ala Ala Gly Gly Glu
        50                  55                  60

Val Cys Met Thr Arg Ala Asp His Gln Ser Gly Thr Glu Arg Leu Ala
65                  70                  75                  80

Glu Val Val Glu Lys Cys Ala Phe Ser Asp Asp Thr Val Ile Val Asn
                85                  90                  95

Val Gln Gly Asp Glu Pro Met Ile Pro Ala Thr Ile Ile Arg Gln Val
            100                 105                 110

Ala Asp Asn Leu Ala Gln Arg Gln Val Gly Met Thr Thr Leu Ala Val
        115                 120                 125

Pro Ile His Asn Ala Glu Glu Ala Phe Asn Pro Asn Ala Val Lys Val
    130                 135                 140

Val Leu Asp Ala Glu Gly Tyr Ala Leu Tyr Phe Ser Arg Ala Thr Ile
145                 150                 155                 160

Pro Trp Asp Arg Asp Arg Phe Ala Glu Gly Leu Glu Thr Val Gly Asp
                165                 170                 175

Asn Phe Leu Arg His Leu Gly Ile Tyr Gly Tyr Arg Ala Gly Phe Ile
            180                 185                 190

Arg Arg Tyr Val Asn Trp Gln Pro Ser Pro Leu Glu His Ile Glu Met
        195                 200                 205

Leu Glu Gln Leu Arg Val Leu Trp Tyr Gly Glu Lys Ile His Val Ala
    210                 215                 220

Val Ala Gln Glu Val Pro Gly Thr Gly Val Asp Thr Pro Glu Asp Leu
225                 230                 235                 240

Asp Pro Ser Thr Asn Ser Thr Met Val Gly Asn Trp Ala Lys Val Leu
                245                 250                 255

Val Val Leu Leu Leu Phe Ala Gly Val Asp Ala Glu Thr His Val Thr
            260                 265                 270

Gly Gly Ser Ala Gly His Thr Val Ser Gly Phe Val Ser Leu Leu Ala
        275                 280                 285

Pro Gly Ala Lys Gln Asn Val Gln Leu Ile Asn Thr Asn Gly Ser Trp
    290                 295                 300

His Leu Asn Ser Thr Ala Leu Asn Cys Asn Asp Ser Leu Asn Thr Gly
305                 310                 315                 320

Trp Leu Ala Gly Leu Phe Tyr His His Lys Phe Asn Ser Ser Gly Cys
                325                 330                 335

Pro Glu Arg Leu Ala Ser Cys Arg Pro Leu Thr Asp Phe Asp Gln Gly
            340                 345                 350

Trp Gly Gln Ile Ser Tyr Ala Asn Gly Ser Gly Pro Asp Gln Arg Pro
        355                 360                 365

Tyr Cys Trp His Tyr Pro Pro Lys Pro Cys Gly Ile Val Pro Ala Lys
370                 375                 380
```

-continued

```
Ser Val Cys Gly Pro Val Tyr Cys Phe Thr Pro Ser Pro Val Val Val
385                 390                 395                 400

Gly Thr Thr Asp Arg Ser Gly Ala Pro Thr Tyr Ser Trp Gly Glu Asn
                405                 410                 415

Asp Thr Asp Val Phe Val Leu Asn Asn Thr Arg Pro Pro Leu Gly Asn
                420                 425                 430

Trp Phe Gly Cys Thr Trp Met Asn Ser Thr Gly Phe Thr Lys Val Cys
            435                 440                 445

Gly Ala Pro Pro Cys Val Ile Gly Pro Pro Cys Val Ile Gly Gly Ala
450                 455                 460

Gly Asn Asn Thr Leu His Cys Pro Thr Asp Cys Phe Arg Lys His Pro
465                 470                 475                 480

Asp Ala Thr Tyr Ser Arg Cys Gly Ser Gly Pro Trp Ile Thr Pro Arg
                485                 490                 495

Cys Leu Val Asp Tyr Pro Tyr Arg Leu Trp His Tyr Pro Cys Thr Ile
                500                 505                 510

Asn Tyr Thr Ile Phe Lys Ile Arg Met Tyr Val Gly Gly Val Glu His
                515                 520                 525

Arg Leu Glu Ala Ala Cys Asn Trp Thr Arg Gly Glu Arg Cys Asp Leu
530                 535                 540

Glu Asp Arg Asp Arg Ser Glu Leu Ser Pro Leu Leu Leu Thr Thr Thr
545                 550                 555                 560

Gln Trp Gln Val Leu Pro Cys Ser Phe Thr Thr Leu Pro Ala Leu Ser
                565                 570                 575

Thr Gly Leu Ile His Leu His Gln Asn Ile Val Asp Val Gln Tyr Leu
                580                 585                 590

Tyr Gly Val Gly Ser Ser Ile Ala Ser Trp Ala Ile Lys Trp Glu Tyr
                595                 600                 605

Val Val Leu Leu Phe Leu Leu Leu Ala Asp Ala Arg Val Cys Ser Cys
                610                 615                 620

Leu Trp Met Met Leu Leu Ile Ser Gln Ala Glu Ala Ala Leu Glu Asn
625                 630                 635                 640

Leu Val Ile Leu Asn Ala Ala Ser Leu Ala Gly Thr His Gly Leu Val
                645                 650                 655

Ser Phe Leu Val Phe Phe Cys Phe Ala Trp Tyr Leu Lys Gly Lys Trp
                660                 665                 670

Val Pro Gly Ala Val Tyr Thr Phe Tyr Gly Met Trp Pro Leu Leu Leu
                675                 680                 685

Leu Leu Leu Ala Leu Pro Gln Arg Ala Tyr Ala Leu Asp Thr Glu Val
690                 695                 700

Ala Ala Ser Cys Gly Gly Val Val Leu Val Gly Leu Met Ala Leu Thr
705                 710                 715                 720

Leu Ser Pro Tyr Tyr Lys Arg Tyr Ile Ser Trp Cys Leu Trp Trp Leu
                725                 730                 735

Gln Xaa
```

(2) INFORMATION FOR SEQ ID NO:36:

(i) SEQUENCE CHARACTERISTICS:
        (A) LENGTH: 798 amino acids
        (B) TYPE: amino acid
        (C) STRANDEDNESS: single
        (D) TOPOLOGY: linear (ii) MOLECULE TYPE: peptide -continued (xi) SEQUENCE DESCRIPTION: SEQ ID NO:36:

```
Met Ser Phe Val Val Ile Ile Pro Ala Arg Tyr Ala Ser Thr Arg Leu
1               5                   10                  15

Pro Gly Lys Pro Leu Val Asp Ile Asn Gly Lys Pro Met Ile Val His
            20                  25                  30

Val Leu Glu Arg Ala Arg Glu Ser Gly Ala Glu Arg Ile Ile Val Ala
        35                  40                  45

Thr Asp His Glu Asp Val Ala Arg Ala Val Glu Ala Ala Gly Gly Glu
    50                  55                  60

Val Cys Met Thr Arg Ala Asp His Gln Ser Gly Thr Glu Arg Leu Ala
65                  70                  75                  80

Glu Val Val Glu Lys Cys Ala Phe Ser Asp Asp Thr Val Ile Val Asn
                85                  90                  95

Val Gln Gly Asp Glu Pro Met Ile Pro Ala Thr Ile Ile Arg Gln Val
            100                 105                 110

Ala Asp Asn Leu Ala Gln Arg Gln Val Gly Met Ala Thr Leu Ala Val
        115                 120                 125

Pro Ile His Asn Ala Glu Glu Ala Phe Asn Pro Asn Ala Val Lys Val
    130                 135                 140

Val Leu Asp Ala Glu Gly Tyr Ala Leu Tyr Phe Ser Arg Ala Thr Ile
145                 150                 155                 160

Pro Trp Asp Arg Asp Arg Phe Ala Glu Gly Leu Glu Thr Val Gly Asp
                165                 170                 175

Asn Phe Leu Arg His Leu Gly Ile Tyr Gly Tyr Arg Ala Gly Phe Ile
            180                 185                 190

Arg Arg Tyr Val Asn Trp Gln Pro Ser Pro Leu Glu His Ile Glu Met
        195                 200                 205

Leu Glu Gln Leu Arg Val Leu Trp Tyr Gly Glu Lys Ile His Val Ala
    210                 215                 220

Val Ala Gln Glu Val Pro Gly Thr Gly Val Asp Thr Pro Glu Asp Leu
225                 230                 235                 240

Asp Pro Ser Thr Asn Ser Pro Trp Thr His Tyr Val Pro Glu Ser Asp
                245                 250                 255

Ala Ala Ala Arg Val Thr Ala Ile Leu Ser Ser Leu Thr Val Thr Gln
            260                 265                 270

Leu Leu Arg Arg Leu His Gln Trp Ile Ser Ser Glu Cys Thr Thr Pro
        275                 280                 285

Cys Ser Gly Ser Trp Leu Arg Asp Ile Trp Asp Trp Ile Cys Glu Val
    290                 295                 300

Leu Ser Asp Phe Lys Thr Trp Leu Lys Ala Lys Leu Met Pro Gln Leu
305                 310                 315                 320

Pro Gly Ile Pro Phe Val Ser Cys Gln Arg Gly Tyr Lys Gly Val Trp
                325                 330                 335

Arg Val Asp Gly Ile Met His Thr Arg Cys His Cys Gly Ala Glu Ile
            340                 345                 350

Thr Gly His Val Lys Asn Gly Thr Met Arg Ile Val Gly Pro Arg Thr
        355                 360                 365

Cys Arg Asn Met Trp Ser Gly Thr Phe Pro Ile Asn Ala Tyr Thr Thr
    370                 375                 380

Gly Pro Cys Thr Pro Leu Pro Ala Pro Asn Tyr Thr Phe Ala Leu Trp
385                 390                 395                 400

Arg Val Ser Ala Glu Glu Tyr Val Glu Ile Arg Gln Val Gly Asp Phe
                405                 410                 415
```

```
His Tyr Val Thr Gly Met Thr Thr Asp Asn Leu Lys Cys Pro Cys Gln
                420                 425                 430

Val Pro Ser Pro Glu Phe Phe Thr Glu Leu Asp Gly Val Arg Leu His
            435                 440                 445

Arg Phe Ala Pro Pro Cys Lys Pro Leu Leu Arg Glu Glu Val Ser Phe
        450                 455                 460

Arg Val Gly Leu His Glu Tyr Pro Val Gly Ser Gln Leu Pro Cys Glu
465                 470                 475                 480

Pro Glu Pro Asp Val Ala Val Leu Thr Ser Met Leu Thr Asp Pro Ser
                485                 490                 495

His Ile Thr Ala Glu Ala Ala Gly Arg Arg Leu Ala Arg Gly Ser Pro
            500                 505                 510

Pro Ser Val Ala Ser Ser Ser Ala Ser Gln Leu Ser Ala Pro Ser Leu
        515                 520                 525

Lys Ala Thr Cys Thr Ala Asn His Asp Ser Pro Asp Ala Glu Leu Ile
530                 535                 540

Glu Ala Asn Leu Leu Trp Arg Gln Glu Met Gly Gly Asn Ile Thr Arg
545                 550                 555                 560

Val Glu Ser Glu Asn Lys Val Val Ile Leu Asp Ser Phe Asp Pro Leu
                565                 570                 575

Val Ala Glu Glu Asp Glu Arg Glu Ile Ser Val Pro Ala Glu Ile Leu
            580                 585                 590

Arg Lys Ser Arg Arg Phe Ala Gln Ala Leu Pro Val Trp Ala Arg Pro
        595                 600                 605

Asp Tyr Asn Pro Pro Leu Val Glu Thr Trp Lys Lys Pro Asp Tyr Glu
610                 615                 620

Pro Pro Val Val His Gly Cys Pro Leu Pro Pro Pro Lys Ser Pro Pro
625                 630                 635                 640

Val Pro Pro Pro Arg Lys Lys Arg Thr Val Val Leu Thr Glu Ser Thr
                645                 650                 655

Leu Ser Thr Ala Leu Ala Glu Leu Ala Thr Arg Ser Phe Gly Ser Ser
            660                 665                 670

Ser Thr Ser Gly Ile Thr Gly Asp Asn Thr Thr Thr Ser Ser Glu Pro
        675                 680                 685

Ala Pro Ser Gly Cys Pro Pro Asp Ser Asp Ala Glu Ser Tyr Ser Ser
690                 695                 700

Met Pro Pro Leu Glu Gly Glu Pro Gly Asp Pro Asp Leu Ser Asp Gly
705                 710                 715                 720

Ser Trp Ser Thr Val Ser Ser Glu Ala Asn Ala Glu Asp Val Val Cys
                725                 730                 735

Cys Ser Met Ser Tyr Ser Trp Thr Gly Ala Leu Val Thr Pro Cys Ala
            740                 745                 750

Ala Glu Glu Gln Lys Leu Pro Ile Asn Ala Leu Ser Asn Ser Leu Leu
        755                 760                 765

Arg His His Asn Leu Val Tyr Ser Thr Thr Ser Arg Ser Ala Cys Gln
770                 775                 780

Arg Gln Lys Lys Val Thr Phe Asp Arg Leu Gln Val Leu Asp
785                 790                 795

(2) INFORMATION FOR SEQ ID NO:37:

(i) SEQUENCE CHARACTERISTICS:
        (A) LENGTH: 342 amino acids
        (B) TYPE: amino acid
```

```
        (C) STRANDEDNESS: single
        (D) TOPOLOGY: linear (ii) MOLECULE TYPE: peptide (xi) SEQUENCE DESCRIPTION: SEQ ID NO:37:

Met Ser Phe Val Val Ile Ile Pro Ala Arg Tyr Ala Ser Thr Arg Leu
1               5                   10                  15

Pro Gly Lys Pro Leu Val Asp Ile Asn Gly Lys Pro Met Ile Val His
            20                  25                  30

Val Leu Glu Arg Ala Arg Glu Ser Gly Ala Glu Arg Ile Ile Val Ala
        35                  40                  45

Thr Asp His Glu Asp Val Ala Arg Ala Val Glu Ala Ala Gly Gly Glu
    50                  55                  60

Val Cys Met Thr Arg Ala Asp His Gln Ser Gly Thr Glu Arg Leu Ala
65                  70                  75                  80

Glu Val Val Glu Lys Cys Ala Phe Ser Asp Asp Thr Val Ile Val Asn
                85                  90                  95

Val Gln Gly Asp Glu Pro Met Ile Pro Ala Thr Ile Ile Arg Gln Val
            100                 105                 110

Ala Asp Asn Leu Ala Gln Arg Gln Val Gly Met Ala Thr Leu Ala Val
        115                 120                 125

Pro Ile His Asn Ala Glu Glu Ala Phe Asn Pro Asn Ala Val Lys Val
    130                 135                 140

Val Leu Asp Ala Glu Gly Tyr Ala Leu Tyr Phe Ser Arg Ala Thr Ile
145                 150                 155                 160

Pro Trp Asp Arg Asp Arg Phe Ala Glu Gly Leu Glu Thr Val Gly Asp
                165                 170                 175

Asn Phe Leu Arg His Leu Gly Ile Tyr Gly Tyr Arg Ala Gly Phe Ile
            180                 185                 190

Arg Arg Tyr Val Asn Trp Gln Pro Ser Pro Leu Glu His Ile Glu Met
        195                 200                 205

Leu Glu Gln Leu Arg Val Leu Trp Tyr Gly Glu Lys Ile His Val Ala
    210                 215                 220

Val Ala Gln Glu Val Pro Gly Thr Gly Val Asp Thr Pro Glu Asp Leu
225                 230                 235                 240

Asp Pro Ser Thr Asn Ser Met Asp Ala His Phe Leu Ser Gln Ala Pro
                245                 250                 255

Pro Pro Ser Trp Asp Gln Met Trp Lys Cys Leu Ile Arg Leu Lys Pro
            260                 265                 270

Thr Leu His Gly Pro Thr Pro Leu Leu Tyr Arg Leu Gly Ala Val Gln
        275                 280                 285

Asn Glu Ile Thr Leu Thr His Pro Val Thr Lys Tyr Ile Met Thr Cys
    290                 295                 300

Met Ser Ala Asp Leu Glu Val Val Thr Ser Thr Trp Val Leu Val Gly
305                 310                 315                 320

Gly Val Leu Ala Ala Leu Ala Tyr Cys Leu Ser Thr Asp Pro Leu
                325                 330                 335

Asp Cys Arg His Ala Lys
            340

(2) INFORMATION FOR SEQ ID NO:38:

(i) SEQUENCE CHARACTERISTICS:
        (A) LENGTH: 344 amino acids
        (B) TYPE: amino acid
```

(C) STRANDEDNESS: single
(D) TOPOLOGY: linear (ii) MOLECULE TYPE: peptide (xi) SEQUENCE DESCRIPTION: SEQ ID NO:38:

```
Met Ser Phe Val Val Ile Ile Pro Ala Arg Tyr Ala Ser Thr Arg Leu
1               5                   10                  15

Pro Gly Lys Pro Leu Val Asp Ile Asn Gly Lys Pro Met Ile Val His
            20                  25                  30

Val Leu Glu Arg Ala Arg Glu Ser Gly Ala Glu Arg Ile Ile Val Ala
            35                  40                  45

Thr Asp His Glu Asp Val Ala Arg Ala Val Glu Ala Ala Gly Gly Glu
50                      55                  60

Val Cys Met Thr Arg Ala Asp His Gln Ser Gly Thr Glu Arg Leu Ala
65                  70                  75                  80

Glu Val Val Glu Lys Cys Ala Phe Ser Asp Asp Thr Val Ile Val Asn
                85                  90                  95

Val Gln Gly Asp Glu Pro Met Ile Pro Ala Thr Ile Ile Arg Gln Val
            100                 105                 110

Ala Asp Asn Leu Ala Gln Arg Gln Val Gly Met Ala Thr Leu Ala Val
            115                 120                 125

Pro Ile His Asn Ala Glu Glu Ala Phe Asn Pro Asn Ala Val Lys Val
            130                 135                 140

Val Leu Asp Ala Glu Gly Tyr Ala Leu Tyr Phe Ser Arg Ala Thr Ile
145                 150                 155                 160

Pro Trp Asp Arg Asp Arg Phe Ala Glu Gly Leu Glu Thr Val Gly Asp
                165                 170                 175

Asn Phe Leu Arg His Leu Gly Ile Tyr Gly Tyr Arg Ala Gly Phe Ile
            180                 185                 190

Arg Arg Tyr Val Asn Trp Gln Pro Ser Pro Leu Glu His Ile Glu Met
            195                 200                 205

Leu Glu Gln Leu Arg Val Leu Trp Tyr Gly Glu Lys Ile His Val Ala
210                 215                 220

Val Ala Gln Glu Val Pro Gly Thr Gly Val Asp Thr Pro Glu Asp Leu
225                 230                 235                 240

Asp Pro Ser Thr Asn Ser Met Asp Ala His Phe Leu Ser Gln Thr Lys
                245                 250                 255

Gln Ser Gly Glu Asn Leu Pro Tyr Leu Val Ala Tyr Gln Ala Thr Val
            260                 265                 270

Cys Ala Arg Ala Gln Ala Pro Thr Pro Leu Leu Tyr Arg Leu Gly Ala
            275                 280                 285

Val Gln Asn Glu Ile Thr Leu Thr His Pro Val Thr Lys Tyr Ile Met
            290                 295                 300

Thr Cys Met Ser Ala Asp Leu Glu Val Val Thr Ser Thr Trp Val Leu
305                 310                 315                 320

Val Gly Gly Val Leu Ala Ala Leu Ala Ala Tyr Cys Leu Ser Thr Asp
                325                 330                 335

Pro Leu Asp Cys Arg His Ala Lys
            340
```

(2) INFORMATION FOR SEQ ID NO:39:

(i) SEQUENCE CHARACTERISTICS:
(A) LENGTH: 352 amino acids
(B) TYPE: amino acid (C) STRANDEDNESS: single
        (D) TOPOLOGY: linear (ii) MOLECULE TYPE: peptide (xi) SEQUENCE DESCRIPTION: SEQ ID NO:39:

```
Met Ser Phe Val Val Ile Ile Pro Ala Arg Tyr Ala Ser Thr Arg Leu
1               5                   10                  15

Pro Gly Lys Pro Leu Val Asp Ile Asn Gly Lys Pro Met Ile Val His
            20                  25                  30

Val Leu Glu Arg Ala Arg Glu Ser Gly Ala Glu Arg Ile Ile Val Ala
        35                  40                  45

Thr Asp His Glu Asp Val Ala Arg Ala Val Glu Ala Ala Gly Gly Glu
    50                  55                  60

Val Cys Met Thr Arg Ala Asp His Gln Ser Gly Thr Glu Arg Leu Ala
65                  70                  75                  80

Glu Val Val Glu Lys Cys Ala Phe Ser Asp Asp Thr Val Ile Val Asn
                85                  90                  95

Val Gln Gly Asp Glu Pro Met Ile Pro Ala Thr Ile Ile Arg Gln Val
            100                 105                 110

Ala Asp Asn Leu Ala Gln Arg Gln Val Gly Met Thr Thr Leu Ala Val
        115                 120                 125

Pro Ile His Asn Ala Glu Glu Ala Phe Asn Pro Asn Ala Val Lys Val
    130                 135                 140

Val Leu Asp Ala Glu Gly Tyr Ala Leu Tyr Phe Ser Arg Ala Thr Ile
145                 150                 155                 160

Pro Trp Asp Arg Asp Arg Phe Ala Glu Gly Leu Glu Thr Val Gly Asp
                165                 170                 175

Asn Phe Leu Arg His Leu Gly Ile Tyr Gly Tyr Arg Ala Gly Phe Ile
            180                 185                 190

Arg Arg Tyr Val Asn Trp Gln Pro Ser Pro Leu Glu His Ile Glu Met
        195                 200                 205

Leu Glu Gln Leu Arg Val Leu Trp Tyr Gly Glu Lys Ile His Val Ala
    210                 215                 220

Val Ala Gln Glu Val Pro Gly Thr Gly Val Asp Thr Pro Glu Asp Leu
225                 230                 235                 240

Asp Pro Ser Thr Asn Ser Met Asp Ala His Phe Leu Ser Gln Thr Lys
                245                 250                 255

Gln Ser Gly Glu Asn Leu Pro Tyr Leu Val Ala Tyr Gln Ala Thr Val
            260                 265                 270

Cys Ala Arg Ala Gln Ala Arg Leu Lys Pro Thr Leu His Gly Pro Thr
        275                 280                 285

Pro Leu Leu Tyr Arg Leu Gly Ala Val Gln Asn Glu Ile Thr Leu Thr
    290                 295                 300

His Pro Val Thr Lys Tyr Ile Met Thr Cys Met Ser Ala Asp Leu Glu
305                 310                 315                 320

Val Val Thr Ser Thr Trp Val Val Gly Gly Val Leu Ala Ala Leu
                325                 330                 335

Ala Ala Tyr Cys Leu Ser Thr Asp Pro Leu Asp Cys Arg His Ala Lys
            340                 345                 350
```

(2) INFORMATION FOR SEQ ID NO:40:

(i) SEQUENCE CHARACTERISTICS:
        (A) LENGTH: 357 amino acids
        (B) TYPE: amino acid (C) STRANDEDNESS: single
            (D) TOPOLOGY: linear (ii) MOLECULE TYPE: peptide (xi) SEQUENCE DESCRIPTION: SEQ ID NO:40:

Met Ser Phe Val Val Ile Ile Pro Ala Arg Tyr Ala Ser Thr Arg Leu
1               5                   10                  15

Pro Gly Lys Pro Leu Val Asp Ile Asn Gly Lys Pro Met Ile Val His
            20                  25                  30

Val Leu Glu Arg Ala Arg Glu Ser Gly Ala Glu Arg Ile Ile Val Ala
        35                  40                  45

Thr Asp His Glu Asp Val Ala Arg Ala Val Glu Ala Ala Gly Gly Glu
    50                  55                  60

Val Cys Met Thr Arg Ala Asp His Gln Ser Gly Thr Glu Arg Leu Ala
65                  70                  75                  80

Glu Val Val Glu Lys Cys Ala Phe Ser Asp Asp Thr Val Ile Val Asn
                85                  90                  95

Val Gln Gly Asp Glu Pro Met Ile Pro Ala Thr Ile Ile Arg Gln Val
            100                 105                 110

Ala Asp Asn Leu Ala Gln Arg Gln Val Gly Met Thr Thr Leu Ala Val
        115                 120                 125

Pro Ile His Asn Ala Glu Glu Ala Phe Asn Pro Asn Ala Val Lys Val
    130                 135                 140

Val Leu Asp Ala Glu Gly Tyr Ala Leu Tyr Phe Ser Arg Ala Thr Ile
145                 150                 155                 160

Pro Trp Asp Arg Asp Arg Phe Ala Glu Gly Leu Glu Thr Val Gly Asp
                165                 170                 175

Asn Phe Leu Arg His Leu Gly Ile Tyr Gly Tyr Arg Ala Gly Phe Ile
            180                 185                 190

Arg Arg Tyr Val Asn Trp Gln Pro Ser Pro Leu Glu His Ile Glu Met
        195                 200                 205

Leu Glu Gln Leu Arg Val Leu Trp Tyr Gly Glu Lys Ile His Val Ala
    210                 215                 220

Val Ala Gln Glu Val Pro Gly Thr Gly Val Asp Thr Pro Glu Asp Leu
225                 230                 235                 240

Asp Pro Ser Thr Asn Ser Met Asp Ala His Phe Leu Ser Gln Thr Lys
                245                 250                 255

Gln Ser Gly Glu Asn Leu Pro Tyr Leu Val Ala Tyr Gln Ala Thr Val
            260                 265                 270

Cys Ala Arg Ala Gln Ala Trp Lys Cys Leu Ile Arg Leu Lys Pro Thr
        275                 280                 285

Leu His Gly Pro Thr Pro Leu Leu Tyr Arg Leu Gly Ala Val Gln Asn
    290                 295                 300

Glu Ile Thr Leu Thr His Pro Val Thr Lys Tyr Ile Met Thr Cys Met
305                 310                 315                 320

Ser Ala Asp Leu Glu Val Val Ser Thr Trp Val Leu Val Gly Gly
                325                 330                 335

Val Leu Ala Ala Leu Ala Ala Tyr Cys Leu Ser Thr Asp Pro Leu Asp
            340                 345                 350

Cys Arg His Ala Lys
            355

(2) INFORMATION FOR SEQ ID NO:41:

(i) SEQUENCE CHARACTERISTICS:
    (A) LENGTH: 362 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:41:

```
Met Ser Phe Val Val Ile Ile Pro Ala Arg Tyr Ala Ser Thr Arg Leu
1               5                   10                  15

Pro Gly Lys Pro Leu Val Asp Ile Asn Gly Lys Pro Met Ile Val His
            20                  25                  30

Val Leu Glu Arg Ala Arg Glu Ser Gly Ala Glu Arg Ile Ile Val Ala
        35                  40                  45

Thr Asp His Glu Asp Val Ala Arg Ala Val Glu Ala Ala Gly Gly Glu
    50                  55                  60

Val Cys Met Thr Arg Ala Asp His Gln Ser Gly Thr Glu Arg Leu Ala
65                  70                  75                  80

Glu Val Val Glu Lys Cys Ala Phe Ser Asp Asp Thr Val Ile Val Asn
                85                  90                  95

Val Gln Gly Asp Glu Pro Met Ile Pro Ala Thr Ile Ile Arg Gln Val
            100                 105                 110

Ala Asp Asn Leu Ala Gln Arg Gln Val Gly Met Thr Thr Leu Ala Val
        115                 120                 125

Pro Ile His Asn Ala Glu Glu Ala Phe Asn Pro Asn Ala Val Lys Val
    130                 135                 140

Val Leu Asp Ala Glu Gly Tyr Ala Leu Tyr Phe Ser Arg Ala Thr Ile
145                 150                 155                 160

Pro Trp Asp Arg Asp Arg Phe Ala Glu Gly Leu Glu Thr Val Gly Asp
                165                 170                 175

Asn Phe Leu Arg His Leu Gly Ile Tyr Gly Tyr Arg Ala Gly Phe Ile
            180                 185                 190

Arg Arg Tyr Val Asn Trp Gln Pro Ser Pro Leu Glu His Ile Glu Met
        195                 200                 205

Leu Glu Gln Leu Arg Val Leu Trp Tyr Gly Glu Lys Ile His Val Ala
    210                 215                 220

Val Ala Gln Glu Val Pro Gly Thr Gly Val Asp Thr Pro Glu Asp Leu
225                 230                 235                 240

Asp Pro Ser Thr Asn Ser Met Asp Ala His Phe Leu Ser Gln Thr Lys
                245                 250                 255

Gln Ser Gly Glu Asn Leu Pro Tyr Leu Val Ala Tyr Gln Ala Thr Val
            260                 265                 270

Cys Ala Arg Ala Gln Ala Ser Trp Asp Gln Met Trp Lys Cys Leu Ile
        275                 280                 285

Arg Leu Lys Pro Thr Leu His Gly Pro Thr Pro Leu Leu Tyr Arg Leu
    290                 295                 300

Gly Ala Val Gln Asn Glu Ile Thr Leu Thr His Pro Val Thr Lys Tyr
305                 310                 315                 320

Ile Met Thr Cys Met Ser Ala Asp Leu Glu Val Val Thr Ser Thr Trp
                325                 330                 335

Val Leu Val Gly Gly Val Leu Ala Leu Ala Ala Tyr Cys Leu Ser
            340                 345                 350

Thr Asp Pro Leu Asp Cys Arg His Ala Lys
    355                 360
```

(2) INFORMATION FOR SEQ ID NO:42:

(i) SEQUENCE CHARACTERISTICS:
        (A) LENGTH: 365 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:42:

```
Met Ser Phe Val Val Ile Ile Pro Ala Arg Tyr Ala Ser Thr Arg Leu
 1               5                  10                  15

Pro Gly Lys Pro Leu Val Asp Ile Asn Gly Lys Pro Met Ile Val His
            20                  25                  30

Val Leu Glu Arg Ala Arg Glu Ser Gly Ala Glu Arg Ile Ile Val Ala
        35                  40                  45

Thr Asp His Glu Asp Val Ala Arg Ala Val Glu Ala Ala Gly Gly Glu
 50                  55                  60

Val Cys Met Thr Arg Ala Asp His Gln Ser Gly Thr Glu Arg Leu Ala
 65                  70                  75                  80

Glu Val Val Glu Lys Cys Ala Phe Ser Asp Asp Thr Val Ile Val Asn
                85                  90                  95

Val Gln Gly Asp Glu Pro Met Ile Pro Ala Thr Ile Ile Arg Gln Val
            100                 105                 110

Ala Asp Asn Leu Ala Gln Arg Gln Val Gly Met Thr Thr Leu Ala Val
        115                 120                 125

Pro Ile His Asn Ala Glu Glu Ala Phe Asn Pro Asn Ala Val Lys Val
130                 135                 140

Val Leu Asp Ala Glu Gly Tyr Ala Leu Tyr Phe Ser Arg Ala Thr Ile
145                 150                 155                 160

Pro Trp Asp Arg Asp Arg Phe Ala Glu Gly Leu Glu Thr Val Gly Asp
                165                 170                 175

Asn Phe Leu Arg His Leu Gly Ile Tyr Gly Tyr Arg Ala Gly Phe Ile
            180                 185                 190

Arg Arg Tyr Val Asn Trp Gln Pro Ser Pro Leu Glu His Ile Glu Met
        195                 200                 205

Leu Glu Gln Leu Arg Val Leu Trp Tyr Gly Glu Lys Ile His Val Ala
210                 215                 220

Val Ala Gln Glu Val Pro Gly Thr Gly Val Asp Thr Pro Glu Asp Leu
225                 230                 235                 240

Asp Pro Ser Thr Asn Ser Met Asp Ala His Phe Leu Ser Gln Thr Lys
                245                 250                 255

Gln Ser Gly Glu Asn Leu Pro Tyr Leu Val Ala Tyr Gln Ala Thr Val
            260                 265                 270

Cys Ala Arg Ala Gln Ala Pro Pro Ser Trp Asp Gln Met Trp Lys
        275                 280                 285

Cys Leu Ile Arg Leu Lys Pro Thr Leu His Gly Pro Thr Pro Leu Leu
290                 295                 300

Tyr Arg Leu Gly Ala Val Gln Asn Glu Ile Thr Leu Thr His Pro Val
305                 310                 315                 320

Thr Lys Tyr Ile Met Thr Cys Met Ser Ala Asp Leu Glu Val Val Thr
                325                 330                 335

Ser Thr Trp Val Leu Val Gly Gly Val Leu Ala Ala Leu Ala Ala Tyr
            340                 345                 350
```

```
Cys Leu Ser Thr Asp Pro Leu Asp Cys Arg His Ala Lys
        355                 360                 365
```

(2) INFORMATION FOR SEQ ID NO:43:

(i) SEQUENCE CHARACTERISTICS:
        (A) LENGTH: 363 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:43:

```
Met Ser Phe Val Val Ile Ile Pro Ala Arg Tyr Ala Ser Thr Arg Leu
1               5                   10                  15

Pro Gly Lys Pro Leu Val Asp Ile Asn Gly Lys Pro Met Ile Val His
            20                  25                  30

Val Leu Glu Arg Ala Arg Glu Ser Gly Ala Glu Arg Ile Ile Val Ala
        35                  40                  45

Thr Asp His Glu Asp Val Ala Arg Ala Val Glu Ala Ala Gly Gly Glu
    50                  55                  60

Val Cys Met Thr Arg Ala Asp His Gln Ser Gly Thr Glu Arg Leu Ala
65                  70                  75                  80

Glu Val Val Glu Lys Cys Ala Phe Ser Asp Thr Val Ile Val Asn
                85                  90                  95

Val Gln Gly Asp Glu Pro Met Ile Pro Ala Thr Ile Ile Arg Gln Val
            100                 105                 110

Ala Asp Asn Leu Ala Gln Arg Gln Val Gly Met Thr Thr Leu Ala Val
        115                 120                 125

Pro Ile His Asn Ala Glu Glu Ala Phe Asn Pro Asn Ala Val Lys Val
    130                 135                 140

Val Leu Asp Ala Glu Gly Tyr Ala Leu Tyr Phe Ser Arg Ala Thr Ile
145                 150                 155                 160

Pro Trp Asp Arg Asp Arg Phe Ala Glu Gly Leu Glu Thr Val Gly Asp
                165                 170                 175

Asn Phe Leu Arg His Leu Gly Ile Tyr Gly Tyr Arg Ala Gly Phe Ile
            180                 185                 190

Arg Arg Tyr Val Asn Trp Gln Pro Ser Pro Leu Glu His Ile Glu Met
        195                 200                 205

Leu Glu Gln Leu Arg Val Leu Trp Tyr Gly Glu Lys Ile His Val Ala
    210                 215                 220

Val Ala Gln Glu Val Pro Gly Thr Gly Val Asp Thr Pro Glu Asp Leu
225                 230                 235                 240

Asp Pro Ser Thr Asn Ser Met Asp Ala His Phe Leu Ser Gln Thr Lys
                245                 250                 255

Gln Ser Gly Glu Asn Leu Pro Tyr Leu Val Ala Tyr Gln Ala Thr Val
            260                 265                 270

Cys Ala Arg Ala Gln Ala Pro Ser Trp Asp Gln Met Trp Lys Cys Leu
        275                 280                 285

Ile Arg Leu Lys Pro Thr Leu His Gly Pro Thr Pro Leu Leu Tyr Arg
    290                 295                 300

Leu Gly Ala Val Gln Asn Glu Ile Thr Leu Thr His Pro Val Thr Lys
305                 310                 315                 320

Tyr Ile Met Thr Cys Met Ser Ala Asp Leu Glu Val Val Thr Ser Thr
                325                 330                 335
```

-continued

```
Trp Val Leu Val Gly Gly Val Leu Ala Leu Ala Ala Tyr Cys Leu
            340                 345                 350

Ser Thr Asp Pro Leu Asp Cys Arg His Ala Lys
            355                 360
```

(2) INFORMATION FOR SEQ ID NO:44:

(i) SEQUENCE CHARACTERISTICS:
        (A) LENGTH: 364 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:44:

```
Met Ser Phe Val Val Ile Ile Pro Ala Arg Tyr Ala Ser Thr Arg Leu
1               5                   10                  15

Pro Gly Lys Pro Leu Val Asp Ile Asn Gly Lys Pro Met Ile Val His
            20                  25                  30

Val Leu Glu Arg Ala Arg Glu Ser Gly Ala Glu Arg Ile Ile Val Ala
            35                  40                  45

Thr Asp His Glu Asp Val Ala Arg Ala Val Glu Ala Ala Gly Gly Glu
        50                  55                  60

Val Cys Met Thr Arg Ala Asp His Gln Ser Gly Thr Glu Arg Leu Ala
65                  70                  75                  80

Glu Val Val Glu Lys Cys Ala Phe Ser Asp Asp Thr Val Ile Val Asn
                85                  90                  95

Val Gln Gly Asp Glu Pro Met Ile Pro Ala Thr Ile Ile Arg Gln Val
            100                 105                 110

Ala Asp Asn Leu Ala Gln Arg Gln Val Gly Met Thr Thr Leu Ala Val
            115                 120                 125

Pro Ile His Asn Ala Glu Glu Ala Phe Asn Pro Asn Ala Val Lys Val
            130                 135                 140

Val Leu Asp Ala Glu Gly Tyr Ala Leu Tyr Phe Ser Arg Ala Thr Ile
145                 150                 155                 160

Pro Trp Asp Arg Asp Arg Phe Ala Glu Gly Leu Glu Thr Val Gly Asp
                165                 170                 175

Asn Phe Leu Arg His Leu Gly Ile Tyr Gly Tyr Arg Ala Gly Phe Ile
            180                 185                 190

Arg Arg Tyr Val Asn Trp Gln Pro Ser Pro Leu Glu His Ile Glu Met
            195                 200                 205

Leu Glu Gln Leu Arg Val Leu Trp Tyr Gly Glu Lys Ile His Val Ala
            210                 215                 220

Val Ala Gln Glu Val Pro Gly Thr Gly Val Asp Thr Pro Glu Asp Leu
225                 230                 235                 240

Asp Pro Ser Thr Asn Ser Met Asp Ala His Phe Leu Ser Gln Thr Lys
                245                 250                 255

Gln Ser Gly Glu Asn Leu Pro Tyr Leu Val Ala Tyr Gln Ala Thr Val
            260                 265                 270

Cys Ala Arg Ala Gln Ala Pro Pro Ser Trp Asp Gln Met Trp Lys Cys
            275                 280                 285

Leu Ile Arg Leu Lys Pro Thr Leu His Gly Pro Thr Pro Leu Leu Tyr
            290                 295                 300

Arg Leu Gly Ala Val Gln Asn Glu Ile Thr Leu Thr His Pro Val Thr
305                 310                 315                 320
```

```
Lys Tyr Ile Met Thr Cys Met Ser Ala Asp Leu Glu Val Val Thr Ser
                325                 330                 335

Thr Trp Val Leu Val Gly Gly Val Leu Ala Ala Leu Ala Ala Tyr Cys
            340                 345                 350

Leu Ser Thr Asp Pro Leu Asp Cys Arg His Ala Lys
        355                 360
```

(2) INFORMATION FOR SEQ ID NO:45:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:45:

```
Trp Asp Pro Leu Asp Cys Arg His Ala Lys
1               5                   10
```

(2) INFORMATION FOR SEQ ID NO:46:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:46:

```
Val His His Lys Arg
1               5
```

(2) INFORMATION FOR SEQ ID NO:47:

(i) SEQUENCE CHARACTERISTICS:
        (A) LENGTH: 592 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:47:

```
Met Ser Phe Val Val Ile Ile Pro Ala Arg Tyr Ala Ser Thr Arg Leu
1               5                   10                  15

Pro Gly Lys Pro Leu Val Asp Ile Asn Gly Lys Pro Met Ile Val His
            20                  25                  30

Val Leu Glu Arg Ala Arg Glu Ser Gly Ala Glu Arg Ile Ile Val Ala
        35                  40                  45

Thr Asp His Glu Asp Val Ala Arg Ala Val Glu Ala Ala Gly Gly Glu
    50                  55                  60

Val Cys Met Thr Arg Ala Asp His Gln Ser Gly Thr Glu Arg Leu Ala
65                  70                  75                  80

Glu Val Val Glu Lys Cys Ala Phe Ser Asp Asp Thr Val Ile Val Asn
                85                  90                  95

Val Gln Gly Asp Glu Pro Met Ile Pro Ala Thr Ile Ile Arg Gln Val
            100                 105                 110

Ala Asp Asn Leu Ala Gln Arg Gln Val Gly Met Ala Thr Leu Ala Val
        115                 120                 125

Pro Ile His Asn Ala Glu Glu Ala Phe Asn Pro Asn Ala Val Lys Val
```

```
            130                 135                 140
Val Leu Asp Ala Glu Gly Tyr Ala Leu Tyr Phe Ser Arg Ala Thr Ile
145                 150                 155                 160

Pro Trp Asp Arg Asp Arg Phe Ala Glu Gly Leu Glu Thr Val Gly Asp
                165                 170                 175

Asn Phe Leu Arg His Leu Gly Ile Tyr Gly Tyr Arg Ala Gly Phe Ile
                180                 185                 190

Arg Arg Tyr Val Asn Trp Gln Pro Ser Pro Leu Glu His Ile Glu Met
            195                 200                 205

Leu Glu Gln Leu Arg Val Leu Trp Tyr Gly Glu Lys Ile His Val Ala
            210                 215                 220

Val Ala Gln Glu Val Pro Gly Thr Gly Val Asp Thr Pro Glu Asp Leu
225                 230                 235                 240

Asp Pro Ser Thr Asn Ser Met Asp Ala His Phe Leu Ser Gln Ala Pro
                245                 250                 255

Pro Pro Ser Trp Asp Gln Met Trp Lys Cys Leu Ile Arg Leu Lys Pro
                260                 265                 270

Thr Leu His Gly Pro Thr Pro Leu Leu Tyr Arg Leu Gly Ala Val Gln
            275                 280                 285

Asn Glu Ile Thr Leu Thr His Pro Val Thr Lys Tyr Ile Met Thr Cys
290                 295                 300

Met Ser Ala Asp Leu Glu Val Thr Ser Thr Trp Val Leu Val Gly
305                 310                 315                 320

Gly Val Leu Ala Ala Leu Ala Ala Tyr Cys Leu Ser Thr Gly Cys Val
                325                 330                 335

Val Ile Val Gly Arg Val Val Leu Ser Gly Lys Pro Ala Ile Ile Pro
                340                 345                 350

Asp Arg Glu Val Leu Tyr Arg Glu Phe Asp Glu Met Glu Glu Cys Ser
                355                 360                 365

Gln His Leu Pro Tyr Ile Glu Gln Gly Met Met Leu Ala Glu Gln Phe
            370                 375                 380

Lys Gln Lys Ala Leu Gly Leu Leu Gln Thr Ala Ser Arg Gln Ala Glu
385                 390                 395                 400

Val Ile Ala Pro Ala Val Gln Thr Asn Trp Gln Lys Leu Glu Thr Phe
                405                 410                 415

Trp Ala Lys His Met Trp Asn Phe Ile Ser Gly Ile Gln Tyr Leu Ala
                420                 425                 430

Gly Leu Ser Thr Leu Pro Gly Asn Pro Ala Ile Ala Ser Leu Met Ala
            435                 440                 445

Phe Thr Ala Ala Val Thr Ser Pro Leu Thr Thr Ser Gln Thr Leu Leu
450                 455                 460

Phe Asn Ile Leu Gly Gly Trp Val Ala Ala Gln Leu Ala Ala Pro Gly
465                 470                 475                 480

Ala Ala Thr Ala Phe Val Gly Ala Gly Leu Ala Gly Ala Ala Ile Gly
                485                 490                 495

Ser Val Gly Leu Gly Lys Val Leu Ile Asp Ile Leu Ala Gly Tyr Gly
                500                 505                 510

Ala Gly Val Ala Gly Ala Leu Val Ala Phe Lys Ile Met Ser Gly Glu
            515                 520                 525

Val Pro Ser Thr Glu Asp Leu Val Asn Leu Leu Pro Ala Ile Leu Ser
            530                 535                 540

Pro Gly Ala Leu Val Val Gly Val Val Cys Ala Ala Ile Leu Arg Arg
545                 550                 555                 560
```

-continued

```
His Val Gly Pro Gly Glu Gly Ala Val Gln Trp Met Asn Arg Leu Ile
                565                 570                 575

Ala Phe Ala Ser Arg Gly Asn His Val Ser Pro Val His His Lys Arg
            580                 585                 590
```

(2) INFORMATION FOR SEQ ID NO:48:

(i) SEQUENCE CHARACTERISTICS:
        (A) LENGTH: 594 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:48:

```
Met Ser Phe Val Val Ile Ile Pro Ala Arg Tyr Ala Ser Thr Arg Leu
1               5                   10                  15

Pro Gly Lys Pro Leu Val Asp Ile Asn Gly Lys Pro Met Ile Val His
                20                  25                  30

Val Leu Glu Arg Ala Arg Glu Ser Gly Ala Glu Arg Ile Ile Val Ala
            35                  40                  45

Thr Asp His Glu Asp Val Ala Arg Ala Val Glu Ala Ala Gly Gly Glu
        50                  55                  60

Val Cys Met Thr Arg Ala Asp His Gln Ser Gly Thr Glu Arg Leu Ala
65                  70                  75                  80

Glu Val Val Glu Lys Cys Ala Phe Ser Asp Thr Val Ile Val Asn
                85                  90                  95

Val Gln Gly Asp Glu Pro Met Ile Pro Ala Thr Ile Ile Arg Gln Val
                100                 105                 110

Ala Asp Asn Leu Ala Gln Arg Gln Val Gly Met Ala Thr Leu Ala Val
            115                 120                 125

Pro Ile His Asn Ala Glu Glu Ala Phe Asn Pro Asn Ala Val Lys Val
        130                 135                 140

Val Leu Asp Ala Glu Gly Tyr Ala Leu Tyr Phe Ser Arg Ala Thr Ile
145                 150                 155                 160

Pro Trp Asp Arg Asp Arg Phe Ala Glu Gly Leu Glu Thr Val Gly Asp
                165                 170                 175

Asn Phe Leu Arg His Leu Gly Ile Tyr Gly Tyr Arg Ala Gly Phe Ile
            180                 185                 190

Arg Arg Tyr Val Asn Trp Gln Pro Ser Pro Leu Glu His Ile Glu Met
        195                 200                 205

Leu Glu Gln Leu Arg Val Leu Trp Tyr Gly Glu Lys Ile His Val Ala
    210                 215                 220

Val Ala Gln Glu Val Pro Gly Thr Gly Val Asp Thr Pro Glu Asp Leu
225                 230                 235                 240

Asp Pro Ser Thr Asn Ser Met Asp Ala His Phe Leu Ser Gln Thr Lys
                245                 250                 255

Gln Ser Gly Glu Asn Leu Pro Tyr Leu Val Ala Tyr Gln Ala Thr Val
            260                 265                 270

Cys Ala Arg Ala Gln Ala Pro Thr Pro Leu Leu Tyr Arg Leu Gly Ala
        275                 280                 285

Val Gln Asn Glu Ile Thr Leu Thr His Pro Val Thr Lys Tyr Ile Met
    290                 295                 300

Thr Cys Met Ser Ala Asp Leu Glu Val Val Thr Ser Thr Trp Val Leu
305                 310                 315                 320
```

```
Val Gly Gly Val Leu Ala Ala Leu Ala Ala Tyr Cys Leu Ser Thr Gly
            325                 330                 335

Cys Val Val Ile Val Gly Arg Val Leu Ser Gly Lys Pro Ala Ile
        340                 345                 350

Ile Pro Asp Arg Glu Val Leu Tyr Arg Glu Phe Asp Glu Met Glu Glu
            355                 360                 365

Cys Ser Gln His Leu Pro Tyr Ile Glu Gln Gly Met Met Leu Ala Glu
        370                 375                 380

Gln Phe Lys Gln Lys Ala Leu Gly Leu Leu Gln Thr Ala Ser Arg Gln
385                 390                 395                 400

Ala Glu Val Ile Ala Pro Ala Val Gln Thr Asn Trp Gln Lys Leu Glu
            405                 410                 415

Thr Phe Trp Ala Lys His Met Trp Asn Phe Ile Ser Gly Ile Gln Tyr
            420                 425                 430

Leu Ala Gly Leu Ser Thr Leu Pro Gly Asn Pro Ala Ile Ala Ser Leu
            435                 440                 445

Met Ala Phe Thr Ala Ala Val Thr Ser Pro Leu Thr Thr Ser Gln Thr
        450                 455                 460

Leu Leu Phe Asn Ile Leu Gly Gly Trp Val Ala Ala Gln Leu Ala Ala
465                 470                 475                 480

Pro Gly Ala Ala Thr Ala Phe Val Gly Ala Gly Leu Ala Gly Ala Ala
            485                 490                 495

Ile Gly Ser Val Gly Leu Gly Lys Val Leu Ile Asp Ile Leu Ala Gly
            500                 505                 510

Tyr Gly Ala Gly Val Ala Gly Ala Leu Val Ala Phe Lys Ile Met Ser
            515                 520                 525

Gly Glu Val Pro Ser Thr Glu Asp Leu Val Asn Leu Leu Pro Ala Ile
        530                 535                 540

Leu Ser Pro Gly Ala Leu Val Val Gly Val Val Cys Ala Ala Ile Leu
545                 550                 555                 560

Arg Arg His Val Gly Pro Gly Glu Gly Ala Val Gln Trp Met Asn Arg
            565                 570                 575

Leu Ile Ala Phe Ala Ser Arg Gly Asn His Val Ser Pro Val His His
            580                 585                 590

Lys Arg (2) INFORMATION FOR SEQ ID NO:49:

(i) SEQUENCE CHARACTERISTICS:
        (A) LENGTH: 613 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:49:

Met Ser Phe Val Val Ile Ile Pro Ala Arg Tyr Ala Ser Thr Arg Leu
1               5                   10                  15

Pro Gly Lys Pro Leu Val Asp Ile Asn Gly Lys Pro Met Ile Val His
            20                  25                  30

Val Leu Glu Arg Ala Arg Glu Ser Gly Ala Glu Arg Ile Ile Val Ala
        35                  40                  45

Thr Asp His Glu Asp Val Ala Arg Ala Val Glu Ala Ala Gly Gly Glu
    50                  55                  60
```

-continued

```
Val Cys Met Thr Arg Ala Asp His Gln Ser Gly Thr Glu Arg Leu Ala
 65                  70                  75                  80

Glu Val Val Glu Lys Cys Ala Phe Ser Asp Thr Val Ile Val Asn
                 85                  90                  95

Val Gln Gly Asp Glu Pro Met Ile Pro Ala Thr Ile Ile Arg Gln Val
                100                 105                 110

Ala Asp Asn Leu Ala Gln Arg Gln Val Gly Met Ala Thr Leu Ala Val
            115                 120                 125

Pro Ile His Asn Ala Glu Glu Ala Phe Asn Pro Asn Ala Val Lys Val
            130                 135                 140

Val Leu Asp Ala Glu Gly Tyr Ala Leu Tyr Phe Ser Arg Ala Thr Ile
145                 150                 155                 160

Pro Trp Asp Arg Asp Arg Phe Ala Glu Gly Leu Glu Thr Val Gly Asp
                165                 170                 175

Asn Phe Leu Arg His Leu Gly Ile Tyr Gly Tyr Arg Ala Gly Phe Ile
            180                 185                 190

Arg Arg Tyr Val Asn Trp Gln Pro Ser Pro Leu Glu His Ile Glu Met
            195                 200                 205

Leu Glu Gln Leu Arg Val Leu Trp Tyr Gly Glu Lys Ile His Val Ala
        210                 215                 220

Val Ala Gln Glu Val Pro Gly Thr Gly Val Asp Thr Pro Glu Asp Leu
225                 230                 235                 240

Asp Pro Ser Thr Asn Ser Met Asp Ala His Phe Leu Ser Gln Thr Lys
                245                 250                 255

Gln Ser Gly Glu Asn Leu Pro Tyr Leu Val Ala Tyr Gln Ala Thr Val
            260                 265                 270

Cys Ala Arg Ala Gln Ala Pro Ser Trp Asp Gln Met Trp Lys Cys Leu
            275                 280                 285

Ile Arg Leu Lys Pro Thr Leu His Gly Pro Thr Pro Leu Leu Tyr Arg
            290                 295                 300

Leu Gly Ala Val Gln Asn Glu Ile Thr Leu Thr His Pro Val Thr Lys
305                 310                 315                 320

Tyr Ile Met Thr Cys Met Ser Ala Asp Leu Glu Val Val Thr Ser Thr
                325                 330                 335

Trp Val Leu Val Gly Gly Val Leu Ala Ala Leu Ala Ala Tyr Cys Leu
            340                 345                 350

Ser Thr Gly Cys Val Val Ile Val Gly Arg Val Val Leu Ser Gly Lys
            355                 360                 365

Pro Ala Ile Ile Pro Asp Arg Glu Val Leu Tyr Arg Glu Phe Asp Glu
370                 375                 380

Met Glu Glu Cys Ser Gln His Leu Pro Tyr Ile Glu Gln Gly Met Met
385                 390                 395                 400

Leu Ala Glu Gln Phe Lys Gln Lys Ala Leu Gly Leu Leu Gln Thr Ala
                405                 410                 415

Ser Arg Gln Ala Glu Val Ile Ala Pro Ala Val Gln Thr Asn Trp Gln
            420                 425                 430

Lys Leu Glu Thr Phe Trp Ala Lys His Met Trp Asn Phe Ile Ser Gly
            435                 440                 445

Ile Gln Tyr Leu Ala Gly Leu Ser Thr Leu Pro Gly Asn Pro Ala Ile
        450                 455                 460

Ala Ser Leu Met Ala Phe Thr Ala Ala Val Thr Ser Pro Leu Thr Thr
465                 470                 475                 480

Ser Gln Thr Leu Leu Phe Asn Ile Leu Gly Gly Trp Val Ala Ala Gln
```

-continued

```
                485                 490                 495
Leu Ala Ala Pro Gly Ala Ala Thr Ala Phe Val Gly Ala Gly Leu Ala
                500                 505                 510
Gly Ala Ala Ile Gly Ser Val Gly Leu Gly Lys Val Leu Ile Asp Ile
                515                 520                 525
Leu Ala Gly Tyr Gly Ala Gly Val Ala Gly Ala Leu Val Ala Phe Lys
            530                 535                 540
Ile Met Ser Gly Glu Val Pro Ser Thr Glu Asp Leu Val Asn Leu Leu
545                 550                 555                 560
Pro Ala Ile Leu Ser Pro Gly Ala Leu Val Val Gly Val Val Cys Ala
                565                 570                 575
Ala Ile Leu Arg Arg His Val Gly Pro Gly Glu Gly Ala Val Gln Trp
                580                 585                 590
Met Asn Arg Leu Ile Ala Phe Ala Ser Arg Gly Asn His Val Ser Pro
                595                 600                 605
Val His His Lys Arg
        610
```

(2) INFORMATION FOR SEQ ID NO:50:

(i) SEQUENCE CHARACTERISTICS:
        (A) LENGTH: 375 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:50:

```
Met Ser Phe Val Val Ile Ile Pro Ala Arg Tyr Ala Ser Thr Arg Leu
1               5                   10                  15
Pro Gly Lys Pro Leu Val Asp Ile Asn Gly Lys Pro Met Ile Val His
                20                  25                  30
Val Leu Glu Arg Ala Arg Glu Ser Gly Ala Glu Arg Ile Ile Val Ala
            35                  40                  45
Thr Asp His Glu Asp Val Ala Arg Ala Val Glu Ala Ala Gly Gly Glu
50                  55                  60
Val Cys Met Thr Arg Ala Asp His Gln Ser Gly Thr Glu Arg Leu Ala
65                  70                  75                  80
Glu Val Val Glu Lys Cys Ala Phe Ser Asp Asp Thr Val Ile Val Asn
                85                  90                  95
Val Gln Gly Asp Glu Pro Met Ile Pro Ala Thr Ile Ile Arg Gln Val
                100                 105                 110
Ala Asp Asn Leu Ala Gln Arg Gln Val Gly Met Ala Thr Leu Ala Val
            115                 120                 125
Pro Ile His Asn Ala Glu Glu Ala Phe Asn Pro Asn Ala Val Lys Val
        130                 135                 140
Val Leu Asp Ala Glu Gly Tyr Ala Leu Tyr Phe Ser Arg Ala Thr Ile
145                 150                 155                 160
Pro Trp Asp Arg Asp Arg Phe Ala Glu Gly Leu Glu Thr Val Gly Asp
                165                 170                 175
Asn Phe Leu Arg His Leu Gly Ile Tyr Gly Tyr Arg Ala Gly Phe Ile
                180                 185                 190
Arg Arg Tyr Val Asn Trp Gln Pro Ser Pro Leu Glu His Ile Glu Met
            195                 200                 205
Leu Glu Gln Leu Arg Val Leu Trp Tyr Gly Glu Lys Ile His Val Ala
```

```
                 210                 215                 220
Val Ala Gln Glu Val Pro Gly Thr Gly Val Asp Thr Pro Glu Asp Leu
225                 230                 235                 240

Asp Pro Ser Thr Glu Phe Val Ile Asp Cys Asn Thr Cys Val Thr Gln
                245                 250                 255

Thr Val Asp Phe Ser Leu Asp Pro Thr Phe Thr Ile Glu Thr Thr Thr
                260                 265                 270

Leu Pro Gln Asp Ala Val Ser Arg Thr Gln Arg Arg Gly Arg Thr Gly
                275                 280                 285

Arg Gly Lys Pro Gly Ile Tyr Arg Phe Val Ala Pro Gly Glu Arg Pro
290                 295                 300

Ser Gly Met Phe Asp Ser Ser Val Leu Cys Glu Cys Tyr Asp Ala Gly
305                 310                 315                 320

Cys Ala Trp Tyr Glu Leu Thr Pro Ala Glu Thr Thr Val Arg Leu Arg
                325                 330                 335

Ala Tyr Met Asn Thr Pro Gly Leu Pro Val Cys Gln Asp His Leu Glu
                340                 345                 350

Phe Trp Glu Gly Val Phe Thr Gly Leu Thr His Ile Ala Met Asp Pro
                355                 360                 365

Leu Asp Cys Arg His Ala Lys
370                 375
```

(2) INFORMATION FOR SEQ ID NO:51:

(i) SEQUENCE CHARACTERISTICS:
        (A) LENGTH: 1414 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:51:

```
GAATTCGTGA TCGATTGCAA TACGTGTGTC ACCCAGACAG TCGACTTCAG CCTTGACCCT      60

ACCTTCACCA TTGAGACAAC CACGCTTCCC CAGGATGCTG TCTCCCGTAC TCAGCGTCGG     120

GGCAGGACTG GTAGGGGGAA GCCAGGCATC TACAGATTTG TGGCACCGGG GGAGCGCCCT     180

TCCGGCATGT TTGACTCGTC CGTCCTCTGC GAGTGCTATG ACGCGGGCTG TGCTTGGTAT     240

GAGCTTACAC CCGCCGAGAC CACAGTTAGG CTACGAGCTT ACATGAACAC TCCGGGGCTT     300

CCCGTGTGCC AAGATCATCT TGAATTTTGG GAGGGCGTCT TTACAGGCCT CACTCATATA     360

GCCATGGACG CTCACTTCCT GTCTCAGGCG CCGCCGCCGT CTTGGGATCA GATGTGGAAA     420

TGCCTGATCC GTCTGAAACC GACCCTGCAC GGCCCGACCC CGCTGCTGTA CCGTCTGGGT     480

GCTGTTCAGA ACGAAATCAC CCTGACCCAC CCGGTTACCA AATACATCAT GACCTGCATG     540

TCTGCTGATC TAGAAGTTGT TACCTCTACC TGGGTTCTGG TTGGTGGTGT TCTGGCTGCT     600

CTGGCTGCTT ACTGCCTGTC GACCGGTTGC GTTGTTATCG TTGGTCGTGT TGTTCTGTCT     660

GGTAAACCGG CCATTATCCC GGACCGTGAA GTTCTGTACC GTGAGTTCGA CGAAATGGAA     720

GAATGCTCTC AGCACCTGCC GTACATCGAA CAGGGTATGA TGCTGGCTGA ACAGTTCAAA     780

CAGAAAGCTC TGGGTCTGCT GCAGACCGCT TCTCGTCAGG CTGAAGTTAT CGCTCCGGCT     840

GTTCAGACCA ACTGGCAGAA ACTCGAGACC TTCTGGGCTA ACACATGTGA ACTTCATC      900

TCTGGTATCC AGTACCTGGC TGGTCTGTCT ACCCTGCCGG GTAACCCGGC TATCGCAAGC     960

TTGATGGCTT TCACCGCTGC TGTTACCTCT CCGCTGACCA CCTCTCAGAC CCTGCTGTTC    1020
```

```
AACATTCTGG GTGGTTGGGT TGCTGCTCAG CTGGCTGCTC CGGGTGCTGC TACCGCTTTC    1080

GTTGGTGCTG GTCTGGCTGG TGCTGCTATC GGTTCTGTAG GCCTGGGTAA AGTTCTGATC    1140

GACATTCTGG CTGGTTACGG TGCTGGTGTT GCTGGAGCTC TGGTTGCTTT CAAAATCATG    1200

TCTGGTGAAG TTCCGTCTAC CGAAGATCTG GTTAACCTGC TGCCGGCTAT CCTGTCTCCG    1260

GGTGCTCTGG TTGTTGGTGT TGTTTGCGCT GCTATCCTGC GTCGTCACGT TGGCCCGGGT    1320

GAAGGTGCTG TTCAGTGGAT GAACCGTCTG ATCGCTTTCG CTTCTCGTGG TAACCACGTT    1380

TCTCCGGTTC ACCACAAACG TTAACCATGG ATCC                                1414
```

(2) INFORMATION FOR SEQ ID NO:52:

(i) SEQUENCE CHARACTERISTICS:
  (A) LENGTH: 971 amino acids
  (B) TYPE: amino acid
  (C) STRANDEDNESS: single
  (D) TOPOLOGY: linear (ii) MOLECULE TYPE: peptide (xi) SEQUENCE DESCRIPTION: SEQ ID NO:52:

```
Met Ser Phe Val Val Ile Ile Pro Ala Arg Tyr Ala Ser Thr Arg Leu
1               5                   10                  15

Pro Gly Lys Pro Leu Val Asp Ile Asn Gly Lys Pro Met Ile Val His
            20                  25                  30

Val Leu Glu Arg Ala Arg Glu Ser Gly Ala Glu Arg Ile Ile Val Ala
        35                  40                  45

Thr Asp His Glu Asp Val Ala Arg Ala Val Glu Ala Ala Gly Gly Glu
    50                  55                  60

Val Cys Met Thr Arg Ala Asp His Gln Ser Gly Thr Glu Arg Leu Ala
65                  70                  75                  80

Glu Val Val Glu Lys Cys Ala Phe Ser Asp Asp Thr Val Ile Val Asn
                85                  90                  95

Val Gln Gly Asp Glu Pro Met Ile Pro Ala Thr Ile Ile Arg Gln Val
            100                 105                 110

Ala Asp Asn Leu Ala Gln Arg Gln Val Gly Met Ala Thr Leu Ala Val
        115                 120                 125

Pro Ile His Asn Ala Glu Glu Ala Phe Asn Pro Asn Ala Val Lys Val
    130                 135                 140

Val Leu Asp Ala Glu Gly Tyr Ala Leu Tyr Phe Ser Arg Ala Thr Ile
145                 150                 155                 160

Pro Trp Asp Arg Asp Arg Phe Ala Glu Gly Leu Glu Thr Val Gly Asp
                165                 170                 175

Asn Phe Leu Arg His Leu Gly Ile Tyr Gly Tyr Arg Ala Gly Phe Ile
            180                 185                 190

Arg Arg Tyr Val Asn Trp Gln Pro Ser Pro Leu Glu His Ile Glu Met
        195                 200                 205

Leu Glu Gln Leu Arg Val Leu Trp Tyr Gly Glu Lys Ile His Val Ala
    210                 215                 220

Val Ala Gln Glu Val Pro Gly Thr Gly Val Asp Thr Pro Glu Asp Leu
225                 230                 235                 240

Asp Pro Ser Thr Asn Ser Met Ala Val Asp Phe Ile Pro Val Glu Asn
                245                 250                 255

Leu Glu Thr Thr Met Arg Ser Pro Val Phe Thr Asp Asn Ser Ser Pro
            260                 265                 270

Pro Val Val Pro Gln Ser Phe Gln Val Ala His Leu His Ala Pro Thr
```

-continued

```
                275                 280                 285
Gly Ser Gly Lys Ser Thr Lys Val Pro Ala Ala Tyr Ala Ala Gln Gly
    290                 295                 300
Tyr Lys Val Leu Val Leu Asn Pro Ser Val Ala Ala Thr Leu Gly Phe
305                 310                 315                 320
Gly Ala Tyr Met Ser Lys Ala His Gly Ile Asp Pro Asn Ile Arg Thr
                325                 330                 335
Gly Val Arg Thr Ile Thr Thr Gly Ser Pro Ile Thr Tyr Ser Thr Tyr
                340                 345                 350
Gly Lys Phe Leu Ala Asp Gly Gly Cys Ser Gly Gly Ala Tyr Asp Ile
                355                 360                 365
Ile Ile Cys Asp Glu Cys His Ser Thr Asp Ala Thr Ser Ile Leu Gly
            370                 375                 380
Ile Gly Thr Val Leu Asp Gln Ala Glu Thr Ala Gly Ala Arg Leu Val
385                 390                 395                 400
Val Leu Ala Thr Ala Thr Pro Pro Gly Ser Val Thr Val Pro His Pro
                405                 410                 415
Asn Ile Glu Glu Val Ala Leu Ser Thr Thr Gly Glu Ile Pro Phe Tyr
                420                 425                 430
Gly Lys Ala Ile Pro Leu Glu Val Ile Lys Gly Gly Arg His Leu Ile
            435                 440                 445
Phe Cys His Ser Lys Lys Lys Cys Asp Glu Leu Ala Ala Lys Leu Val
        450                 455                 460
Ala Leu Gly Ile Asn Ala Val Ala Tyr Tyr Arg Gly Leu Asp Val Ser
465                 470                 475                 480
Val Ile Pro Thr Ser Gly Asp Val Val Val Ala Thr Asp Ala Leu
                485                 490                 495
Met Thr Gly Tyr Thr Gly Asp Phe Asp Ser Val Ile Asp Cys Asn Thr
                500                 505                 510
Cys Val Thr Gln Thr Val Asp Phe Ser Leu Asp Pro Thr Phe Thr Ile
            515                 520                 525
Glu Thr Thr Thr Leu Pro Gln Asp Ala Val Ser Arg Thr Gln Arg Arg
        530                 535                 540
Gly Arg Thr Gly Arg Gly Lys Pro Gly Ile Tyr Arg Phe Val Ala Pro
545                 550                 555                 560
Gly Glu Arg Pro Ser Gly Met Phe Asp Ser Ser Val Leu Cys Glu Cys
                565                 570                 575
Tyr Asp Ala Gly Cys Ala Trp Tyr Glu Leu Thr Pro Ala Glu Thr Thr
                580                 585                 590
Val Arg Leu Arg Ala Tyr Met Asn Thr Pro Gly Leu Pro Val Cys Gln
            595                 600                 605
Asp His Leu Glu Phe Trp Glu Gly Val Phe Thr Gly Leu Thr His Ile
        610                 615                 620
Ala Met Asp Ala His Phe Leu Ser Gln Ala Pro Pro Ser Trp Asp
625                 630                 635                 640
Gln Met Trp Lys Cys Leu Ile Arg Leu Lys Pro Thr Leu His Gly Pro
                645                 650                 655
Thr Pro Leu Leu Tyr Arg Leu Gly Ala Val Gln Asn Glu Ile Thr Leu
                660                 665                 670
Thr His Pro Val Thr Lys Tyr Ile Met Thr Cys Met Ser Ala Asp Leu
            675                 680                 685
Glu Val Val Thr Ser Thr Trp Val Leu Val Gly Gly Val Leu Ala Ala
        690                 695                 700
```

```
Leu Ala Ala Tyr Cys Leu Ser Thr Gly Cys Val Ile Val Gly Arg
705                 710                 715                 720

Val Val Leu Ser Gly Lys Pro Ala Ile Ile Pro Asp Arg Glu Val Leu
            725                 730                 735

Tyr Arg Glu Phe Asp Glu Met Glu Cys Ser Gln His Leu Pro Tyr
                740                 745                 750

Ile Glu Gln Gly Met Met Leu Ala Glu Gln Phe Lys Gln Lys Ala Leu
            755                 760                 765

Gly Leu Leu Gln Thr Ala Ser Arg Gln Ala Glu Val Ile Ala Pro Ala
        770                 775                 780

Val Gln Thr Asn Trp Gln Lys Leu Glu Thr Phe Trp Ala Lys His Met
785                 790                 795                 800

Trp Asn Phe Ile Ser Gly Ile Gln Tyr Leu Ala Gly Leu Ser Thr Leu
                805                 810                 815

Pro Gly Asn Pro Ala Ile Ala Ser Leu Met Ala Phe Thr Ala Ala Val
                820                 825                 830

Thr Ser Pro Leu Thr Thr Ser Gln Thr Leu Leu Phe Asn Ile Leu Gly
            835                 840                 845

Gly Trp Val Ala Ala Gln Leu Ala Ala Pro Gly Ala Ala Thr Ala Phe
850                 855                 860

Val Gly Ala Gly Leu Ala Gly Ala Ala Ile Gly Ser Val Gly Leu Gly
865                 870                 875                 880

Lys Val Leu Ile Asp Ile Leu Ala Gly Tyr Gly Ala Gly Val Ala Gly
                885                 890                 895

Ala Leu Val Ala Phe Lys Ile Met Ser Gly Glu Val Pro Ser Thr Glu
                900                 905                 910

Asp Leu Val Asn Leu Leu Pro Ala Ile Leu Ser Pro Gly Ala Leu Val
            915                 920                 925

Val Gly Val Val Cys Ala Ala Ile Leu Arg Arg His Val Gly Pro Gly
            930                 935                 940

Glu Gly Ala Val Gln Trp Met Asn Arg Leu Ile Ala Phe Ala Ser Arg
945                 950                 955                 960

Gly Asn His Val Ser Pro Val His His Lys Arg
                965                 970

(2) INFORMATION FOR SEQ ID NO:53:

(i) SEQUENCE CHARACTERISTICS:
        (A) LENGTH: 973 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:53:

Met Ser Phe Val Val Ile Ile Pro Ala Arg Tyr Ala Ser Thr Arg Leu
1               5                   10                  15

Pro Gly Lys Pro Leu Val Asp Ile Asn Gly Lys Pro Met Ile Val His
            20                  25                  30

Val Leu Glu Arg Ala Arg Glu Ser Gly Ala Glu Arg Ile Ile Val Ala
        35                  40                  45

Thr Asp His Glu Asp Val Ala Arg Ala Val Glu Ala Ala Gly Gly Glu
    50                  55                  60

Val Cys Met Thr Arg Ala Asp His Gln Ser Gly Thr Glu Arg Leu Ala
65                  70                  75                  80
```

-continued

```
Glu Val Val Glu Lys Cys Ala Phe Ser Asp Asp Thr Val Ile Val Asn
                85                  90                  95
Val Gln Gly Asp Glu Pro Met Ile Pro Ala Thr Ile Ile Arg Gln Val
            100                 105                 110
Ala Asp Asn Leu Ala Gln Arg Gln Val Gly Met Ala Thr Leu Ala Val
            115                 120                 125
Pro Ile His Asn Ala Glu Glu Ala Phe Asn Pro Asn Ala Val Lys Val
            130                 135                 140
Val Leu Asp Ala Glu Gly Tyr Ala Leu Tyr Phe Ser Arg Ala Thr Ile
145                 150                 155                 160
Pro Trp Asp Arg Asp Arg Phe Ala Glu Gly Leu Glu Thr Val Gly Asp
                165                 170                 175
Asn Phe Leu Arg His Leu Gly Ile Tyr Gly Tyr Arg Ala Gly Phe Ile
                180                 185                 190
Arg Arg Tyr Val Asn Trp Gln Pro Ser Pro Leu Glu His Ile Glu Met
            195                 200                 205
Leu Glu Gln Leu Arg Val Leu Trp Tyr Gly Lys Ile His Val Ala
            210                 215                 220
Val Ala Gln Glu Val Pro Gly Thr Gly Val Asp Thr Pro Glu Asp Leu
225                 230                 235                 240
Asp Pro Ser Thr Asn Ser Met Ala Val Asp Phe Ile Pro Val Glu Asn
                245                 250                 255
Leu Glu Thr Thr Met Arg Ser Pro Val Phe Thr Asp Asn Ser Ser Pro
                260                 265                 270
Pro Val Val Pro Gln Ser Phe Gln Val Ala His Leu His Ala Pro Thr
            275                 280                 285
Gly Ser Gly Lys Ser Thr Lys Val Pro Ala Ala Tyr Ala Ala Gln Gly
            290                 295                 300
Tyr Lys Val Leu Val Leu Asn Pro Ser Val Ala Ala Thr Leu Gly Phe
305                 310                 315                 320
Gly Ala Tyr Met Ser Lys Ala His Gly Ile Asp Pro Asn Ile Arg Thr
                325                 330                 335
Gly Val Arg Thr Ile Thr Thr Gly Ser Pro Ile Thr Tyr Ser Thr Tyr
                340                 345                 350
Gly Lys Phe Leu Ala Asp Gly Gly Cys Ser Gly Gly Ala Tyr Asp Ile
            355                 360                 365
Ile Ile Cys Asp Glu Cys His Ser Thr Asp Ala Thr Ser Ile Leu Gly
            370                 375                 380
Ile Gly Thr Val Leu Asp Gln Ala Glu Thr Ala Gly Ala Arg Leu Val
385                 390                 395                 400
Val Leu Ala Thr Ala Thr Pro Pro Gly Ser Val Thr Val Pro His Pro
                405                 410                 415
Asn Ile Glu Glu Val Ala Leu Ser Thr Thr Gly Glu Ile Pro Phe Tyr
            420                 425                 430
Gly Lys Ala Ile Pro Leu Glu Val Ile Lys Gly Gly Arg His Leu Ile
            435                 440                 445
Phe Cys His Ser Lys Lys Cys Asp Glu Leu Ala Ala Lys Leu Val
            450                 455                 460
Ala Leu Gly Ile Asn Ala Val Ala Tyr Tyr Arg Gly Leu Asp Val Ser
465                 470                 475                 480
Val Ile Pro Thr Ser Gly Asp Val Val Val Ala Thr Asp Ala Leu
                485                 490                 495
```

-continued

```
Met Thr Gly Tyr Thr Gly Asp Phe Asp Ser Val Ile Asp Cys Asn Thr
            500                 505                 510

Cys Val Thr Gln Thr Val Asp Phe Ser Leu Asp Pro Thr Phe Thr Ile
        515                 520                 525

Glu Thr Thr Thr Leu Pro Gln Asp Ala Val Ser Arg Thr Gln Arg Arg
    530                 535                 540

Gly Arg Thr Gly Arg Gly Lys Pro Gly Ile Tyr Arg Phe Val Ala Pro
545                 550                 555                 560

Gly Glu Arg Pro Ser Gly Met Phe Asp Ser Ser Val Leu Cys Glu Cys
                565                 570                 575

Tyr Asp Ala Gly Cys Ala Trp Tyr Glu Leu Thr Pro Ala Glu Thr Thr
            580                 585                 590

Val Arg Leu Arg Ala Tyr Met Asn Thr Pro Gly Leu Pro Val Cys Gln
        595                 600                 605

Asp His Leu Glu Phe Trp Glu Gly Val Phe Thr Gly Leu Thr His Ile
    610                 615                 620

Ala Met Asp Ala His Phe Leu Ser Gln Thr Lys Gln Ser Gly Glu Asn
625                 630                 635                 640

Leu Pro Tyr Leu Val Ala Tyr Gln Ala Thr Val Cys Ala Arg Ala Gln
                645                 650                 655

Ala Pro Thr Pro Leu Leu Tyr Arg Leu Gly Ala Val Gln Asn Glu Ile
            660                 665                 670

Thr Leu Thr His Pro Val Thr Lys Tyr Ile Met Thr Cys Met Ser Ala
        675                 680                 685

Asp Leu Glu Val Val Thr Ser Thr Trp Val Leu Val Gly Gly Val Leu
    690                 695                 700

Ala Ala Leu Ala Ala Tyr Cys Leu Ser Thr Gly Cys Val Val Ile Val
705                 710                 715                 720

Gly Arg Val Val Leu Ser Gly Lys Pro Ala Ile Ile Pro Asp Arg Glu
                725                 730                 735

Val Leu Tyr Arg Glu Phe Asp Glu Met Glu Glu Cys Ser Gln His Leu
            740                 745                 750

Pro Tyr Ile Glu Gln Gly Met Met Leu Ala Glu Gln Phe Lys Gln Lys
        755                 760                 765

Ala Leu Gly Leu Leu Gln Thr Ala Ser Arg Gln Ala Glu Val Ile Ala
    770                 775                 780

Pro Ala Val Gln Thr Asn Trp Gln Lys Leu Glu Thr Phe Trp Ala Lys
785                 790                 795                 800

His Met Trp Asn Phe Ile Ser Gly Ile Gln Tyr Leu Ala Gly Leu Ser
                805                 810                 815

Thr Leu Pro Gly Asn Pro Ala Ile Ala Ser Leu Met Ala Phe Thr Ala
            820                 825                 830

Ala Val Thr Ser Pro Leu Thr Thr Ser Gln Thr Leu Leu Phe Asn Ile
        835                 840                 845

Leu Gly Gly Trp Val Ala Ala Gln Leu Ala Ala Pro Gly Ala Ala Thr
    850                 855                 860

Ala Phe Val Gly Ala Gly Leu Ala Gly Ala Ala Ile Gly Ser Val Gly
865                 870                 875                 880

Leu Gly Lys Val Leu Ile Asp Ile Leu Ala Gly Tyr Gly Ala Gly Val
                885                 890                 895

Ala Gly Ala Leu Val Ala Phe Lys Ile Met Ser Gly Glu Val Pro Ser
            900                 905                 910

Thr Glu Asp Leu Val Asn Leu Leu Pro Ala Ile Leu Ser Pro Gly Ala
```

```
                915                 920                 925
Leu Val Val Gly Val Val Cys Ala Ala Ile Leu Arg Arg His Val Gly
    930                 935                 940

Pro Gly Glu Gly Ala Val Gln Trp Met Asn Arg Leu Ile Ala Phe Ala
945                 950                 955                 960

Ser Arg Gly Asn His Val Ser Pro Val His His Lys Arg
                965                 970
```

(2) INFORMATION FOR SEQ ID NO:54:

(i) SEQUENCE CHARACTERISTICS:
        (A) LENGTH: 992 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:54:

```
Met Ser Phe Val Val Ile Ile Pro Ala Arg Tyr Ala Ser Thr Arg Leu
1               5                   10                  15

Pro Gly Lys Pro Leu Val Asp Ile Asn Gly Lys Pro Met Ile Val His
                20                  25                  30

Val Leu Glu Arg Ala Arg Glu Ser Gly Ala Glu Arg Ile Ile Val Ala
            35                  40                  45

Thr Asp His Glu Asp Val Ala Arg Ala Val Glu Ala Ala Gly Gly Glu
50                  55                  60

Val Cys Met Thr Arg Ala Asp His Gln Ser Gly Thr Glu Arg Leu Ala
65                  70                  75                  80

Glu Val Val Glu Lys Cys Ala Phe Ser Asp Thr Val Ile Val Asn
                85                  90                  95

Val Gln Gly Asp Glu Pro Met Ile Pro Ala Thr Ile Ile Arg Gln Val
            100                 105                 110

Ala Asp Asn Leu Ala Gln Arg Gln Val Gly Met Ala Thr Leu Ala Val
            115                 120                 125

Pro Ile His Asn Ala Glu Glu Ala Phe Asn Pro Asn Ala Val Lys Val
130                 135                 140

Val Leu Asp Ala Glu Gly Tyr Ala Leu Tyr Phe Ser Arg Ala Thr Ile
145                 150                 155                 160

Pro Trp Asp Arg Asp Arg Phe Ala Glu Gly Leu Glu Thr Val Gly Asp
                165                 170                 175

Asn Phe Leu Arg His Leu Gly Ile Tyr Gly Tyr Arg Ala Gly Phe Ile
            180                 185                 190

Arg Arg Tyr Val Asn Trp Gln Pro Ser Pro Leu Glu His Ile Glu Met
        195                 200                 205

Leu Glu Gln Leu Arg Val Leu Trp Tyr Gly Glu Lys Ile His Val Ala
    210                 215                 220

Val Ala Gln Glu Val Pro Gly Thr Gly Val Asp Thr Pro Glu Asp Leu
225                 230                 235                 240

Asp Pro Ser Thr Asn Ser Met Ala Val Asp Phe Ile Pro Val Glu Asn
                245                 250                 255

Leu Glu Thr Thr Met Arg Ser Pro Val Phe Thr Asp Asn Ser Ser Pro
            260                 265                 270

Pro Val Val Pro Gln Ser Phe Gln Val Ala His Leu His Ala Pro Thr
            275                 280                 285

Gly Ser Gly Lys Ser Thr Lys Val Pro Ala Ala Tyr Ala Ala Gln Gly
```

-continued

```
            290                 295                 300
Tyr Lys Val Leu Val Leu Asn Pro Ser Val Ala Ala Thr Leu Gly Phe
305                 310                 315                 320
Gly Ala Tyr Met Ser Lys Ala His Gly Ile Asp Pro Asn Ile Arg Thr
                325                 330                 335
Gly Val Arg Thr Ile Thr Thr Gly Ser Pro Ile Thr Tyr Ser Thr Tyr
                340                 345                 350
Gly Lys Phe Leu Ala Asp Gly Gly Cys Ser Gly Gly Ala Tyr Asp Ile
                355                 360                 365
Ile Ile Cys Asp Glu Cys His Ser Thr Asp Ala Thr Ser Ile Leu Gly
370                 375                 380
Ile Gly Thr Val Leu Asp Gln Ala Glu Thr Ala Gly Ala Arg Leu Val
385                 390                 395                 400
Val Leu Ala Thr Ala Thr Pro Pro Gly Ser Val Thr Val Pro His Pro
                405                 410                 415
Asn Ile Glu Glu Val Ala Leu Ser Thr Thr Gly Glu Ile Pro Phe Tyr
                420                 425                 430
Gly Lys Ala Ile Pro Leu Glu Val Ile Lys Gly Gly Arg His Leu Ile
                435                 440                 445
Phe Cys His Ser Lys Lys Lys Cys Asp Glu Leu Ala Ala Lys Leu Val
            450                 455                 460
Ala Leu Gly Ile Asn Ala Val Ala Tyr Tyr Arg Gly Leu Asp Val Ser
465                 470                 475                 480
Val Ile Pro Thr Ser Gly Asp Val Val Val Ala Thr Asp Ala Leu
                485                 490                 495
Met Thr Gly Tyr Thr Gly Asp Phe Asp Ser Val Ile Asp Cys Asn Thr
                500                 505                 510
Cys Val Thr Gln Thr Val Asp Phe Ser Leu Asp Pro Thr Phe Thr Ile
            515                 520                 525
Glu Thr Thr Thr Leu Pro Gln Asp Ala Val Ser Arg Thr Gln Arg Arg
530                 535                 540
Gly Arg Thr Gly Arg Gly Lys Pro Gly Ile Tyr Arg Phe Val Ala Pro
545                 550                 555                 560
Gly Glu Arg Pro Ser Gly Met Phe Asp Ser Ser Val Leu Cys Glu Cys
                565                 570                 575
Tyr Asp Ala Gly Cys Ala Trp Tyr Glu Leu Thr Pro Ala Glu Thr Thr
                580                 585                 590
Val Arg Leu Arg Ala Tyr Met Asn Thr Pro Gly Leu Pro Val Cys Gln
                595                 600                 605
Asp His Leu Glu Phe Trp Glu Gly Val Phe Thr Gly Leu Thr His Ile
            610                 615                 620
Ala Met Asp Ala His Phe Leu Ser Gln Thr Lys Gln Ser Gly Glu Asn
625                 630                 635                 640
Leu Pro Tyr Leu Val Ala Tyr Gln Ala Thr Val Cys Ala Arg Ala Gln
                645                 650                 655
Ala Pro Ser Trp Asp Gln Met Trp Lys Cys Leu Ile Arg Leu Lys Pro
                660                 665                 670
Thr Leu His Gly Pro Thr Pro Leu Leu Tyr Arg Leu Gly Ala Val Gln
            675                 680                 685
Asn Glu Ile Thr Leu Thr His Pro Val Thr Lys Tyr Ile Met Thr Cys
            690                 695                 700
Met Ser Ala Asp Leu Glu Val Val Thr Ser Thr Trp Val Leu Val Gly
705                 710                 715                 720
```

```
Gly Val Leu Ala Ala Leu Ala Ala Tyr Cys Leu Ser Thr Gly Cys Val
                725                 730                 735

Val Ile Val Gly Arg Val Val Leu Ser Gly Lys Pro Ala Ile Ile Pro
            740                 745                 750

Asp Arg Glu Val Leu Tyr Arg Glu Phe Asp Glu Met Glu Glu Cys Ser
                755                 760                 765

Gln His Leu Pro Tyr Ile Glu Gln Gly Met Met Leu Ala Glu Gln Phe
            770                 775                 780

Lys Gln Lys Ala Leu Gly Leu Leu Gln Thr Ala Ser Arg Gln Ala Glu
785                 790                 795                 800

Val Ile Ala Pro Ala Val Gln Thr Asn Trp Gln Lys Leu Glu Thr Phe
                805                 810                 815

Trp Ala Lys His Met Trp Asn Phe Ile Ser Gly Ile Gln Tyr Leu Ala
            820                 825                 830

Gly Leu Ser Thr Leu Pro Gly Asn Pro Ala Ile Ala Ser Leu Met Ala
            835                 840                 845

Phe Thr Ala Ala Val Thr Ser Pro Leu Thr Thr Ser Gln Thr Leu Leu
850                 855                 860

Phe Asn Ile Leu Gly Gly Trp Val Ala Ala Gln Leu Ala Ala Pro Gly
865                 870                 875                 880

Ala Ala Thr Ala Phe Val Gly Ala Gly Leu Ala Gly Ala Ala Ile Gly
                885                 890                 895

Ser Val Gly Leu Gly Lys Val Leu Ile Asp Ile Leu Ala Gly Tyr Gly
            900                 905                 910

Ala Gly Val Ala Gly Ala Leu Val Ala Phe Lys Ile Met Ser Gly Glu
            915                 920                 925

Val Pro Ser Thr Glu Asp Leu Val Asn Leu Leu Pro Ala Ile Leu Ser
930                 935                 940

Pro Gly Ala Leu Val Val Gly Val Val Cys Ala Ala Ile Leu Arg Arg
945                 950                 955                 960

His Val Gly Pro Gly Glu Gly Ala Val Gln Trp Met Asn Arg Leu Ile
                965                 970                 975

Ala Phe Ala Ser Arg Gly Asn His Val Ser Pro Val His His Lys Arg
                980                 985                 990

(2) INFORMATION FOR SEQ ID NO:55:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:55:

Pro Pro Pro Ser Tyr Asp Gln Met Trp Lys Cys Leu Ile Arg Leu Lys
1               5                   10                  15

Pro Thr Leu His Gly
            20

(2) INFORMATION FOR SEQ ID NO:56:

(i) SEQUENCE CHARACTERISTICS:
        (A) LENGTH: 382 base pairs
        (B) TYPE: nucleic acid
        (C) STRANDEDNESS: single
        (D) TOPOLOGY: linear
```

(ii) MOLECULE TYPE: DNA (genomic)

(xi) SEQUENCE DESCRIPTION: SEQ ID NO:56:

| | | | | | |
|---|---|---|---|---|---|
| CTCCACTCTA | TGAATTCGTG | ATCGATTGCA | ATACGTGTGT | CACCCAGACA | GTCGACTTCA | 60 |
| GCCTTGACCC | TACCTTCACC | ATTGAGACAA | CCACGCTTCC | CCAGGATGCT | GTCTCCCGTA | 120 |
| CTCAGCGTCG | GGGCAGGACT | GGTAGGGGGA | AGCCAGGCAT | CTACAGATTT | GTGGCACCGG | 180 |
| GGGAGCGCCC | TTCCGGCATG | TTTGACTCGT | CCGTCCTCTG | CGAGTGCTAT | GACGCGGGCT | 240 |
| GTGCTTGGTA | TGAGCTTACA | CCCGCCGAGA | CCACAGTTAG | GCTACGAGCT | TACATGAACA | 300 |
| CTCCGGGGCT | TCCCGTGTGC | AAGATCATC | TTGAATTTTG | GGAGGGCGTC | TTTACAGGCC | 360 |
| TCACTCATAT | AGCCATGGAT | CC | | | | 382 |

(2) INFORMATION FOR SEQ ID NO:57:

(i) SEQUENCE CHARACTERISTICS:
        (A) LENGTH: 1420 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:57:

| | | | | | |
|---|---|---|---|---|---|
| GAATTCGTGA | TCGATTGCAA | TACGTGTGTC | ACCCAGACAG | TCGACTTCAG | CCTTGACCCT | 60 |
| ACCTTCACCA | TTGAGACAAC | CACGCTTCCC | CAGGATGCTG | TCTCCCGTAC | TCAGCGTCGG | 120 |
| GGCAGGACTG | GTAGGGGAA | GCCAGGCATC | TACAGATTTG | TGGCACCGGG | GGAGCGCCCT | 180 |
| TCCGGCATGT | TTGACTCGTC | CGTCCTCTGC | GAGTGCTATG | ACGCGGGCTG | TGCTTGGTAT | 240 |
| GAGCTTACAC | CCGCCGAGAC | CACAGTTAGG | CTACGAGCTT | ACATGAACAC | TCCGGGGCTT | 300 |
| CCCGTGTGCC | AAGATCATCT | TGAATTTTGG | GAGGGCGTCT | TTACAGGCCT | CACTCATATA | 360 |
| GCCATGGACG | CTCACTTCCT | GTCTCAGACC | AAACAGTCTG | GTGAAAACCT | TCCGTACCTG | 420 |
| GTTGCTTACC | AGGCTACCGT | TTGCGCTCGT | GCTCAGGCCC | CGACCCCGCT | GCTGTACCGT | 480 |
| CTGGGTGCTG | TTCAGAACGA | AATCACCCTG | ACCCACCCGG | TTACCAAATA | CATCATGACC | 540 |
| TGCATGTCTG | CTGATCTAGA | AGTTGTTACC | TCTACCTGGG | TTCTGGTTGG | TGGTGTTCTG | 600 |
| GCTGCTCTGG | CTGCTTACTG | CCTGTCGACC | GGTTGCGTTG | TTATCGTTGG | TCGTGTTGTT | 660 |
| CTGTCTGGTA | AACCGGCCAT | TATCCCGGAC | CGTGAAGTTC | TGTACCGTGA | GTTCGACGAA | 720 |
| ATGGAAGAAT | GCTCTCAGCA | CCTGCCGTAC | ATCGAACAGG | GTATGATGCT | GGCTGAACAG | 780 |
| TTCAAACAGA | AAGCTCTGGG | TCTGCTGCAG | ACCGCTTCTC | GTCAGGCTGA | AGTTATCGCT | 840 |
| CCGGCTGTTC | AGACCAACTG | GCAGAAACTC | GAGACCTTCT | GGGCTAAACA | CATGTGGAAC | 900 |
| TTCATCTCTG | GTATCCAGTA | CCTGGCTGGT | CTGTCTACCC | TGCCGGGTAA | CCCGGCTATC | 960 |
| GCAAGCTTGA | TGGCTTTCAC | CGCTGCTGTT | ACCTCTCCGC | TGACCACCTC | TCAGACCCTG | 1020 |
| CTGTTCAACA | TTCTGGGTGG | TTGGGTTGCT | GCTCAGCTGG | CTGCTCCGGG | TGCTGCTACC | 1080 |
| GCTTTCGTTG | GTGCTGGTCT | GGCTGGTGCT | GCTATCGGTT | CTGTAGGCCT | GGGTAAAGTT | 1140 |
| CTGATCGACA | TTCTGGCTGG | TTACGGTGCT | GGTGTTGCTG | GAGCTCTGGT | TGCTTTCAAA | 1200 |
| ATCATGTCTG | GTGAAGTTCC | GTCTACCGAA | GATCGGTTA | ACCTGCTGCC | GGCTATCCTG | 1260 |
| TCTCCGGGTG | CTCTGGTTGT | TGGTGTTGTT | TGCGCTGCTA | TCCTGCGTCG | TCACGTTGGC | 1320 |
| CCGGGTGAAG | GTGCTGTTCA | GTGGATGAAC | CGTCTGATCG | CTTTCGCTTC | TCGTGGTAAC | 1380 |
| CACGTTTCTC | CGGTTCACCA | CAAACGTTAA | CCATGGATCC | | | 1420 |

(2) INFORMATION FOR SEQ ID NO:58:

(i) SEQUENCE CHARACTERISTICS:
        (A) LENGTH: 512 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:58:

```
Met Ser Phe Val Val Ile Ile Pro Ala Arg Tyr Ala Ser Thr Arg Leu
 1               5                  10                  15

Pro Gly Lys Pro Leu Val Asp Ile Asn Gly Lys Pro Met Ile Val His
            20                  25                  30

Val Leu Glu Arg Ala Arg Glu Ser Gly Ala Glu Arg Ile Ile Val Ala
        35                  40                  45

Thr Asp His Glu Asp Val Ala Arg Ala Val Glu Ala Ala Gly Gly Glu
    50                  55                  60

Val Cys Met Thr Arg Ala Asp His Gln Ser Gly Thr Glu Arg Leu Ala
65                  70                  75                  80

Glu Val Val Glu Lys Cys Ala Phe Ser Asp Asp Thr Val Ile Val Asn
                85                  90                  95

Val Gln Gly Asp Glu Pro Met Ile Pro Ala Thr Ile Ile Arg Gln Val
            100                 105                 110

Ala Asp Asn Leu Ala Gln Arg Gln Val Gly Met Ala Thr Leu Ala Val
        115                 120                 125

Pro Ile His Asn Ala Glu Glu Ala Phe Asn Pro Asn Ala Val Lys Val
    130                 135                 140

Val Leu Asp Ala Glu Gly Tyr Ala Leu Tyr Phe Ser Arg Ala Thr Ile
145                 150                 155                 160

Pro Trp Asp Arg Asp Arg Phe Ala Glu Gly Leu Glu Thr Val Gly Asp
                165                 170                 175

Asn Phe Leu Arg His Leu Gly Ile Gly Tyr Arg Ala Gly Phe Ile
            180                 185                 190

Arg Arg Tyr Val Asn Trp Gln Pro Ser Pro Leu Glu His Ile Glu Met
        195                 200                 205

Leu Glu Gln Leu Arg Val Leu Trp Tyr Gly Glu Lys Ile His Val Ala
    210                 215                 220

Val Ala Gln Glu Val Pro Gly Thr Gly Val Asp Thr Pro Glu Asp Leu
225                 230                 235                 240

Asp Pro Ser Thr Asn Ser Ser Thr Gly Cys Val Val Ile Val Gly Arg
                245                 250                 255

Val Val Leu Ser Gly Lys Pro Ala Ile Ile Pro Asp Arg Glu Val Leu 260
Tyr Arg Glu Phe Asp Glu Met Glu Glu Cys Ser Gln His Leu Pro Tyr
            275                 280                 285

Ile Glu Gln Gly Met Met Leu Ala Glu Gln Phe Lys Gln Lys Ala Leu
    290                 295                 300

Gly Leu Leu Gln Thr Ala Ser Arg Gln Ala Glu Val Ile Ala Pro Ala
305                 310                 315                 320

Val Gln Thr Asn Trp Gln Lys Leu Glu Thr Phe Trp Ala Lys His Met
                325                 330                 335

Trp Asn Phe Ile Ser Gly Ile Gln Tyr Leu Ala Gly Leu Ser Thr Leu
            340                 345                 350

Pro Gly Asn Pro Ala Ile Ala Ser Leu Met Ala Phe Thr Ala Ala Val
```

```
                355                 360                 365
Thr Ser Pro Leu Thr Thr Ser Gln Thr Leu Leu Phe Asn Ile Leu Gly
    370                 375                 380

Gly Trp Val Ala Ala Gln Leu Ala Ala Pro Gly Ala Ala Thr Ala Phe
385                 390                 395                 400

Val Gly Ala Gly Leu Ala Gly Ala Ala Ile Gly Ser Val Gly Leu Gly
                405                 410                 415

Lys Val Leu Ile Asp Ile Leu Ala Gly Tyr Gly Ala Gly Val Ala Gly
                420                 425                 430

Ala Leu Val Ala Phe Lys Ile Met Ser Gly Glu Val Pro Ser Thr Glu
                435                 440                 445

Asp Leu Val Asn Leu Leu Pro Ala Ile Leu Ser Pro Gly Ala Leu Val
    450                 455                 460

Val Gly Val Val Cys Ala Ala Ile Leu Arg Arg His Val Gly Pro Gly
465                 470                 475                 480

Glu Gly Ala Val Gln Trp Met Asn Arg Leu Ile Ala Phe Ala Ser Arg
                485                 490                 495

Gly Asn His Val Ser Pro Trp Asp Pro Leu Asp Cys Arg His Ala Lys
                500                 505                 510

(2) INFORMATION FOR SEQ ID NO:59:

(i) SEQUENCE CHARACTERISTICS:
        (A) LENGTH: 513 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:59:

Met Ser Phe Val Val Ile Ile Pro Ala Pro Tyr Ala Ser Thr Arg Leu
1               5                   10                  15

Pro Gly Lys Pro Leu Val Asp Ile Asn Gly Lys Pro Met Ile Val His
                20                  25                  30

Val Leu Glu Arg Ala Arg Glu Ser Gly Ala Glu Arg Ile Ile Val Ala
                35                  40                  45

Thr Asp His Glu Asp Val Ala Arg Ala Val Glu Ala Ala Gly Gly Glu
    50                  55                  60

Val Cys Met Thr Arg Ala Asp His Gln Ser Gly Thr Glu Arg Leu Ala
65                  70                  75                  80

Glu Val Val Glu Lys Cys Ala Phe Ser Asp Asp Thr Val Ile Val Asn
                85                  90                  95

Val Gln Gly Asp Glu Pro Met Ile Pro Ala Thr Ile Ile Arg Gln Val
                100                 105                 110

Ala Asp Asn Leu Ala Gln Arg Gln Val Gly Met Ala Thr Leu Ala Val
            115                 120                 125

Pro Ile His Asn Ala Glu Glu Ala Phe Asn Pro Asn Ala Val Lys Val
            130                 135                 140

Val Leu Asp Ala Glu Gly Tyr Ala Leu Tyr Phe Ser Arg Ala Thr Ile
145                 150                 155                 160

Pro Trp Asp Arg Asp Arg Phe Ala Glu Gly Leu Glu Thr Val Gly Asp
                165                 170                 175

Asn Phe Leu Arg His Leu Gly Ile Tyr Gly Tyr Arg Ala Gly Phe Ile
            180                 185                 190

Arg Arg Tyr Val Asn Trp Gln Pro Ser Pro Leu Glu His Ile Glu Met
```

-continued

```
                195                 200                 205
Leu Glu Gln Leu Arg Val Leu Trp Tyr Gly Glu Lys Ile His Val Ala
            210                 215                 220
Val Ala Gln Glu Val Pro Gly Thr Gly Val Asp Thr Pro Glu Asp Leu
225                 230                 235                 240
Asp Pro Ser Thr Asn Ser Met Ala Val Asp Phe Ile Pro Val Glu Asn
            245                 250                 255
Leu Glu Thr Thr Met Arg Ser Pro Val Phe Thr Asp Asn Ser Ser Pro
            260                 265                 270
Pro Val Val Pro Gln Ser Phe Gln Val Ala His Leu His Ala Pro Thr
            275                 280                 285
Gly Ser Gly Lys Ser Thr Lys Val Pro Ala Ala Tyr Ala Ala Gln Gly
            290                 295                 300
Tyr Lys Val Leu Val Leu Asn Pro Ser Val Ala Ala Thr Leu Gly Phe
305                 310                 315                 320
Gly Ala Tyr Met Ser Lys Ala His Gly Ile Asp Pro Asn Ile Arg Thr
                325                 330                 335
Gly Val Arg Thr Ile Thr Thr Gly Ser Pro Ile Thr Tyr Ser Thr Tyr
            340                 345                 350
Gly Lys Phe Leu Ala Asp Gly Gly Cys Ser Gly Gly Ala Tyr Asp Ile
            355                 360                 365
Ile Ile Cys Asp Glu Cys His Ser Thr Asp Ala Thr Ser Ile Leu Gly
370                 375                 380
Ile Gly Thr Val Leu Asp Gln Ala Glu Thr Ala Gly Ala Arg Leu Val
385                 390                 395                 400
Val Leu Ala Thr Ala Thr Pro Pro Gly Ser Val Thr Val Pro His Pro
                405                 410                 415
Asn Ile Glu Glu Val Ala Leu Ser Thr Thr Gly Glu Ile Pro Phe Tyr
            420                 425                 430
Gly Lys Ala Ile Pro Leu Glu Val Ile Lys Gly Gly Arg His Leu Ile
            435                 440                 445
Phe Cys His Ser Lys Lys Lys Cys Asp Glu Leu Ala Ala Lys Leu Val
    450                 455                 460
Ala Leu Gly Ile Asn Ala Val Ala Tyr Tyr Arg Gly Leu Asp Val Ser
465                 470                 475                 480
Val Ile Pro Thr Ser Gly Asp Val Val Val Ala Thr Asp Ala Leu
            485                 490                 495
Met Thr Gly Tyr Thr Gly Asp Phe Asp Ser Val Ile Asp Cys Asn Thr
            500                 505                 510
Cys
```